US012590076B2

(12) United States Patent
Ito et al.

(10) Patent No.: US 12,590,076 B2
(45) Date of Patent: Mar. 31, 2026

(54) COMPOUND, MATERIAL FOR ORGANIC ELECTROLUMINESCENT ELEMENT, ORGANIC ELECTROLUMINESCENT ELEMENT, AND ELECTRONIC DEVICE

(71) Applicant: IDEMITSU KOSAN CO., LTD., Chiyoda-ku (JP)

(72) Inventors: Hirokatsu Ito, Sodegaura (JP); Tasuku Haketa, Sodegaura (JP); Yu Kudo, Sodegaura (JP)

(73) Assignee: IDEMITSU KOSAN CO., LTD., Chiyoda-ku (JP)

(*) Notice: Subject to any disclaimer, the term of this patent is extended or adjusted under 35 U.S.C. 154(b) by 400 days.

(21) Appl. No.: 17/053,630

(22) PCT Filed: May 10, 2019

(86) PCT No.: PCT/JP2019/018737
§ 371 (c)(1),
(2) Date: Nov. 6, 2020

(87) PCT Pub. No.: WO2019/216411
PCT Pub. Date: Nov. 14, 2019

(65) Prior Publication Data
US 2021/0253546 A1 Aug. 19, 2021

(30) Foreign Application Priority Data
May 10, 2018 (JP) ................................ 2018-091763

(51) Int. Cl.
*C07D 307/91* (2006.01)
*H10K 50/15* (2023.01)
*H10K 85/60* (2023.01)

(52) U.S. Cl.
CPC ......... *C07D 307/91* (2013.01); *H10K 85/615* (2023.02); *H10K 85/636* (2023.02);
(Continued)

(58) Field of Classification Search
CPC .............. C07D 307/91; H01L 51/0052; H01L 51/0059; H01L 51/006; H01L 51/0061;
(Continued)

(56) References Cited

U.S. PATENT DOCUMENTS

2015/0179940 A1 6/2015 Mujica-Fernaud et al.
2015/0243891 A1 8/2015 Kato et al.
(Continued)

FOREIGN PATENT DOCUMENTS

CN 101851210 A 10/2010
CN 104603111 A 5/2015
(Continued)

OTHER PUBLICATIONS

WO-2017022727-A1 machine translation (Year: 2017).*
(Continued)

*Primary Examiner* — Elizabeth M. Dahlburg
(74) *Attorney, Agent, or Firm* — Oblon, McClelland, Maier & Neustadt, L.L.P.

(57) ABSTRACT

Provided is an organic electroluminescent element including a compound that is represented by formula (1) and having a
(Continued)

more improved lifetime. In the formula, X, $R^1$-$R^8$, $R^{11}$-$R^{17}$, $R^{21}$-$R^{30}$, $L^1$, $L^2$, n, and $Ar^1$-$Ar^3$ are as defined in the description:

(1)

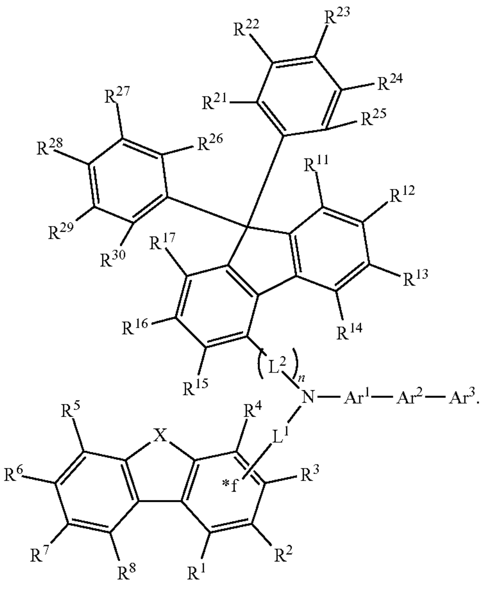

26 Claims, 1 Drawing Sheet

(52) U.S. Cl.
CPC ....... *H10K 85/6574* (2023.02); *H10K 50/156* (2023.02); *H10K 50/157* (2023.02)

(58) Field of Classification Search
CPC ............. H01L 51/0073; H01L 51/0074; H01L 51/5056; H01L 51/5064; H01L 51/5068; H10K 50/15; H10K 50/156; H10K 50/157; H10K 85/615; H10K 85/631; H10K 85/633; H10K 85/636; H10K 85/6574; H10K 50/6576
See application file for complete search history.

(56) References Cited

U.S. PATENT DOCUMENTS

| | | | |
|---|---|---|---|
| 2016/0176801 A1 | 6/2016 | Kato et al. | |
| 2016/0181525 A1 | 6/2016 | Kato et al. | |
| 2016/0329492 A1 | 11/2016 | Funahashi et al. | |
| 2017/0186969 A1 | 6/2017 | Kim et al. | |
| 2017/0229661 A1 | 8/2017 | Haketa et al. | |
| 2018/0097178 A1 | 4/2018 | Mujica-Fernaud et al. | |
| 2018/0114907 A1 | 4/2018 | Takada et al. | |
| 2018/0123043 A1 | 5/2018 | Kato et al. | |
| 2018/0145265 A1 | 5/2018 | Haketa et al. | |
| 2018/0190904 A1 | 7/2018 | Kato et al. | |
| 2018/0219157 A1 | 8/2018 | Yamaki et al. | |
| 2018/0331290 A1 | 11/2018 | Miyake et al. | |
| 2020/0365814 A1* | 11/2020 | Ha | H01L 51/0073 |

FOREIGN PATENT DOCUMENTS

| | | | |
|---|---|---|---|
| CN | 107459478 A | 12/2017 | |
| JP | 2015-530364 A | 10/2015 | |
| JP | 2018-65806 A | 4/2018 | |
| KR | 10-2015-0144823 | 12/2015 | |
| KR | 10-2016-0143627 A | 12/2016 | |
| KR | 10-2017-0134163 A | 12/2017 | |
| KR | 10-1854886 B1 | 5/2018 | |
| WO | WO 2013/118847 A1 | 8/2013 | |
| WO | WO 2014/015935 A2 | 1/2014 | |
| WO | WO 2014/034795 A1 | 3/2014 | |
| WO | WO 2015/129896 A1 | 9/2015 | |
| WO | WO 2016/006709 A1 | 1/2016 | |
| WO | WO 2017/022727 A1 | 2/2017 | |
| WO | WO-2019135665 A1 * | 7/2019 | H01L 51/006 |

OTHER PUBLICATIONS

International Search Report issued Jul. 16, 2019 in PCT/JP2019/018737 filed May 10, 2019, 3 pages.
Chinese Office Action dated Mar. 21, 2023, in Chinese Patent Application No. 201980031310.0 (with English Translation).
Chinese Office Action dated Sep. 28, 2023, in Chinese Patent Application No. 201980031310.0 (with English Translation).
Official Communication Issued in Korean application 10-2020-7032038 on Nov. 30, 2023 w/Engilsh language translation.
Official communication issued in CN application 201980031310.0 on Jan. 29, 2024 (w/English Machine Translation).

* cited by examiner

COMPOUND, MATERIAL FOR ORGANIC ELECTROLUMINESCENT ELEMENT, ORGANIC ELECTROLUMINESCENT ELEMENT, AND ELECTRONIC DEVICE

TECHNICAL FIELD

The present invention relates to compounds, materials for organic electroluminescence devices comprising the compounds, organic electroluminescence devices comprising the compounds, and electronic devices comprising the organic electroluminescence devices.

BACKGROUND ART

An organic electroluminescence device ("organic EL device") is generally composed of an anode, a cathode, and an organic layer sandwiched between the anode and the cathode. When a voltage is applied between electrodes, electrons are injected from the cathode and holes are injected from the anode into a light emitting region. The injected electrons recombine with the injected holes in the light emitting region to form excited states. When the excited states return to the ground state, the energy is released as light. Therefore, it is important for obtaining an organic EL device with high efficiency to develop a compound that transports electrons or holes into the light emitting region efficiently and facilitates the recombination of electrons and holes.

Patent Literature 1 describes an amine compound (formula 140) wherein a biphenylyl group, a 4-(4-dibenzofuranyl)phenyl group, and a 9,9-diphenylfluorene-4-yl group are bonded to the central nitrogen atom.

Patent Literature 2 describes an amine compound (Compound 119) wherein a biphenylyl group, a 4-(4-dibenzothiophenyl)phenyl group, and a 9,9-diphenylfluorene-2-yl group are bonded to the central nitrogen atom and an amine compound (Compound 28) wherein a biphenylyl group, 4-(4-dibenzofuranyl)phenyl group, and a 9,9'-spirobifluorene-4-yl group are bonded to the central nitrogen atom.

Patent Literature 3 describes an amine compound (page 20) wherein a p-terphenylyl group, a 4-(4-dibenzofuranyl) phenyl group, and a 9,9-diphenylfluorene-2-yl group are bonded to the central nitrogen atom.

CITATION LIST

Patent Literature

Patent Literature 1: WO 2014/015935A1
Patent Literature 2: KR 10-2016-0143627A1
Patent Literature 3: WO 2014/034795A1

SUMMARY OF INVENTION

Technical Problem

Various compounds have been reported as materials for the production of organic EL devices. However, compounds that further improve the performance of organic EL devices have been still demanded.

The present invention has been made to solve the above problem and an object of the invention is to provide organic EL devices having further improved lifetime and novel compounds providing such organic EL devices.

Solution to Problem

As a result of intensive research to achieve the above object, the inventors have found that a specific amine compound provides organic EL devices having a further improved lifetime as compared with amine compounds described in the prior art documents mentioned above. The specific amine compound is a compound wherein a 9,9-diphenylfluorene-4-yl structure, an aryl group comprising a dibenzofuran ring or a dibenzothiophene ring, and a structure wherein at least three aromatic hydrocarbon rings (a single ring or a fused ring) are successively bonded to each other via a single bond are bonded to the central nitrogen atom.

In an aspect, the invention provides a compound represented by formula (1) (hereinafter also referred to as "Compound (1)"):

(1)

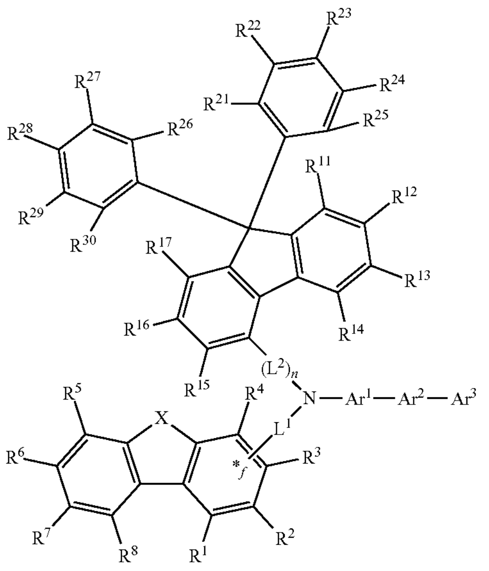

wherein:

X is an oxygen atom or a sulfur atom;

one selected from $R^1$ to $R^4$ is a single bond bonded to *f;

$R^5$ to $R^8$ and $R^1$ to Ra not the single bond bonded to *f are each independently a hydrogen or a substituent, wherein the substituent is selected from the group consisting of a substituted or unsubstituted alkyl group having 1 to 30 carbon atoms and a substituted or unsubstituted aryl group having 6 to 30 ring carbon atoms;

provided that adjacent two selected from $R^5$ to $R^8$ and adjacent two selected from $R^1$ to $R^4$ not the single bond bonded to *f are each independently a hydrogen or the substituent or bonded to each other to form an aliphatic or aromatic ring structure;

$R^{11}$ to $R^{17}$ are each independently, a hydrogen or a substituent, wherein the substituent is selected from the group consisting of a substituted or unsubstituted alkyl group having 1 to 30 carbon atoms and a substituted or unsubstituted aryl group having 6 to 30 ring carbon atoms;

provided that adjacent two selected from $R^{1'}$ to $R^{14}$ and adjacent two selected from $R^{15}$ to $R^{17}$ are each independently a hydrogen or the substituent or bonded to each other to form an aliphatic or aromatic ring structure;

$R^{21}$ to $R^{30}$ are each independently, a hydrogen or a substituent, wherein the substituent is selected from the group consisting of a substituted or unsubstituted alkyl group having 1 to 30 carbon atoms and a substituted or unsubstituted aryl group having 6 to 30 ring carbon atoms;

provided that adjacent two selected from $R^{21}$ to $R^{25}$ and adjacent two selected from $R^{26}$ to $R^{30}$ are each independently a hydrogen or the substituent or bonded to each other to form an aliphatic or aromatic ring structure, $R^{21}$ is not bonded to $R^{26}$ or $R^{30}$, and $R^{25}$ is not bonded to $R^{26}$ or $R^{30}$;

$L^1$ and $L^2$ are each independently a substituted or unsubstituted arylene group having 6 to 30 ring carbon atoms;

n is 0 or 1, when n is 0, $-(L^2)_0-$ is a single bond;

$Ar^1$ and $Ar^2$ are each independently a substituted or unsubstituted phenylene group or a substituted or unsubstituted fused arylene group, wherein the fused arylene group comprises 2 to 4 benzene rings that are fused to each other;

$Ar^3$ is a substituted or unsubstituted phenyl group or a substituted or unsubstituted fused aryl group, wherein the fused aryl group comprises 2 to 4 benzene rings that are fused to each other;

$Ar^1$ and $Ar^2$ are boned to each other by only one single bond and not crosslinked;

$Ar^2$ and $A^3$ are boned to each other by only one single bond and not crosslinked; and the optional substituent referred to by "substituted or unsubstituted" is selected from the group consisting of a halogen atom, a cyano group, an alkyl group having 1 to 30 carbon atoms, a cycloalkyl group having 3 to 30 ring carbon atoms, an aryl group having 6 to 30 ring carbon atoms, an aralkyl group having 7 to 36 carbon atoms, an alkoxy group having 1 to 30 carbon atoms, an aryloxy group having 6 to 30 ring carbon atoms, a mono-, di- or tri-substituted silyl group having a substituent selected from an alkyl group having 1 to 30 carbon atoms and an aryl group having 6 to 30 ring carbon atom, and a heteroaryl group having 5 to 30 ring atoms.

In another aspect, the present invention provides a material for organic EL device comprising Compound (1).

In another aspect, the present invention provides an organic electroluminescence device comprising an anode, a cathode, and an organic layer between the anode and the cathode, wherein the organic layer comprises a light emitting layer and at least one layer of the organic layer comprises Compound (1).

In another aspect, the present invention provides an electronic device comprising the organic electroluminescence device.

Advantageous Effects of Invention

The compound (1) provides an organic EL device having a further improved lifetime.

DESCRIPTION OF EMBODIMENTS

Figure 1:
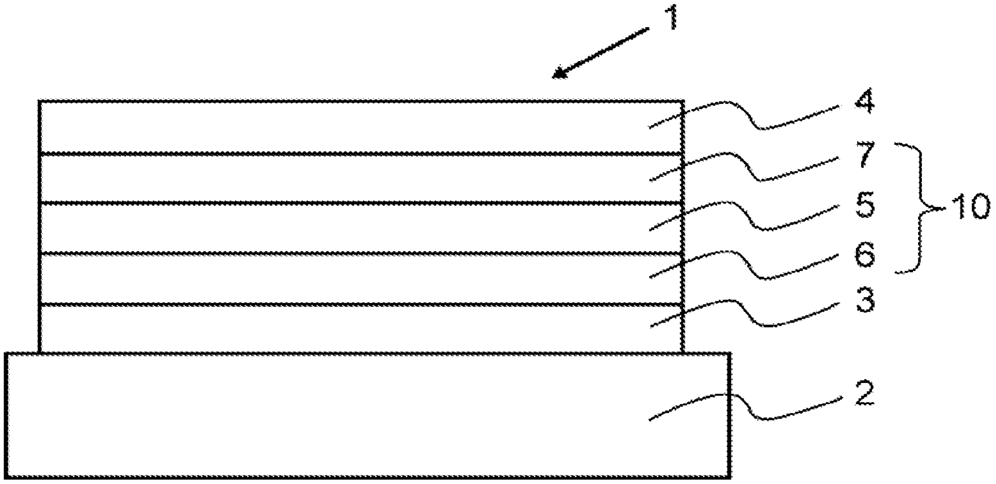
FIG. 1 is a schematic view showing an example of the layered structure of an organic EL device in an embodiment of the invention.

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ.

The term of "unsubstituted group ZZ" referred to by "substituted or unsubstituted group ZZ" used herein means that no hydrogen atom in the group ZZ is substituted by a substituent.

The definition of "hydrogen atom" used herein includes isotopes different in the neutron numbers, i.e., light hydrogen (protium), heavy hydrogen (deuterium), and tritium.

The number of ring carbon atoms referred to herein means the number of the carbon atoms included in the atoms that form the ring itself of a compound in which a series of atoms are bonded to form a cyclic compound (for example, a monocyclic compound, a fused ring compound, a cross-linked compound, a carbocyclic compound, and a heterocyclic compound). If the ring has a substituent, the carbon atom in the substituent is not included in the ring carbon atom. Unless otherwise noted, the same applies to the number of ring carbon atoms mentioned below.

For example, a benzene ring has 6 ring carbon atoms, a naphthalene ring has 10 ring carbon atoms, a pyridinyl group has 5 ring carbon atoms, a furan ring has 4 ring carbon atoms. If a benzene ring or a naphthalene ring has, for example, an alkyl substituent, the carbon atom in the alkyl substituent is not counted as the ring carbon atom. When a fluorene ring has a fluorene substituent (inclusive of a spirofluorene ring), the carbon atoms in the fluorene substituent is not counted as the ring carbon atom.

The number of ring atom referred to herein means the number of the atoms which forms the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) on the ring atom) and the atom in a substituent, if the ring is substituted, are not counted as the ring atom. The same applies to the number of ring atoms described below, unless otherwise noted. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. When a fluorene ring has a fluorene substituent (inclusive of a spirofluorene ring), the atom in the fluorene substituent is not counted as the ring atom of the fluorene ring.

The term "aryl group" used herein is a monovalent residue of an aromatic hydrocarbon and does not include a heteroaryl group. The term "arylene group" is a divalent residue of an aromatic hydrocarbon and does not include a heteroarylene group.

The compound in an aspect of the invention is represented by formula 1:

(1)

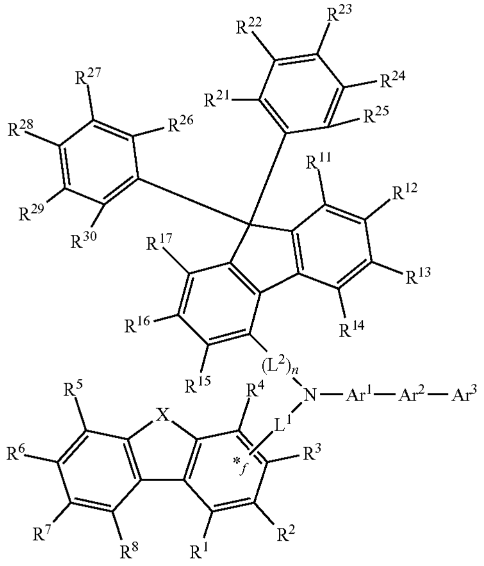

X is an oxygen atom or a sulfur atom, preferably an oxygen atom.

One selected from $R^1$ to $R^4$ is a single bond bonded to *f. $R^5$ to $R^8$ and $R^1$ to $R^4$ not the single bond bonded to *f are each independently a hydrogen or a substituent. The substituent is selected from the group consisting of a substituted or unsubstituted alkyl group having 1 to 30, preferably 1 to 18, more preferably 1 to 8 carbon atoms and a substituted or unsubstituted aryl group having 6 to 30, preferably 6 to 25, more preferably 6 to 18 ring carbon atoms.

Provided that adjacent two selected from $R^5$ to $R^8$ and adjacent two selected from $R^1$ to $R^4$ not the single bond bonded to *f are each independently a hydrogen or the substituent or bonded to each other to form an aliphatic or aromatic ring structure. Two or more aliphatic or aromatic ring structures may be formed on the same benzene ring.

Examples of the alkyl group having 1 to 30 carbon atoms of the substituted or unsubstituted alkyl group having 1 to 30 carbon atoms include a methyl group, an ethyl group, a propyl group (a n-propyl group, an isopropyl group), a butyl group (a n-butyl group, an isobutyl group, a s-butyl group, a t-butyl group), a pentyl group, a hexyl group, a heptyl group, an octyl group, a nonyl group, a decyl group, an undecyl group, and a dodecyl group. Preferred are a methyl group, an ethyl group, a propyl group (a n-propyl group, an isopropyl group), and a butyl group (a n-butyl group, an isobutyl group, a s-butyl group, a t-butyl group). More preferred are a methyl group and a t-butyl group.

The alkyl group having 1 to 30 carbon atoms includes isomeric groups, if present.

Examples of the aryl group having 6 to 30 ring carbon atoms of the substituted or unsubstituted aryl group having 6 to 30 ring carbon atoms include a phenyl group, a biphenylyl group, a terphenylyl group, a biphenylenyl group, a naphthyl group, an anthryl group, a benzanthryl group, a phenanthryl group, a benzophenanthryl group, a phenalenyl group, a picenyl group, a pentaphenyl group, a pyrenyl group, a chrysenyl group, a benzochrysenyl group, a fluorenyl group, a fluoranthenyl group, a perylenyl group, and a triphenylenyl group. Preferred are a phenyl group, a naphthyl group, and a phenanthryl group. More preferred are a phenyl group and a naphthyl group (a 1-naphthyl group, a 2-naphthyl group).

The aryl group having 6 to 30 ring carbon atoms includes isomeric groups, if present.

In an embodiment of the invention, adjacent two selected from $R^5$ to $R^8$ and adjacent two selected from $R^1$ to $R^4$ not the single bond bonded to *f are each independently a hydrogen atom or the substituent without forming the aliphatic or aromatic ring structure. In another embodiment of the invention, at least one set of "adjacent two" are bonded to each other to form the aliphatic or aromatic ring structure.

Examples of the aliphatic or aromatic ring structure include a substituted or unsubstituted aromatic hydrocarbon ring having 6 to 18 ring carbon atoms, a substituted or unsubstituted aliphatic hydrocarbon ring having 5 to 18 ring carbon atoms, a substituted or unsubstituted aromatic heterocyclic ring having 5 to 18 ring atoms, and a substituted or unsubstituted aliphatic heterocyclic ring having 5 to 18 ring atoms.

Examples of the aromatic hydrocarbon ring having 6 to 18 ring carbon atoms include a benzene ring, a biphenylene ring, a naphthalene ring, an anthracene ring, a benzanthracene ring, a phenanthrene ring, a benzophenanthrene ring, a phenalene ring, a pyrene ring, a chrysene ring, and a triphenylene ring, with a benzene ring and a naphthalene ring being preferred and a benzene ring being more preferred.

Examples of the aliphatic hydrocarbon ring having 5 to 18 ring carbon atoms include aliphatic rings obtained by partially hydrogenating the above aromatic hydrocarbon ring having 6 to 18 ring carbon atoms, for example, a cyclopentene ring, a cyclopentadiene ring, a cyclohexene ring, or a cyclohexadiene ring.

Examples of the aromatic heterocyclic ring having 5 to 18 ring atoms include a pyrrole ring, a furan ring, a thiophene ring, a pyridine ring, an imidazole ring, a pyrazole ring, an indole ring, an isoindole ring, a benzofuran ring, an isobenzofuran ring, a benzothiophene ring, a benzimidazole ring, an indazole ring, a dibenzofuran ring, a naphthobenzofuran ring, a dibenzothiophene ring, a naphthobenzothiophene ring, a carbazole ring, and a benzocarbazole ring.

The aliphatic heterocyclic ring having 5 to 18 ring atoms is, for example, an aliphatic heterocyclic ring obtained by partially hydrogenating the above aromatic heterocyclic ring having 5 to 18 ring atoms.

In an embodiment of the invention, $R^5$ to $R^8$ and $R^1$ to $R^4$ not the single bond bonded to *f are preferably all hydrogen atoms.

$R^{11}$ to $R^{17}$ are each independently a hydrogen or a substituent. The substituent is selected from the group consisting of a substituted or unsubstituted alkyl group having 1 to 30, preferably 1 to 18, more preferably 1 to 8 carbon atoms and a substituted or unsubstituted aryl group having 6 to 30, preferably 6 to 25, more preferably 6 to 18 ring carbon atoms.

Provided that adjacent two selected from $R^{11}$ to $R^{14}$ and adjacent two selected from $R^{15}$ to $R^{17}$ are each independently a hydrogen or the substituent or bonded to each other to form an aliphatic or aromatic ring structure. Two or more aliphatic or aromatic ring structures may be formed on the same benzene ring.

The details of the substituted or unsubstituted alkyl group having 1 to 30 carbon atoms and the substituted or unsubstituted aryl group having 6 to 30 ring carbon atoms for $R^{11}$ to $R^{17}$ are the same as described above with respect to $R^1$ to $R^8$.

The details of the aliphatic or aromatic ring structure that is optionally formed by the adjacent two selected from $R^{11}$ to $R^{14}$ and the adjacent two selected from $R^{15}$ to $R^{17}$ are the same as described above with respect to $R^1$ to $R^8$.

In an embodiment of the invention, adjacent two selected from $R^1$ to $R^{14}$, and adjacent two selected from $R^{15}$ to $R^{17}$ are each independently a hydrogen atom or the substituent without forming the aliphatic or aromatic ring structure. In another embodiment of the invention, at least one set of "adjacent two" are bonded to each other to form the aliphatic or aromatic ring structure.

In an embodiment of the invention, $R^{11}$ to $R^{17}$ are preferably all hydrogen atoms.

$R^{21}$ to $R^{30}$ are each independently a hydrogen or a substituent. The substituent is selected from the group consisting of a substituted or unsubstituted alkyl group having 1 to 30, preferably 1 to 18, more preferably 1 to 8 carbon atoms and a substituted or unsubstituted aryl group having 6 to 30, preferably 6 to 25, more preferably 6 to 18 ring carbon atoms.

Provided that adjacent two selected from $R^{21}$ to $R^{25}$ and adjacent two selected from $R^{26}$ to $R^{30}$ are each independently a hydrogen or the substituent or bonded to each other to form an aliphatic or aromatic ring structure. Two or more aliphatic or aromatic ring structures may be formed on the same benzene ring.

$R^{21}$ is not bonded to $R^{26}$ or $R^{30}$. $R^{25}$ is not bonded to $R^{26}$ or $R^{30}$. Thus, in formula (1) and each formula described below as a preferred embodiment of formula (1), the 9,9-diphenylfluorene structure does not form a spirobifluorene structure.

The details of the substituted or unsubstituted alkyl group having 1 to 30 carbon atoms and the substituted or unsubstituted aryl group having 6 to 30 ring carbon atoms for $R^{21}$ to $R^{30}$ are the same as described above with respect to $R^1$ to $R^8$.

The details of the aliphatic or aromatic ring structure that is optimally formed by the adjacent two selected from $R^{21}$ to $R^{25}$ and the adjacent two selected from $R^{26}$ to $R^{30}$ are the same as described above with respect to $R^1$ to $R^8$.

In an embodiment of the invention, the adjacent two selected from $R^{21}$ to $R^{25}$ and the adjacent two selected from $R^{26}$ to $R^{30}$ are each independently a hydrogen atom or the substituent without forming the aliphatic or aromatic ring structure. In another embodiment of the invention, at least one set of "adjacent two" are bonded to each other to form the aliphatic or aromatic ring structure.

In an embodiment of the invention, $R^{21}$ to $R^{30}$ are preferably all hydrogen atoms.

$L^1$ and $L^2$ are each independently a substituted or unsubstituted arylene group having 6 to 30, preferably 6 to 25, more preferably 6 to 18 ring carbon atoms.

n is 0 or 1. When n is 0, $-(L^2)_0-$ is a single bond. In an embodiment of the invention, n is preferably 0. In another embodiment of the invention, n is preferably 1.

Examples of the arylene group having 6 to 30 ring carbon atoms of the substituted or unsubstituted arylene group having 6 to 30 ring carbon atoms for $L^1$ and $L^2$ include a phenylene group, a biphenylene group, a terphenylene group, a biphenylenylene group, a naphthylene group, an anthrylene group, a benzanthrylene group, a phenanthrylene group, a benzophenanthrylene group, a phenalenylene group, a picenylene group, a pentaphenylene group, a pyrenylene group, a chrysenylene group, a benzochrysenylene group, a fluorenylene group, a fluoranthenylene group, a perylenylene group, and a triphenylenylene group. Preferred are a phenylene group, a biphenylene group, and a naphthylene group, with a phenylene group (a 1,4-phenylene group, a 1,3-phenylene group, or a 1,2-phenylene group) being more preferred and a 1,4-phenylene group being still more preferred.

The arylene group having 6 to 30 ring carbon atoms includes isomeric groups, if present.

$Ar^1$ and $Ar^2$ are each independently a substituted or unsubstituted phenylene group or a substituted or unsubstituted fused arylene group, wherein the fused arylene group comprises 2 to 4 benzene rings that are fused to each other.

The fused arylene group is preferably selected from the group consisting of a naphthylene group, an anthrylene group, a benzanthrylene group, a phenanthrylene group, a benzophenanthrylene group, a phenalenylene group, a pyrenylene group, a chrysenylene group, and a triphenylenylene group.

The phenylene group and the fused arylene group includes isomeric groups.

$Ar^1$ and $Ar^2$ are each independently, preferably a substituted or unsubstituted phenylene group, a substituted or unsubstituted naphthylene group, or a substituted or unsubstituted phenanthrylene group, more preferably a substituted or unsubstituted phenylene group (1,4-phenylene group, 1,3-phenylene group, or 1,2-phenylene group) or a substituted or unsubstituted naphthylene group (inclusive of 1,4-naphthylene group and 2,6-naphthylene group), still more preferably a substituted or unsubstituted phenylene group (1,4-phenylene group, 1,3-phenylene group, or 1,2-phenylene group), and particularly preferably a substituted or unsubstituted 1,4-phenylene group.

$Ar^3$ is a substituted or unsubstituted phenyl group or a substituted or unsubstituted fused aryl group, wherein the fused aryl group comprises 2 to 4 benzene rings that are fused to each other.

The fused aryl group is preferably selected from the group consisting of a naphthyl group, an anthryl group, a benzanthryl group, a phenanthryl group, a benzophenanthryl group, a phenalenyl group, a pyrenyl group, a chrysenyl group, and a triphenylenyl group.

The fused aryl group includes isomeric groups.

$Ar^3$ is preferably a substituted or unsubstituted phenyl group, a substituted or unsubstituted naphthyl group, or a substituted or unsubstituted phenanthryl group, more preferably a substituted or unsubstituted phenyl group or a substituted or unsubstituted naphthyl group, still more preferably a substituted or unsubstituted phenyl group, a substituted or unsubstituted 1-naphthyl group, or a substituted or unsubstituted 2-naphthyl group, and particularly preferably a substituted or unsubstituted phenyl group.

$Ar^1$ and $Ar^2$ are bonded to each other only via a single bond. Namely, $Ar^1$ and $Ar^2$ are not crosslinked by a single bond other the above single bond or a group.

$Ar^2$ and $Ar^3$ are bonded to each other only via a single bond. Namely, $Ar^2$ and $Ar^3$ are not crosslinked by a single bond other the above single bond or a group.

Formula (1) is preferably represented by formula (2):

(2)
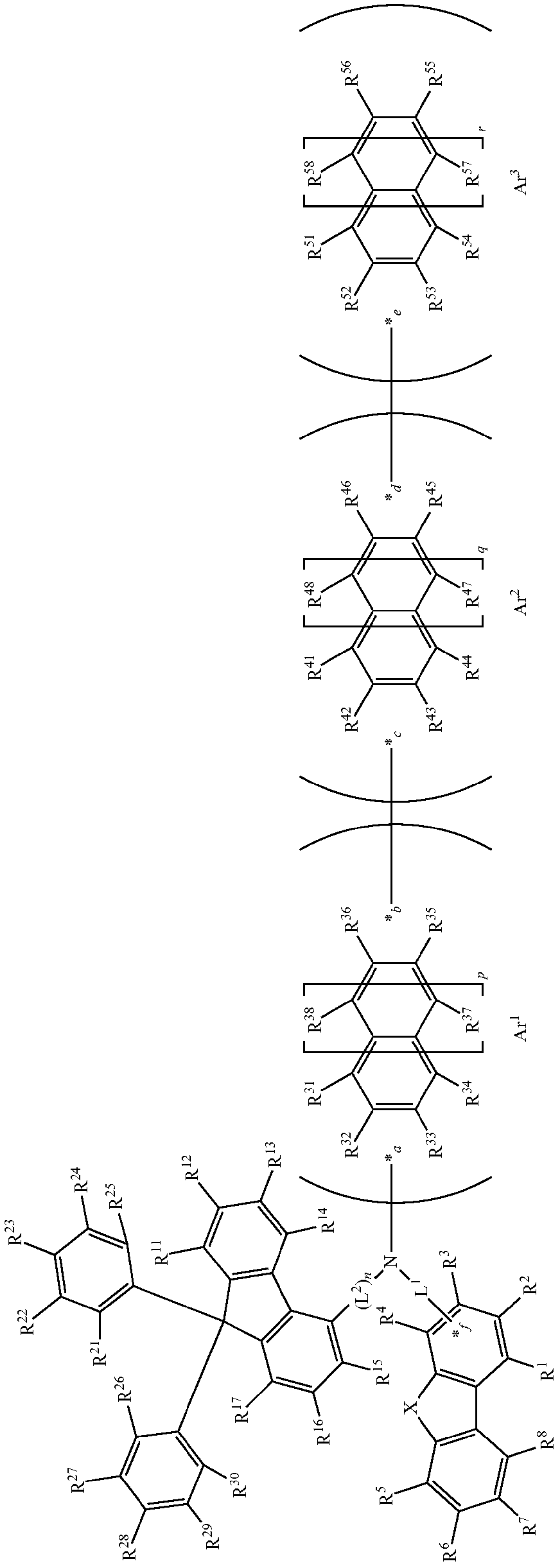

wherein X, $R^1$ to $R^8$, $R^{11}$ to $R^{17}$, $R^{21}$ to $R^{30}$, $L^1$, $L^2$, and n are the same as defined in formula (1) and $R^{31}$ to $R^{38}$, $R^{41}$ to $R^{48}$, $R^{51}$ to $R^{58}$, p, q, and r will be described below.

$Ar^1$ in formula (2) is represented by formula (2a):

(2a)

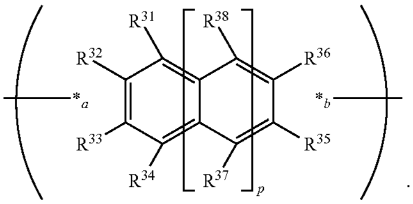

One selected from $R^{31}$ to $R^{34}$ is a single bond bonded to *a and one selected from $R^{35}$ to $R^{38}$ and $R^{31}$ to $R^{34}$ not the single bond bonded to *a is a single bond bonded to *b.

$R^{31}$ to $R^{38}$ that are not the single bond bonded to *a and not the single bond bonded to *b are each independently a hydrogen or a substituent, wherein the substituent is selected from the group consisting of a substituted or unsubstituted alkyl group having 1 to 30, preferably 1 to 18, more preferably 1 to 8 carbon atoms and a substituted or unsubstituted aryl group having 6 to 30, preferably 6 to 25, more preferably 6 to 18 ring carbon atoms.

Provided that adjacent two selected from $R^{31}$ to $R^{38}$ that are not the single bond bonded to *a and not the single bond bonded to *b are each independently a hydrogen or the substituent or bonded to each other to form an aliphatic or aromatic ring structure. Two or more aliphatic or aromatic ring structures may be formed on the same benzene ring or the same naphthalene ring.

p is 0 or 1. When p is 0, $Ar^1$ is represented by formula (2a-1). When p is 1, $Ar^1$ is represented by formula (2a-2).

(2a-1)

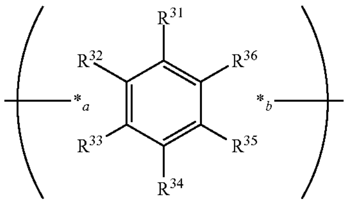

(2a-2)

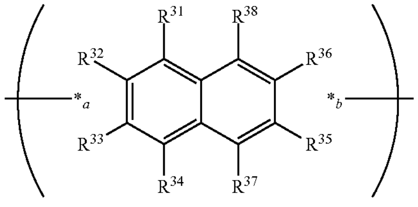

wherein $R^{31}$ to $R^{38}$ are the same as defined in formula (2a).

$Ar^2$ of formula (2) is represented by formula (2b):

(2b)

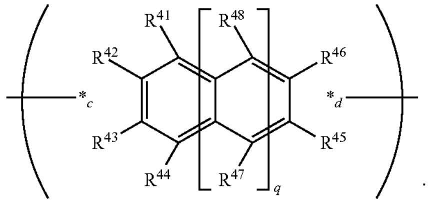

One selected from $R^{41}$ to $R^{44}$ is a single bond bonded to *c and one selected from $R^{45}$ to $R^{48}$ and $R^{41}$ to $R^{44}$ not the single bond bonded to *c is a single bond bonded to *d.

$R^{41}$ to $R^{48}$ that are not the single bond bonded to *c and not the single bond bonded to *d are each independently a hydrogen or a substituent, wherein the substituent is selected from the group consisting of a substituted or unsubstituted alkyl group having 1 to 30, preferably 1 to 18, more preferably 1 to 8 carbon atoms and a substituted or unsubstituted aryl group having 6 to 30, preferably 6 to 25, more preferably 6 to 18 ring carbon atoms.

Provided that adjacent two selected from $R^{41}$ to $R^{48}$ that are not the single bond bonded to *c and not the single bond bonded to *d are each independently a hydrogen or the substituent or bonded to each other to form an aliphatic or aromatic ring structure. Two or more aliphatic or aromatic ring structures may be formed on the same benzene ring or the same naphthalene ring.

q is 0 or 1. When q is 0, $Ar^2$ is represented by formula (2b-1). When q is 1, $Ar^2$ is represented by formula (2b-2).

(2b-1)

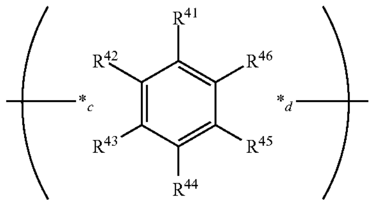

(2b-2)

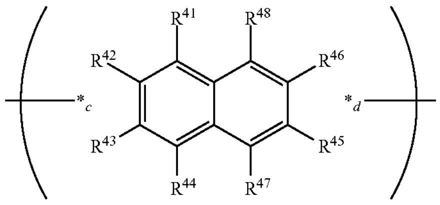

wherein $R^{41}$ to $R^{48}$ are the same as defined in formula (2b).

$Ar^3$ of formula (2) is represented by formula (2c):

(2c)

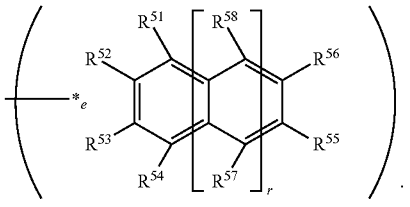

One selected from $R^{51}$ to $R^{54}$ is a single bond bonded to *e.

$R^{55}$ to $R^{58}$ and $R^{51}$ to $R^{54}$ not the single bond bonded to *e are each independently a hydrogen or a substituent, wherein the substituent is selected from the group consisting of a substituted or unsubstituted alkyl group having 1 to 30, preferably 1 to 18, more preferably 1 to 8 carbon atoms and a substituted or unsubstituted aryl group having 6 to 30, preferably 6 to 25, more preferably 6 to 18 ring carbon atoms.

Provided that adjacent two selected from $R^{55}$ to $R^{58}$ and $R^{51}$ to $R^{54}$ that are not the single bond bonded to *e are each independently a hydrogen or the substituent or bonded to each other to form an aliphatic or aromatic ring structure. Two or more aliphatic or aromatic ring structures may be formed on the same benzene ring or the same naphthalene ring.

r is 0 or 1. When r is 0, $Ar^3$ is represented by formula (2c-1). When r is 1, $Ar^3$ is represented by formula (2c-2).

(2c-1)

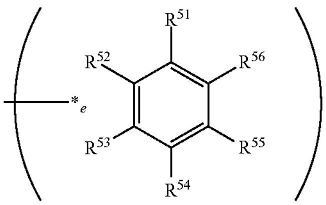

-continued (2c-2)

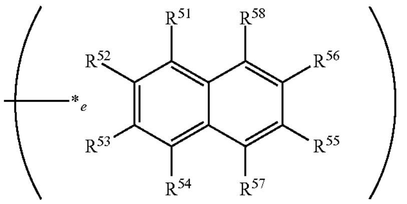

wherein $R^{51}$ to $R^{58}$ are the same as defined in formula (2c).

The details of the substituted or unsubstituted alkyl group having 1 to 30 carbon atoms, the substituted or unsubstituted aryl group having 6 to 30 ring carbon atoms, and the aliphatic or aromatic ring structure in the definitions of formulae (2a), (2b), and (2c) are the same as described above with respect to $R^1$ to $R^8$.

In a particularly preferred embodiment of the invention, p, q, and r are all 0.

In an embodiment of the invention, $R^{31}$ to $R^{38}$ that are not the single bond bonded to *a and not the single bond bonded to *b, $R^{41}$ to $R^{48}$ that are not the single bond bonded to *c and not the single bond bonded to *d, $R^{55}$ to $R^{58}$, and $R^{51}$ to $R^{54}$ that are not the single bond bonded to *e are preferably all hydrogen atoms.

The formulae (1) and (2) are preferably represented by any of formulae (3) to (6) and more preferably by formula (3):

(3)

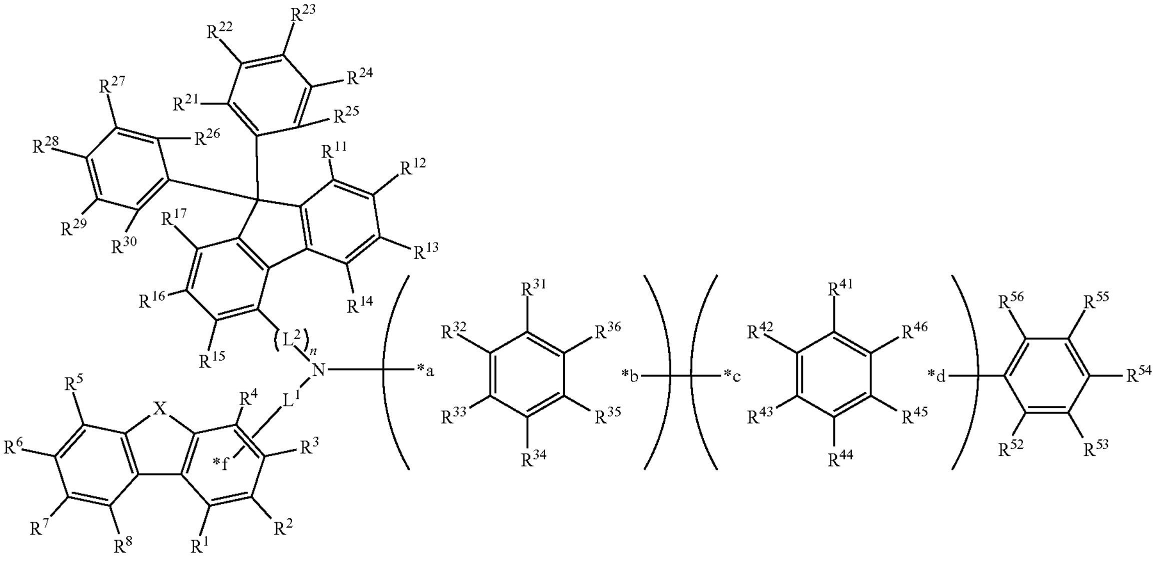

-continued
(4)
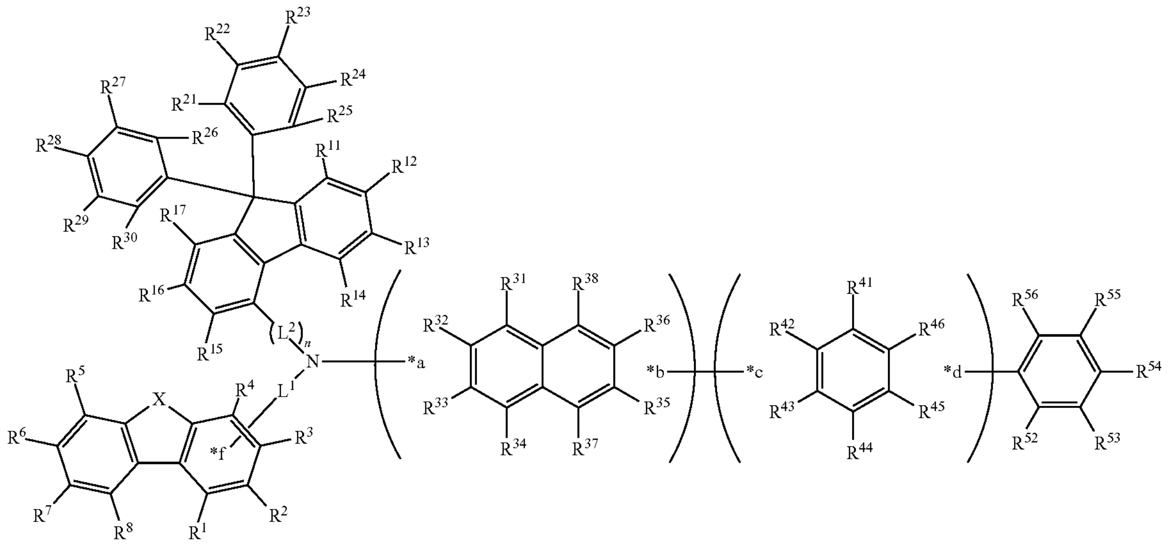
(5)
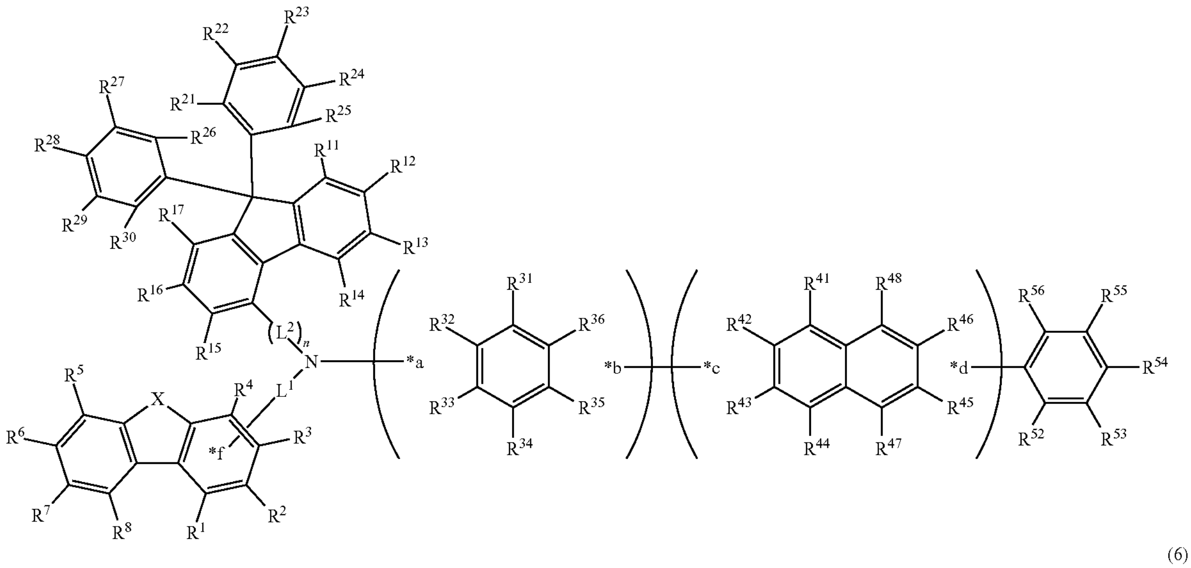
(6)
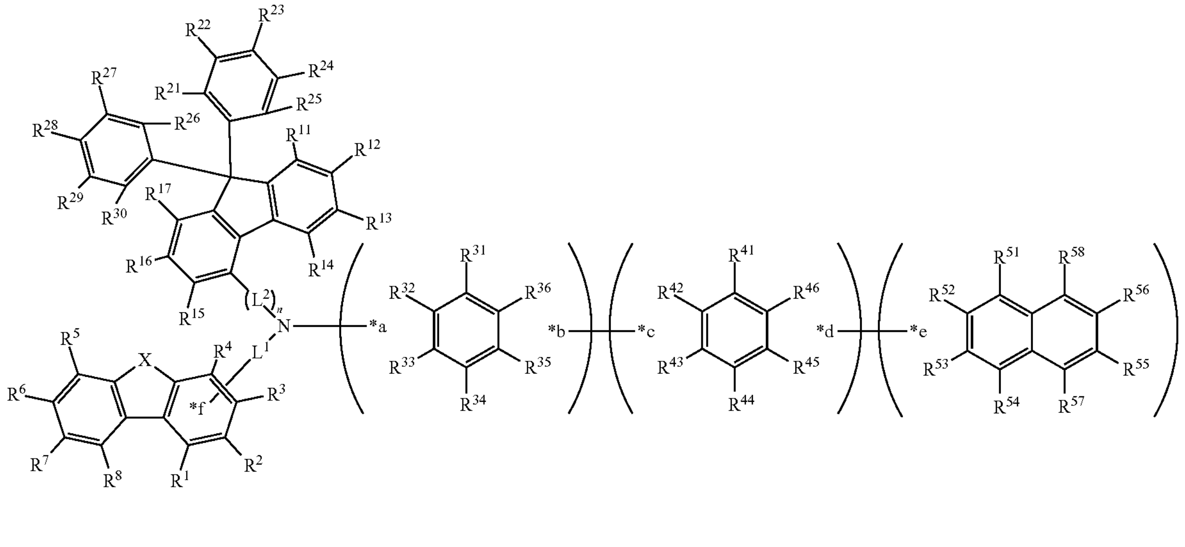

wherein X, $R^1$ to $R^8$, $R^{11}$ to $R^{17}$, $R^{21}$ to $R^{30}$, $L^1$, $L^2$, and n are the same as defined in formula (1) and $R^{31}$ to $R^{38}$, $R^{41}$ to $R^{48}$, and $R^{51}$ to $R^{58}$ are the same as defined in formulae (2a) to (2c).

Formula (3) is preferably represented by formula (3a):

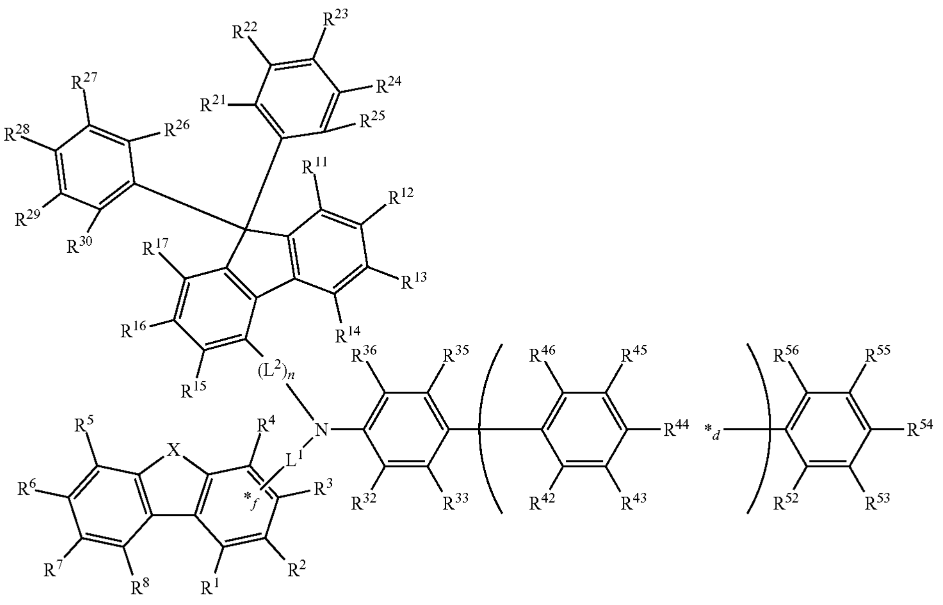

(3a)

wherein X, $R^1$ to $R^8$, $R^{11}$ to $R^{17}$, $R^{21}$ to $R^{30}$, $L^1$, $L^2$, and n are the same as defined in formula (1) and $R^{32}$, $R^{33}$, $R^{35}$, $R^{36}$, $R^{42}$ to $R^{46}$, and $R^{52}$ to $R^{56}$ are the same as defined in formulae (2a) to (2c).

Formula (3a) is preferably represented by any of formulae (3a-1) to (3a-3), more preferably by formula (3a-1) or (3a-2), and still more preferably by formula (3a-1):

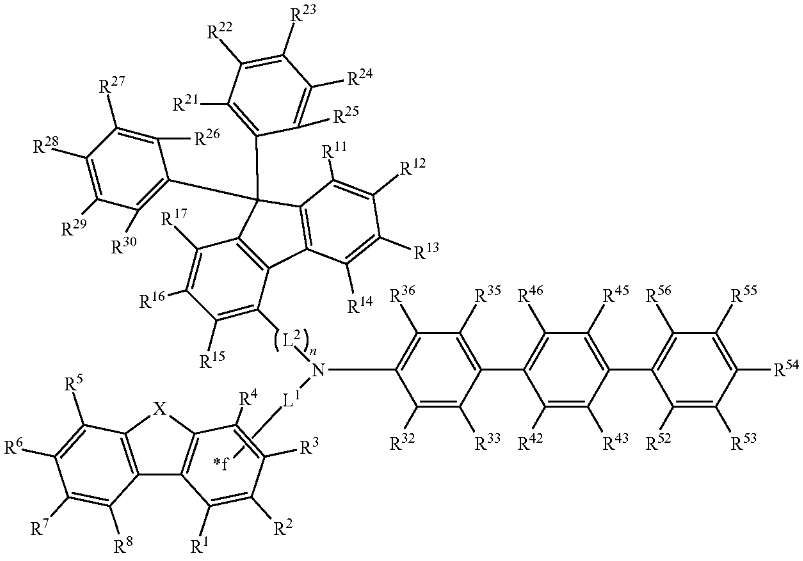

(3a-1)

-continued
(3a-2)
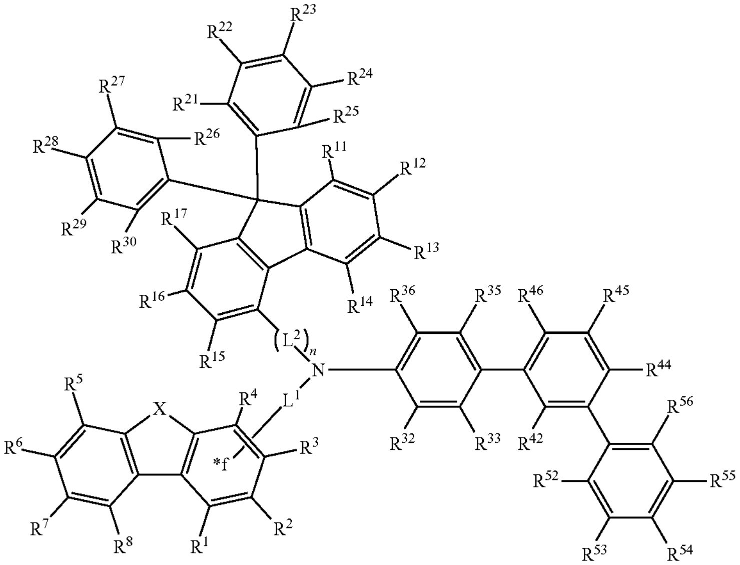
(3a-3)
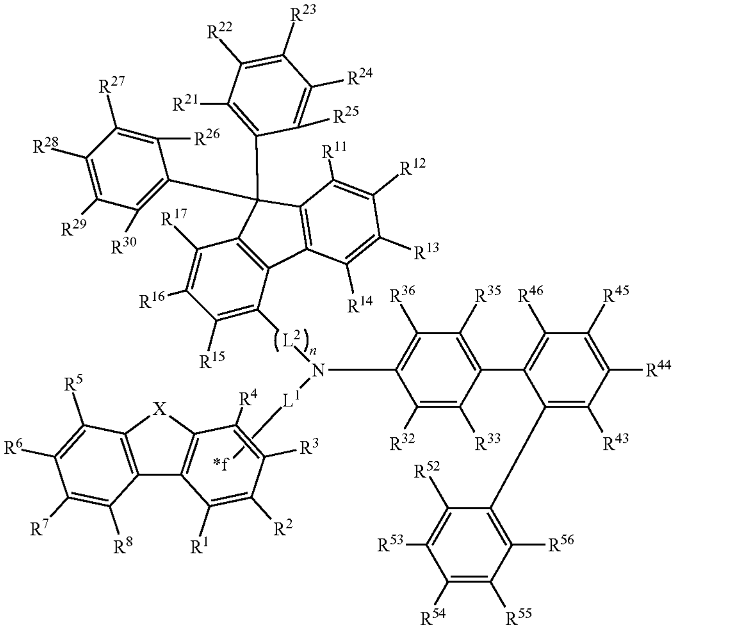
wherein X, $R^1$ to $R^3$, $R^{11}$ to $R^{17}$, $R^{21}$ to $R^{30}$, $L^1$, $L^2$, and n are the same as defined in formula (1) and $R^{32}$, $R^{33}$, $R^{35}$, $R^{36}$, $R^{42}$ to $R^{46}$, and $R^{52}$ to $R^{56}$ are the same as defined in formulae (2a) to (2c).

Formula (4) is preferably represented by formula (4a).
(4a)
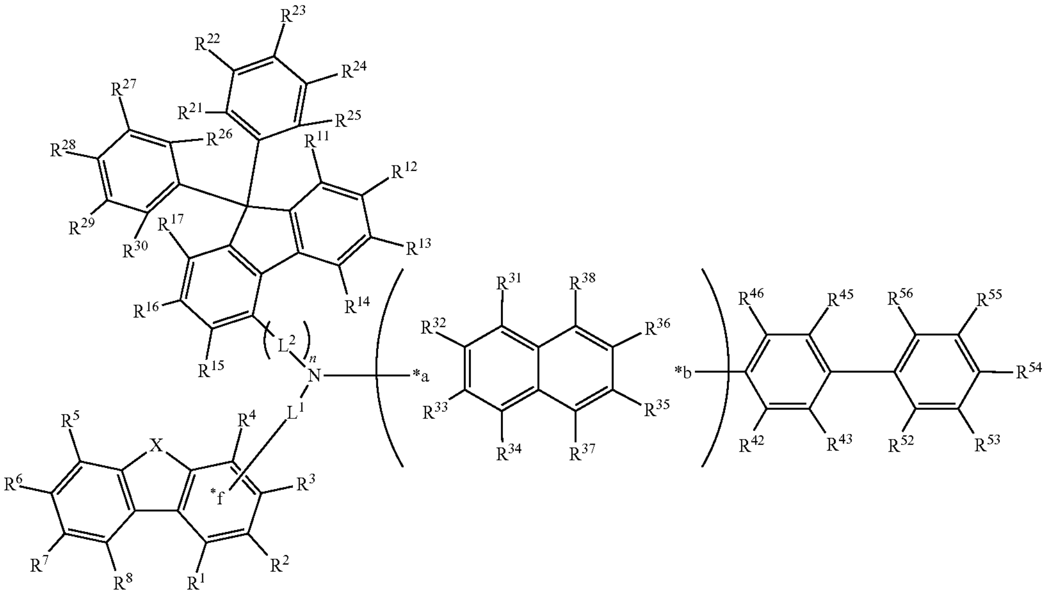
wherein X, $R^1$ to $R^8$, $R^{11}$ to $R^{17}$, $R^{21}$ to $R^{30}$, $L^1$, $L^2$, and n are the same as defined in formula (1) and $R^{31}$ to $R^{38}$, $R^{42}$, $R^{43}$, $R^{45}$, $R^{46}$, and $R^{52}$ to $R^{56}$ are the same as defined in formulae (2a) to (2c).
Formula (4a) is preferably represented by formula (4a-1) or (4a-2):
(4a-1)
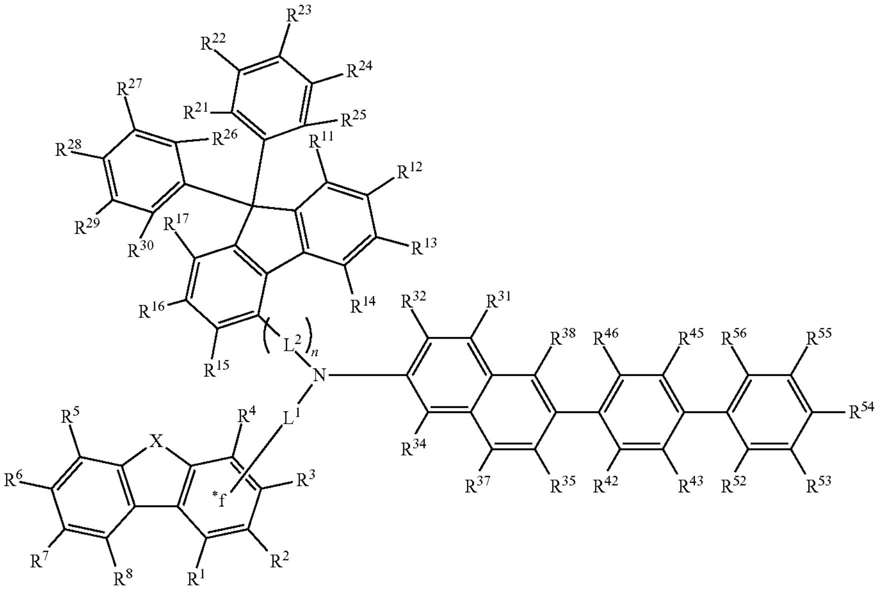

-continued (4a-2)

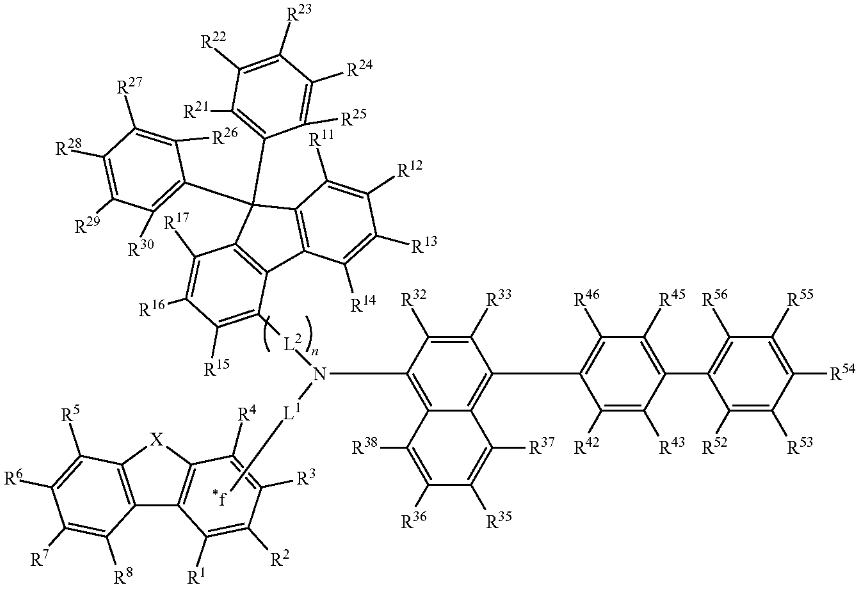

wherein X, $R^1$ to $R^8$, $R^{11}$ to $R^{17}$, $R^{21}$ to $R^{30}$, $L^1$, $L^2$, and n are the same as defined in formula (1) and $R^{31}$ to $R^{38}$, $R^{42}$, $R^{43}$, $R^{45}$, $R^{46}$, and $R^{52}$ to $R^{56}$ are the same as defined in formulae (2a) to (2c).

Formula (5) is preferably represented by formula (5a):

(5a)

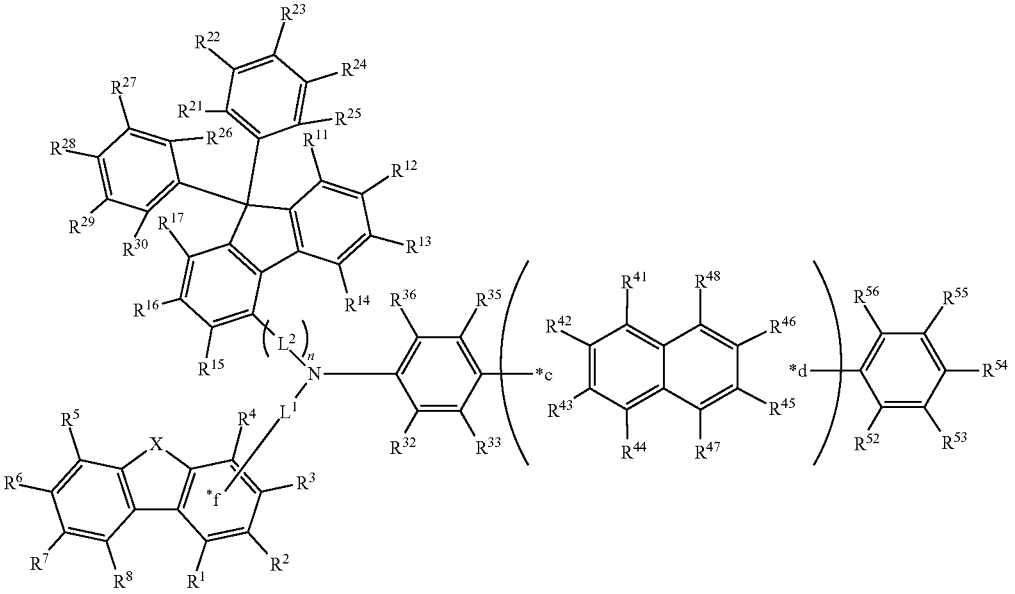

wherein X, $R^1$ to $R^8$, $R^{11}$ to $R^{17}$, $R^{21}$ to $R^{30}$, $L^1$, $L^2$, and n are the same as defined in formula (1) and $R^{32}$, $R^{33}$, $R^{35}$, $R^{36}$, $R^{41}$ to $R^{48}$, and $R^{52}$ to $R^{56}$ are the same as defined in formulae (2a) to (2c).

Formula (5a) is preferably represented by formula (5a-1) or (5a-2):

(5a-1)
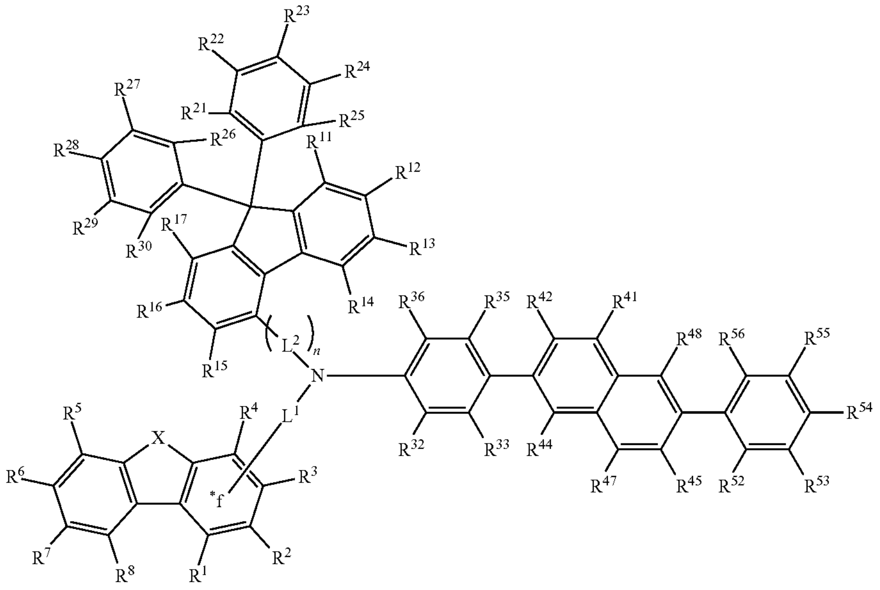
(5a-2)
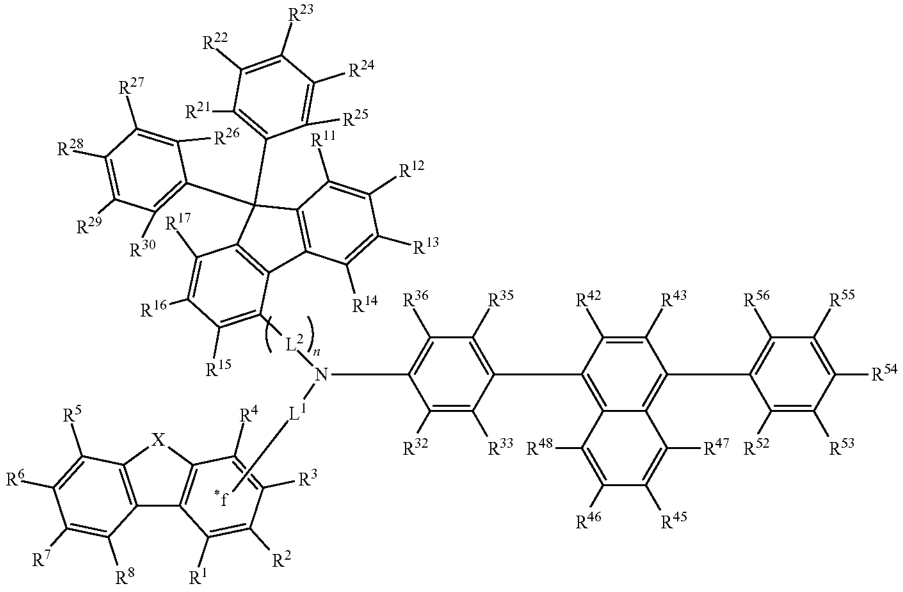
wherein X, $R^1$ to $R^8$, $R^{11}$ to $R^{17}$, $R^{21}$ to $R^{30}$, $L^1$, $L^2$, and n are the same as defined in formula (1) and $R^{32}$, $R^{33}$, $R^{35}$, $R^{36}$, $R^{41}$ to $R^{48}$, and $R^{52}$ to $R^{56}$ are the same as defined in formulae (2a) to (2c).

Formula (6) is preferably represented by formula (6a):
(6a)
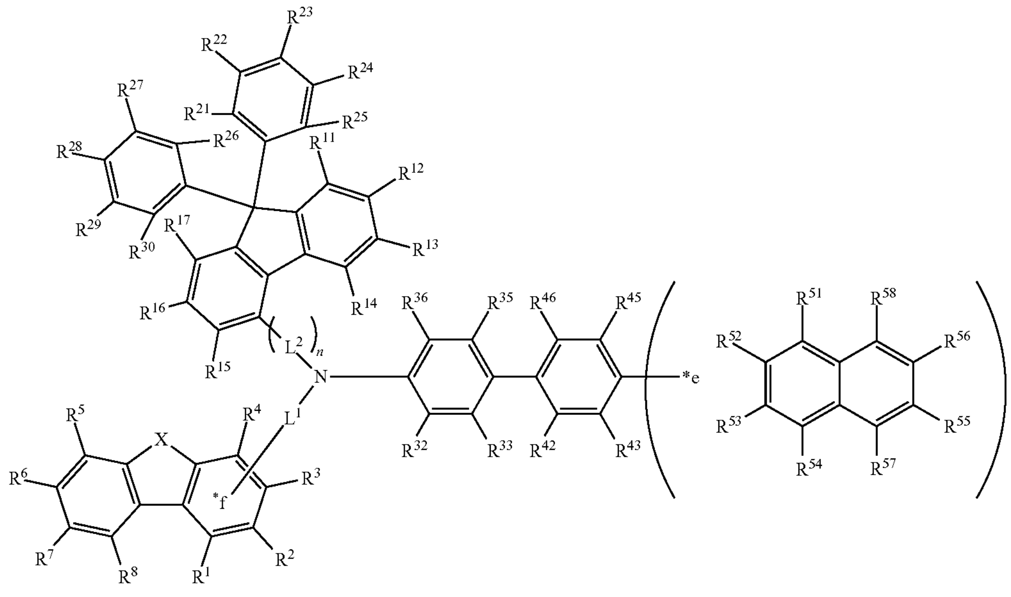
wherein X, $R^1$ to $R^8$, $R^{11}$ to $R^{17}$, $R^{21}$ to $R^{30}$, $L^1$, $L^2$, and n are the same as defined in formula (1) and $R^{32}$, $R^{33}$, $R^{35}$, $R^{36}$, $R^{42}$, $R^{43}$, $R^{45}$, $R^{46}$, and $R^{51}$ to $R^{58}$ are the same as defined in formulae (2a) to (2c).
Formula (Ga) is preferably represented by formula (Ga-1) or (Ga-2):
(6a-1)
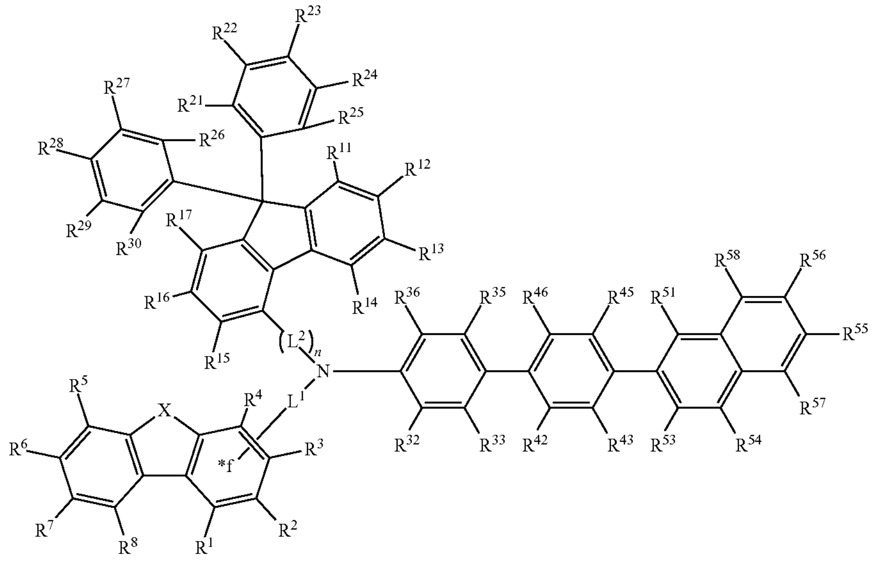

-continued (6a-2)

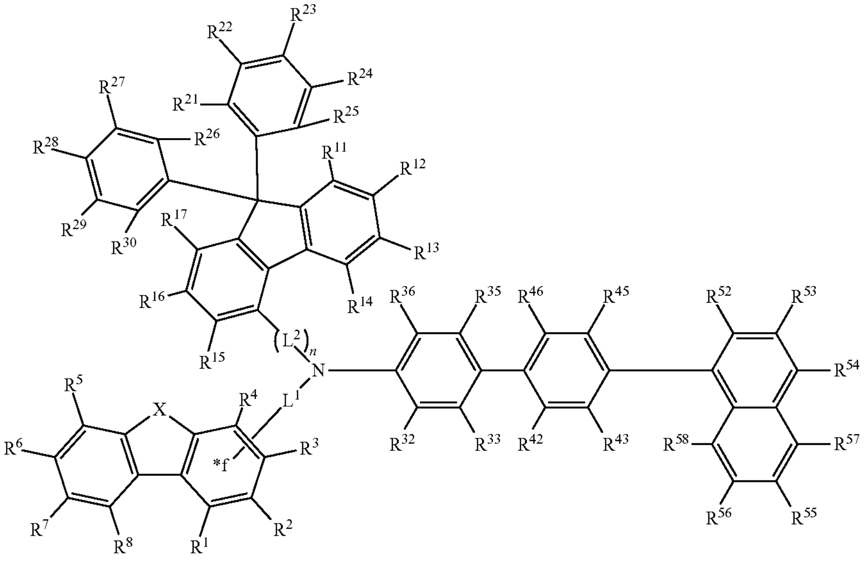

wherein X, $R^1$ to $R^8$, $R^{11}$ to $R^{17}$, $R^{21}$ to $R^{30}$, $L^1$, $L^2$, and n are the same as defined in formula (1) and $R^{32}$, $R^{33}$, $R^{35}$ 1136, $R^{42}$, $R^{43}$, $R^{45}$, $R^{46}$, and $R^{51}$ to $R^{58}$ are the same as defined in formulae (2a) to (2c).

The optional substituent referred to by "substituted or unsubstituted" used herein is, unless otherwise noted, selected from the group consisting of a halogen atom; a cyano group; an alkyl group having 1 to 30, preferably 1 to 18, more preferably 1 to 8 carbon atoms; a cycloalkyl group having 3 to 30, preferably 3 to 10, more preferably 3 to 8, still more preferably 5 or 6 ring carbon atoms; an aryl group having 6 to 30, preferably 6 to 25, more preferably 6 to 18 ring carbon atoms; an aralkyl group having 7 to 36, preferably 7 to 26, more preferably 7 to 20 carbon atoms; an alkoxy group having 1 to 30, preferably 1 to 18, more preferably 1 to 8 carbon atoms; an aryloxy group having 6 to 30, preferably 6 to 25, more preferably 6 to 18 ring carbon atoms; a mono-, di- or tri-substituted silyl group wherein the substituent is selected from an alkyl group having 1 to 30, preferably 1 to 18, more preferably 1 to 8 carbon atoms and an aryl group having 6 to 30, preferably 6 to 25, more preferably 6 to 18 ring carbon atoms; and a heteroaryl group having 5 to 30, preferably 5 to 24, more preferably 5 to 13 ring atoms.

The details of the optional substituent are as follows.

The halogen atom is a fluorine atom, a chlorine atom, a bromine atom or an iodine atom, with a fluorine atom being preferred.

Examples of the alkyl group having 1 to 30 carbon atoms include a methyl group, an ethyl group, a n-propyl group, an isopropyl group, a n-butyl group, an isobutyl group, a s-butyl group, a t-butyl group, a pentyl group, a hexyl group, a heptyl group, an octyl group, a nonyl group, a decyl group, an undecyl group, and a dodecyl group. Preferred are a methyl group, an ethyl group, a n-propyl group, an isopropyl group, a n-butyl group, an isobutyl group, a s-butyl group, a t-butyl group, and a pentyl group. More preferred are a methyl group, an ethyl group, a n-propyl group, an isopropyl group, a n-butyl group, an isobutyl group, a s-butyl group, and a t-butyl group. Still more preferred are a methyl group and a t-butyl group.

Examples of the cycloalkyl group having 3 to 30 ring carbon atoms include a cyclopropyl group, a cyclobutyl group, a cyclopentyl group, a cyclohexyl group, and a cycloheptyl group, with a cyclopentyl group and a cyclohexyl group being preferred.

Examples of the aryl group having 6 to 30 ring carbon atoms include a phenyl group, a biphenylyl group, a terphenylyl group, a biphenylenyl group, a naphthyl group, an anthryl group, a benzanthryl group, a phenanthryl group, a benzophenanthryl group, a phenalenyl group, a picenyl group, a pentaphenyl group, a pyrenyl group, a chrysenyl group, a benzochrysenyl group, a fluorenyl group, a fluoranthenyl group, a perylenyl group, and a triphenylenyl group. Preferred are a phenyl group, a biphenylyl group, a terphenylyl group, and a naphthyl group. More preferred are a phenyl group, a 2-, 3- or 4-biphenylyl group, a 2-, 3-, or 4-o-terphenylyl group, a 2-, 3-, or 4-m-terphenylyl group, a 2-, 3-, or 4-p-terphenylyl group, or a 1- or 2-naphthyl group. Still more preferred are a phenyl group, a 2-, 3-, or 4-biphenylyl group, or a 1- or 2-naphthyl group. A phenyl group is particularly preferred.

In the aralkyl group having 7 to 36 carbon atoms, the aryl portion is selected from the above aryl group having 6 to 30, preferably 6 to 25, more preferably 6 to 18 ring carbon atoms and the alkyl portion is selected from the above alkyl group having 1 to 30, preferably 1 to 18, more preferably 1 to 8 carbon atoms. Examples of the aralkyl group having 7 to 36 carbon atoms include a benzyl group, a phenethyl group, a phenylpropyl group, with a benzyl group being preferred.

In the alkoxy group having 1 to 30 carbon atoms, the alkyl portion is selected from the above alkyl group having 1 to 30, preferably 1 to 18, more preferably 1 to 8 carbon atoms. Examples of the alkoxy group having 1 to 30 carbon atoms include a t-butoxy group, a propoxy group, an ethoxy group, and a methoxy group, with an ethoxy group and a methoxy group being preferred and a methoxy group being more preferred.

In the aryloxy group having 6 to 30 ring carbon atoms, the aryl portion is selected from the above aryl group having 6 to 30, preferably 6 to 25, more preferably 6 to 18 ring carbon atoms. Examples of the aryloxy group having 6 to 30 ring carbon atoms include a terphenyloxy group, a biphenyloxy group and a phenoxy group, with a biphenyloxy group and a phenoxy group being preferred and a phenoxy group being more preferred.

The substituent of the mono, di or tri-substituted silyl group is selected from the above alkyl group having 1 to 30, preferably 1 to 18, more preferably 1 to 8 carbon atoms and the above aryl group having 6 to 30, preferably 6 to 25, more preferably 6 to 18 ring carbon atoms. Preferred is a tri-substituted silyl group, with a trimethylsilyl group, a triethylsilyl group, a t-butyldimethylsilyl group, a propyldimethylsilyl group, an isopropyldimethylsilyl group, a triphenylsilyl group, a phenyldimethylsilyl group, a t-butyldiphenylsilyl group, and a tritolylsilyl group being more preferred.

The heteroaryl group having 5 to 30 ring atoms includes 1 to 5, preferably 1 to 3, more preferably 1 to 2 ring hetero atoms. The ring hetero atom is selected from, for example, a nitrogen atom, a sulfur atom, and an oxygen atom. The free valence of the heteroaryl group is present on a ring carbon atom or on a ring nitrogen atom.

Examples of the heteroaryl group having 5 to 30 ring atoms include a pyrrolyl group, a furyl group, a thienyl group, a pyridyl group, an imidazopyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a phenanthridinyl group, an acridinyl group, a phenanthrolinyl group, a phenazinyl group, a phenothiazinyl group, a phenoxazinyl group, a xanthenyl group, a benzofuranyl group, an isobenzofuranyl group, a naphthobenzofuranyl group, a dibenzofuranyl group, a benzothiophenyl group (a benzothienyl group, the same applies below), an isobenzothiophenyl group (an isobenzothienyl group, the same applies below), a naphthobenzothiophenyl group (a naphthobenzothienyl group, the same applies below), a dibenzothiophenyl group (a dibenzothienyl group, the same applies below), and a carbazolyl group.

The production method of Compound (1) is not particularly limited and one of ordinary skill in the art could easily produce Compound (1) by a method described in the examples mentioned below and a modified method thereof by referring to known synthesis methods.

Examples of Compound (1) of the invention are shown below, although not limited thereto.

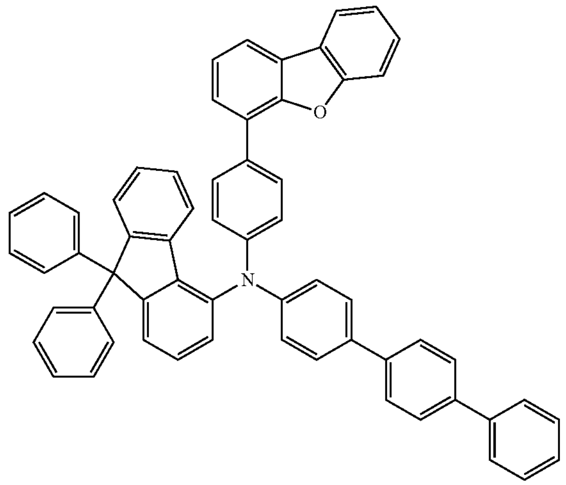

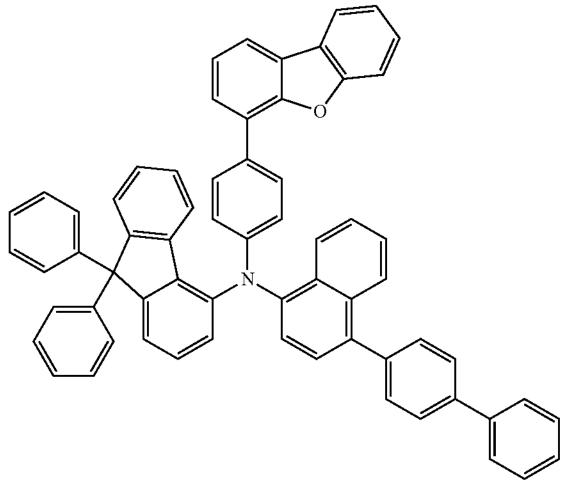

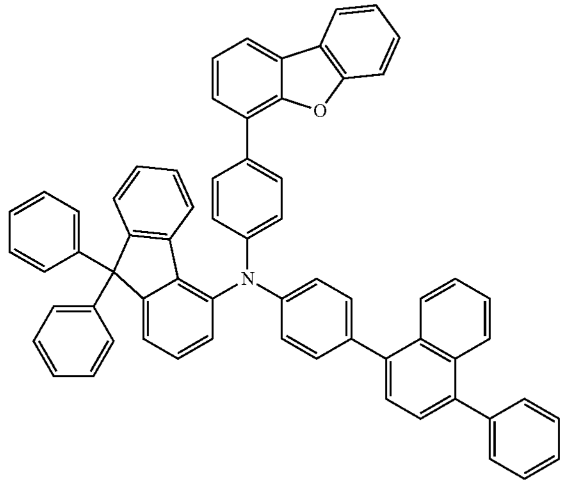

-continued
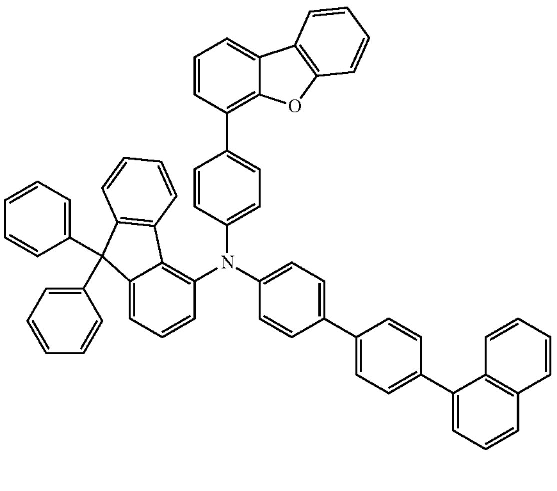
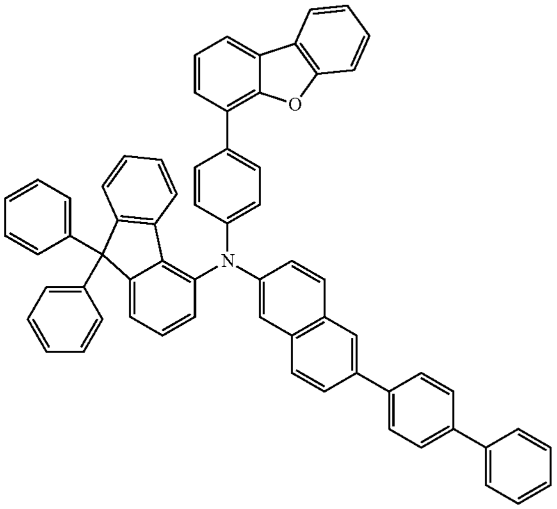
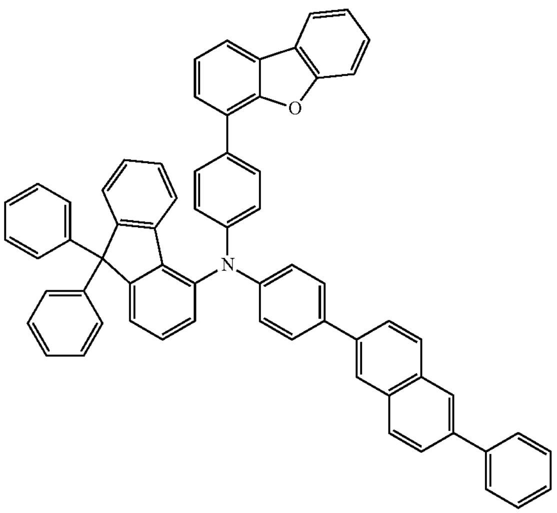
-continued
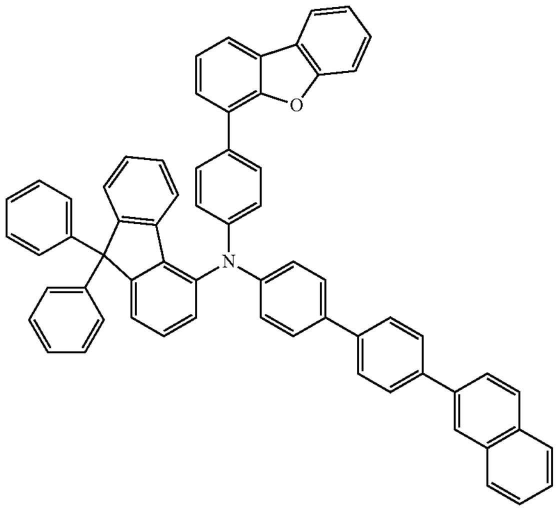
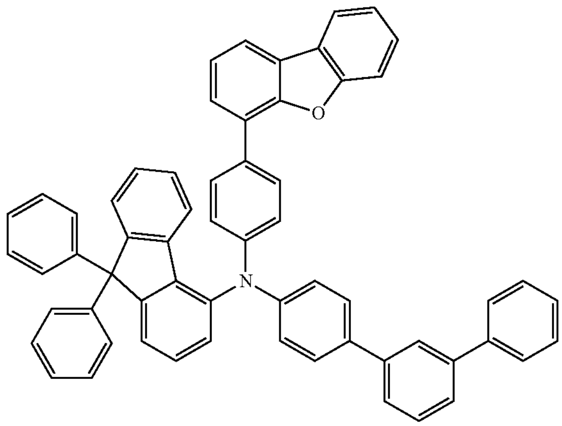
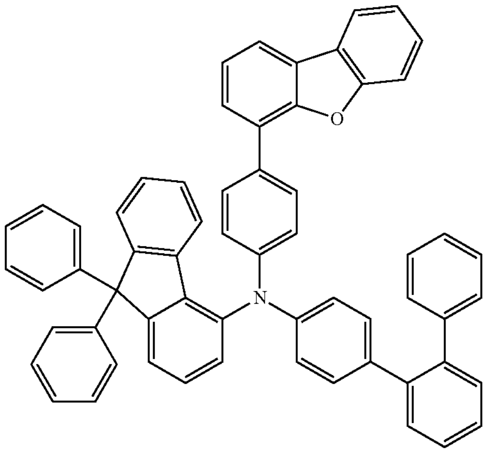

-continued
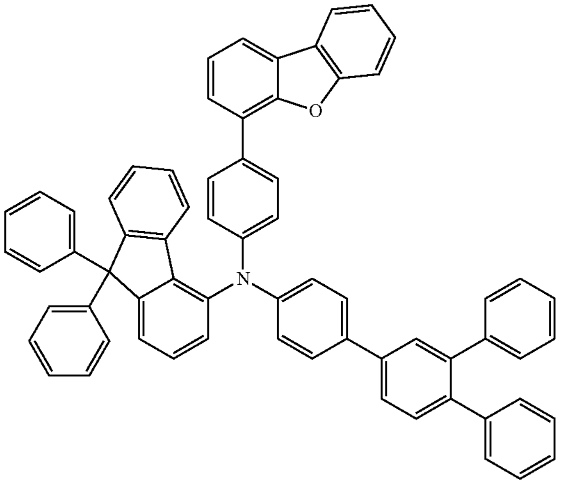
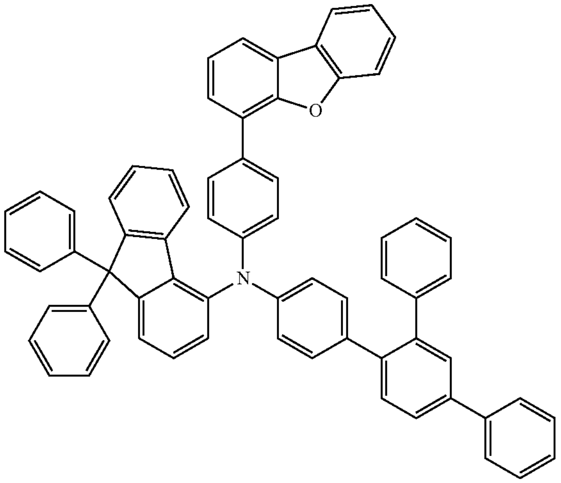
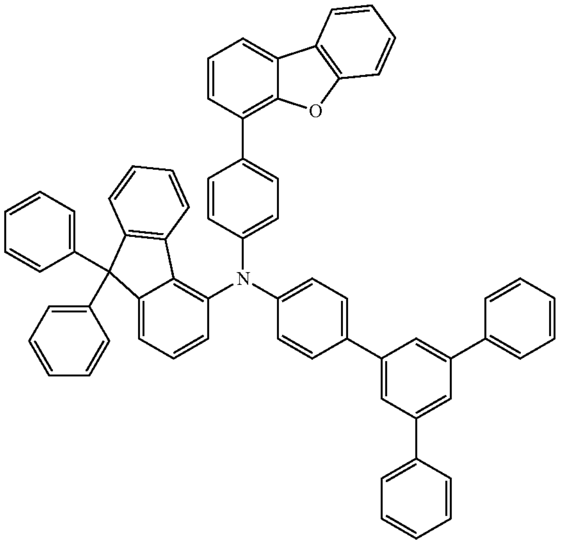
-continued
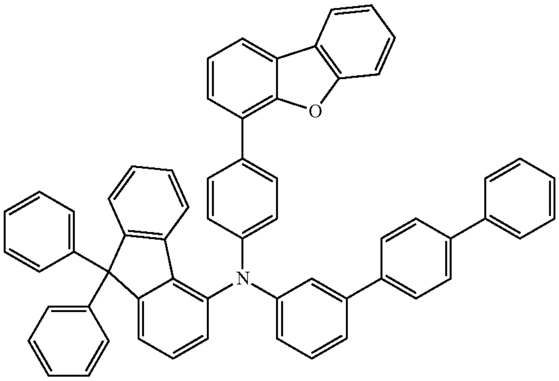
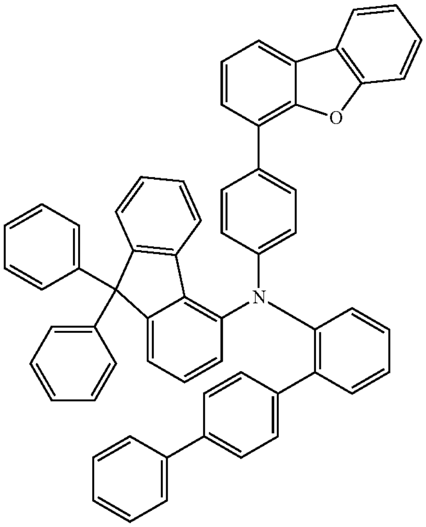
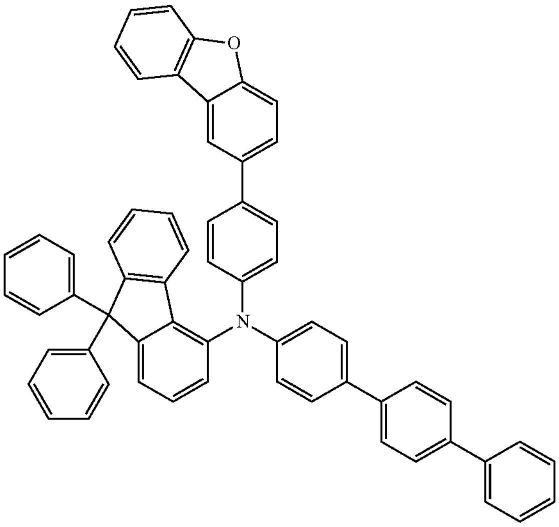

-continued
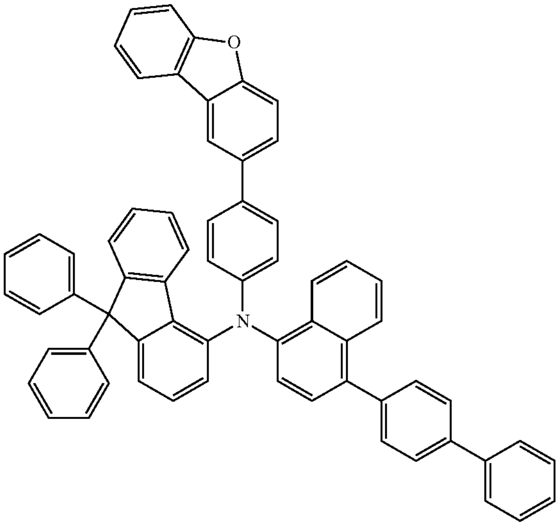
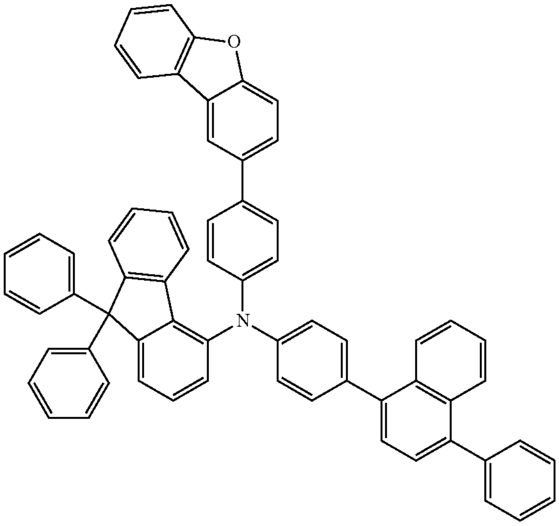
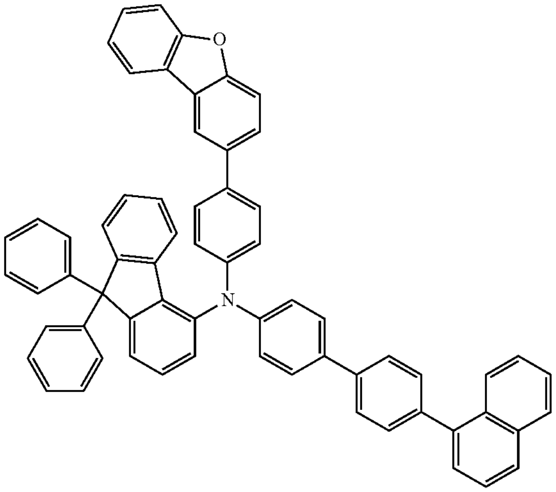
-continued
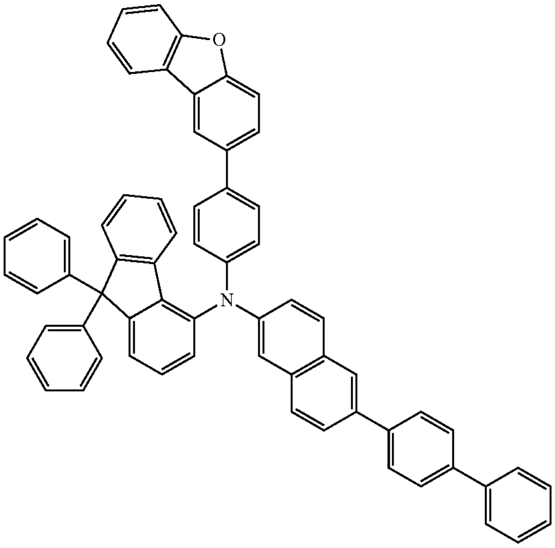
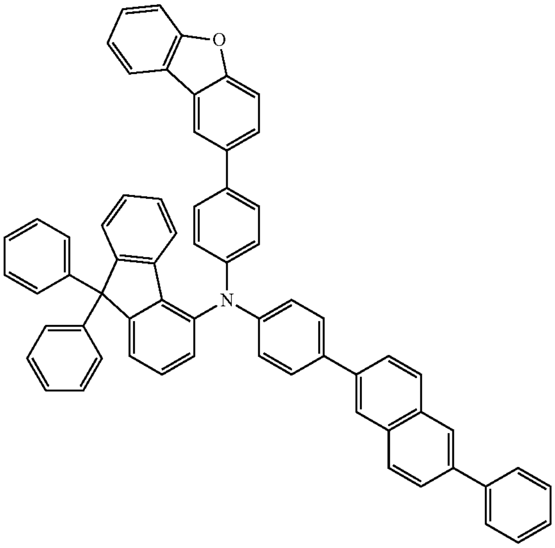
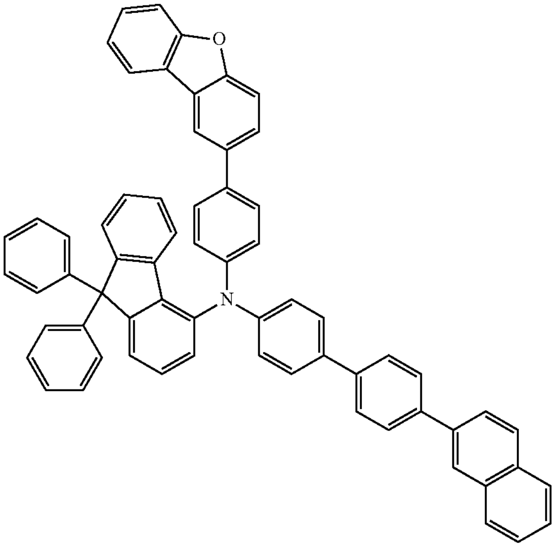

-continued
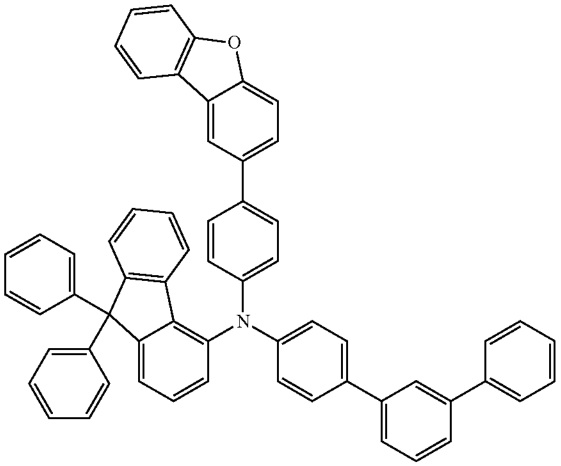
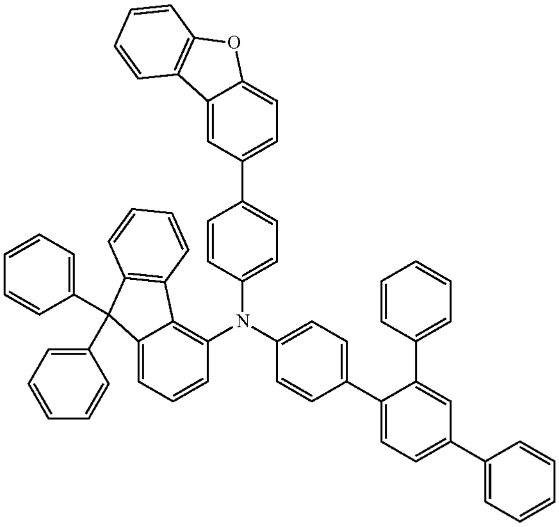
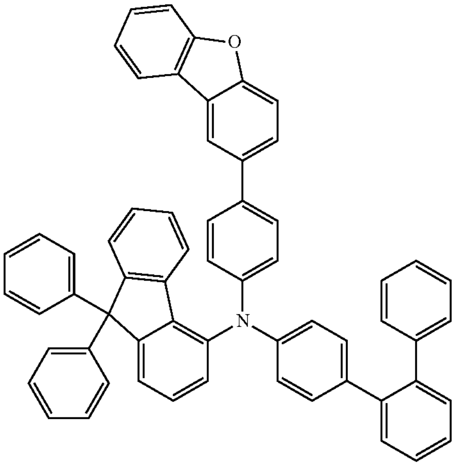
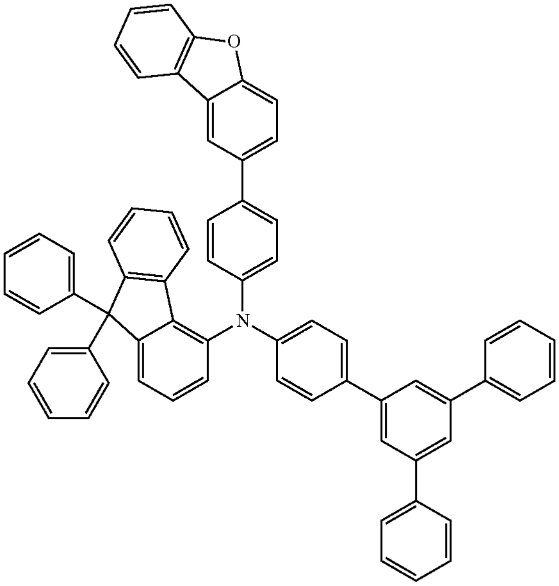
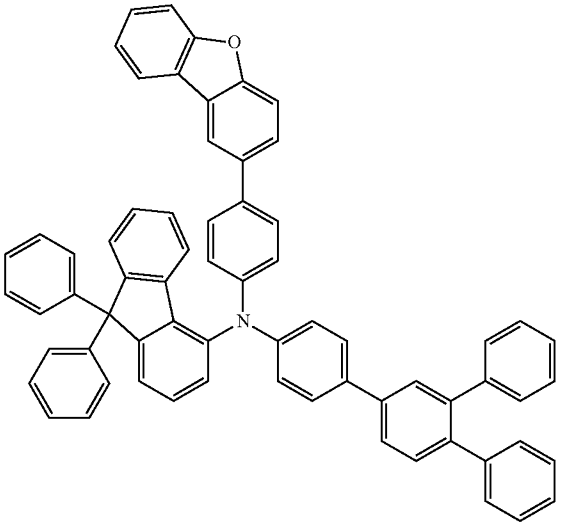
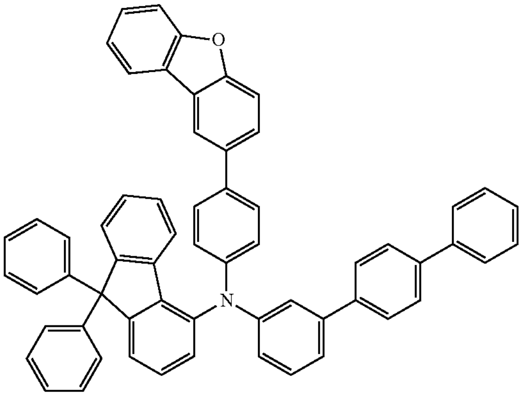

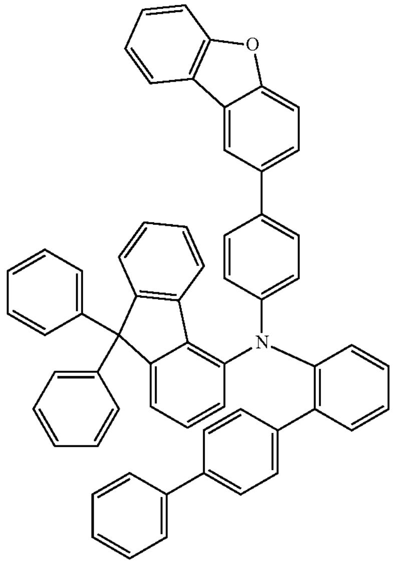
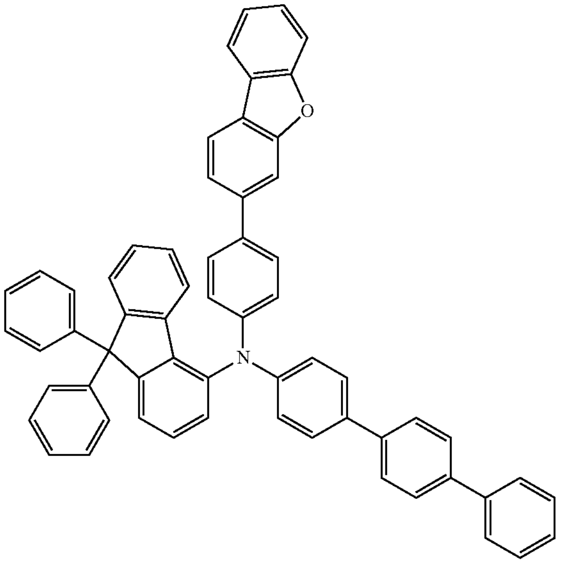
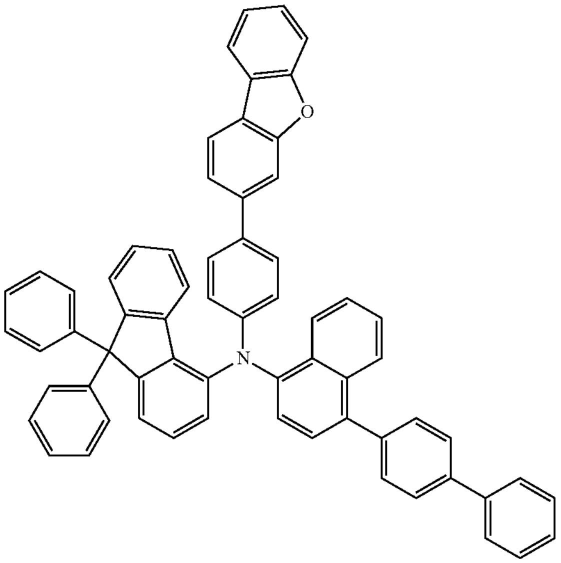
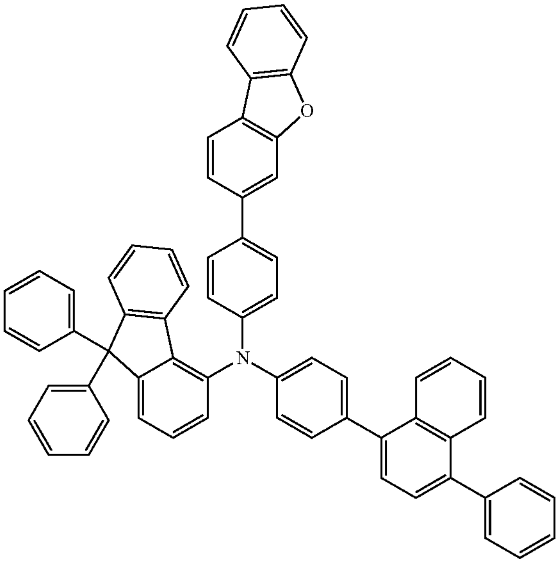
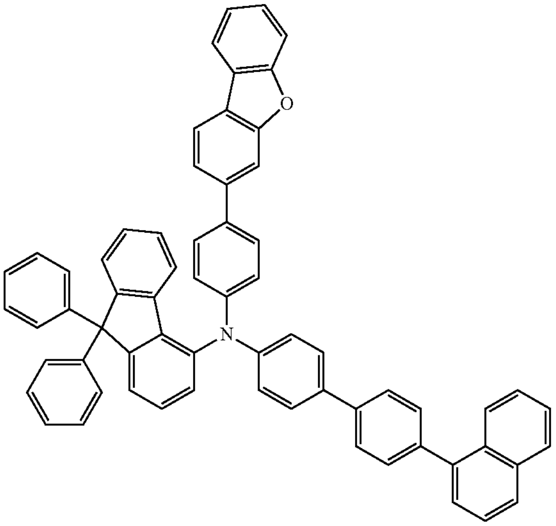
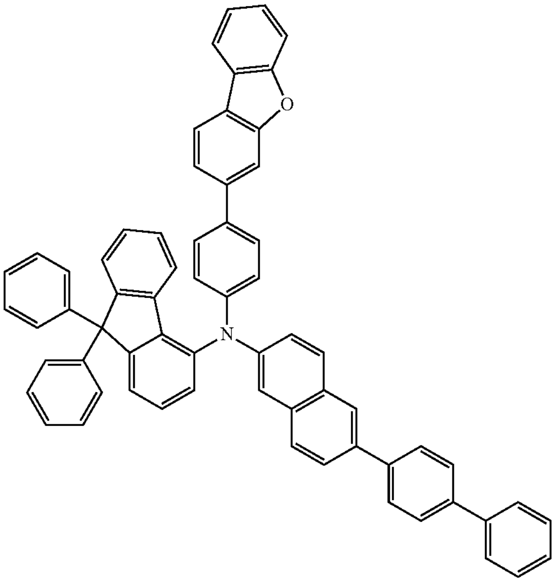

-continued
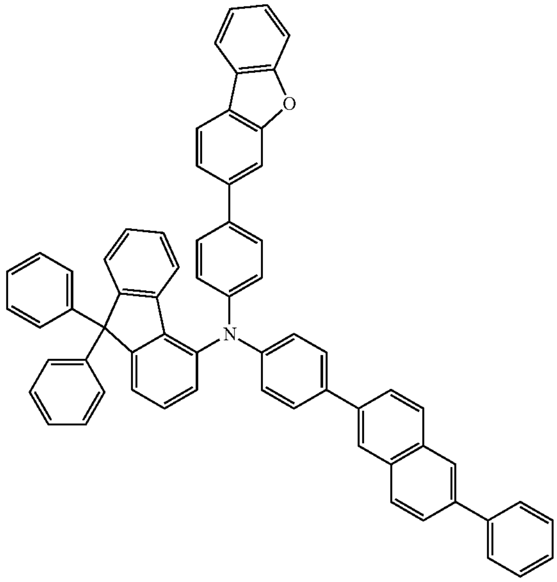
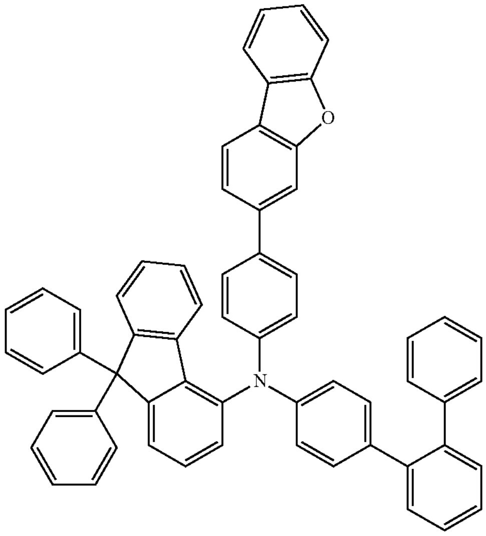
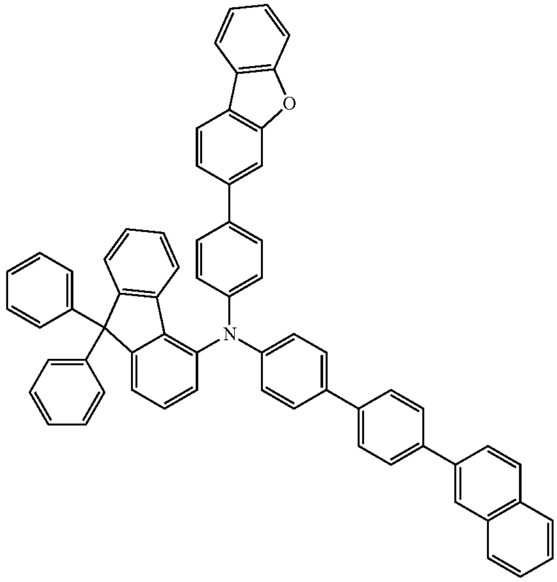
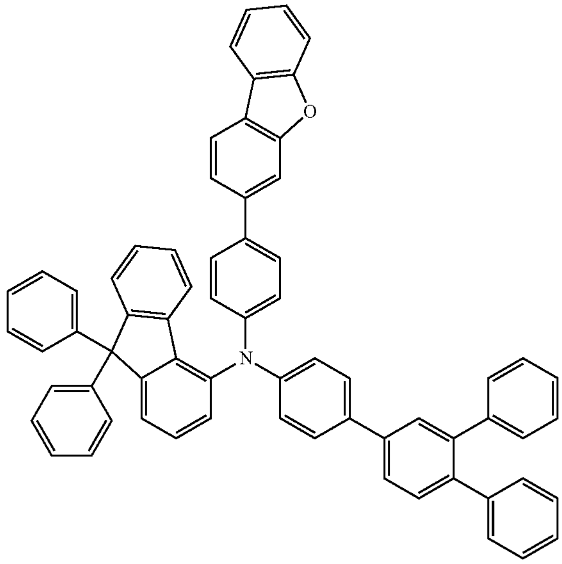
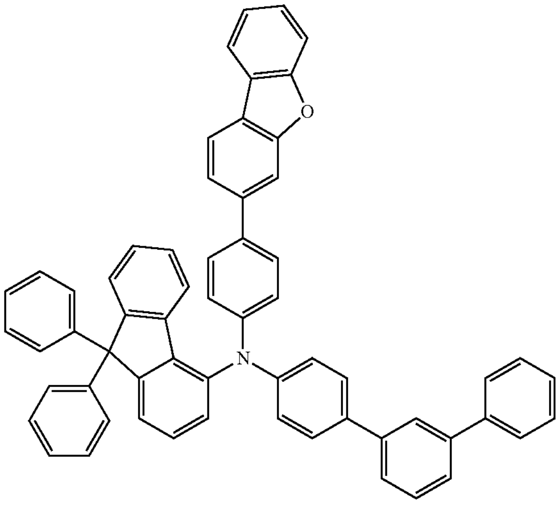
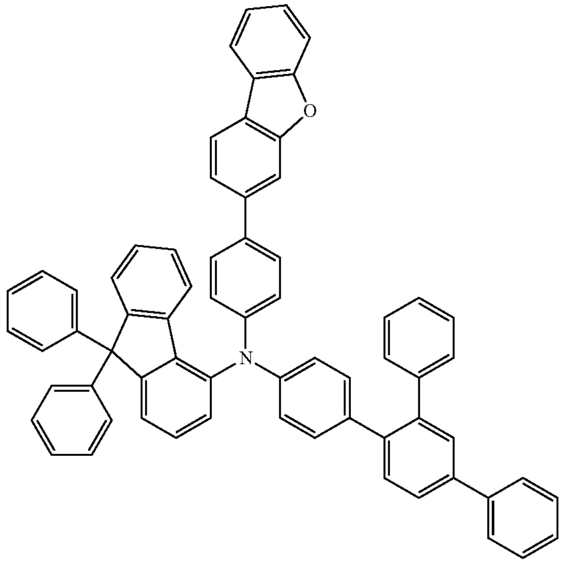
-continued -continued
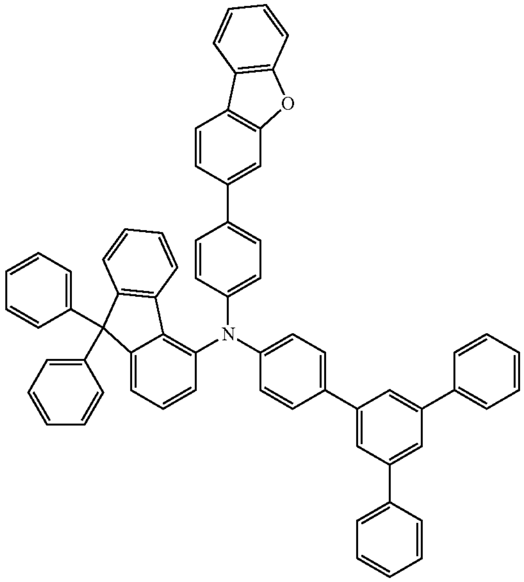
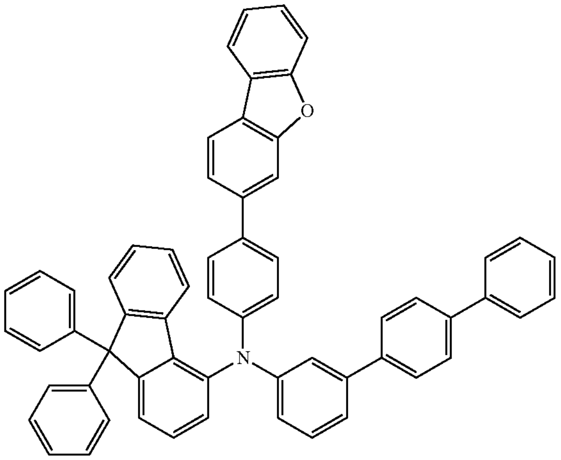
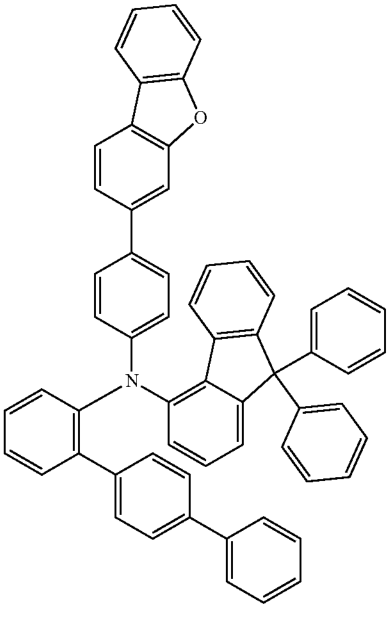
-continued
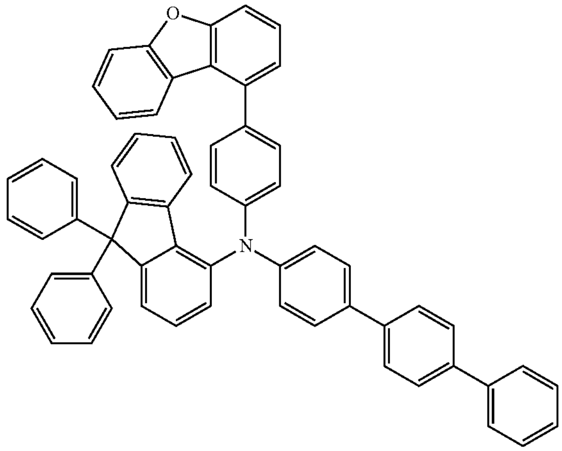
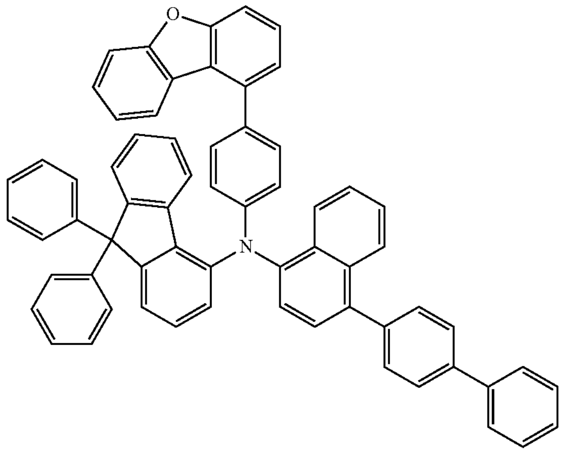
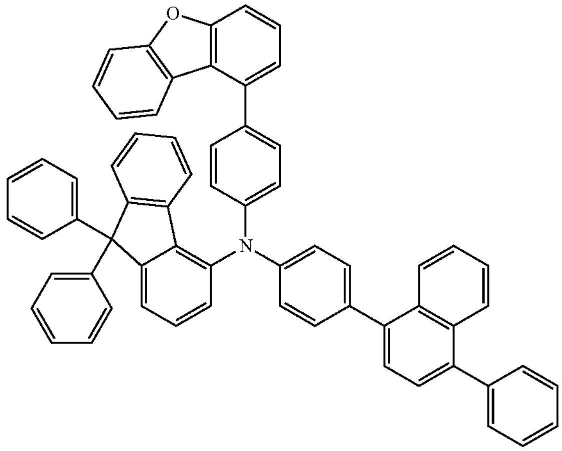

-continued
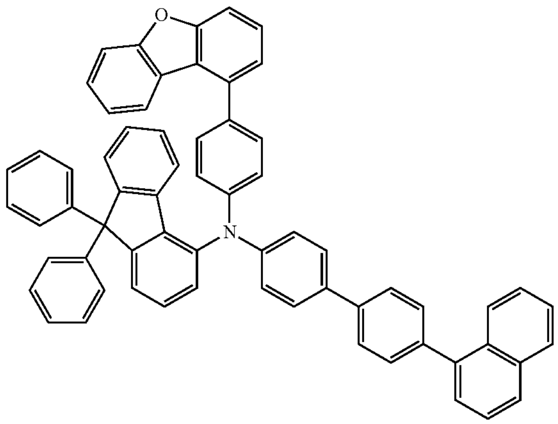
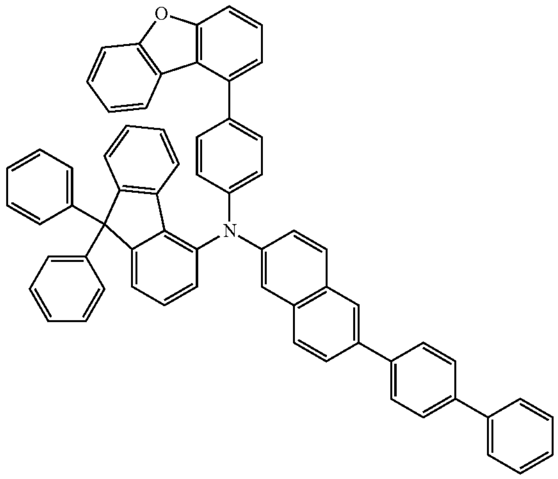
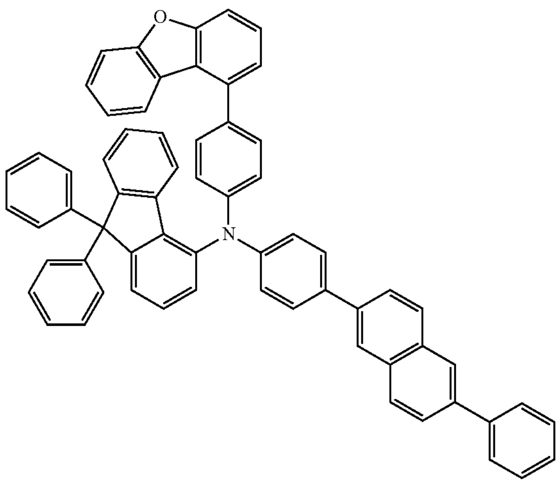
-continued
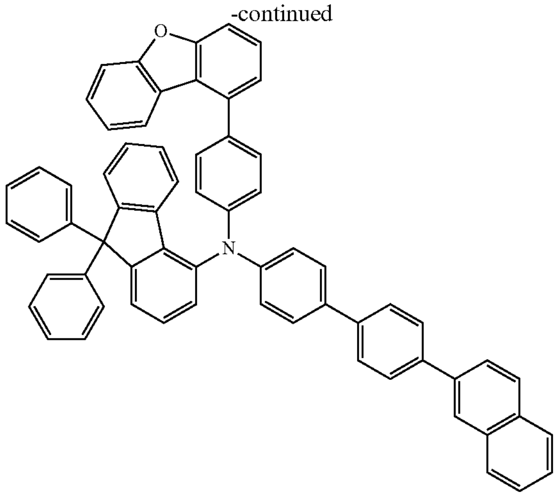
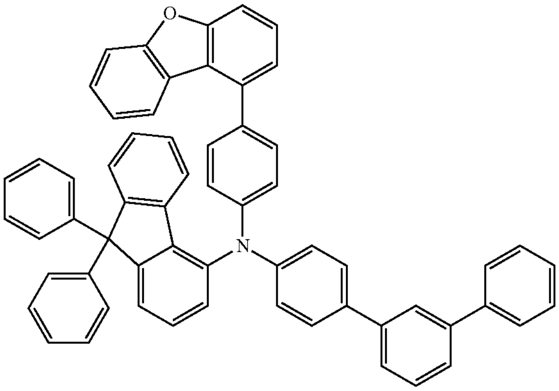
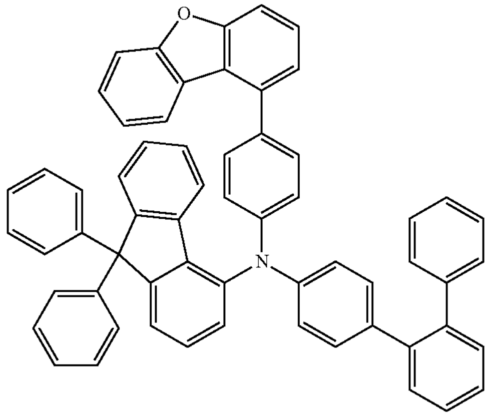
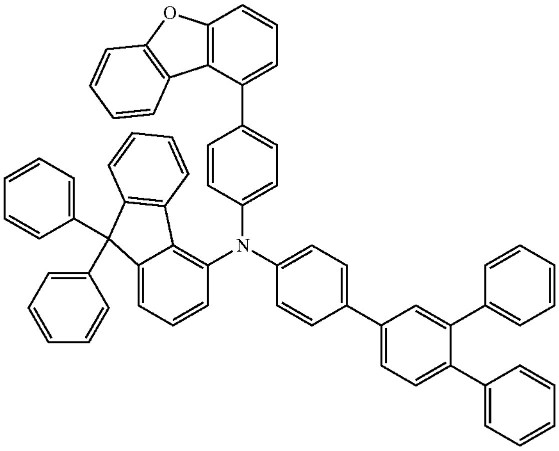

-continued
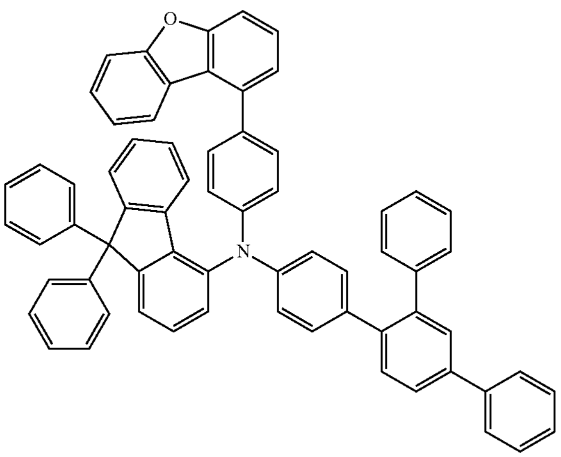
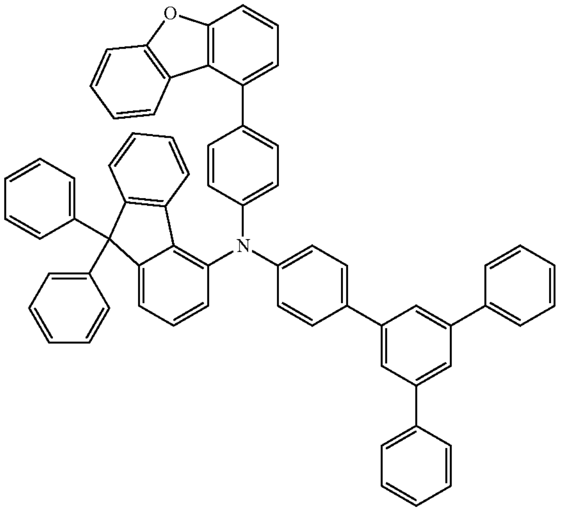
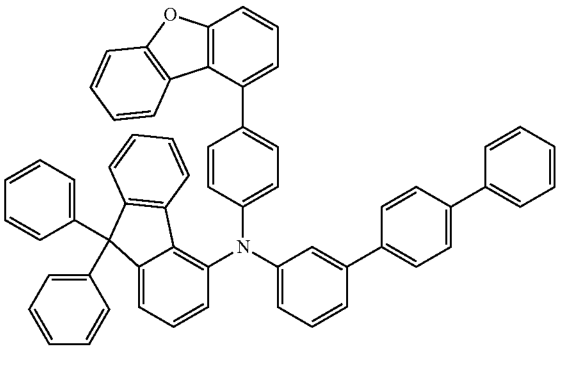
-continued
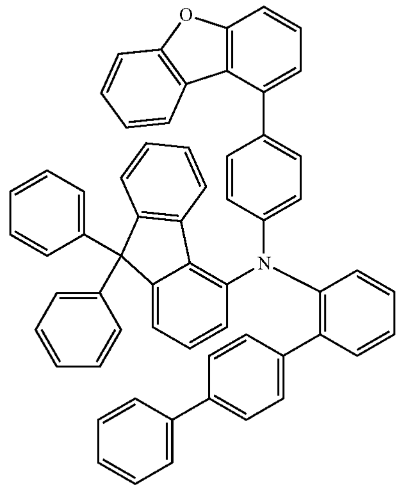
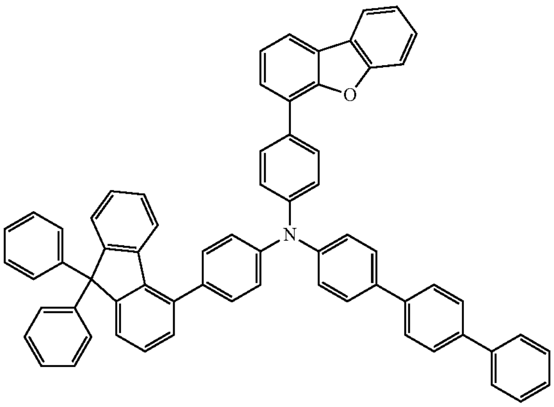
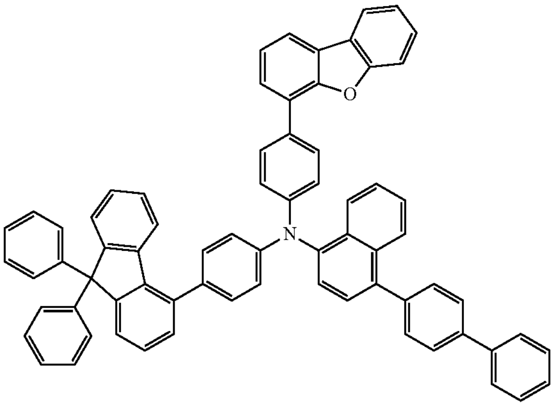
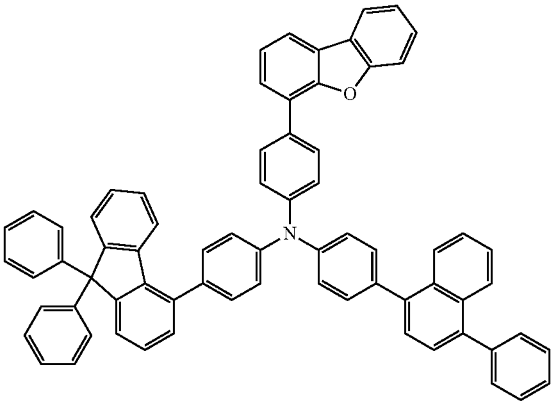

-continued
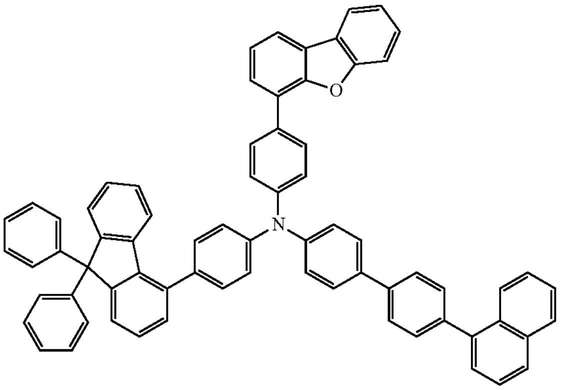
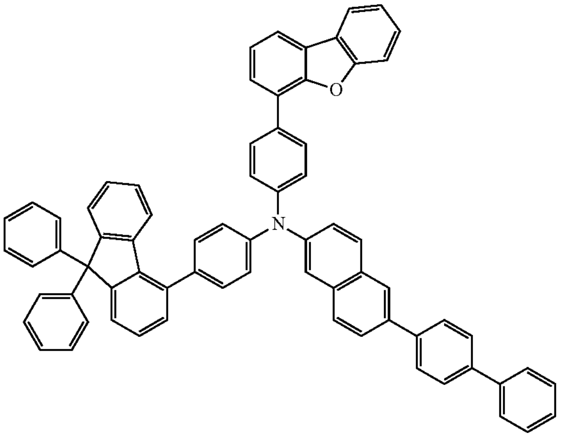
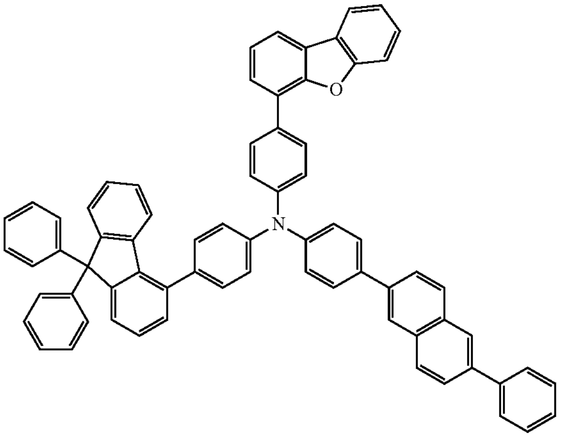
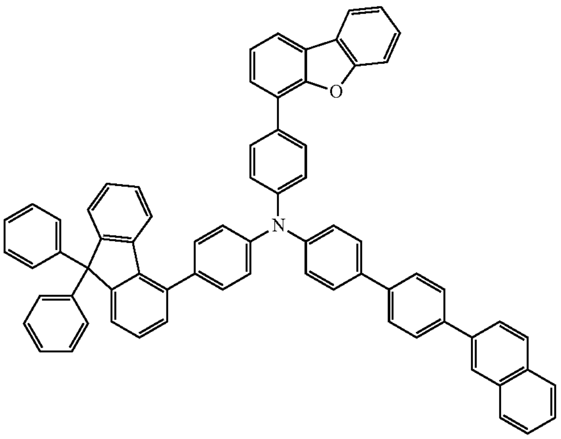
-continued
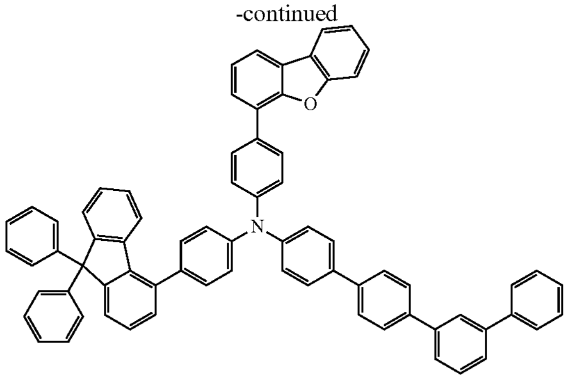
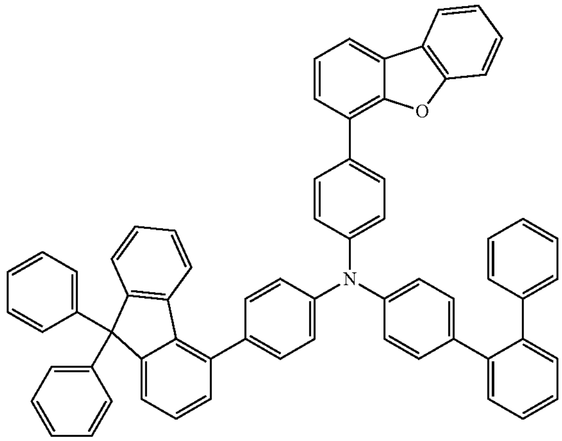
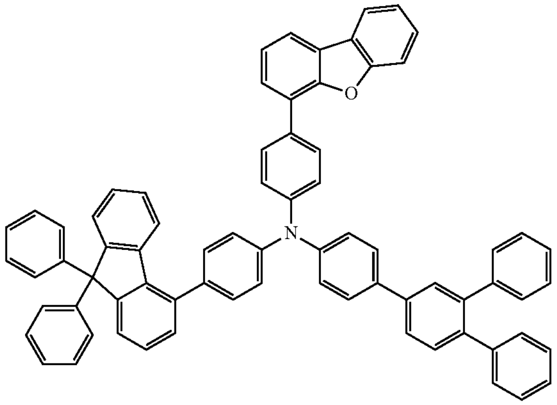
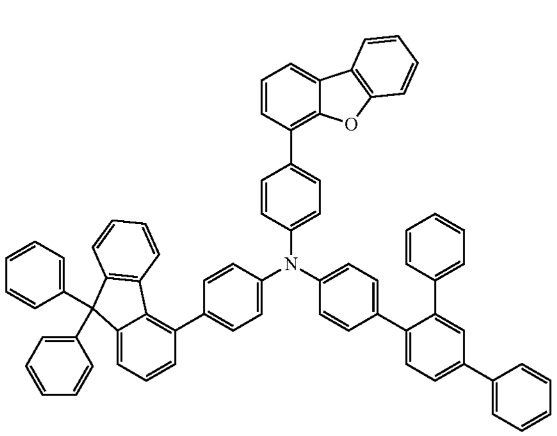

-continued
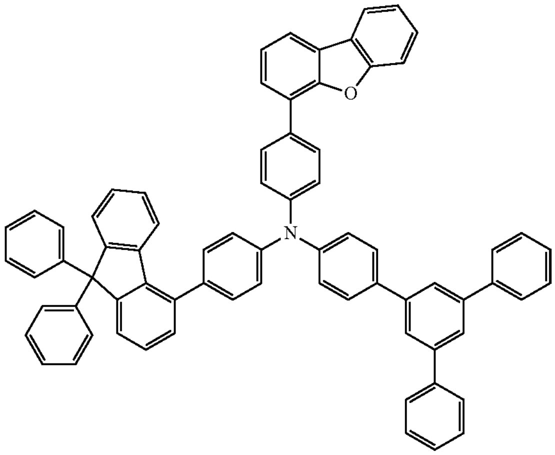
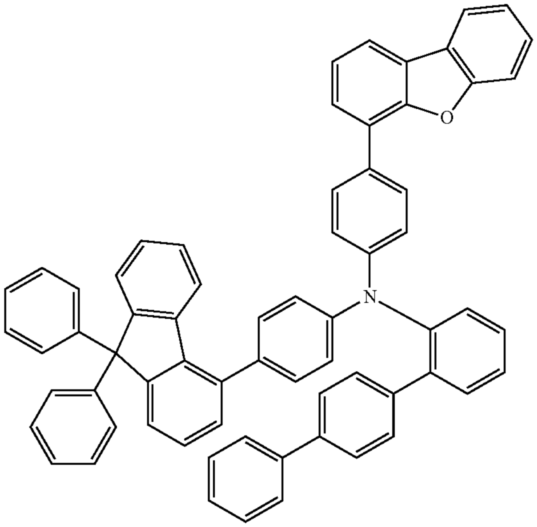
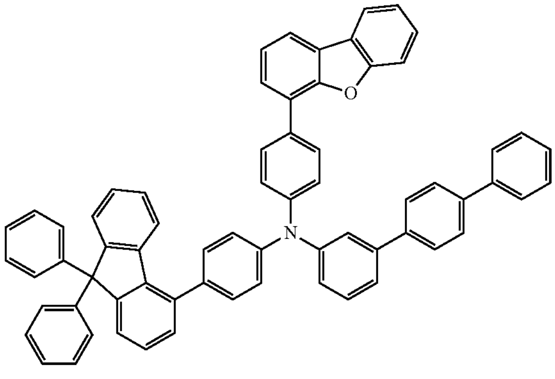
-continued
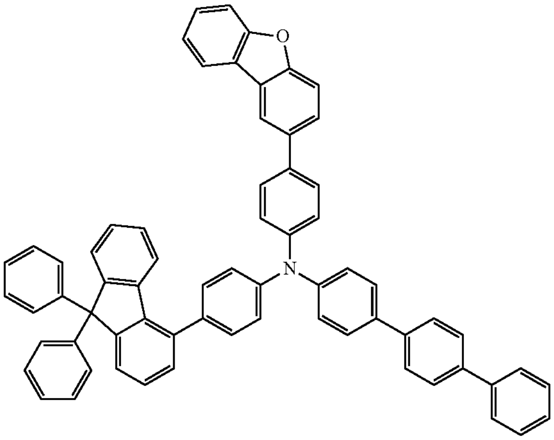
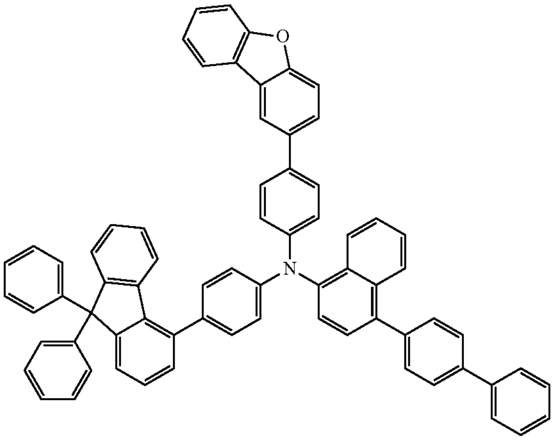
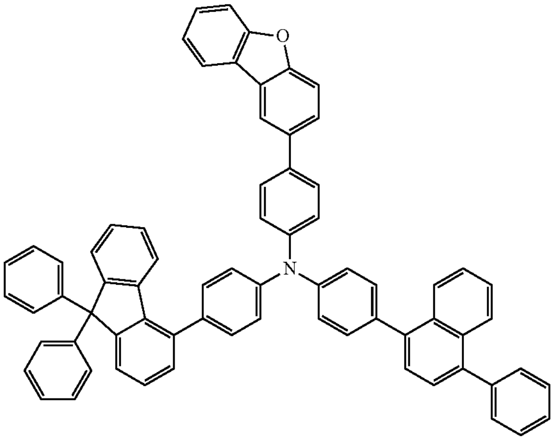

-continued
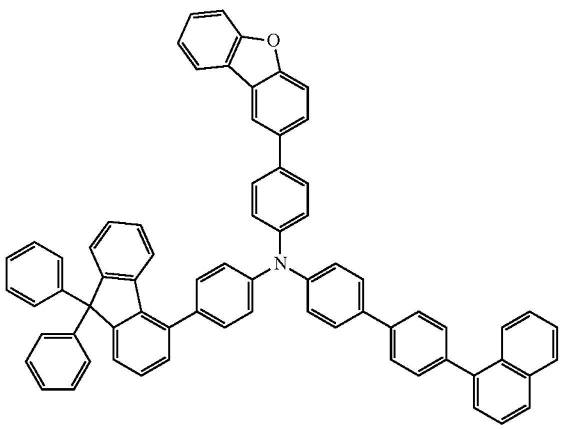
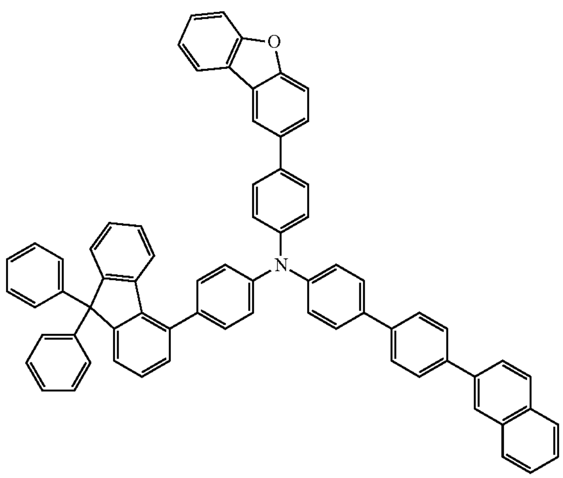
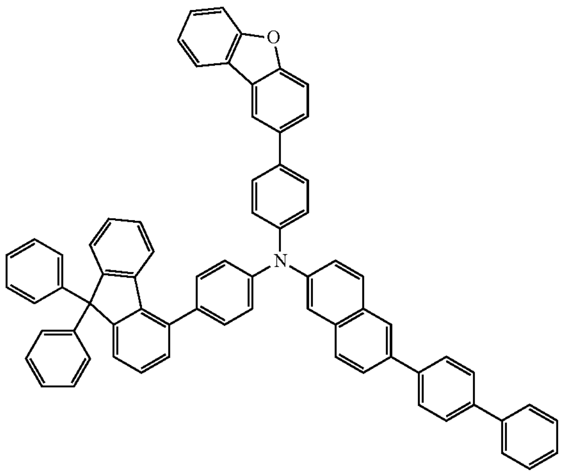
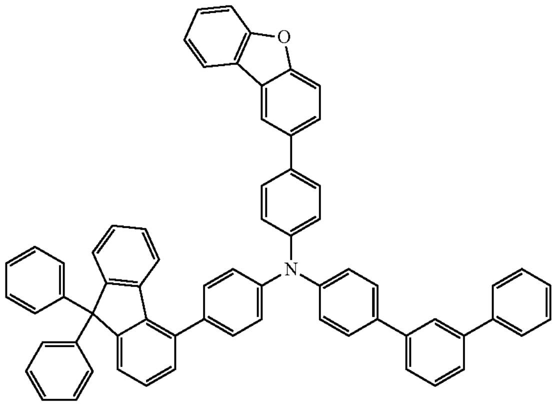
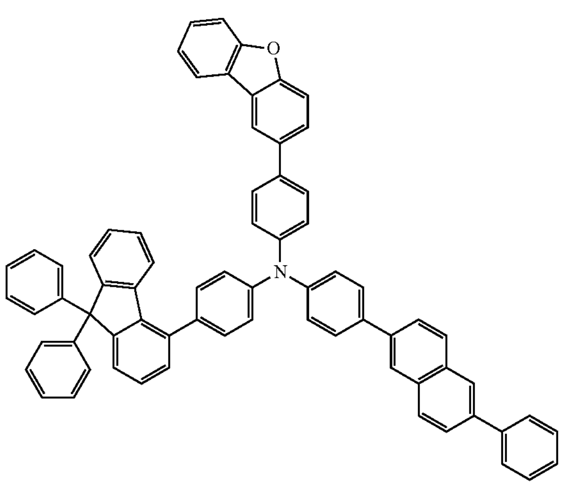
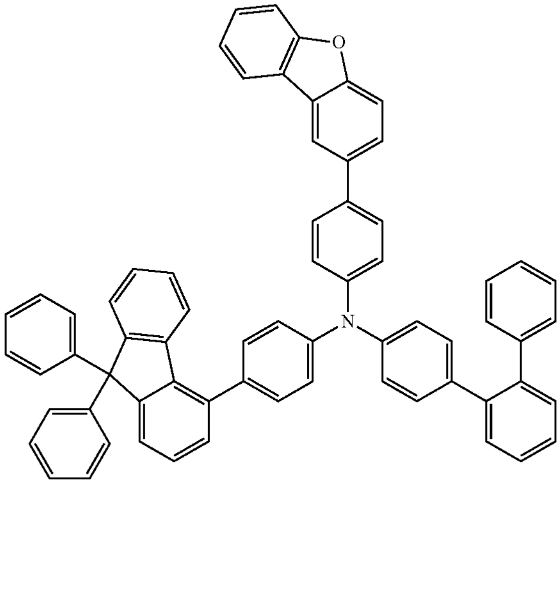
-continued -continued
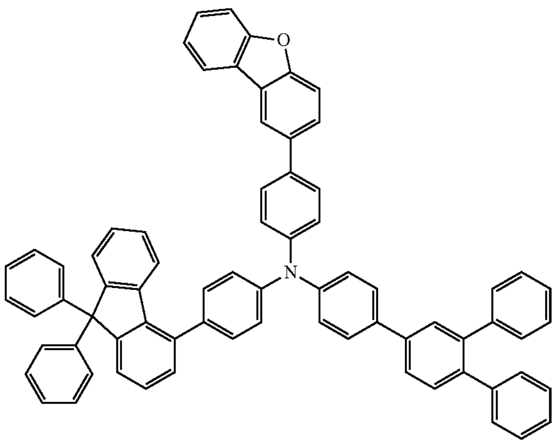
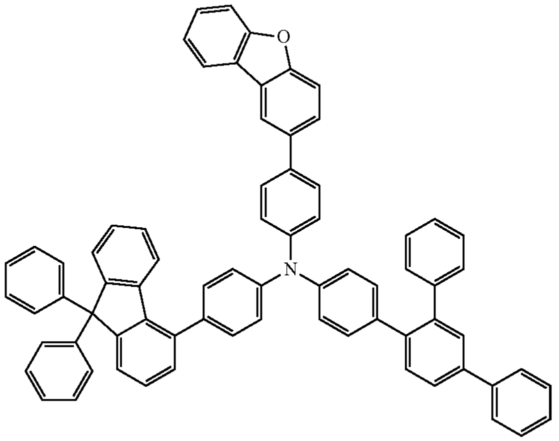
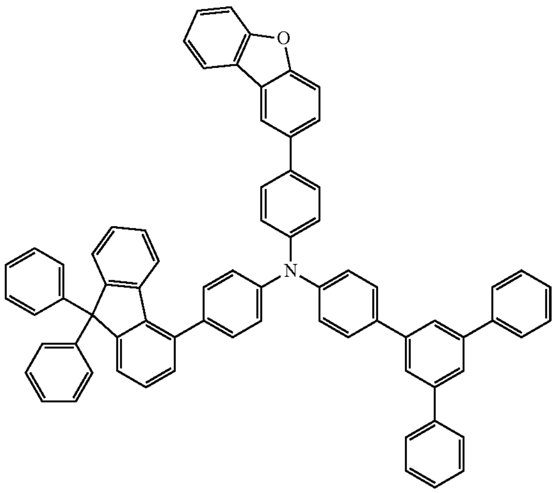
-continued
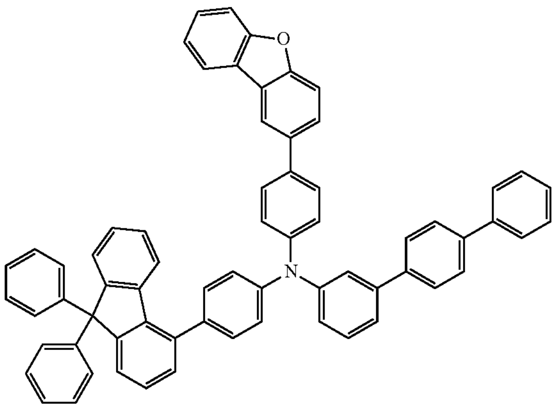
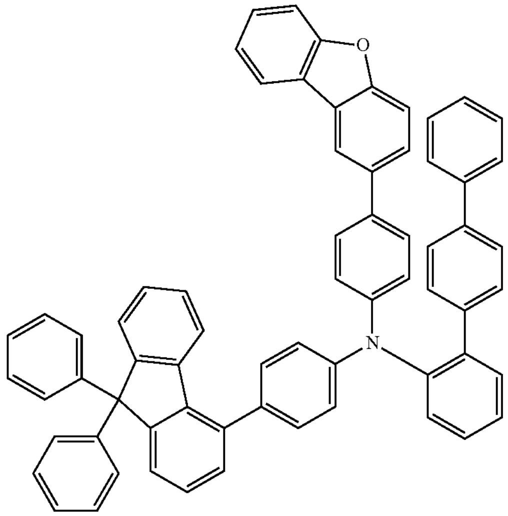
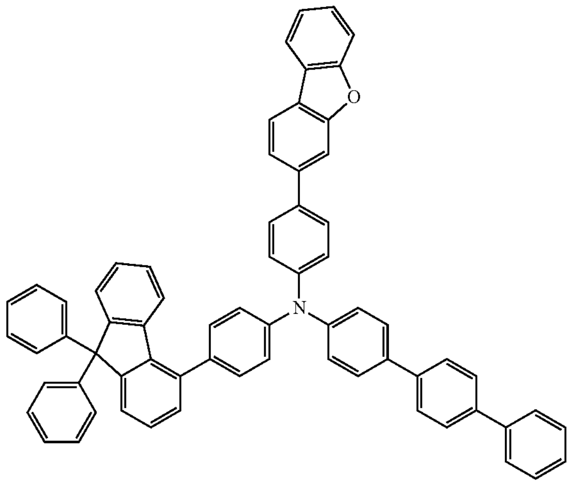

-continued
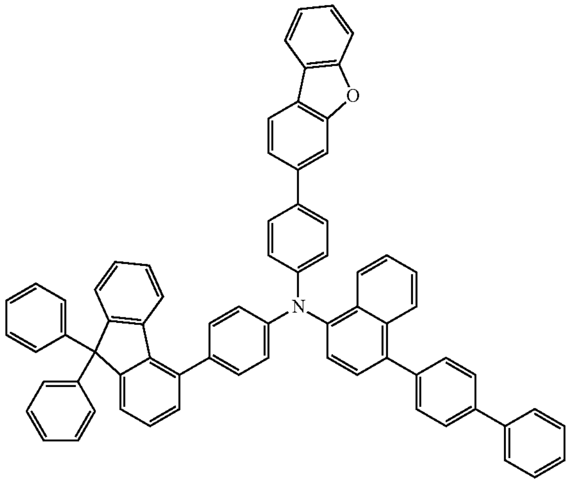
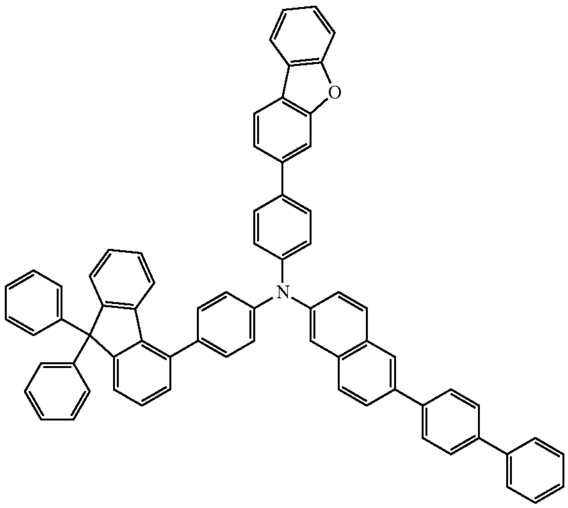
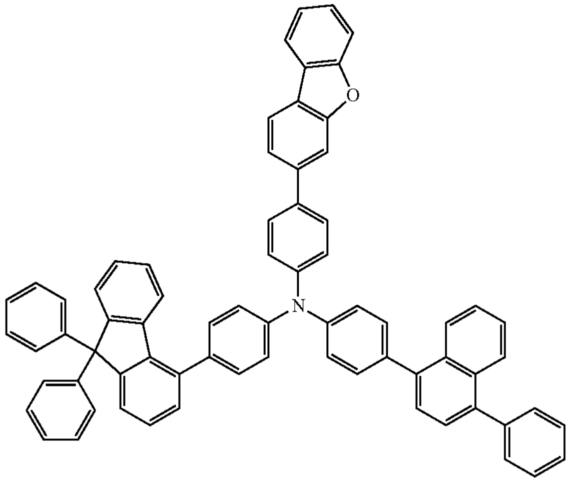
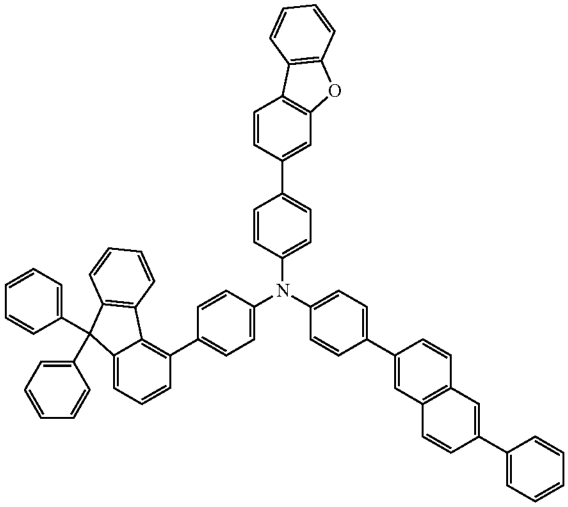
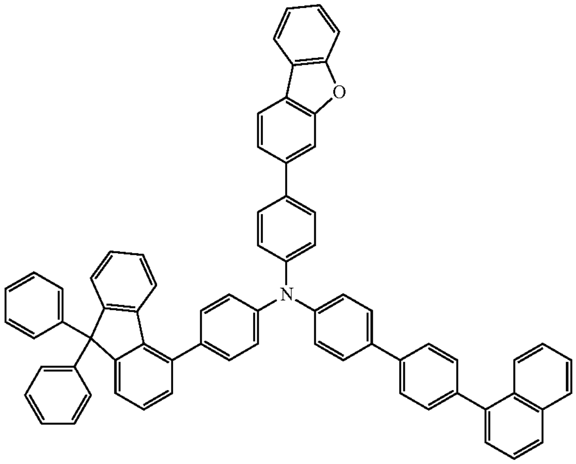
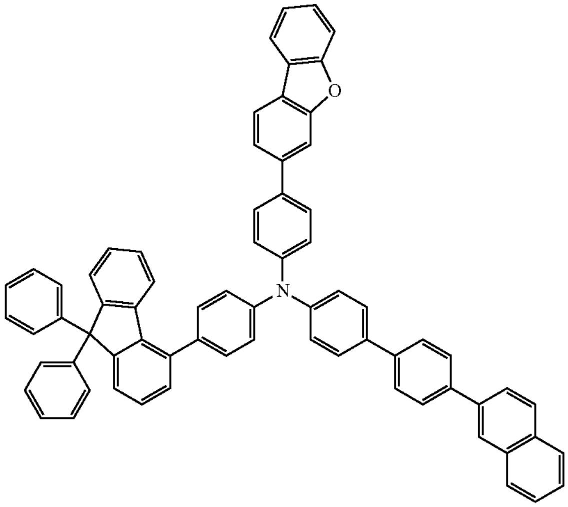
-continued -continued
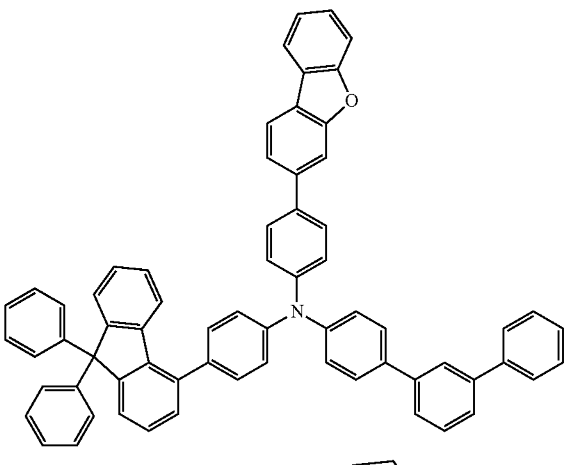
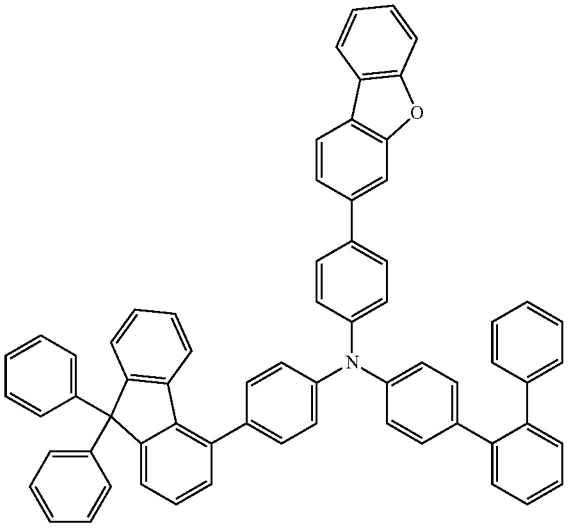
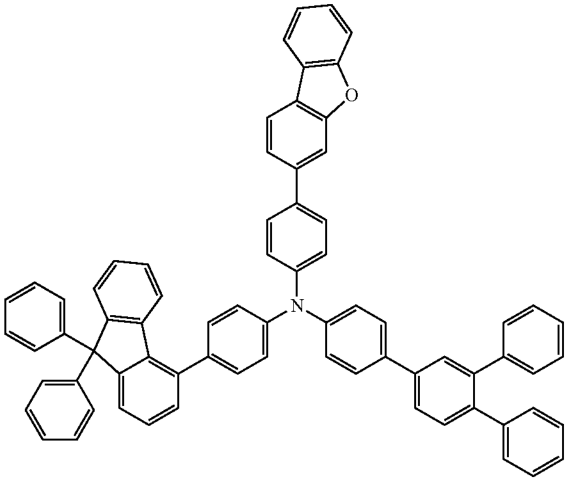
-continued
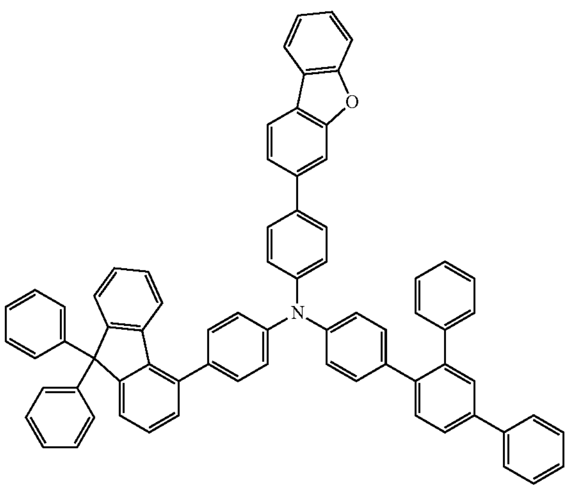
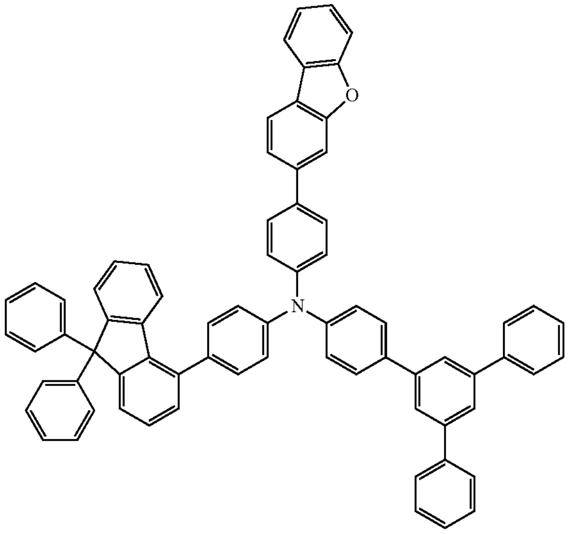
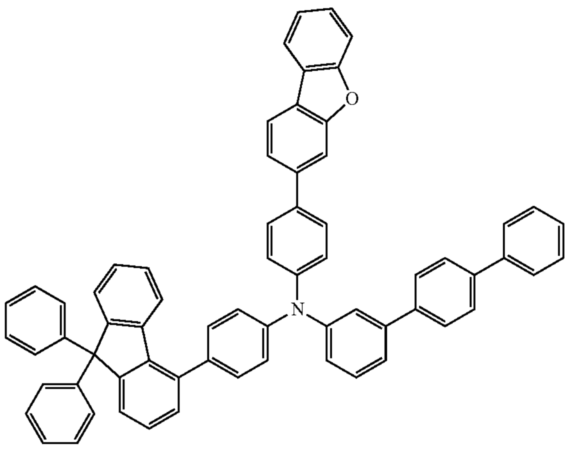

-continued
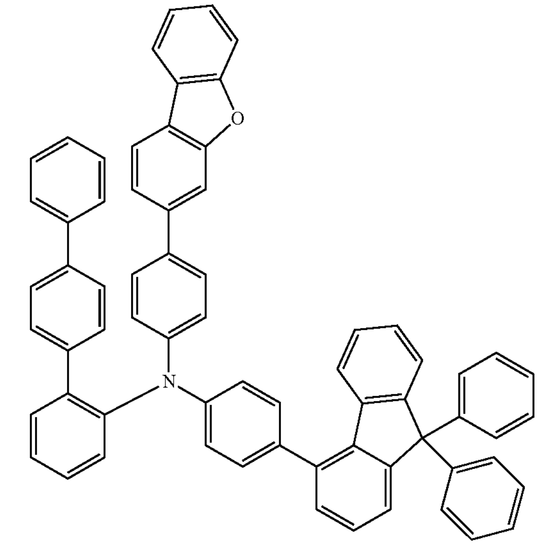
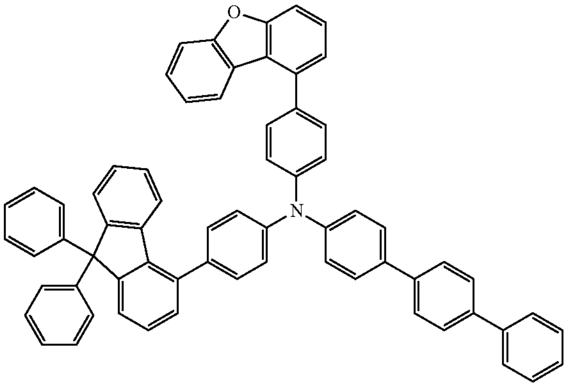
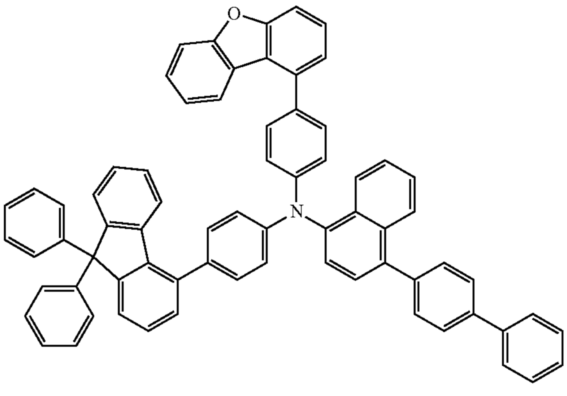
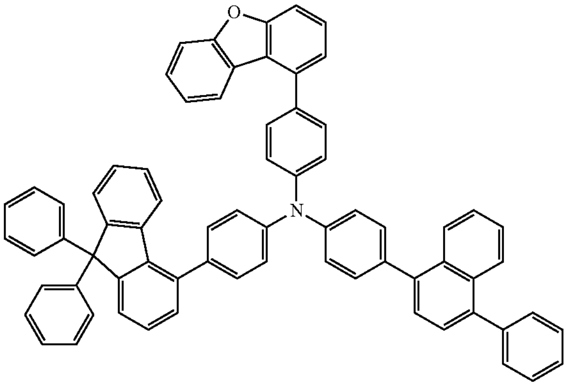
-continued
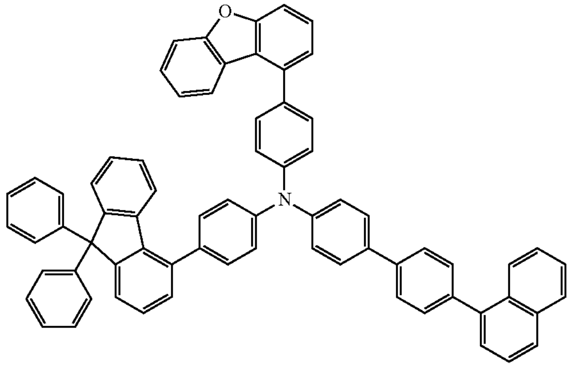
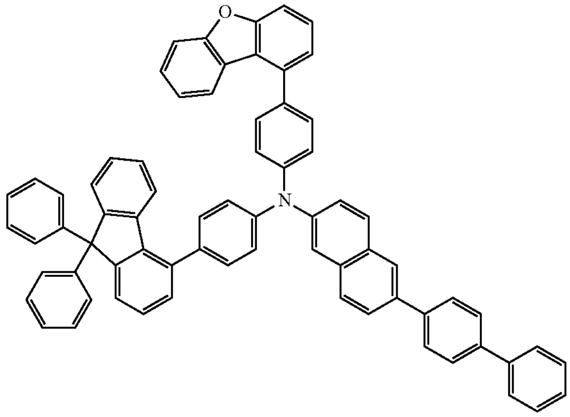
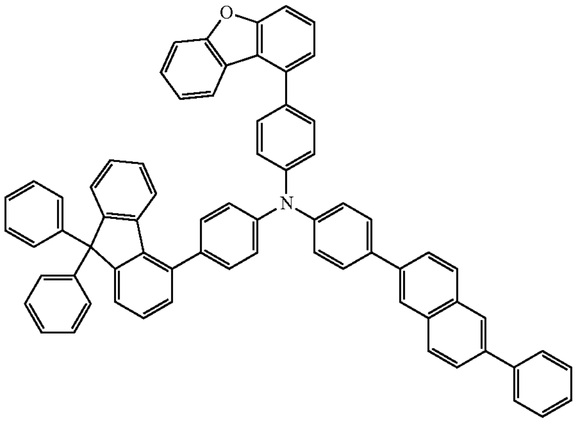
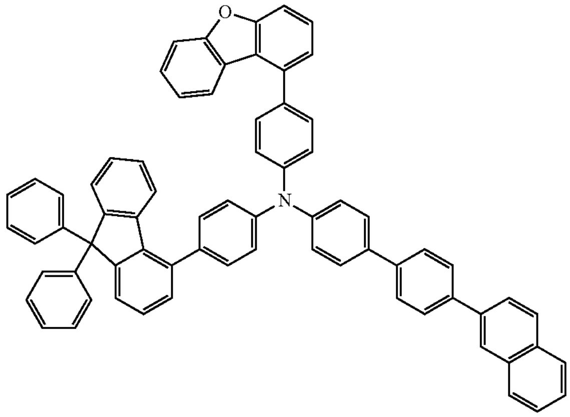

-continued
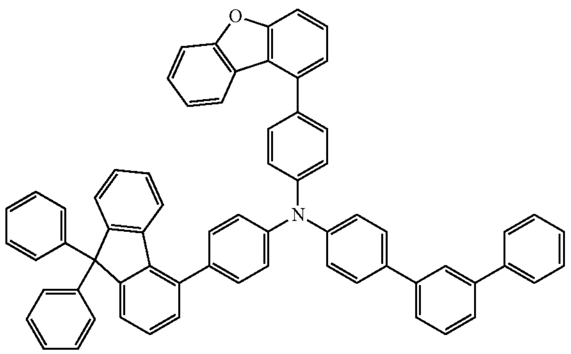
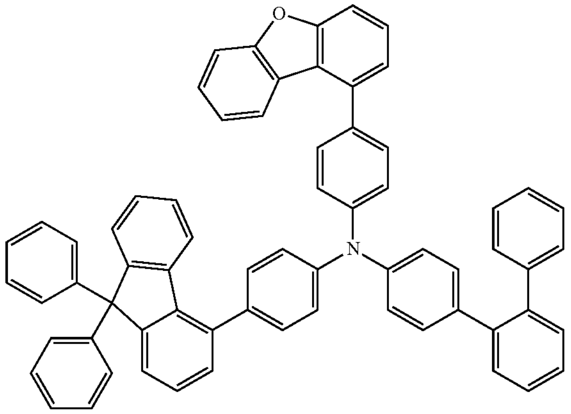
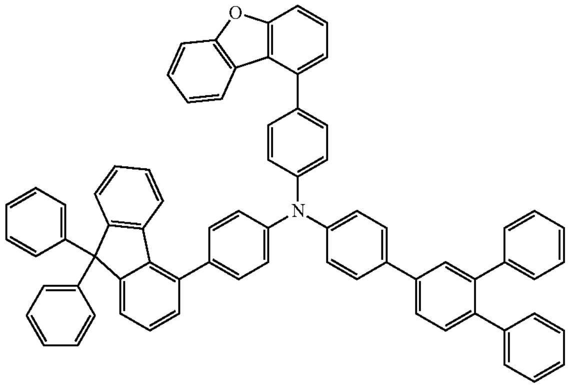
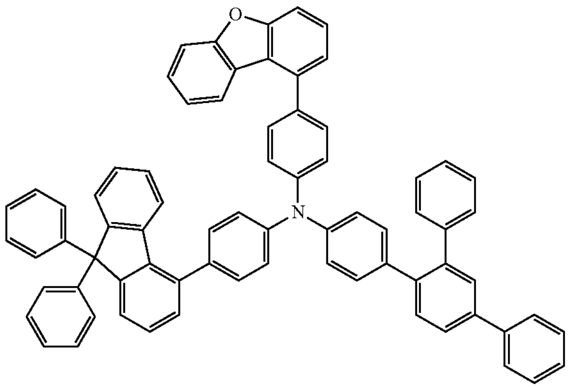
-continued
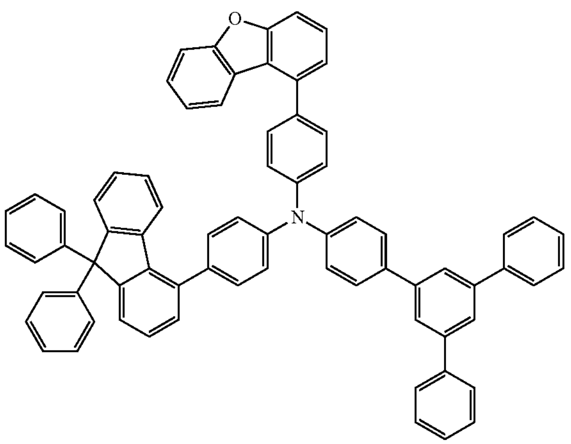
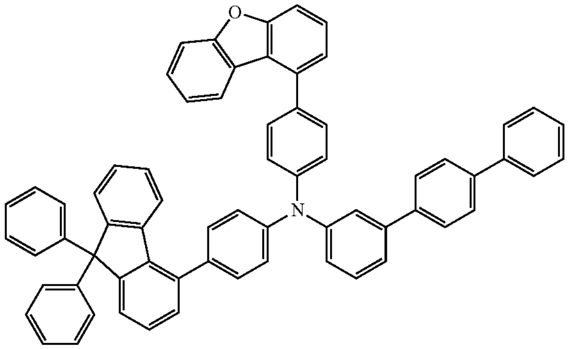
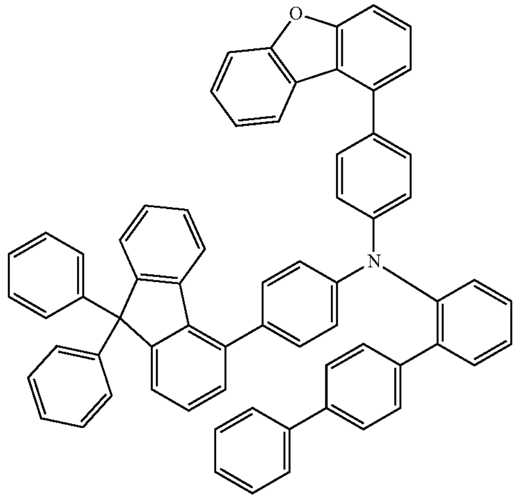

-continued
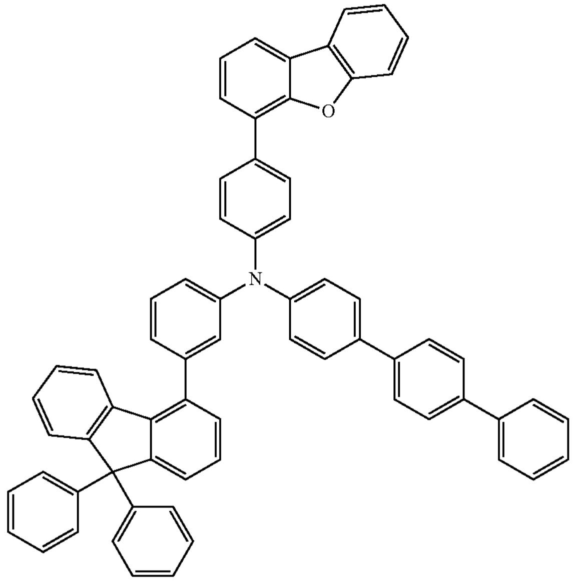
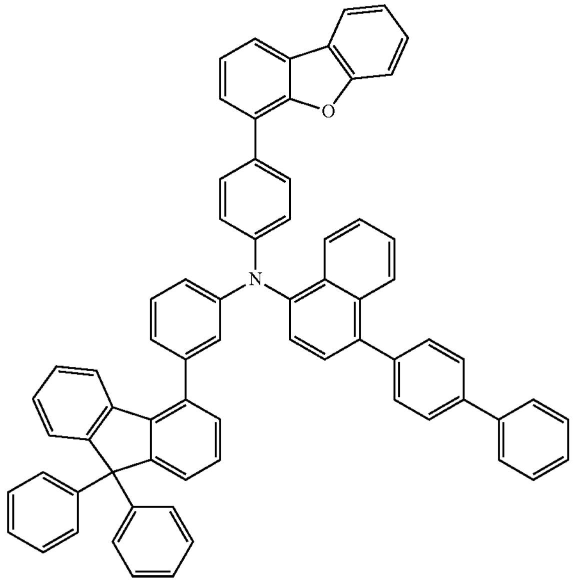
-continued
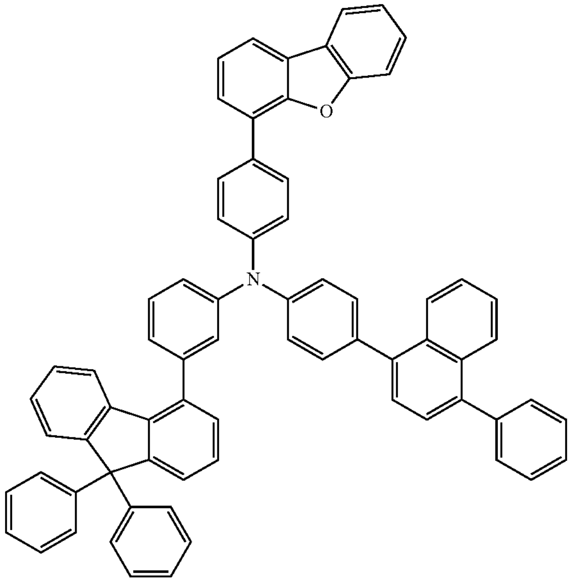
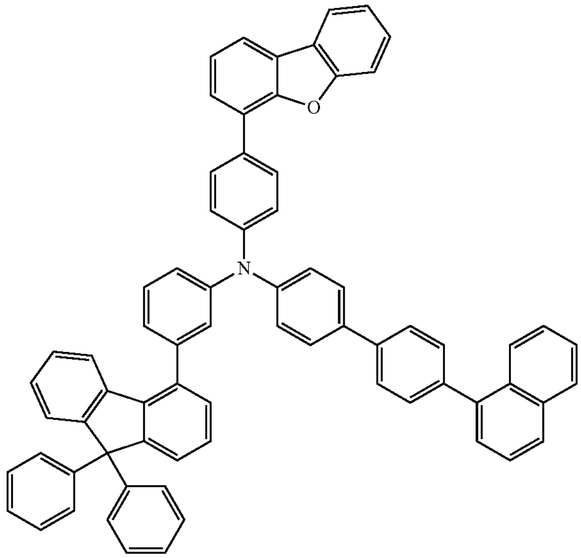
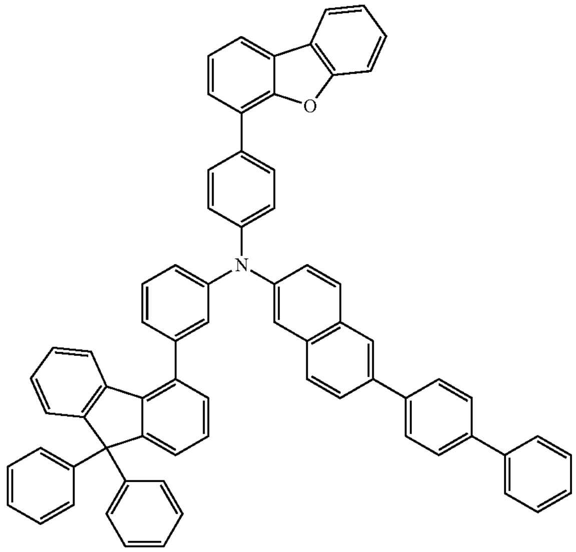

-continued
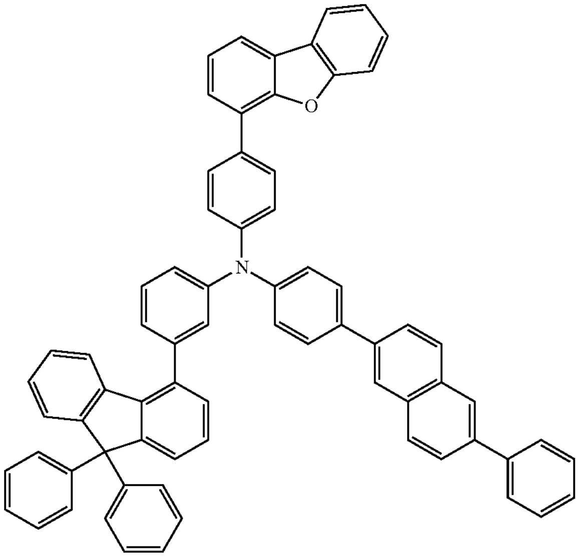
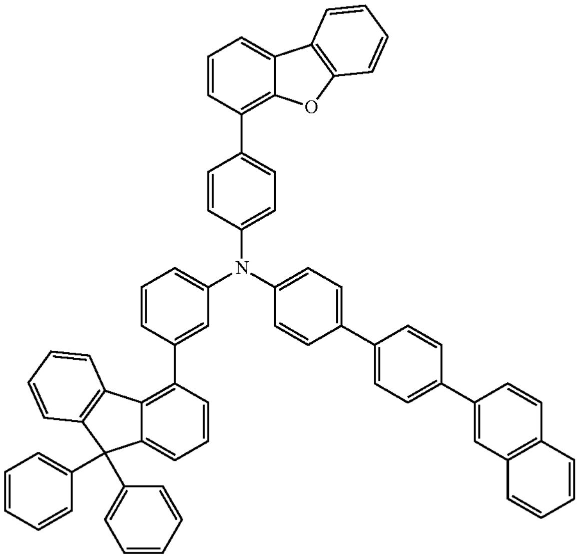
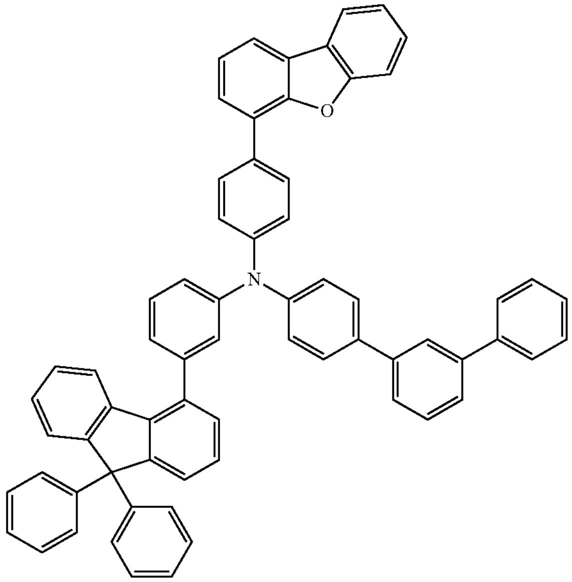
-continued
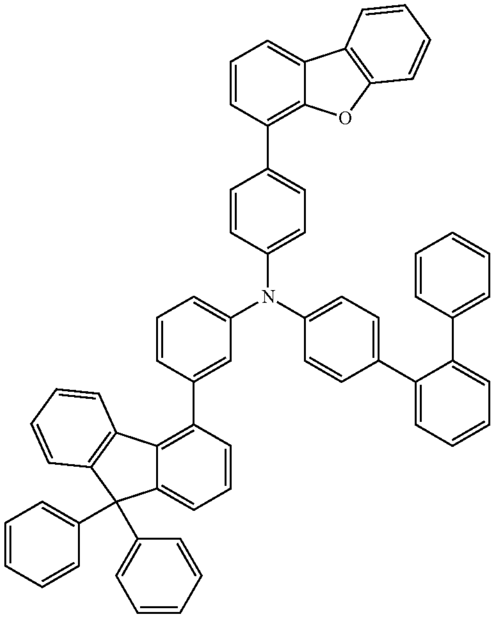
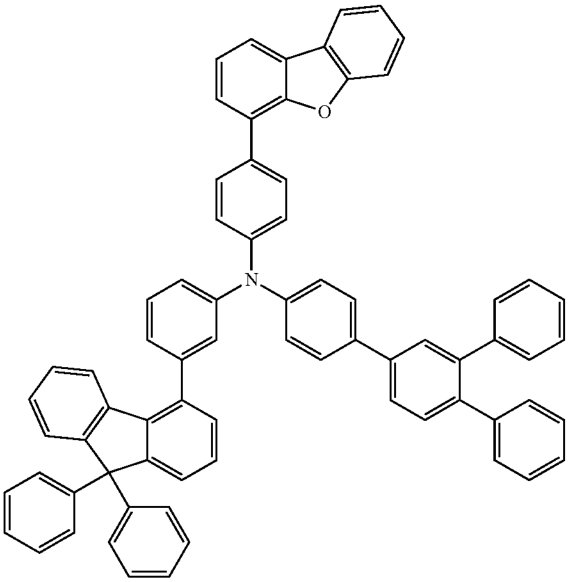

-continued
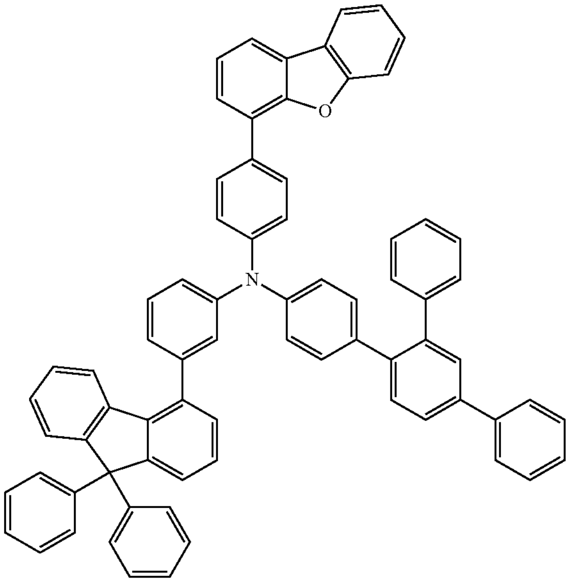
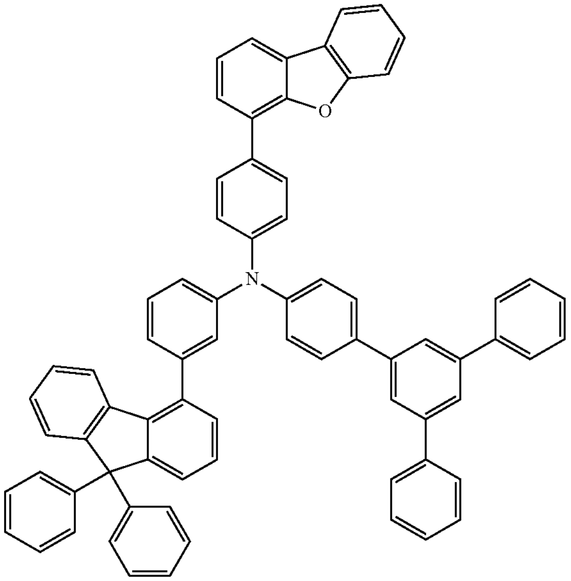
-continued
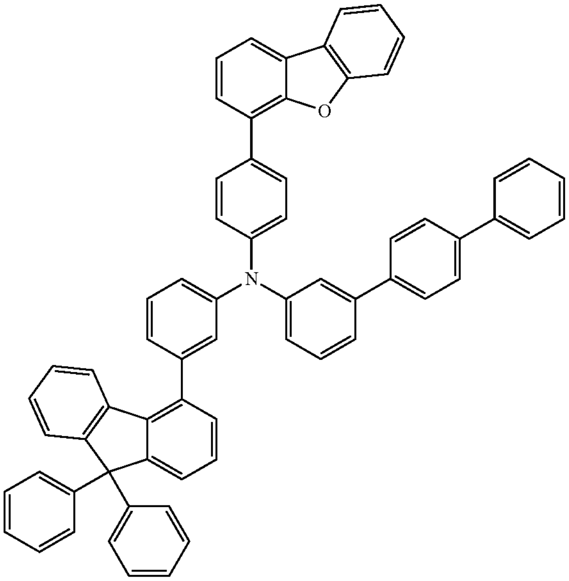
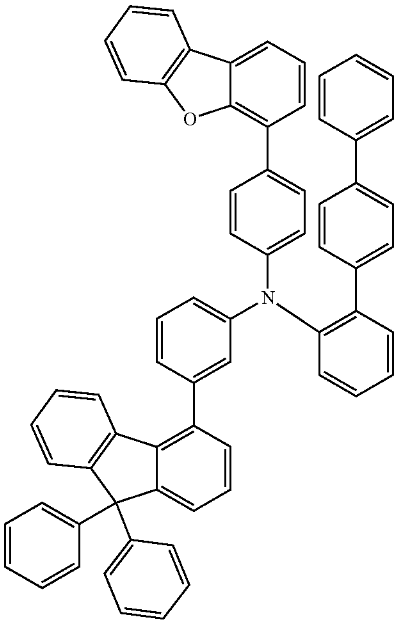

-continued
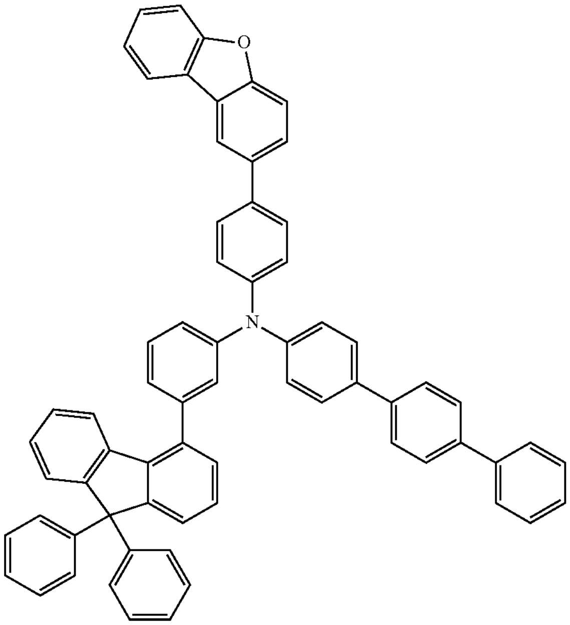
-continued
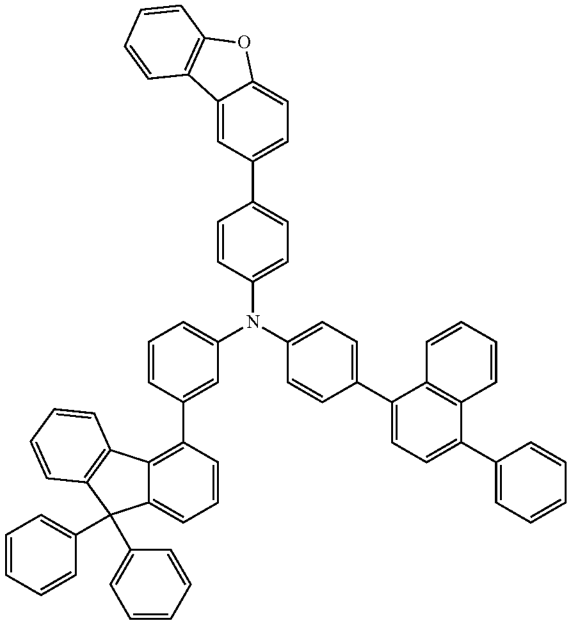
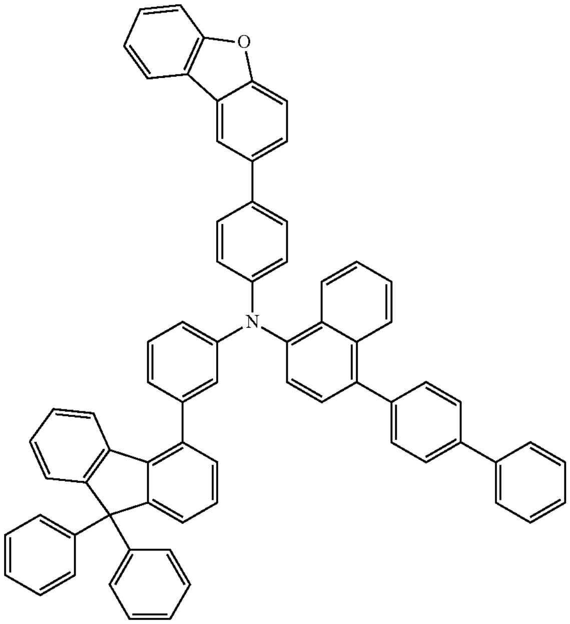
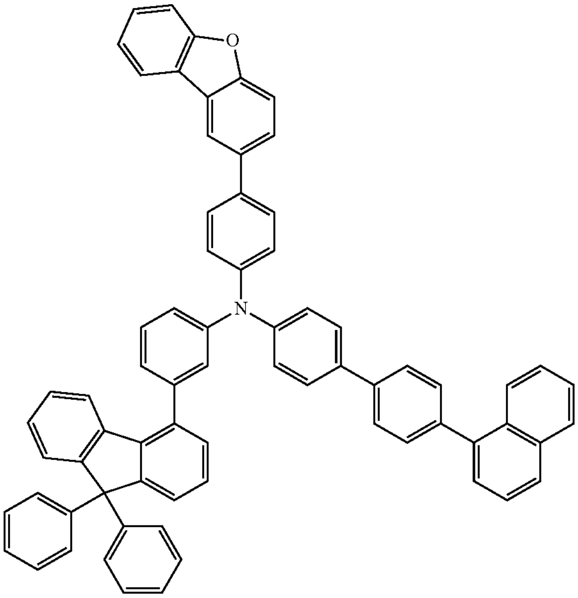

-continued
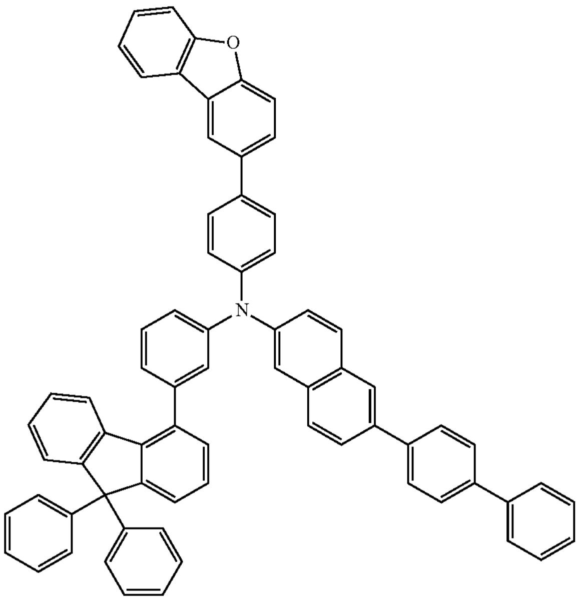
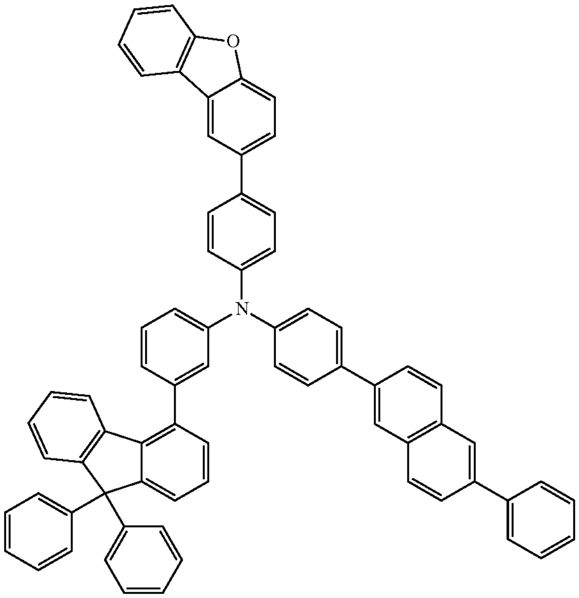
-continued
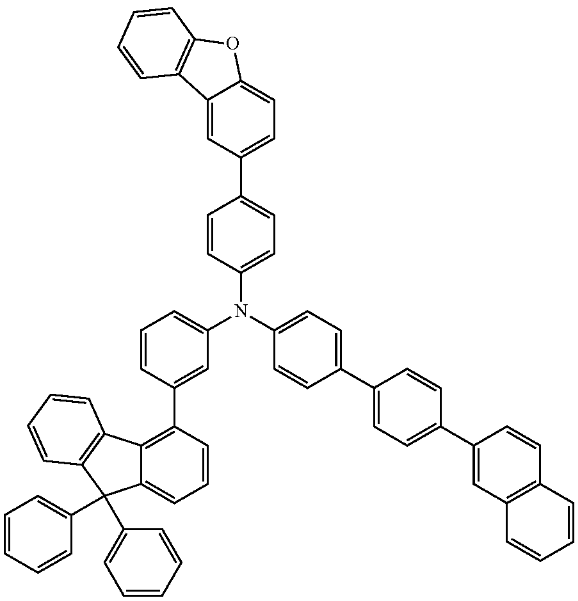
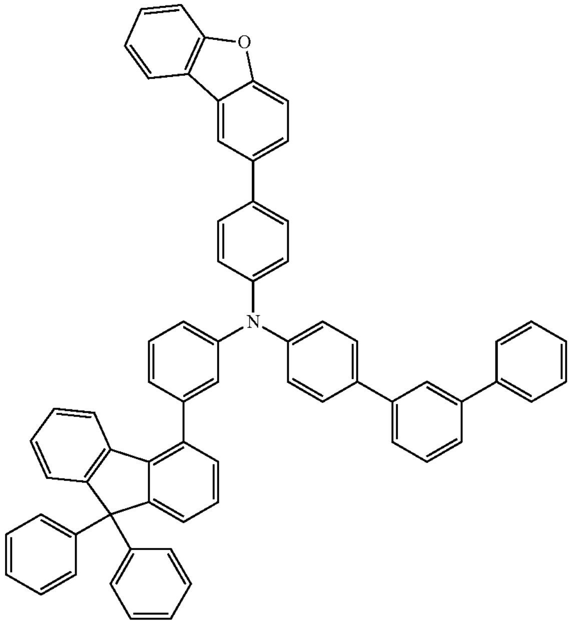

-continued
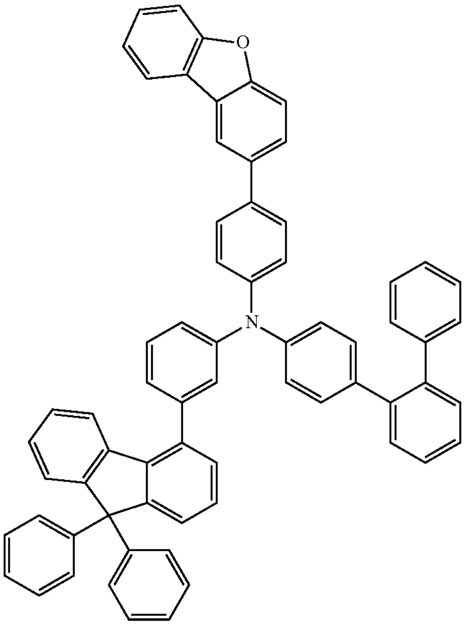
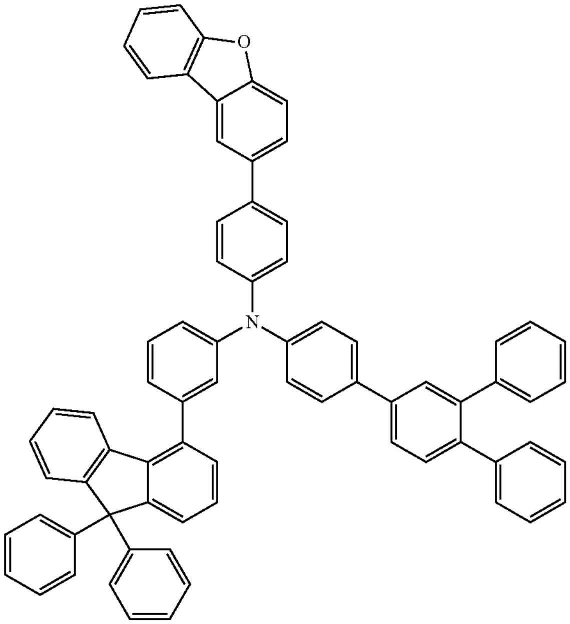
-continued
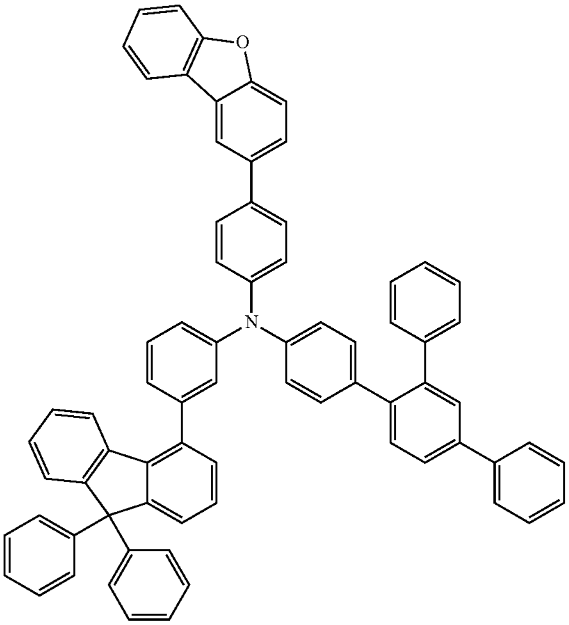
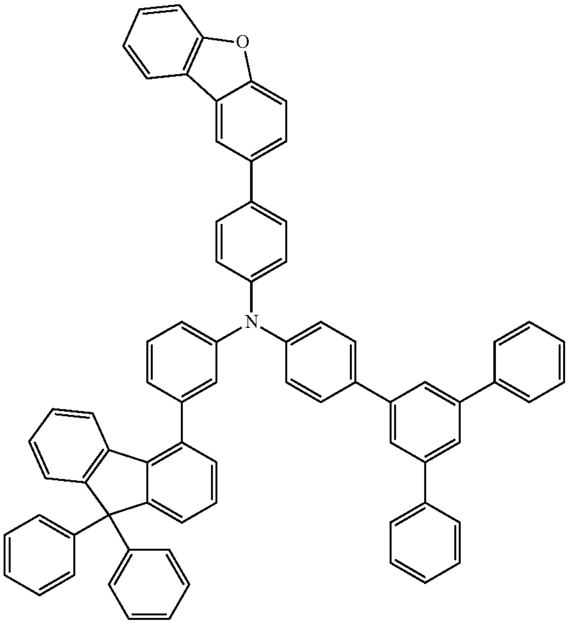

-continued
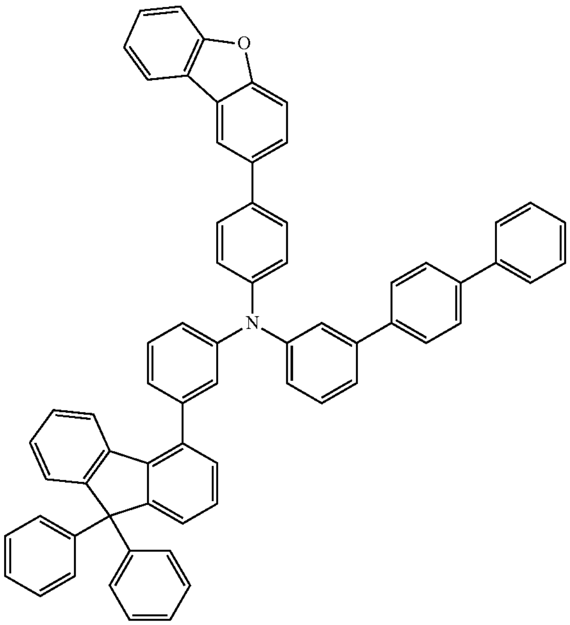
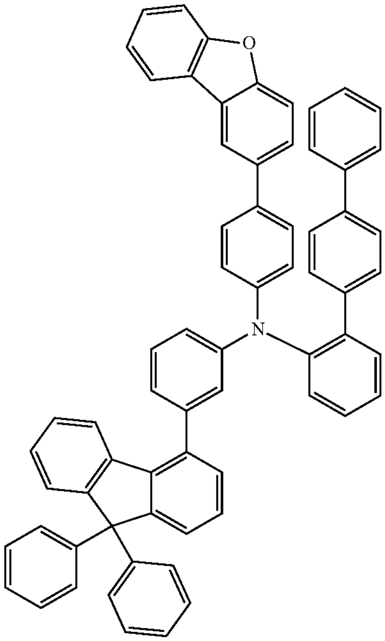
-continued
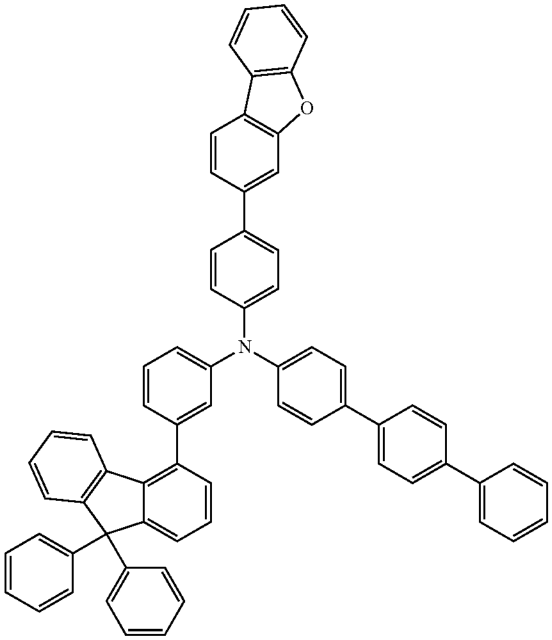
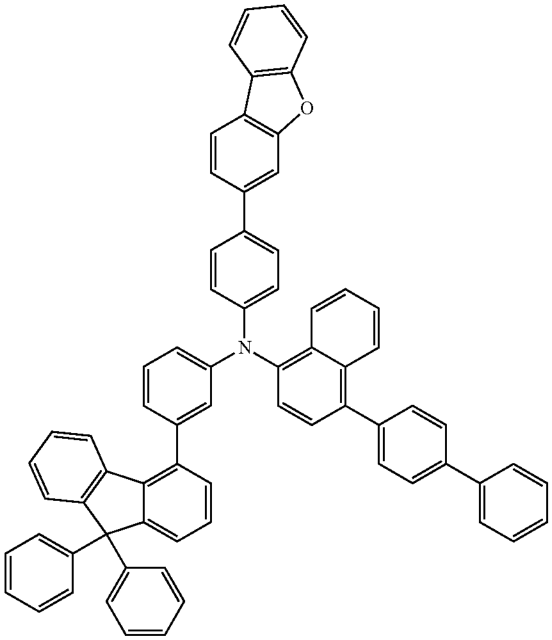

-continued
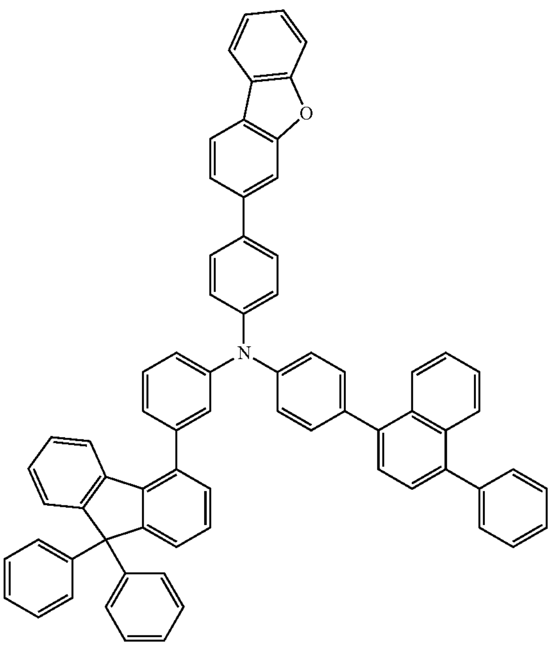
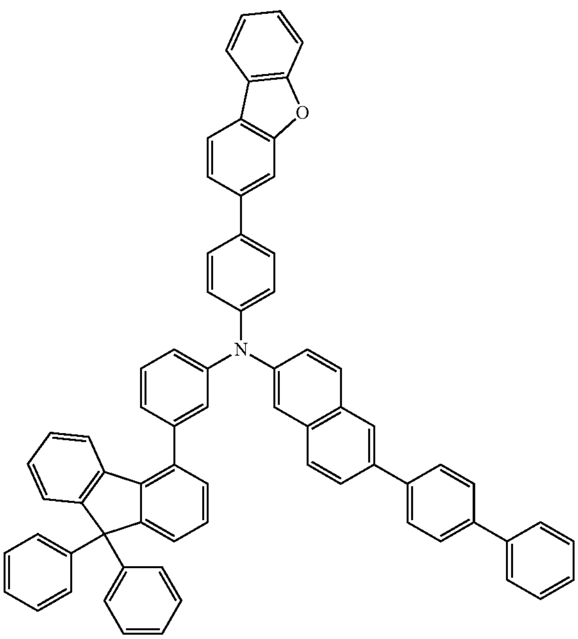
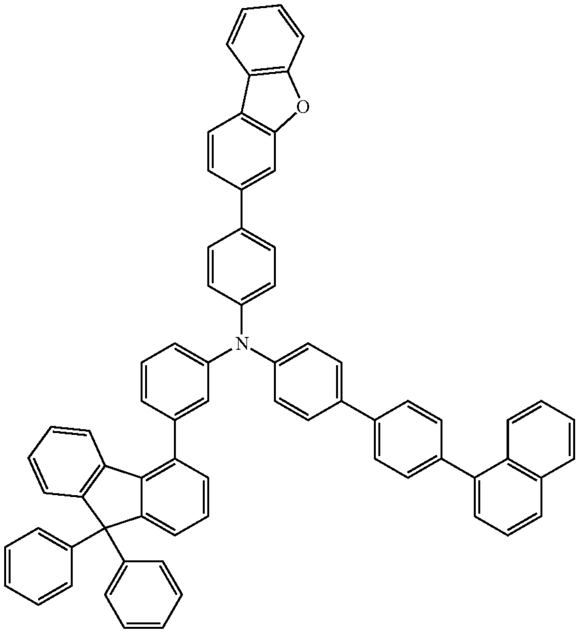
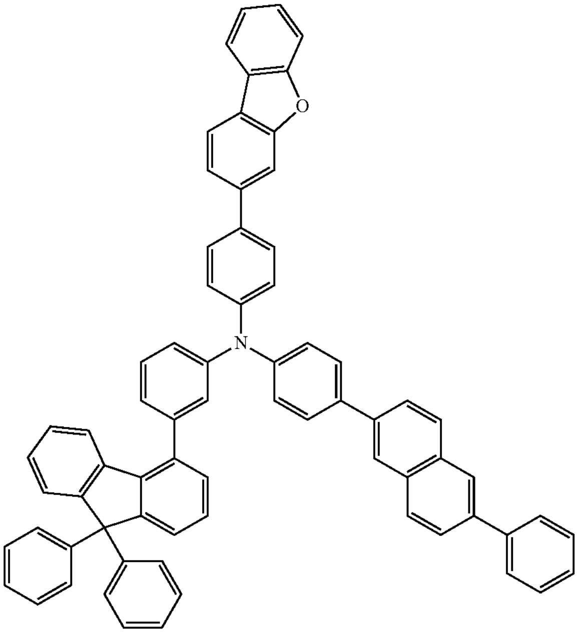
-continued

-continued
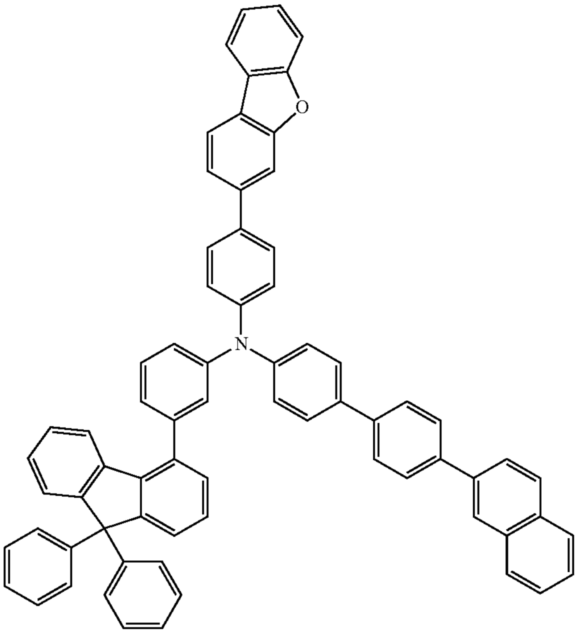
-continued
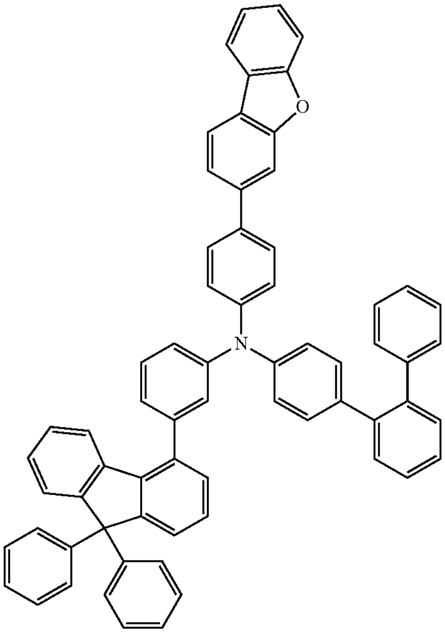
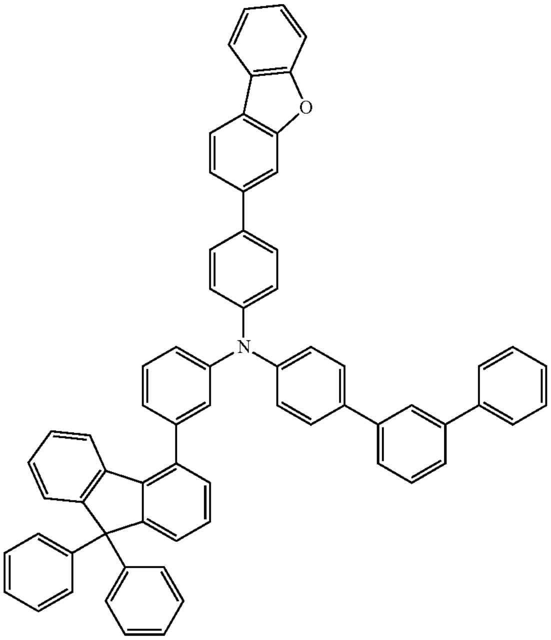
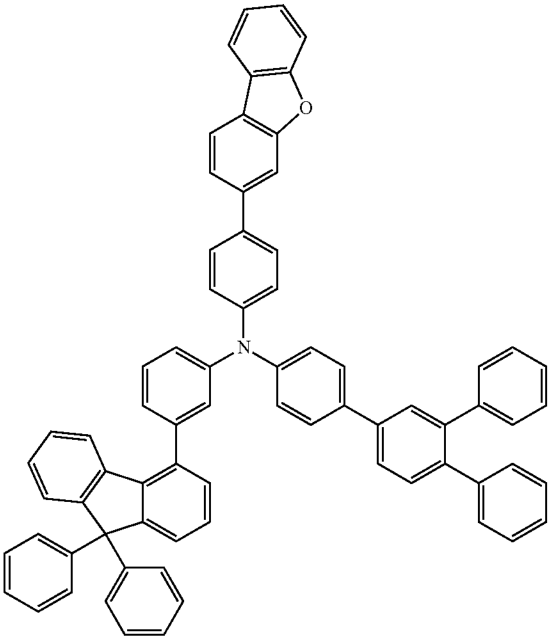

-continued
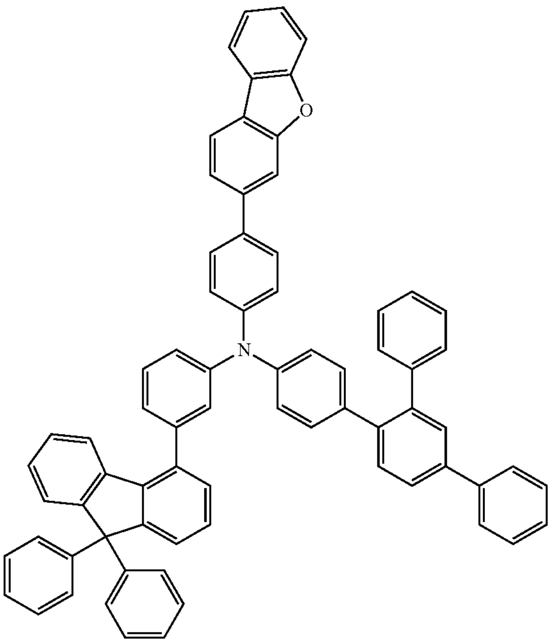
-continued
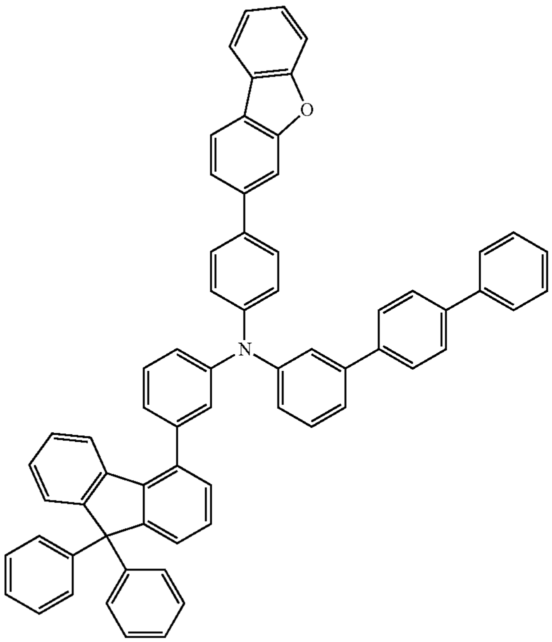
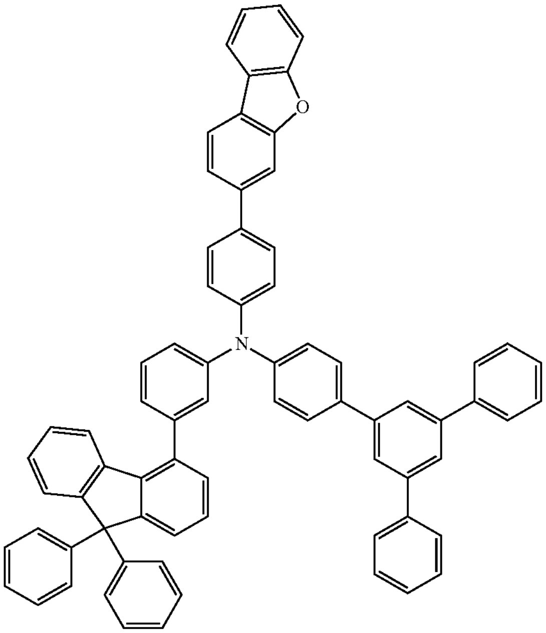
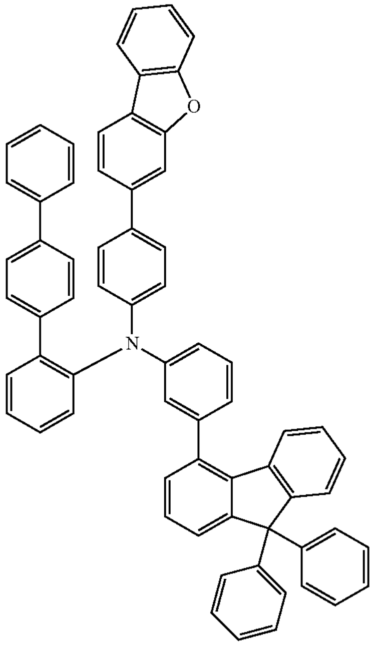

-continued
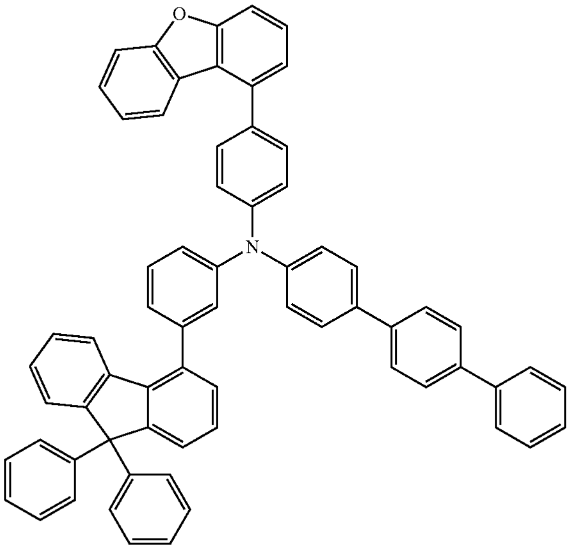
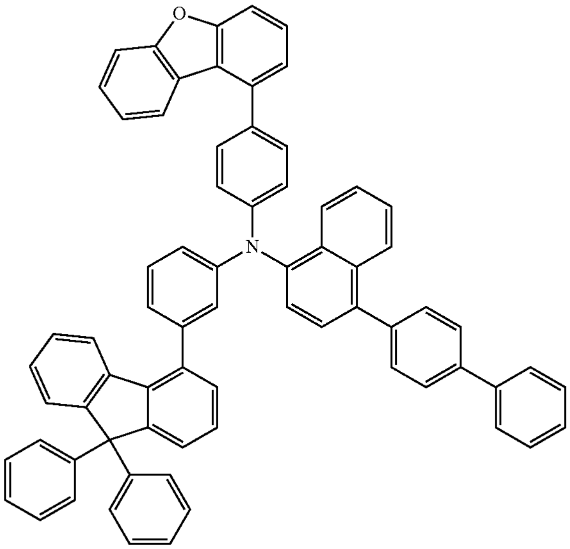
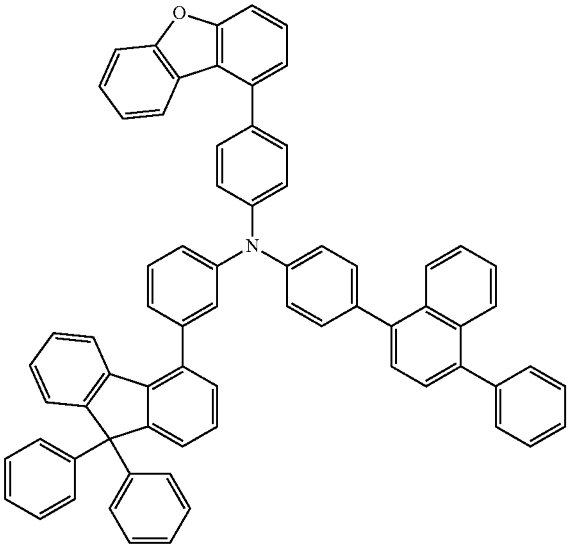
-continued
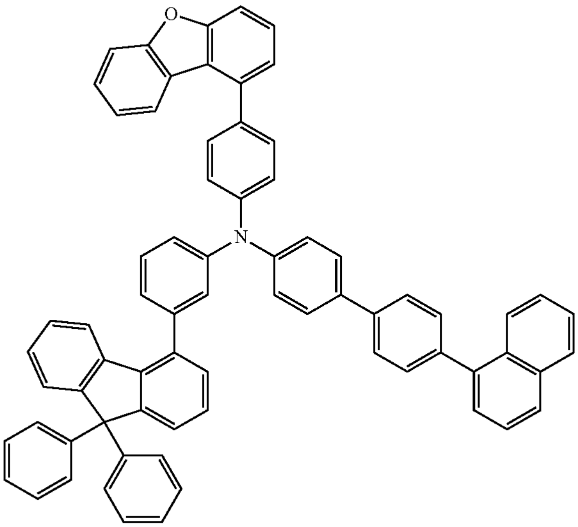
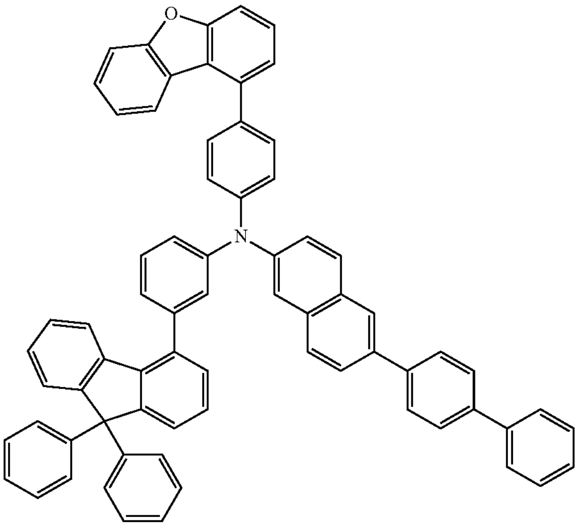
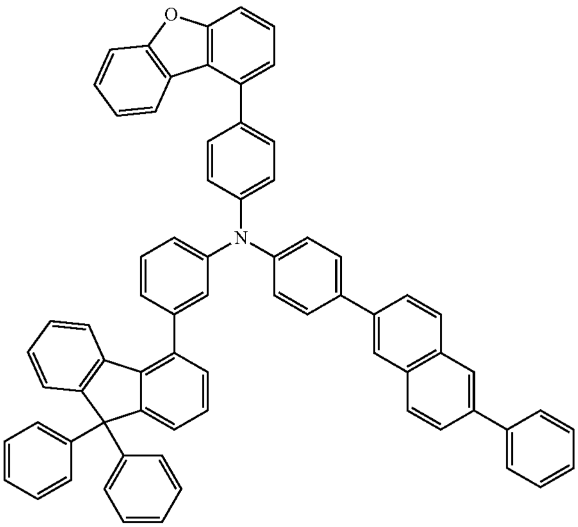

-continued
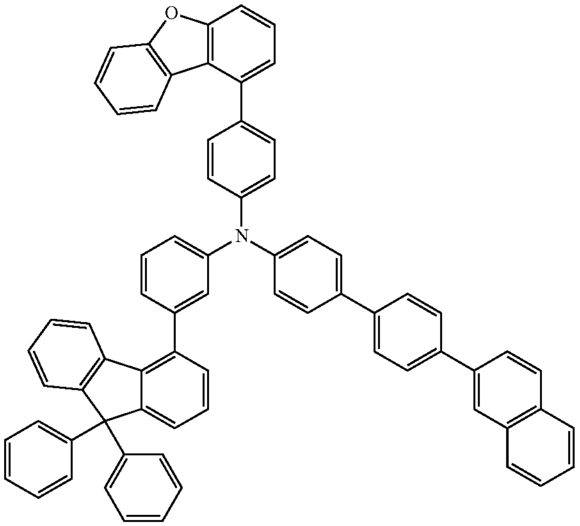
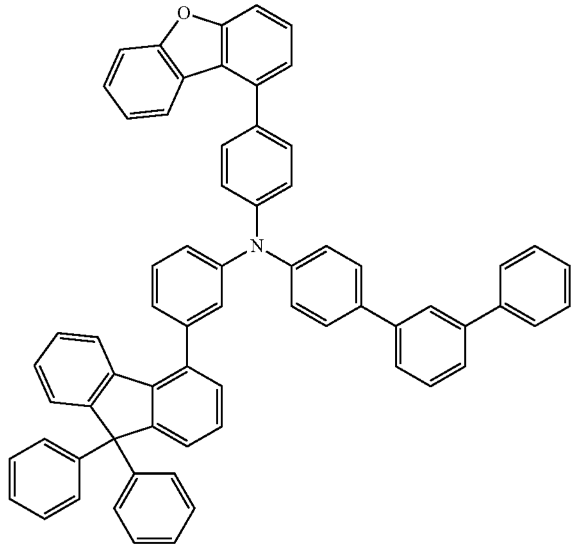
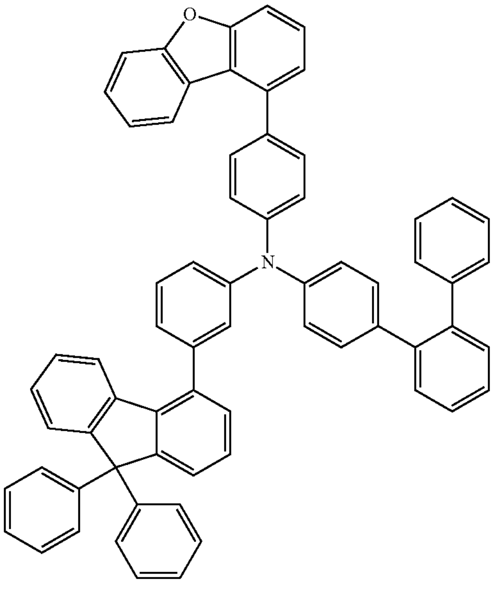
-continued
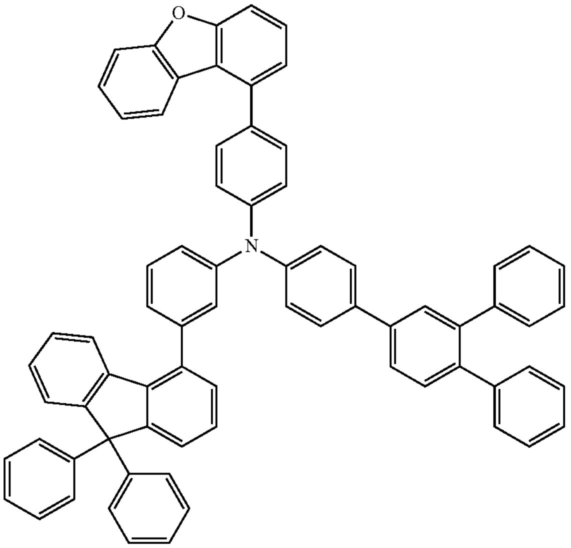
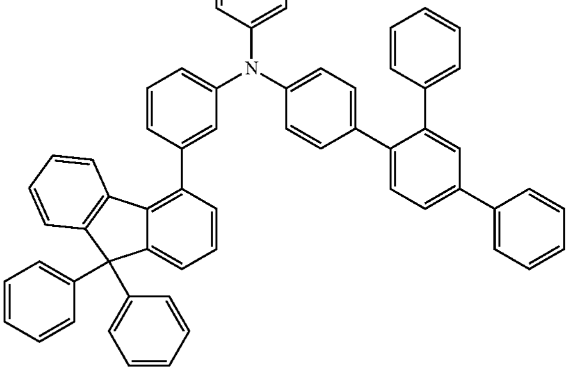
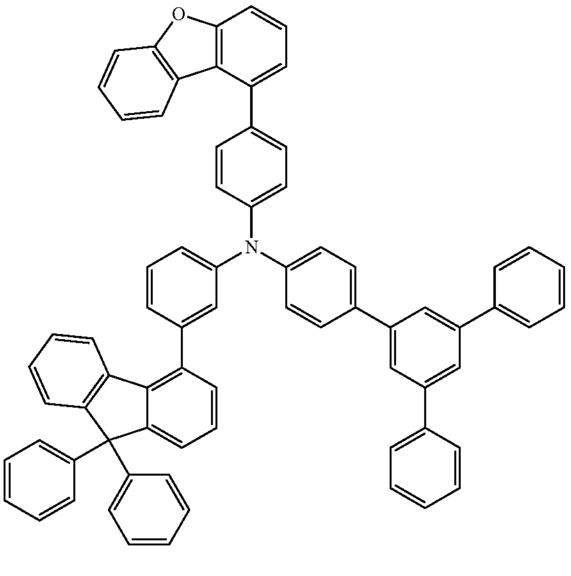

-continued
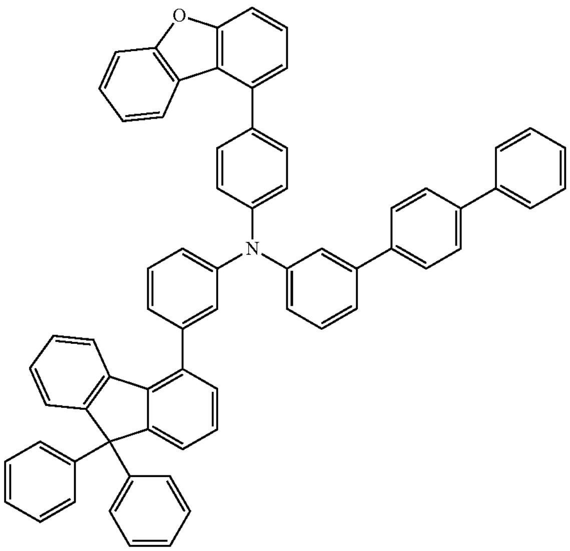
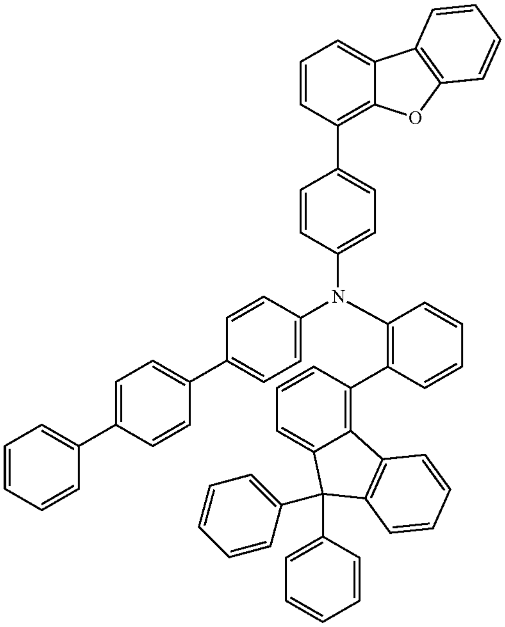
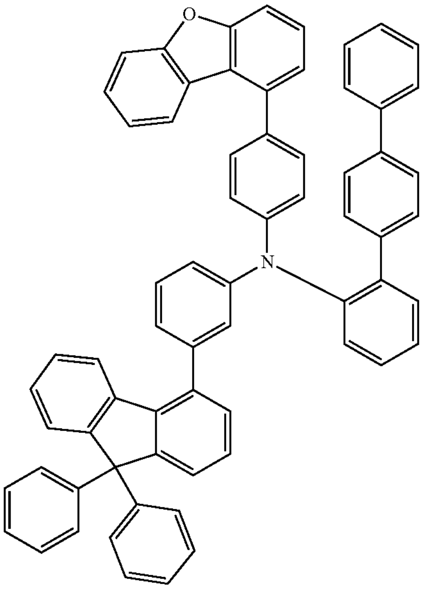 [SMILES: c1ccc(-c2ccc(-c3ccccc3N(c3ccc(-c4cccc5oc6ccccc6c45)cc3)c3cccc(-c4cccc5c4-c4ccccc4C5(c4ccccc4)c4ccccc4)c3)cc2)cc1]
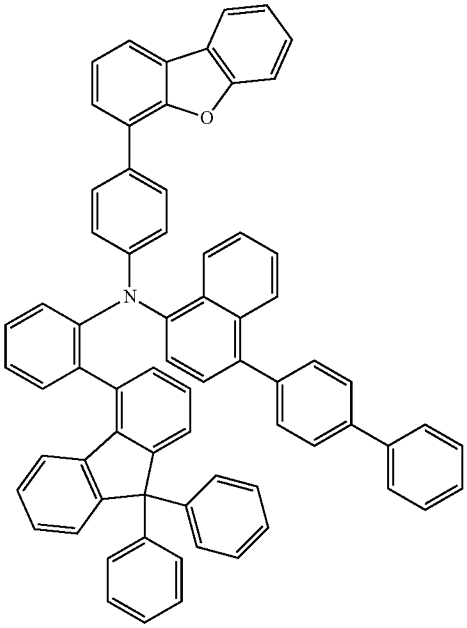

-continued
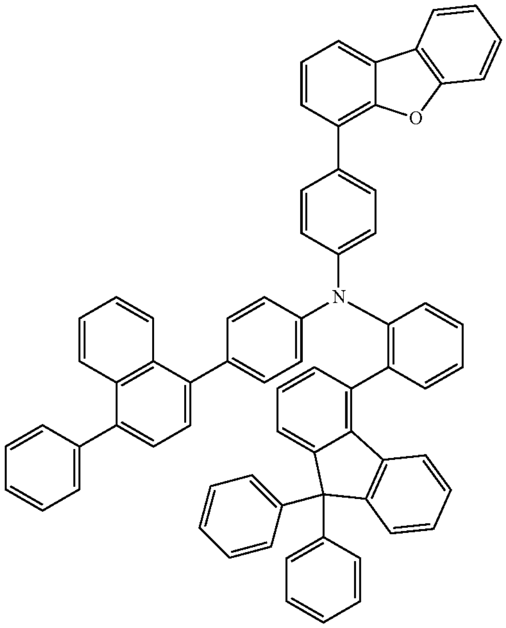
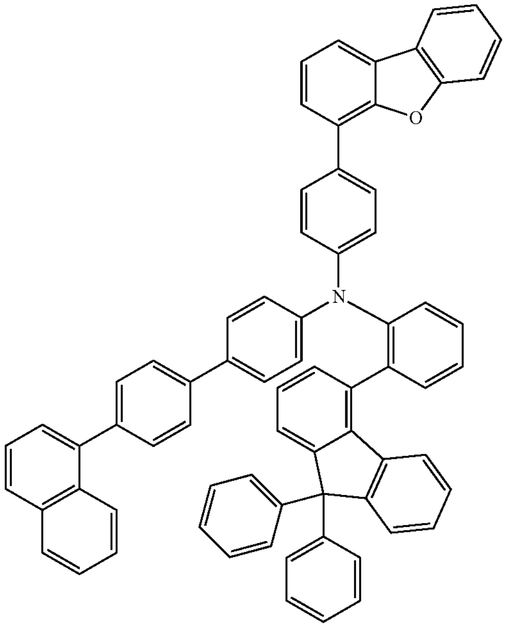
-continued
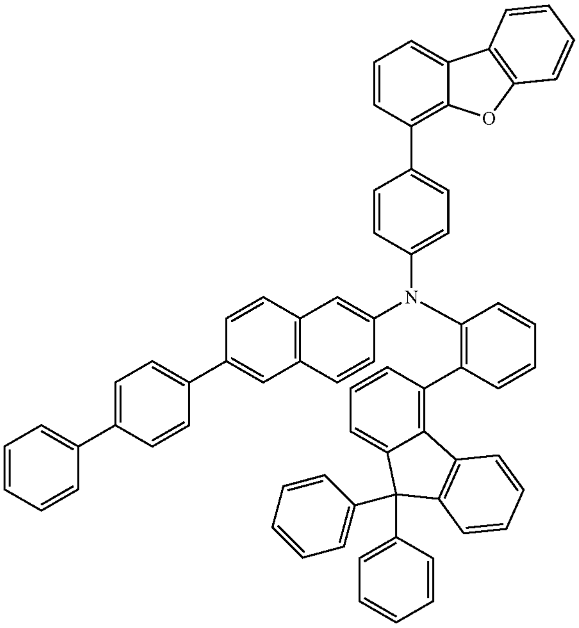
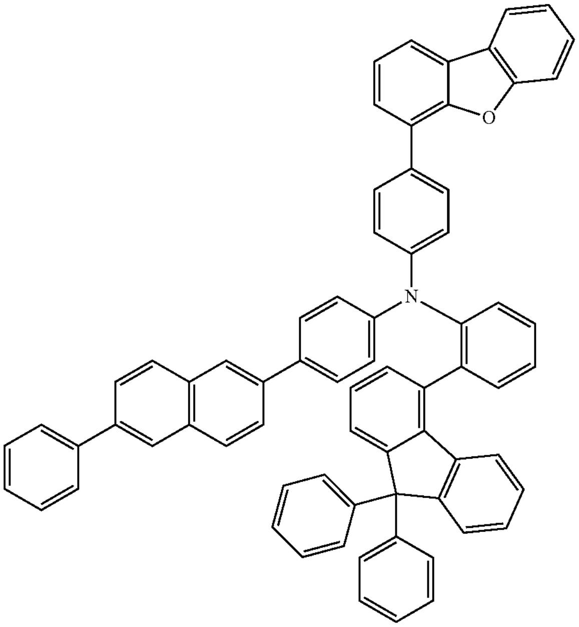

-continued
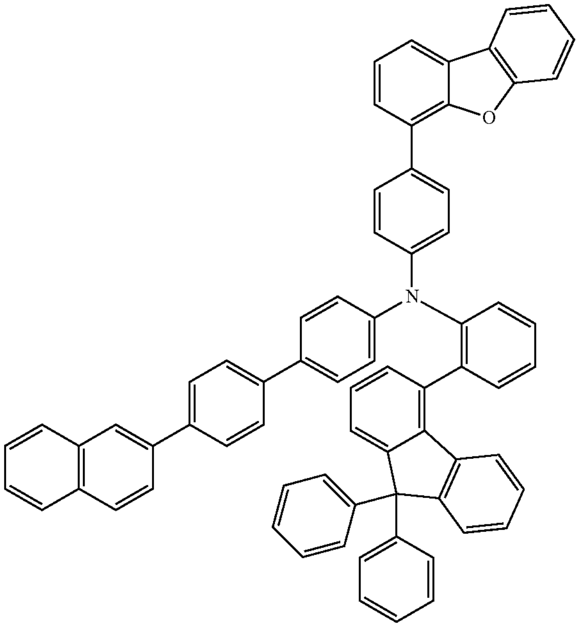
-continued
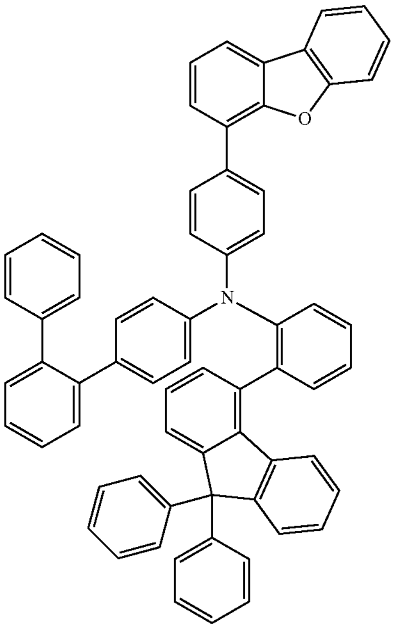
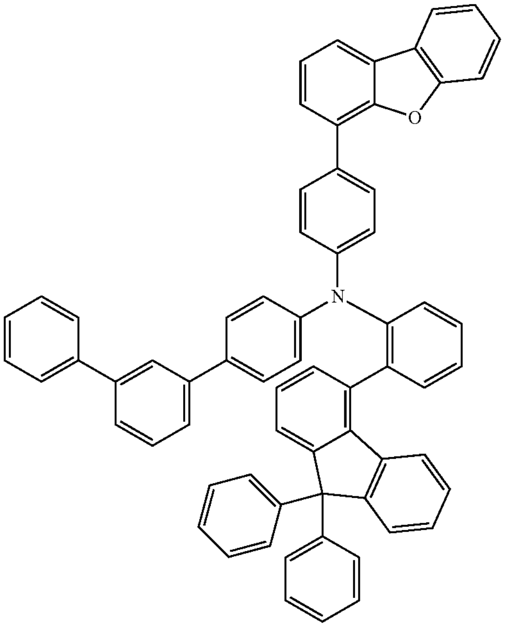
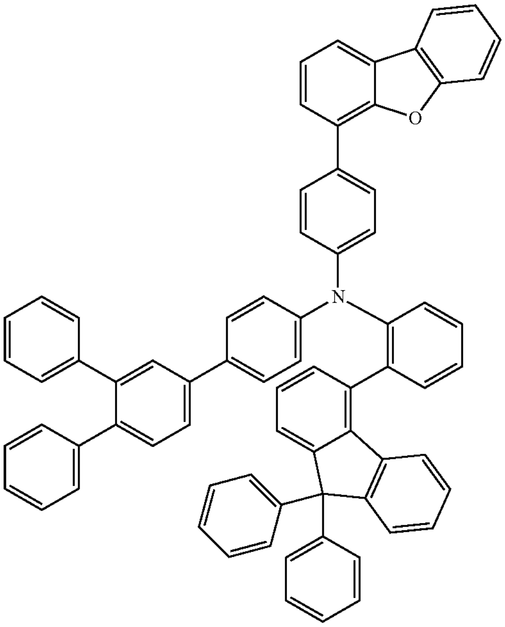

-continued
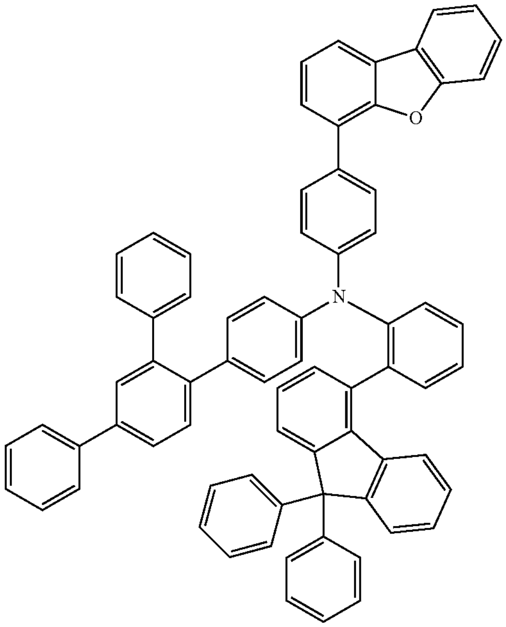
-continued
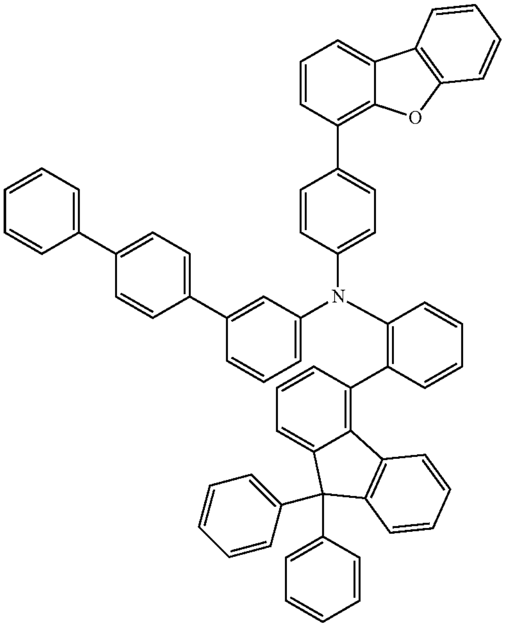
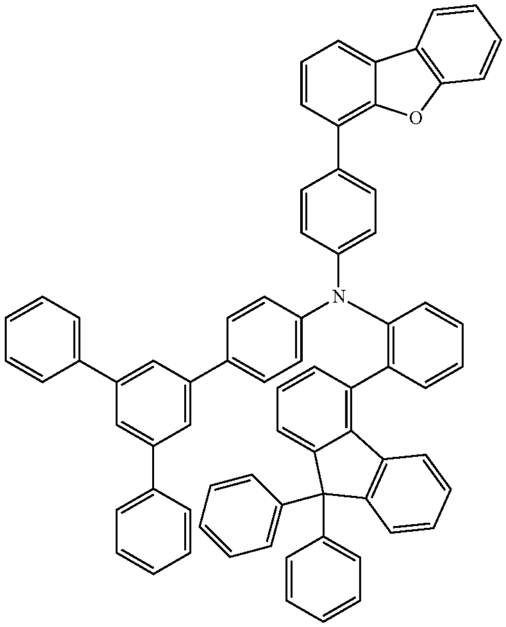
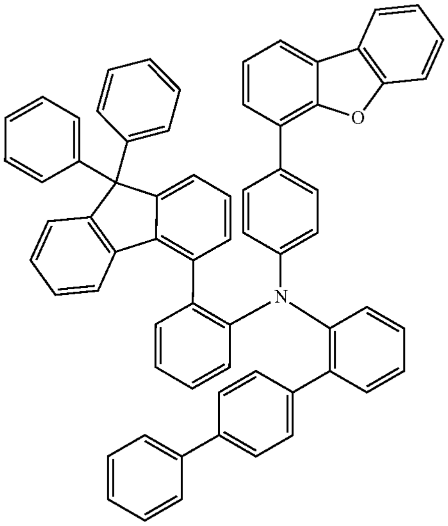

-continued
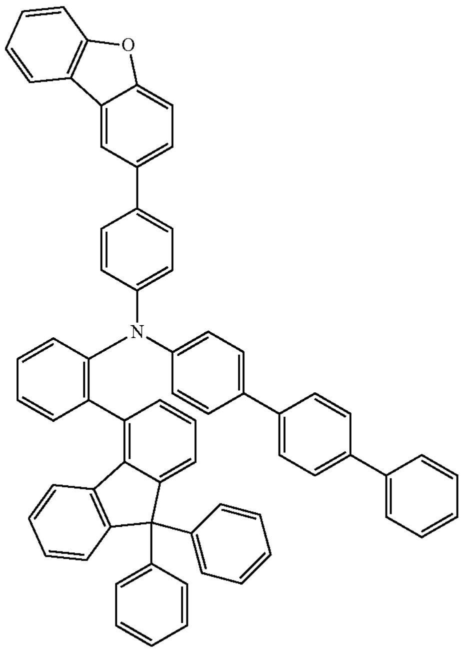
-continued
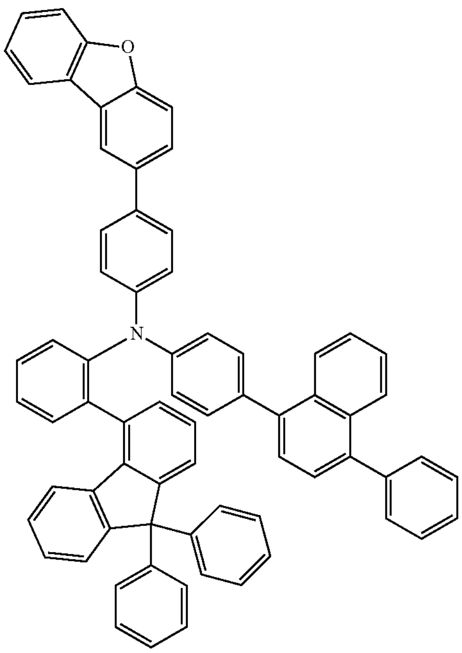
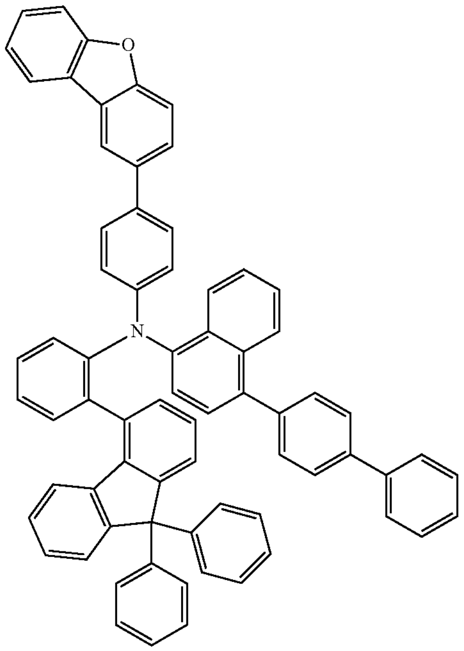
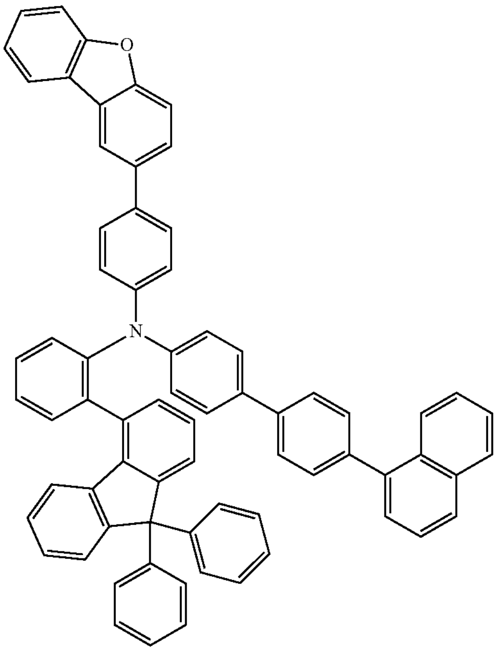

-continued
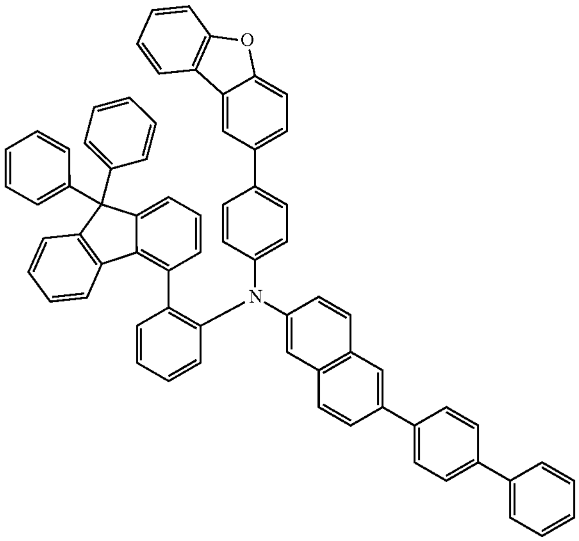
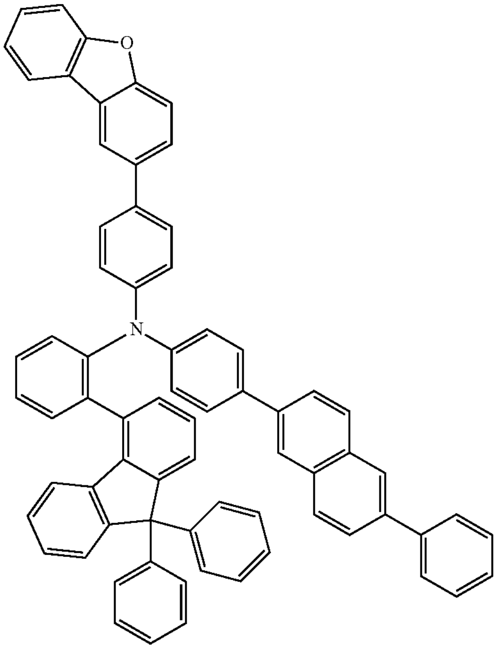 [SMILES: c1ccc(-c2ccc3cc(-c4ccc(N(c5ccc(-c6ccc7oc8ccccc8c7c6)cc5)c5ccccc5-c5cccc6c5-c5ccccc5C6(c5ccccc5)c5ccccc5)cc4)ccc3c2)cc1]
-continued
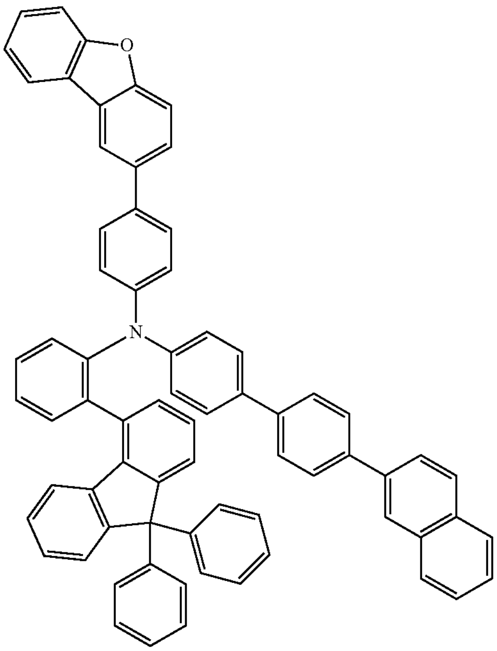
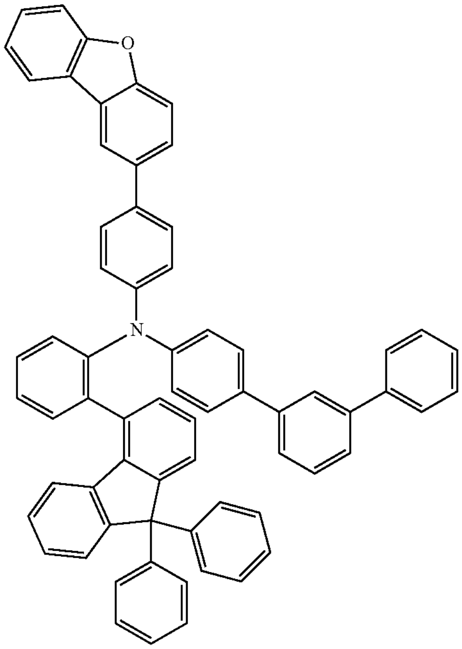

-continued
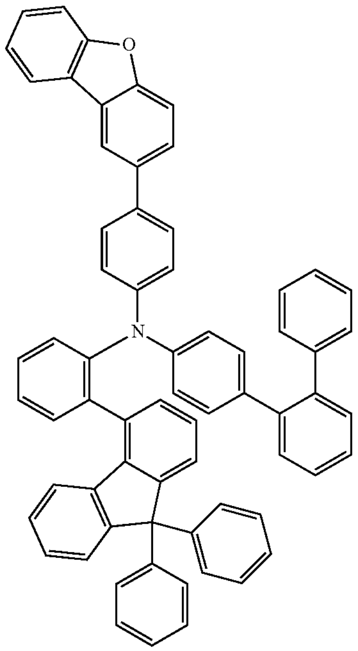
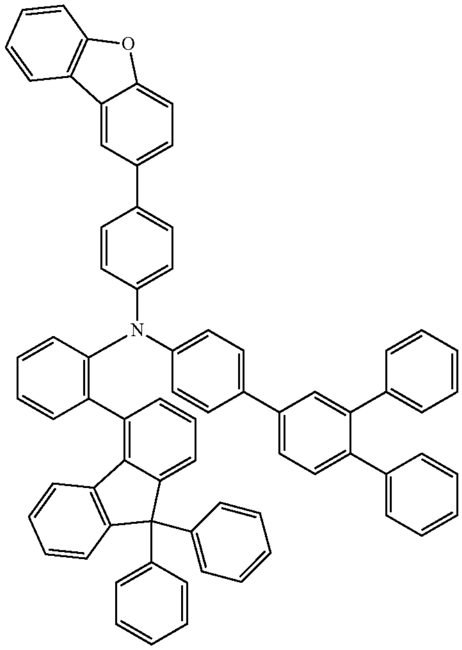
-continued
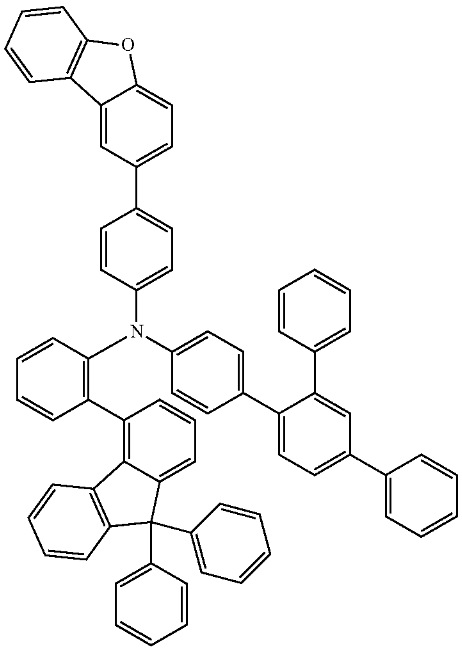
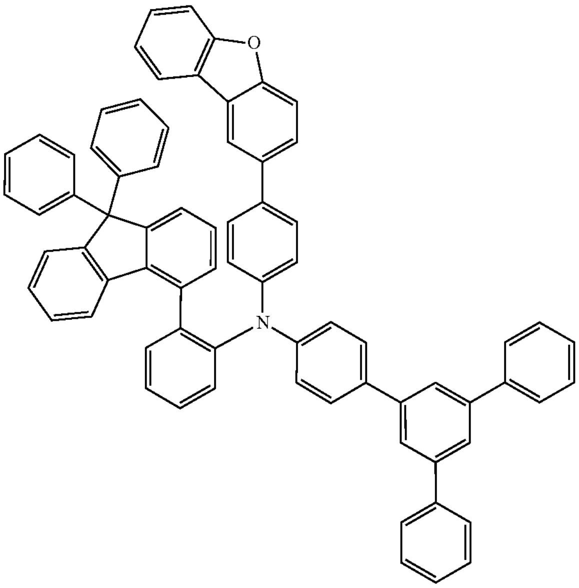

-continued
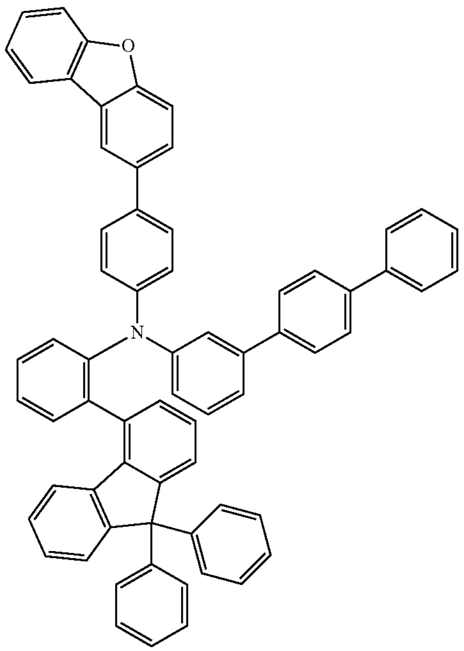
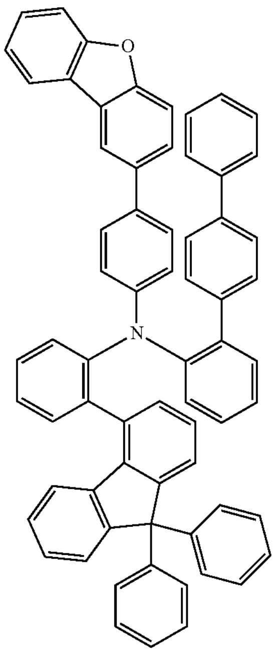
-continued
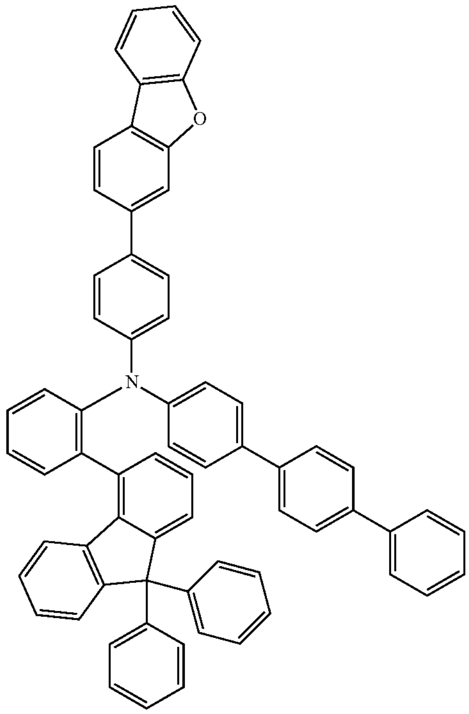
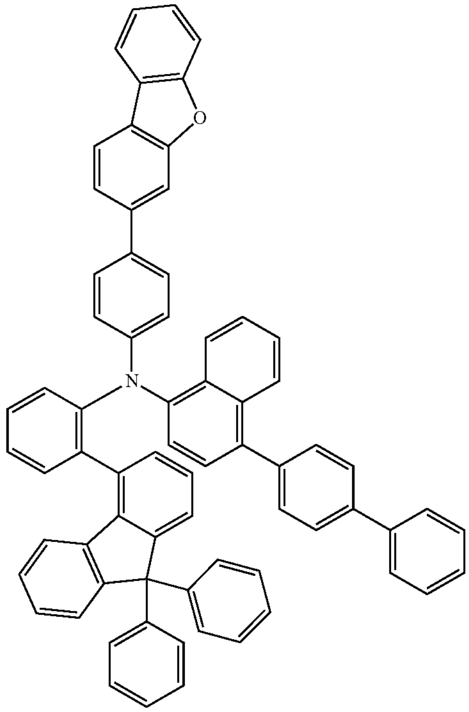

-continued
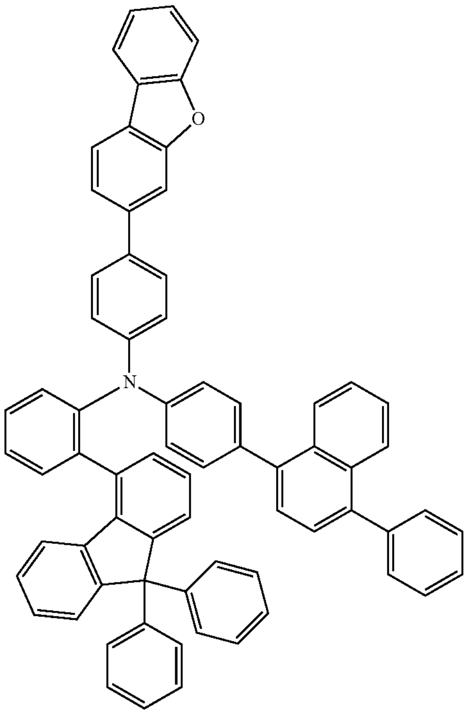
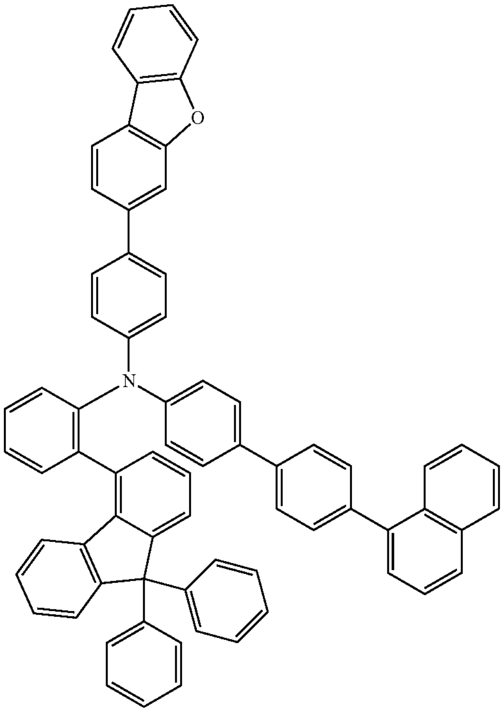
-continued
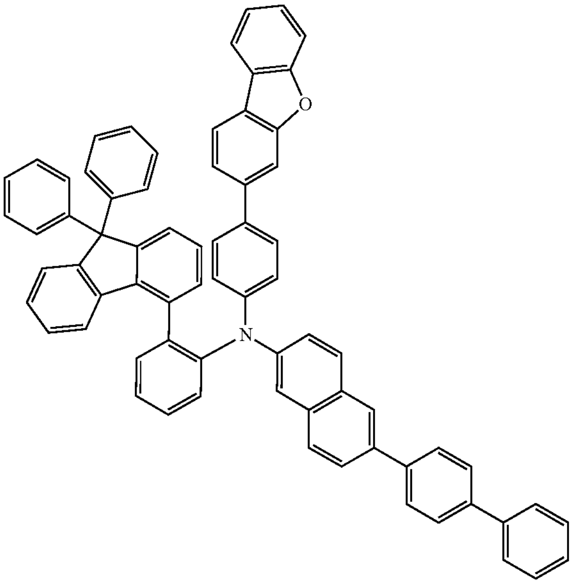
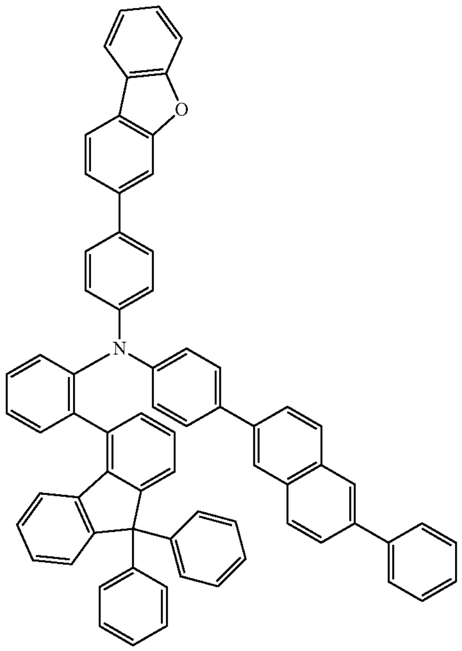

-continued
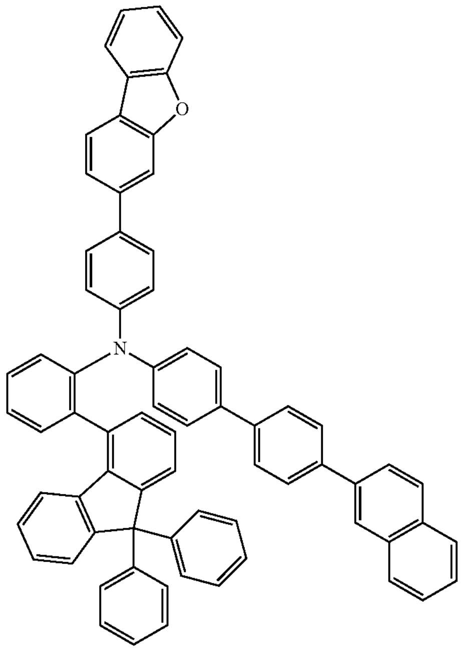
-continued
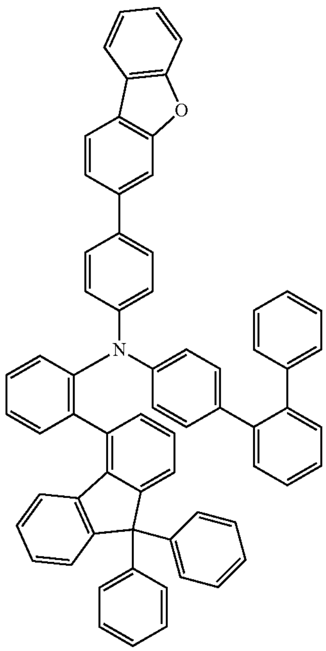
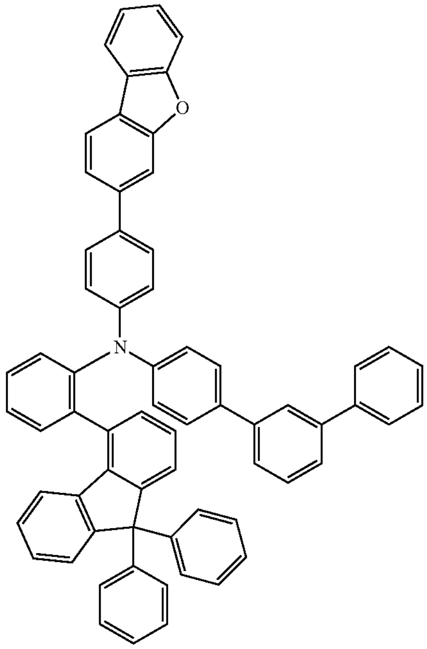
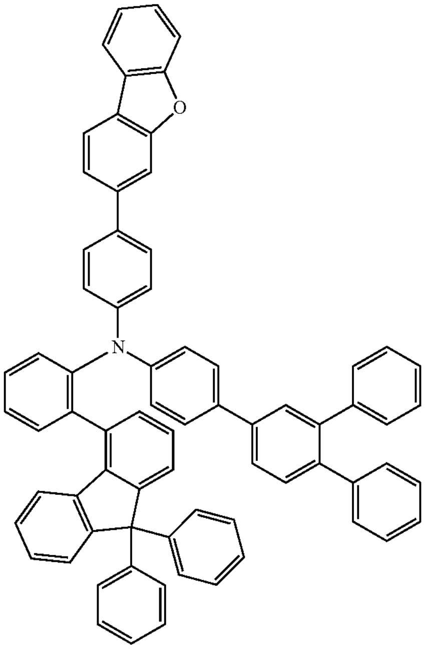

-continued
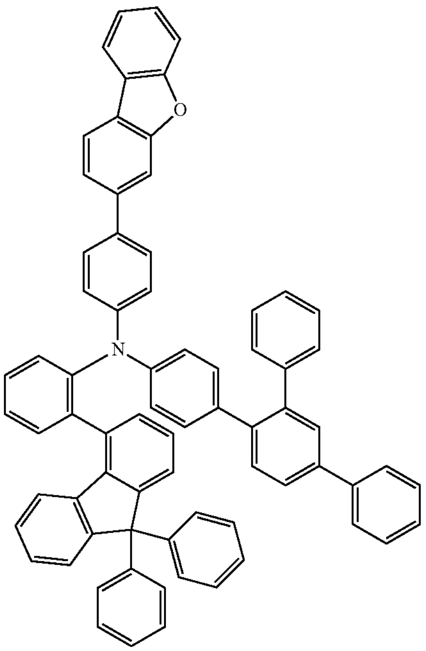
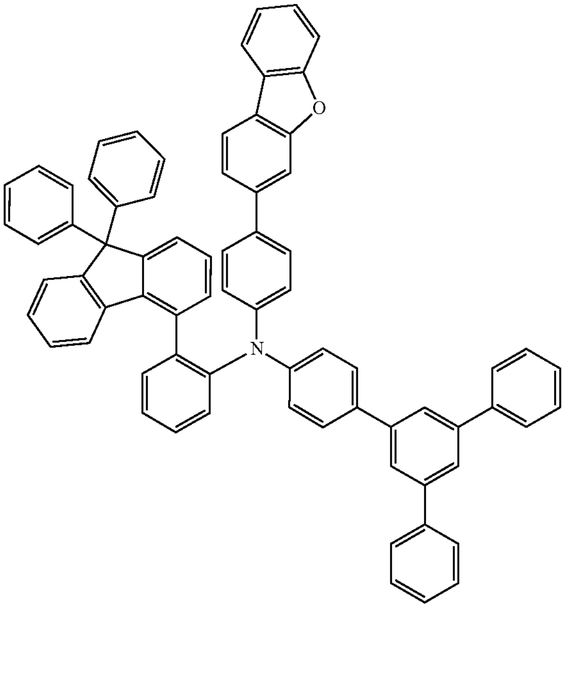
-continued
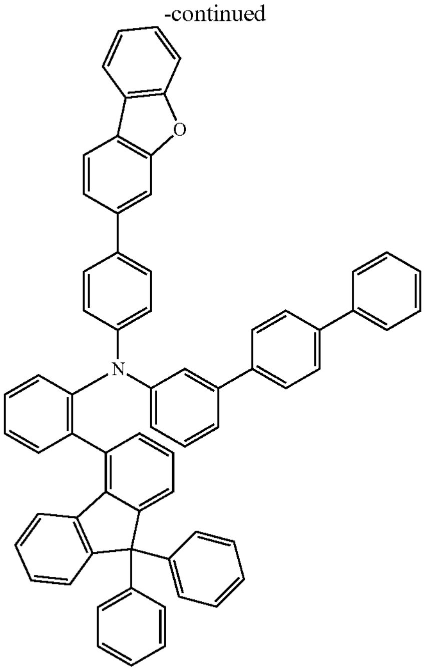
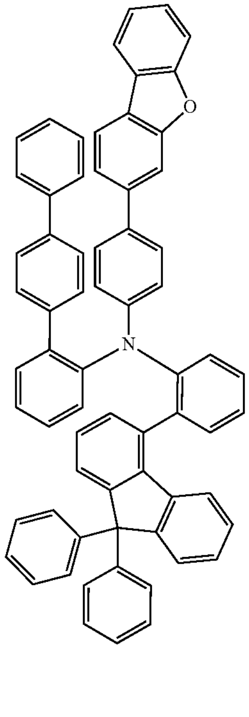

-continued
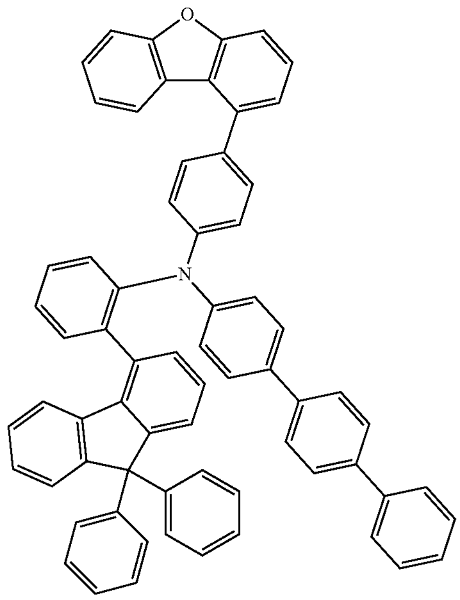
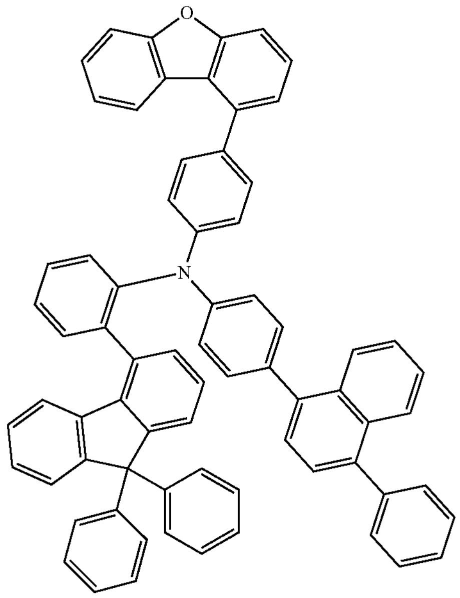
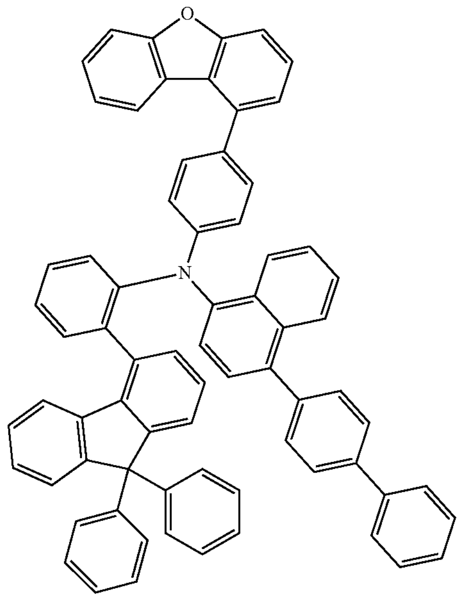
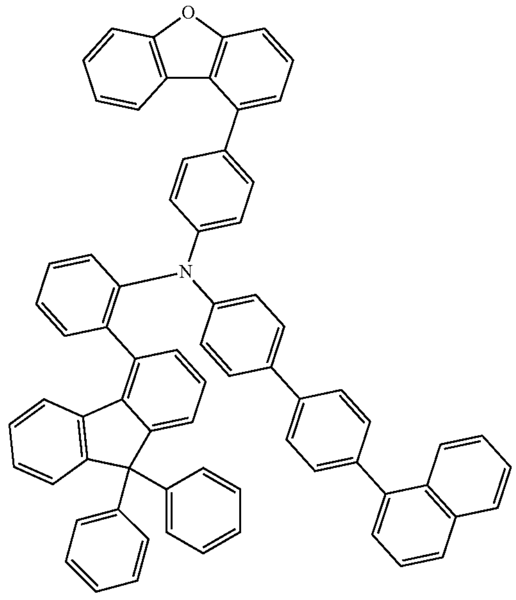
-continued

-continued
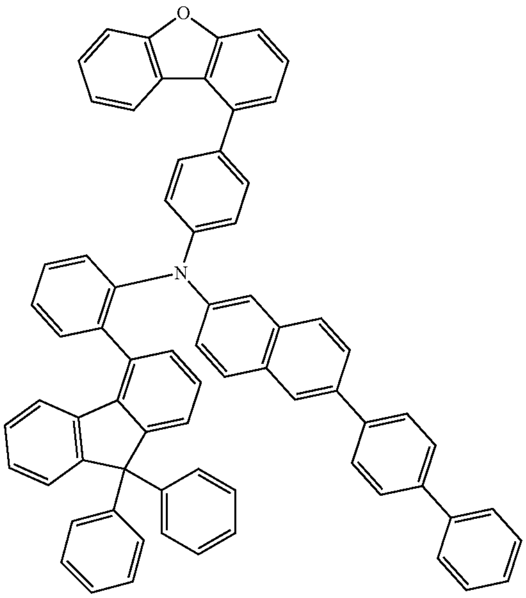
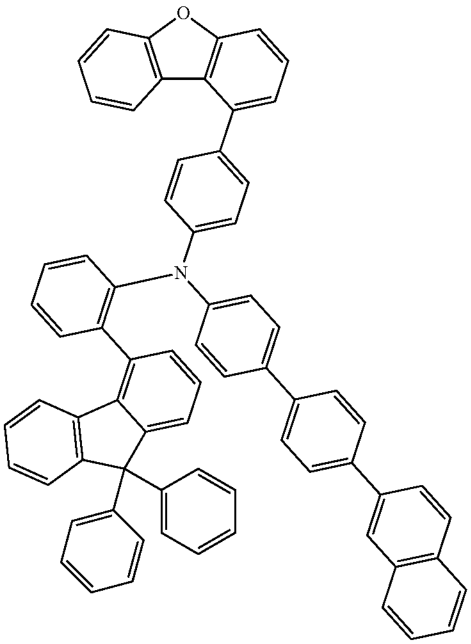
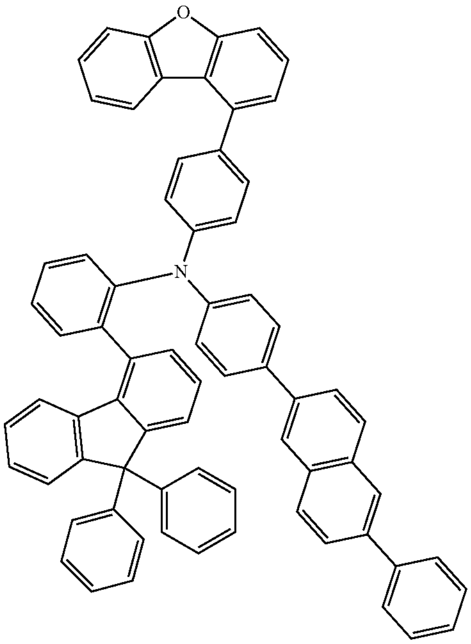
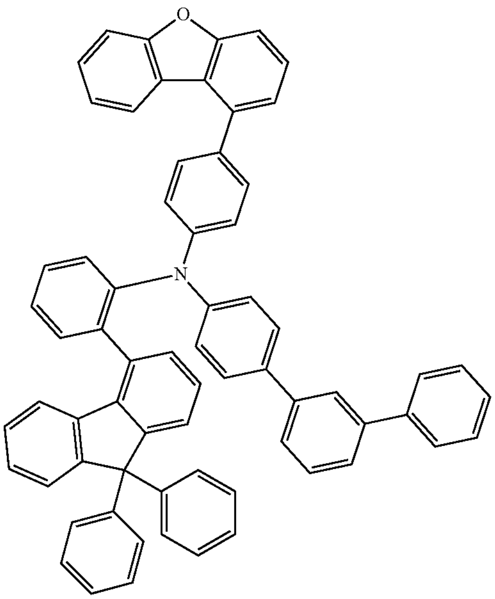

-continued
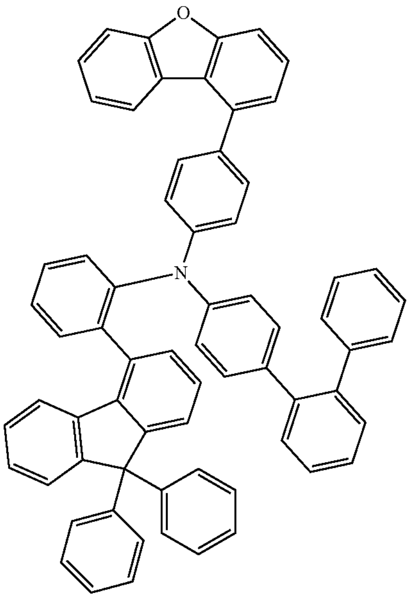
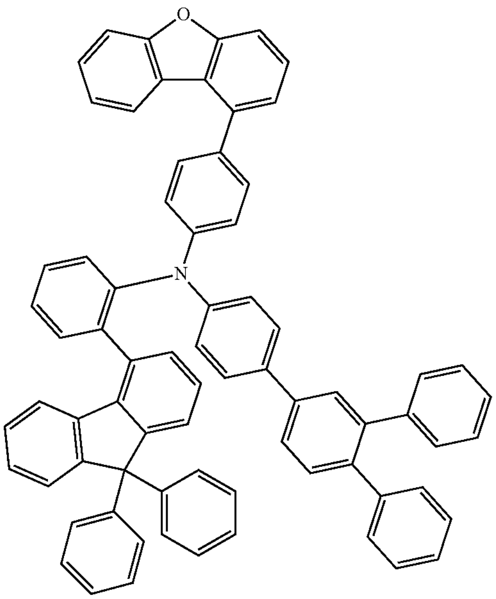
-continued
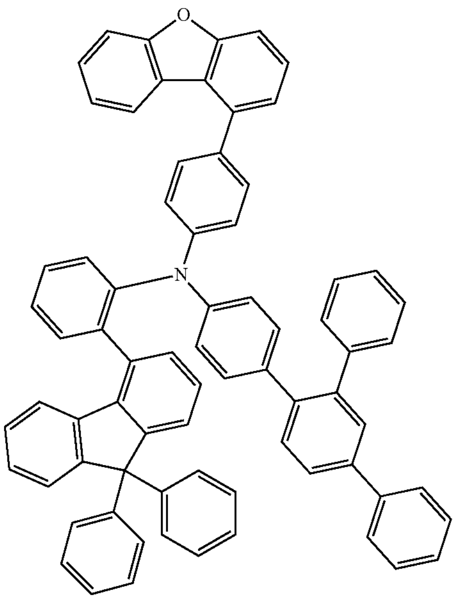
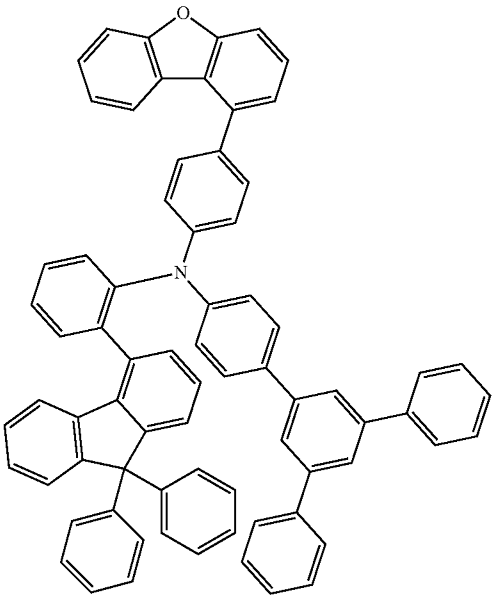

-continued
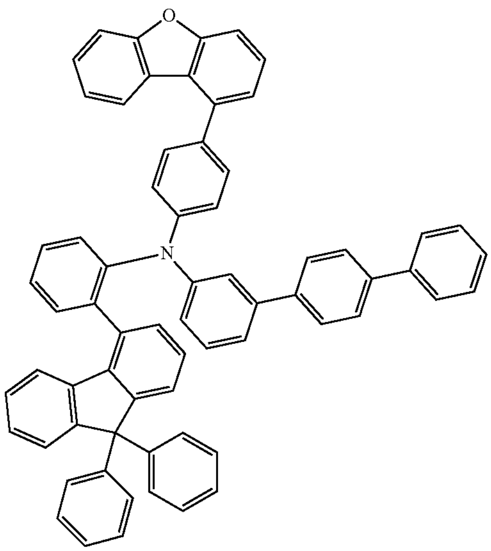
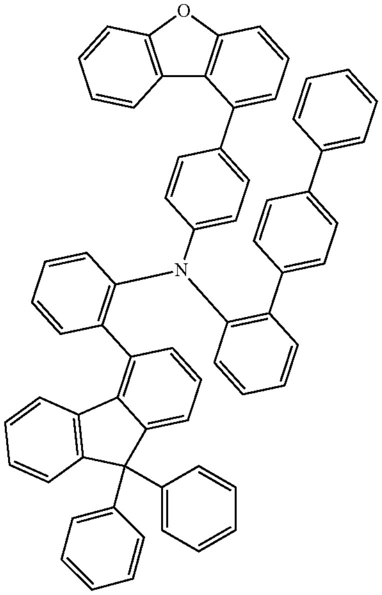
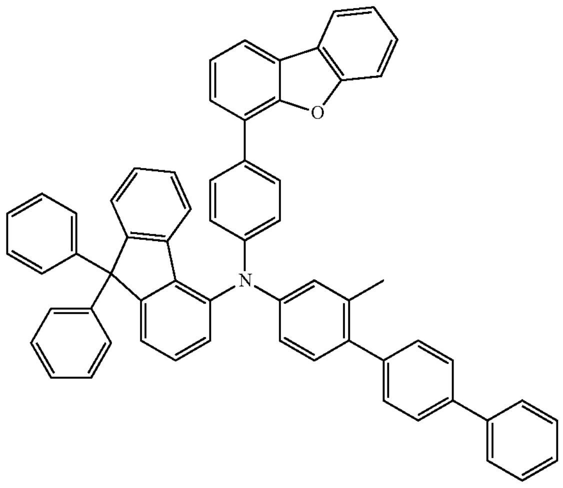
-continued
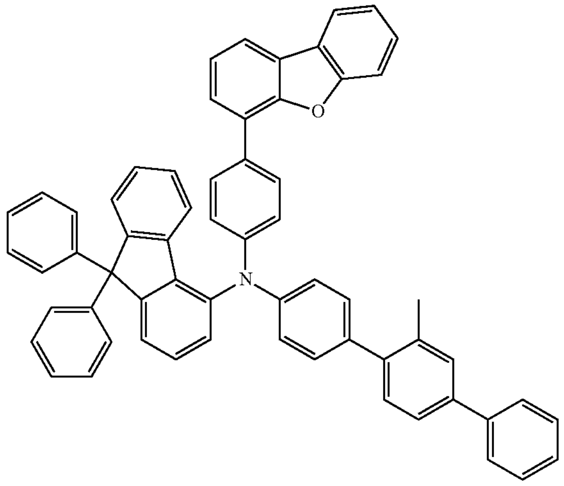
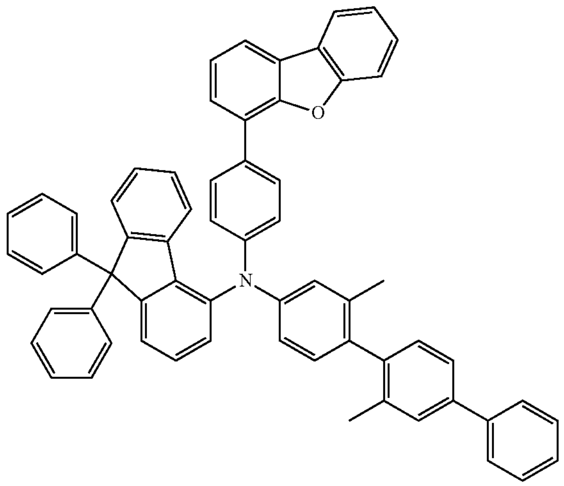
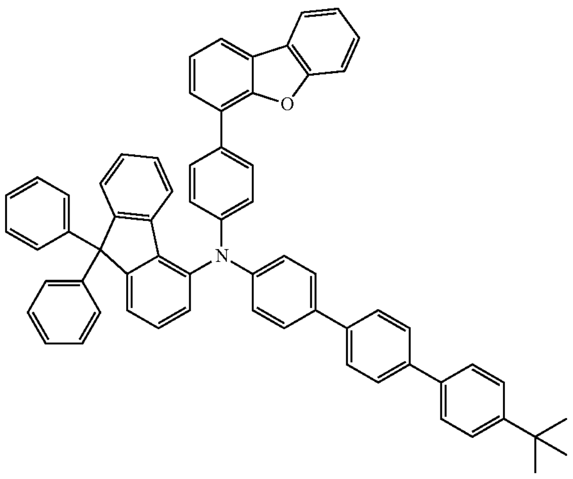 [SMILES: c1ccc(C2(c3ccccc3)c3ccccc3-c3c(N(c4ccc(-c5ccc(-c6ccc7ccccc7c6)cc5)cc4)c4ccc(-c5cccc6c5oc5ccccc56)cc4)cccc32)cc1]

-continued
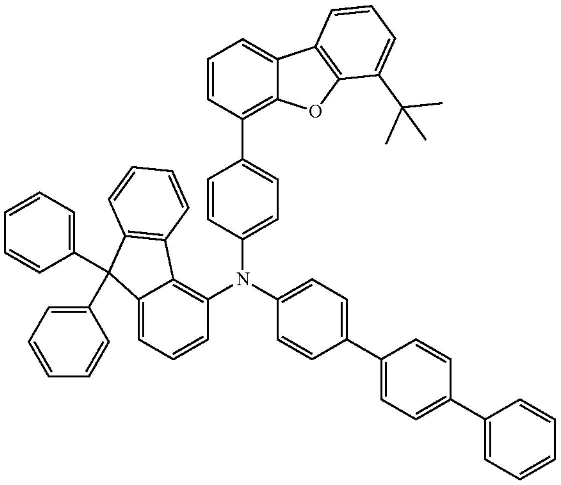
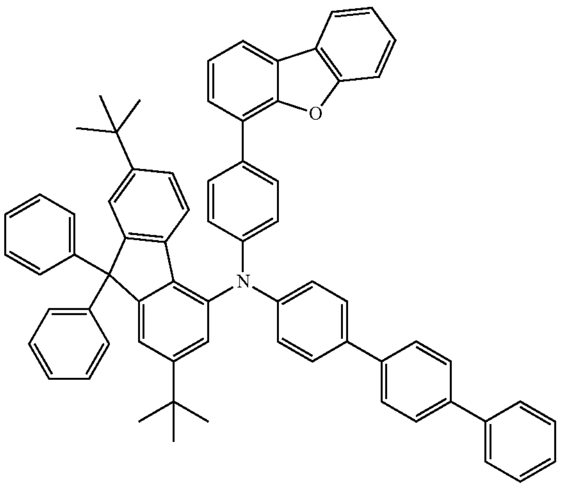
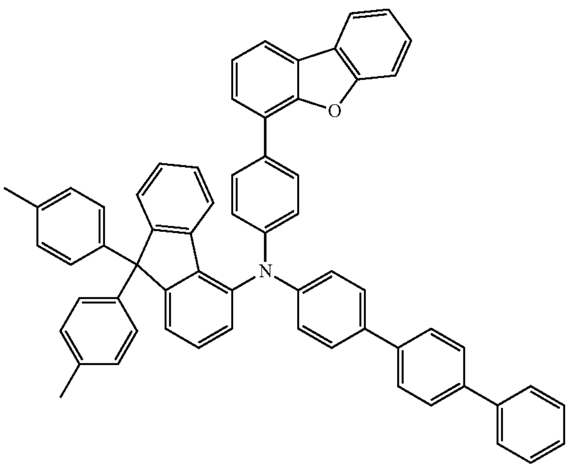
-continued
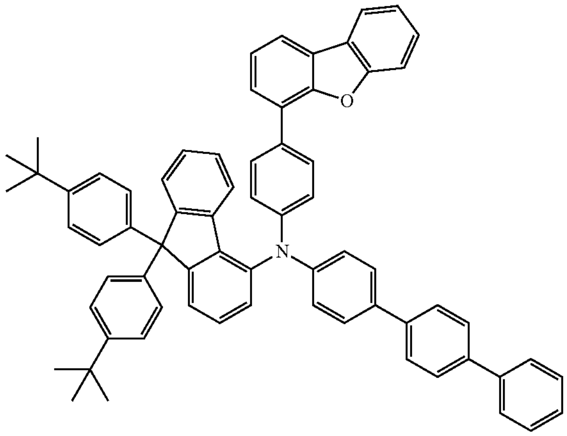
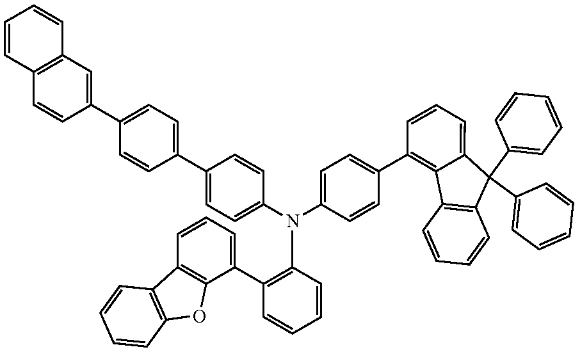
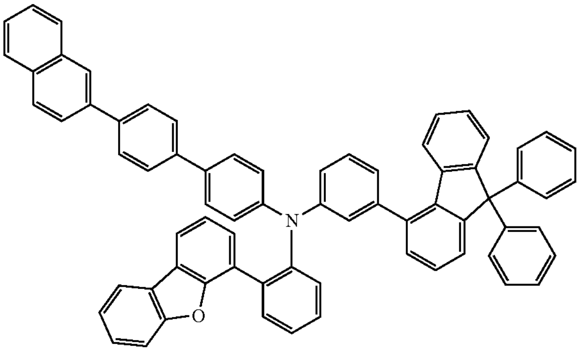
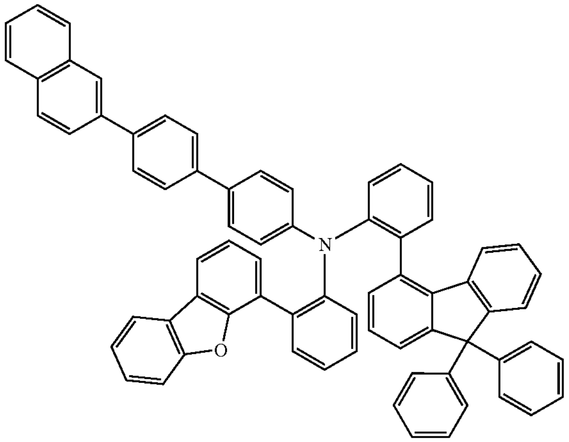

-continued
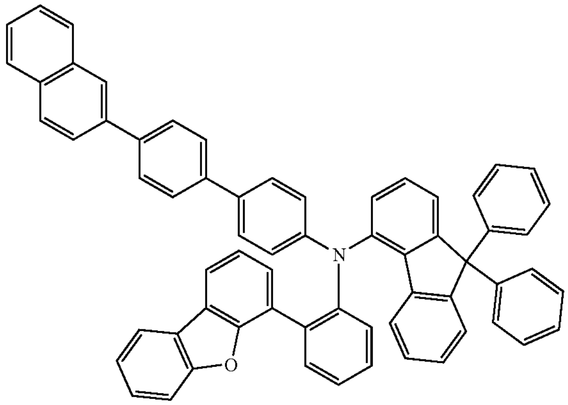
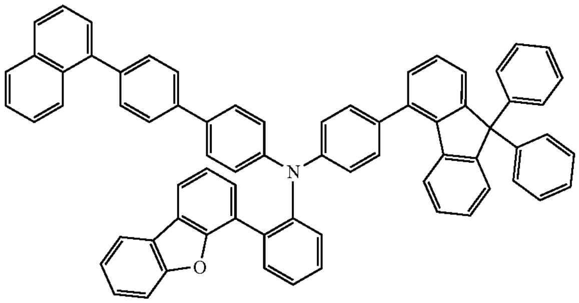
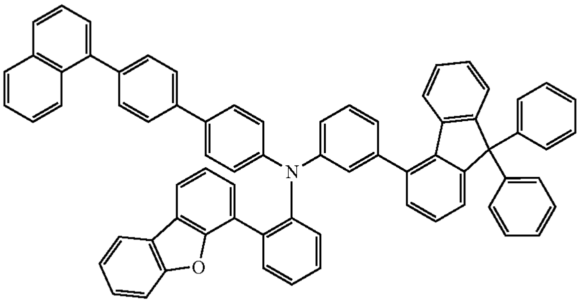
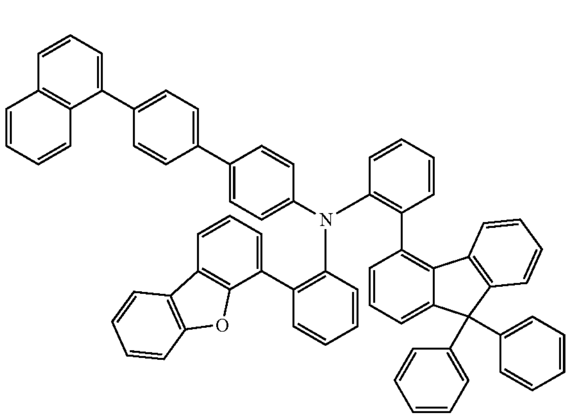
-continued
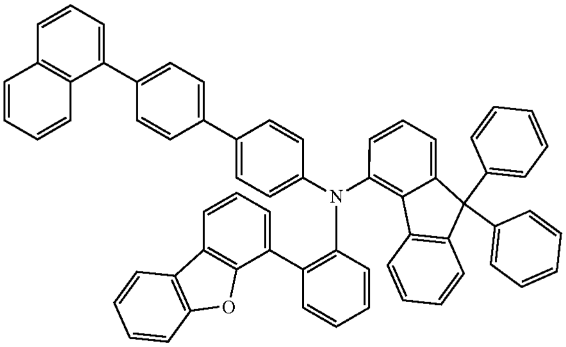
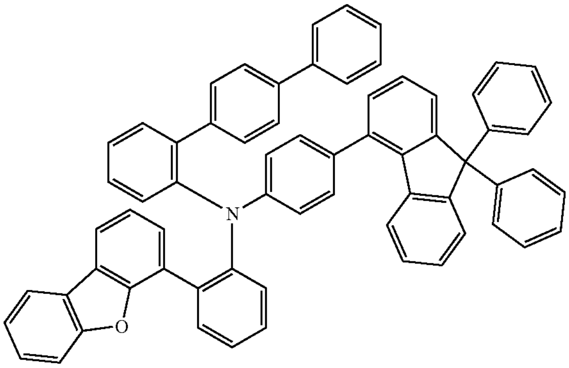
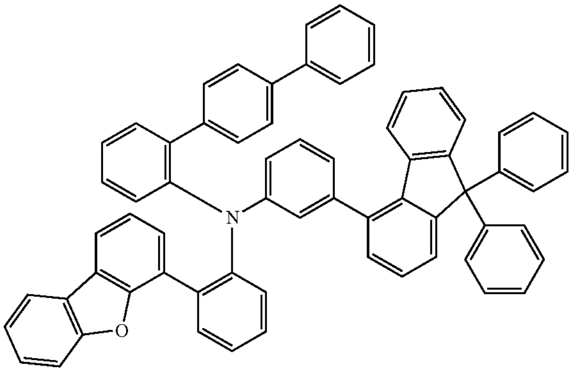
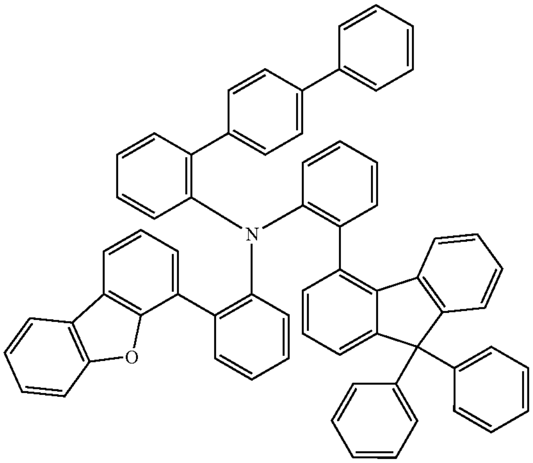

-continued
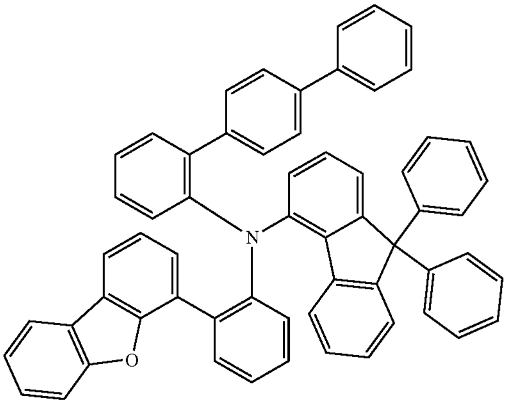
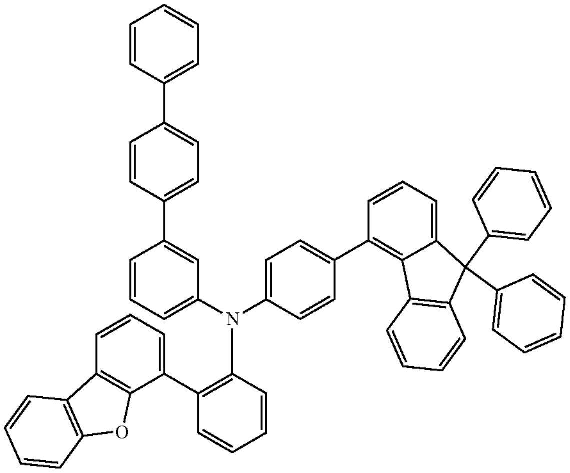
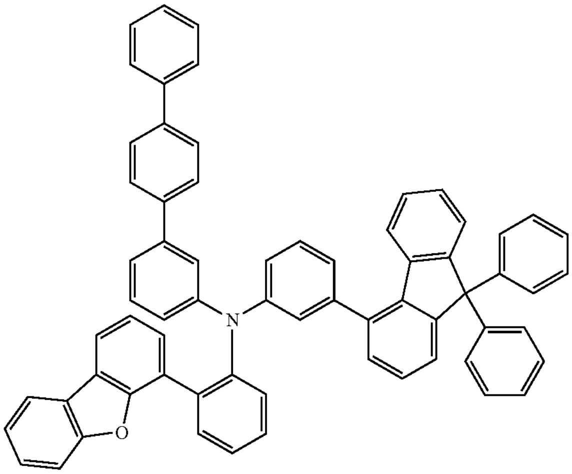
-continued
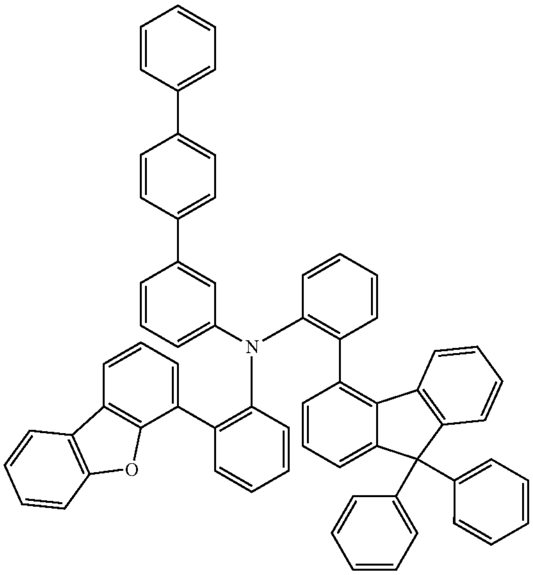
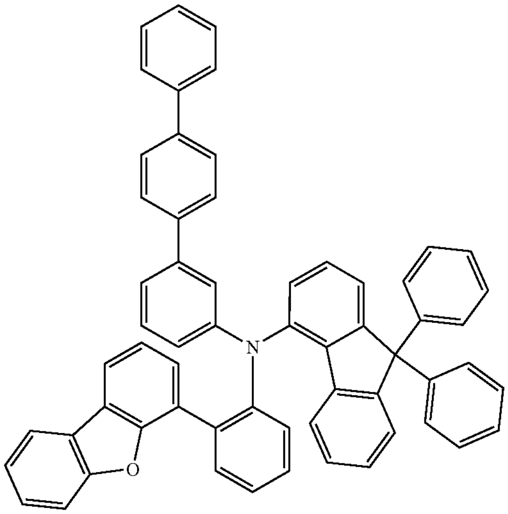
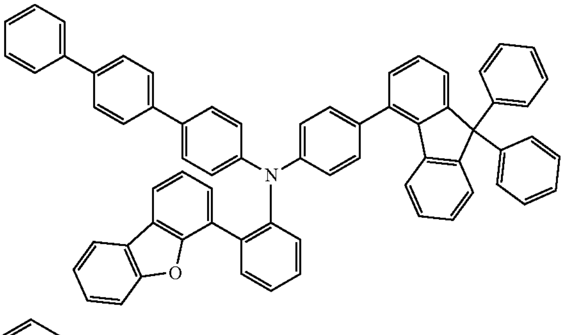
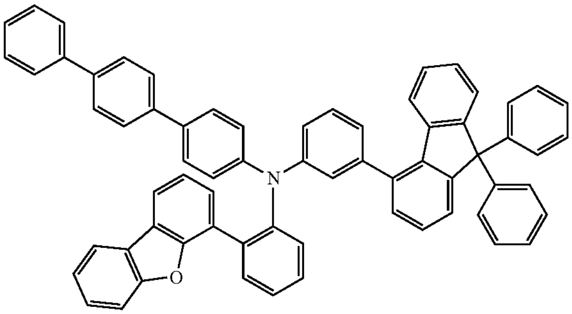

-continued
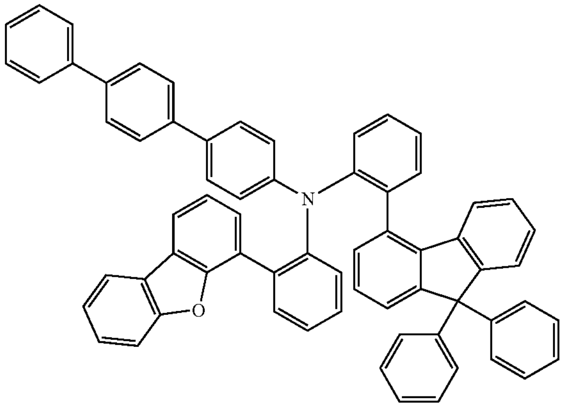
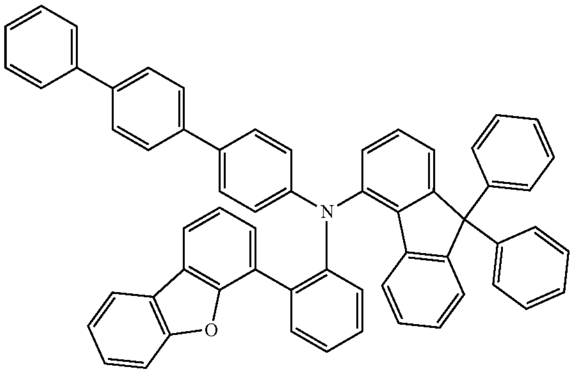
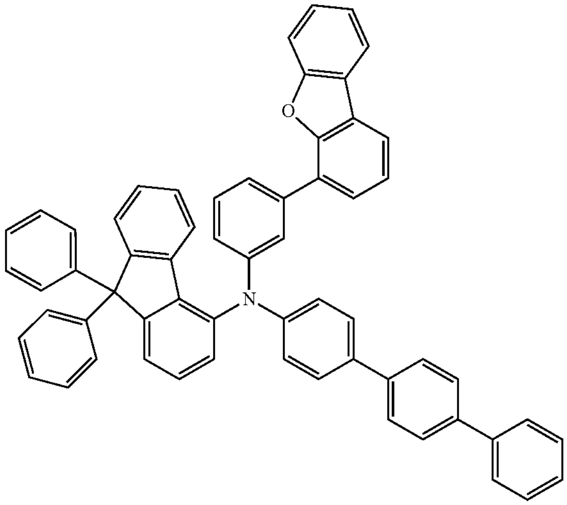
-continued
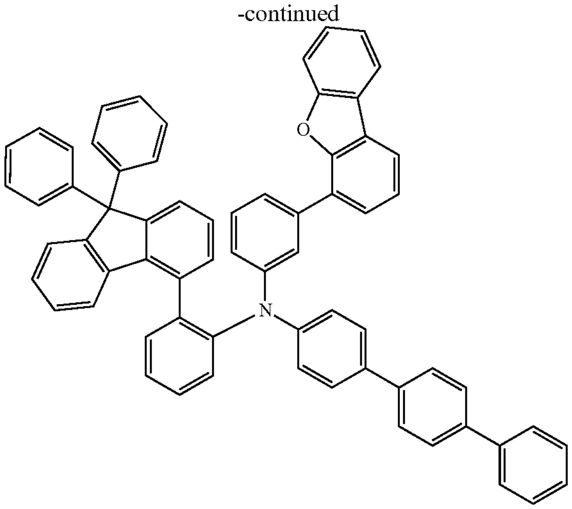
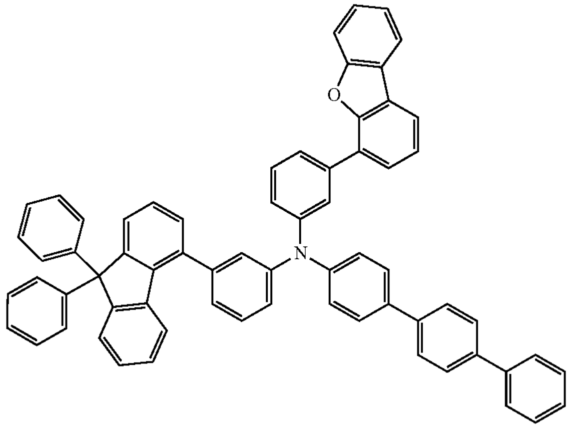
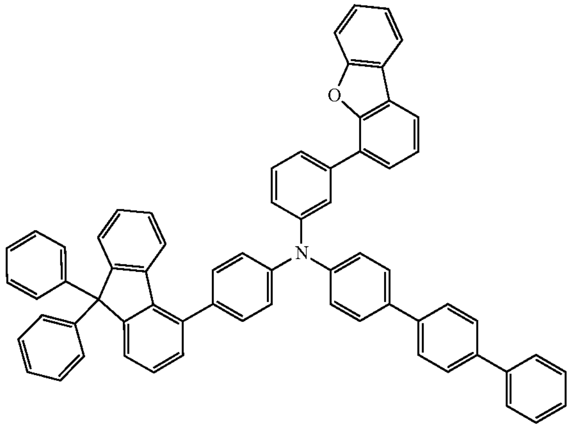
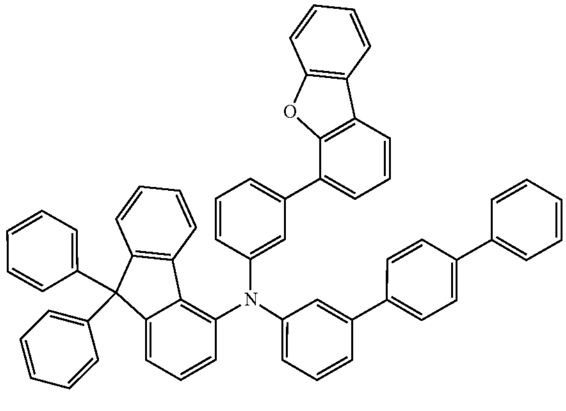

-continued
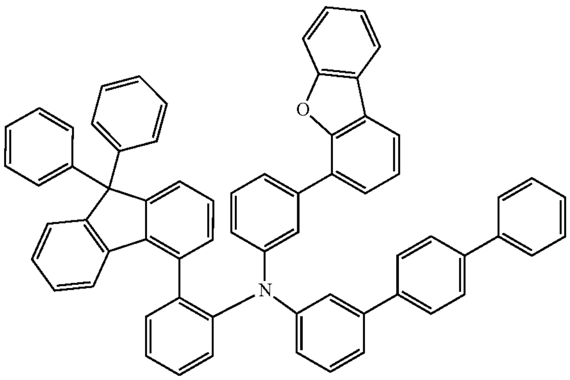
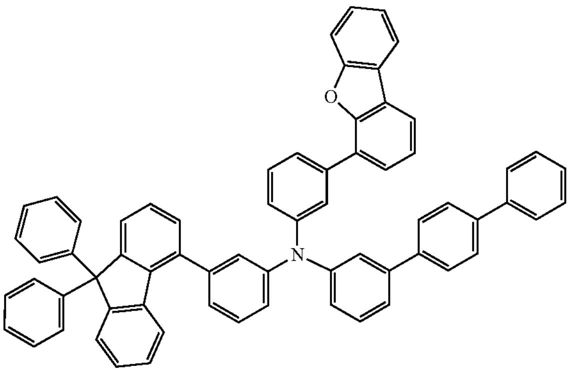
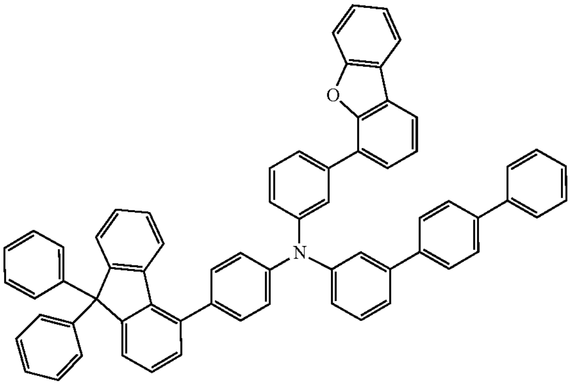
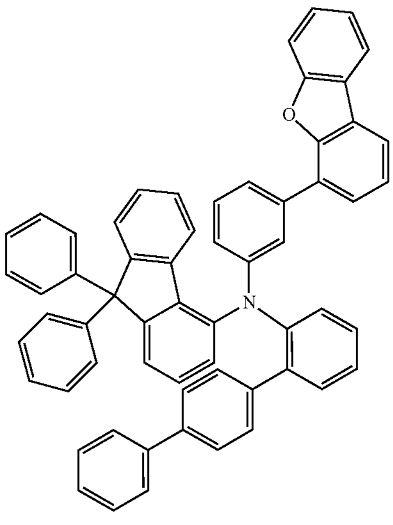
-continued
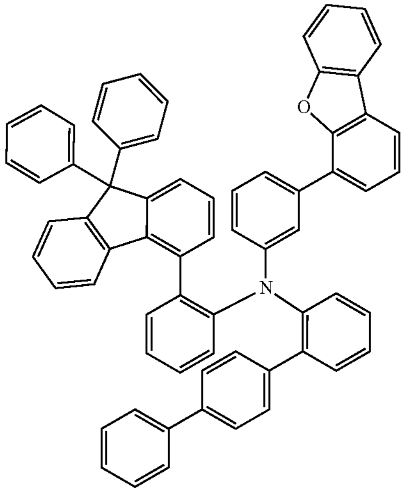
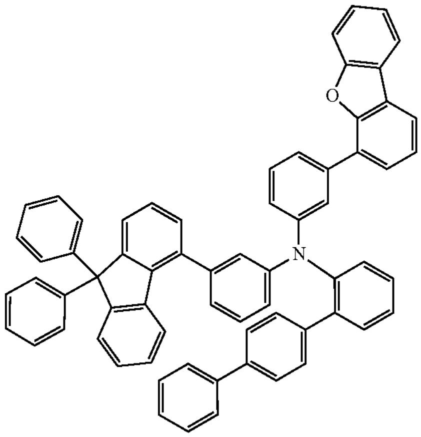
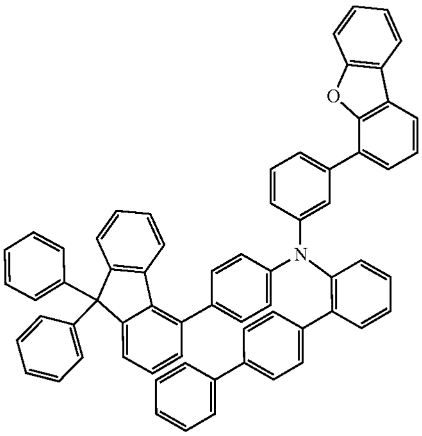

-continued
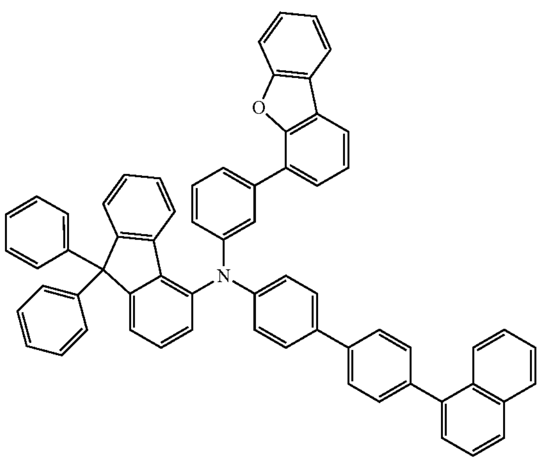
-continued
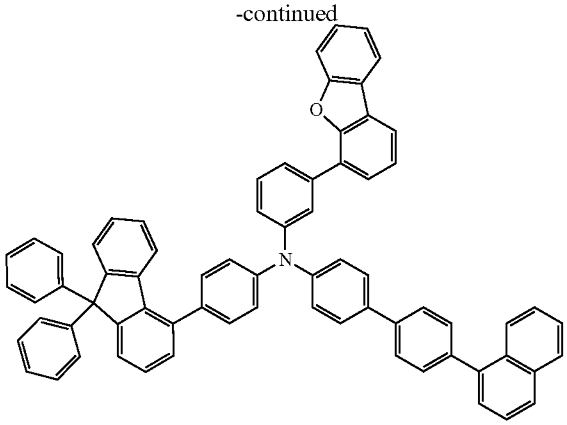
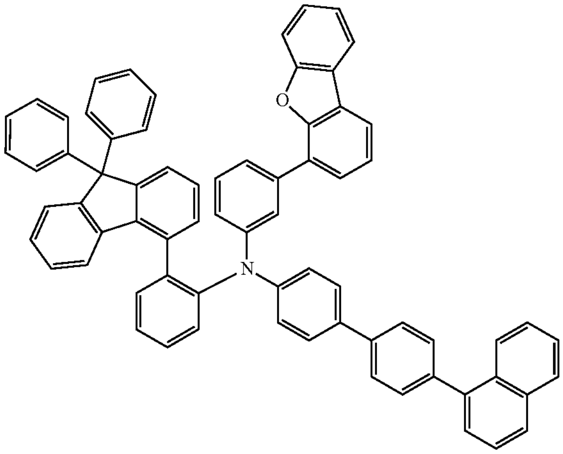
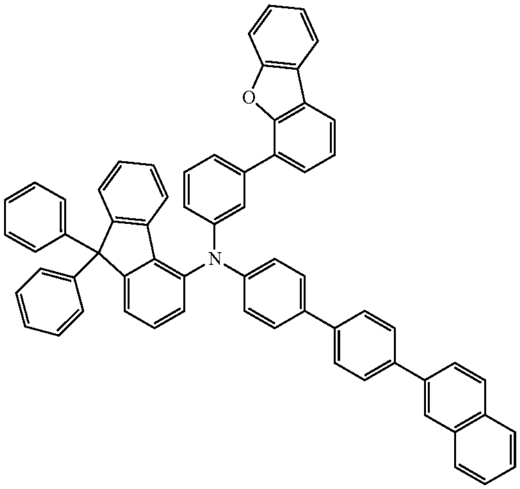
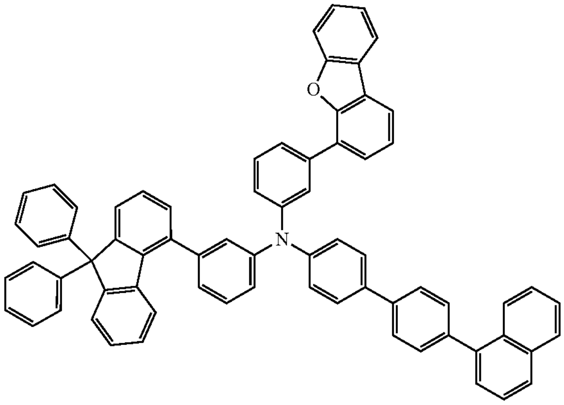
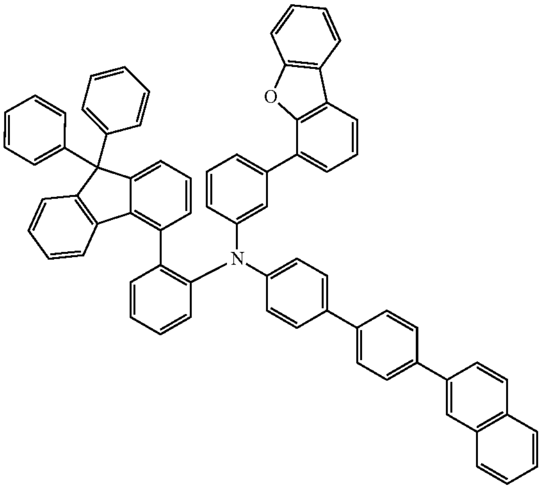

-continued
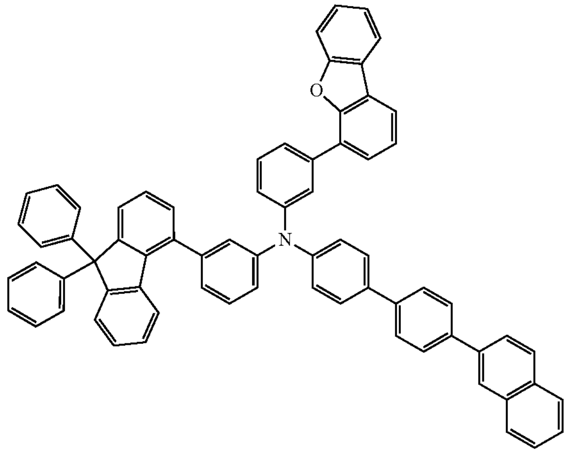
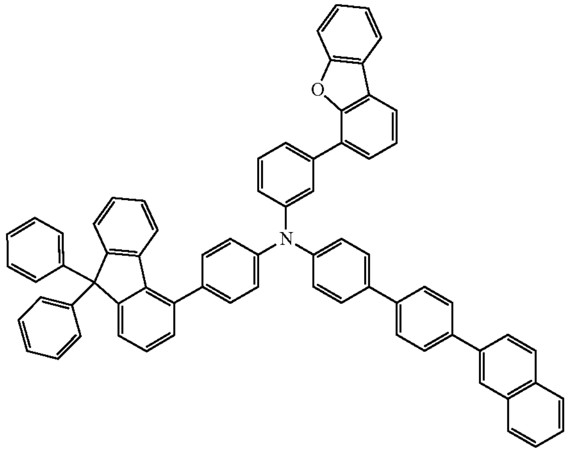
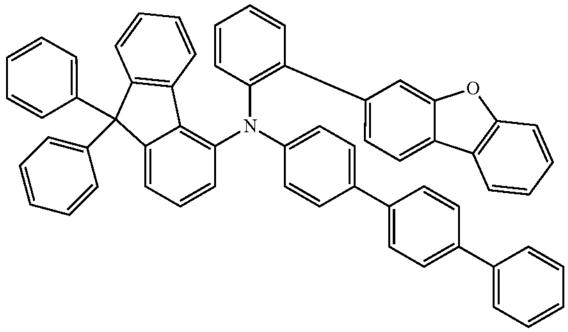
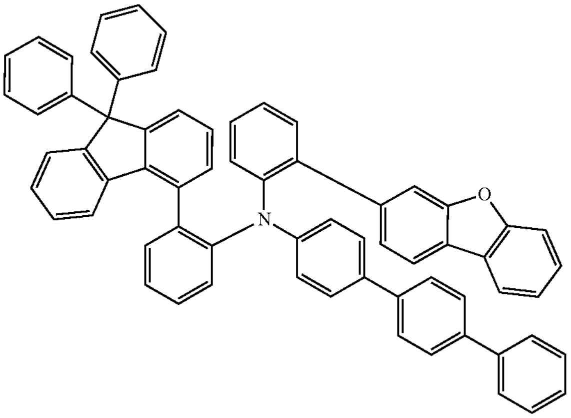
-continued
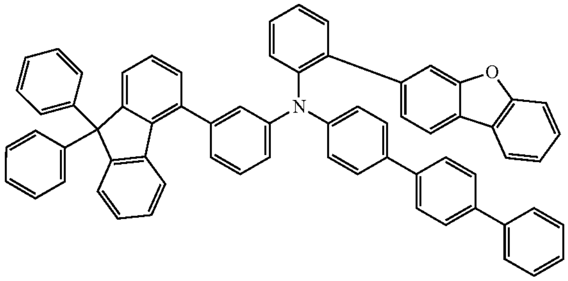
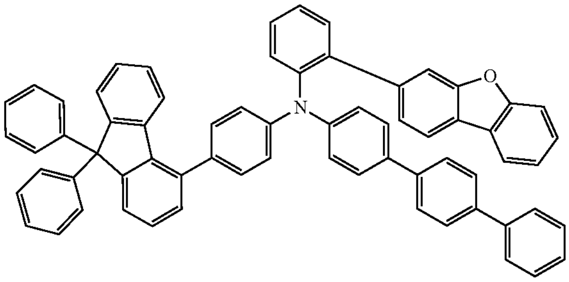
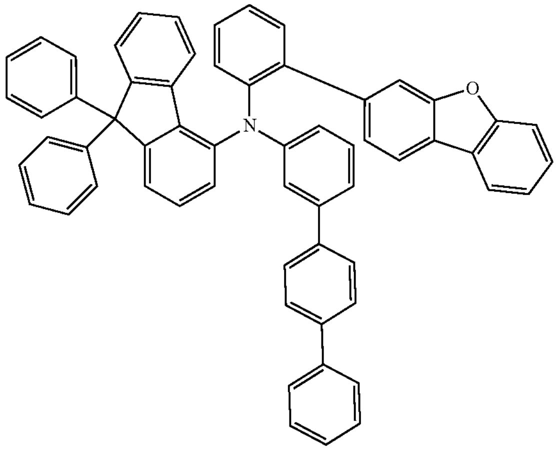
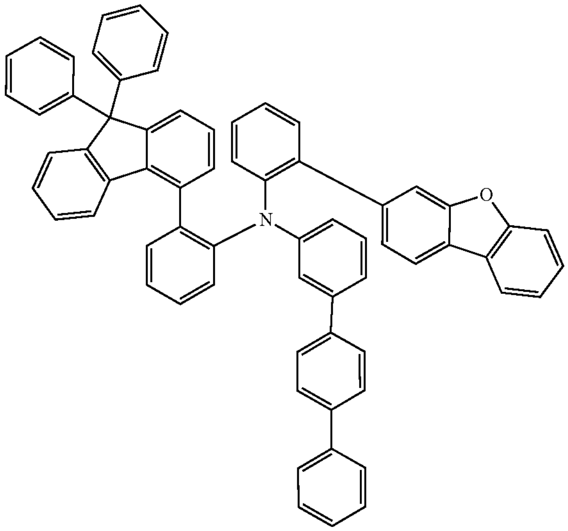

-continued
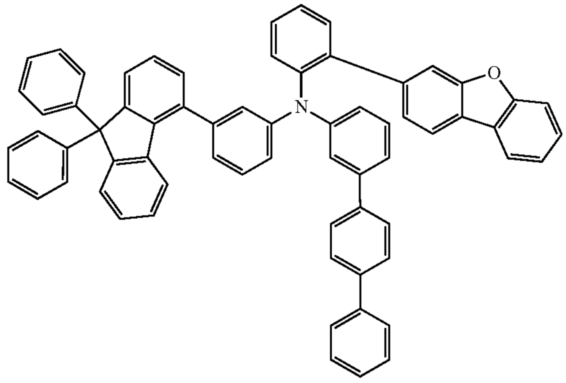
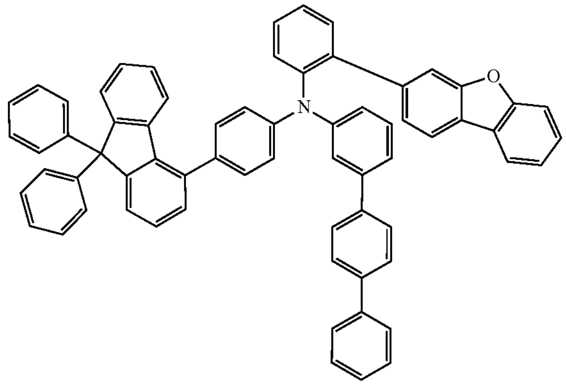
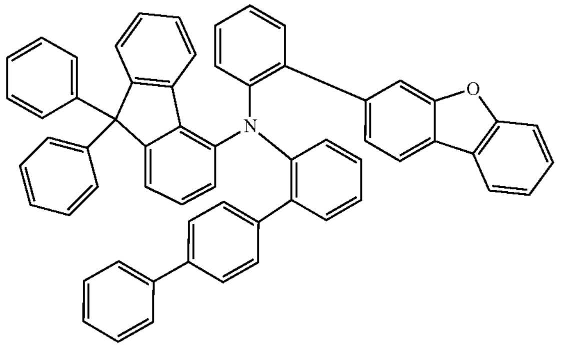
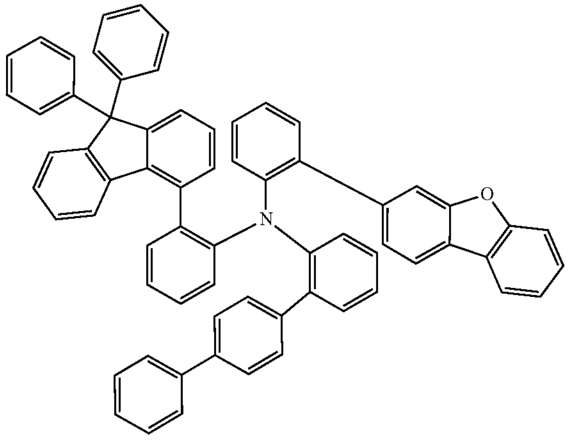
-continued
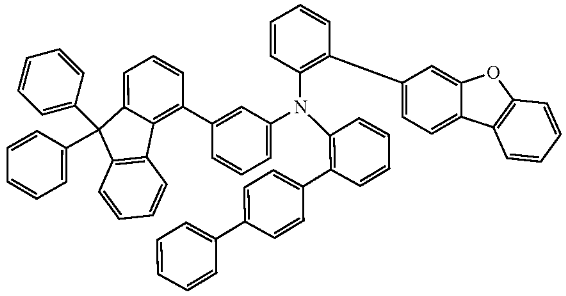
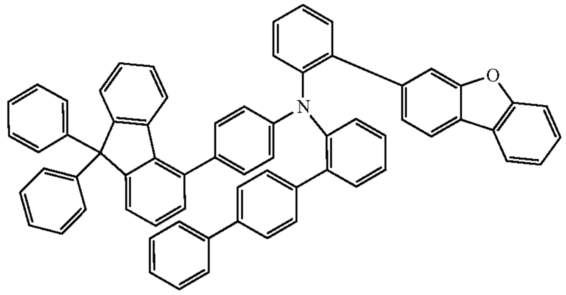
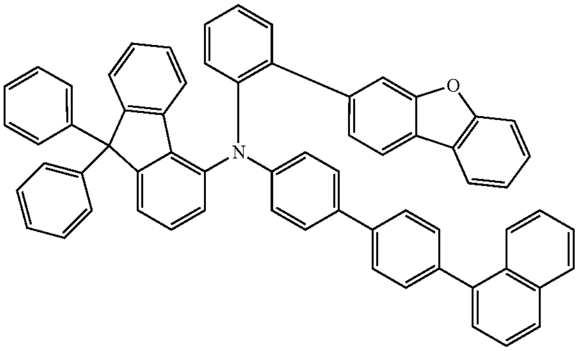
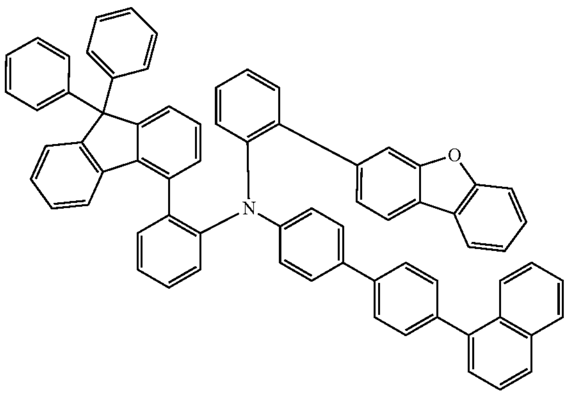
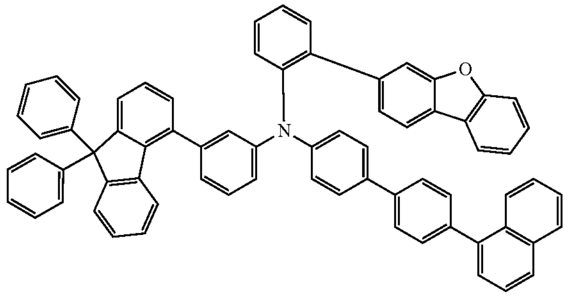

-continued
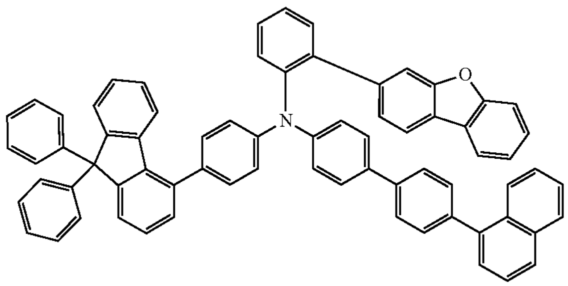
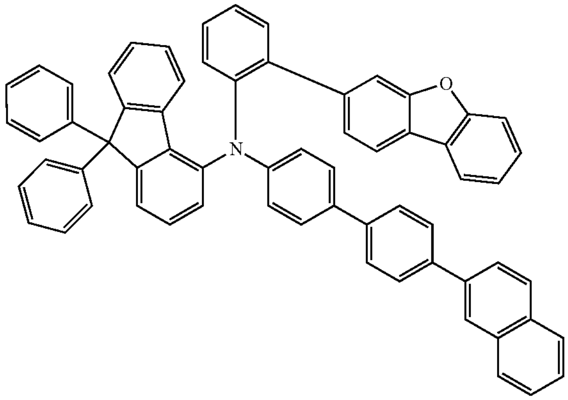
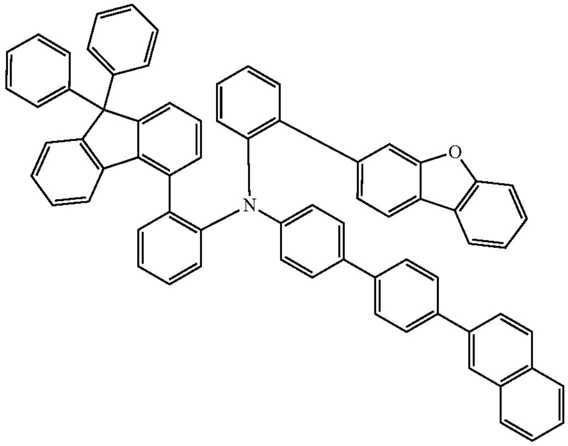
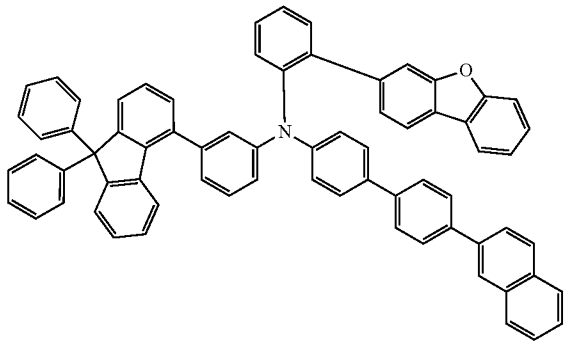
-continued
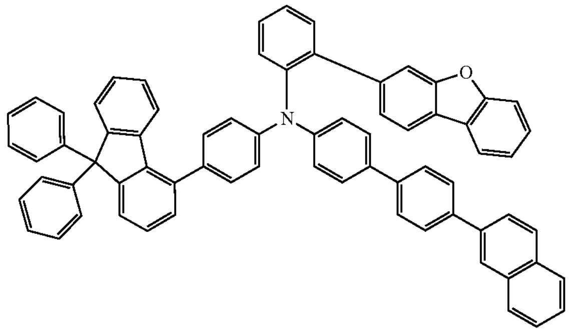
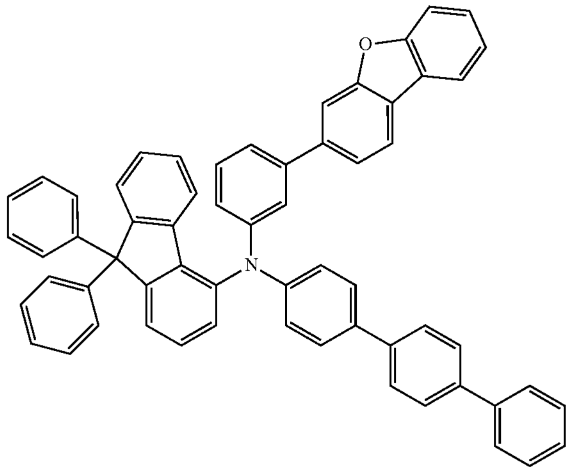
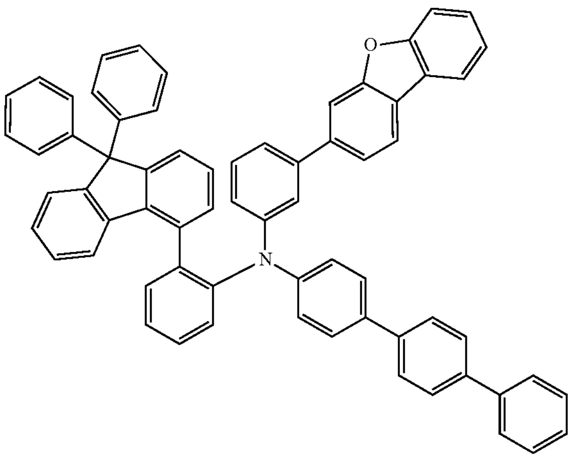
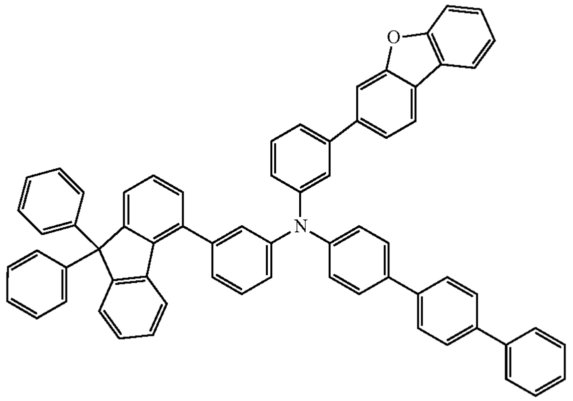

-continued
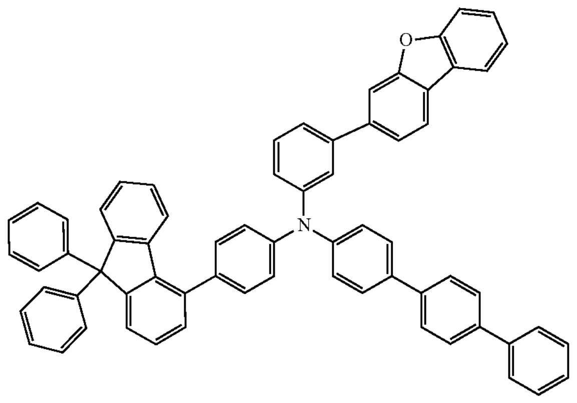
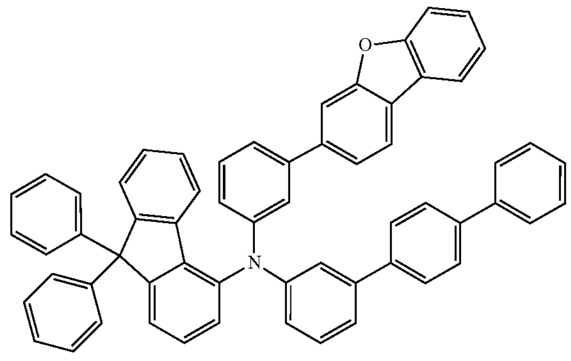
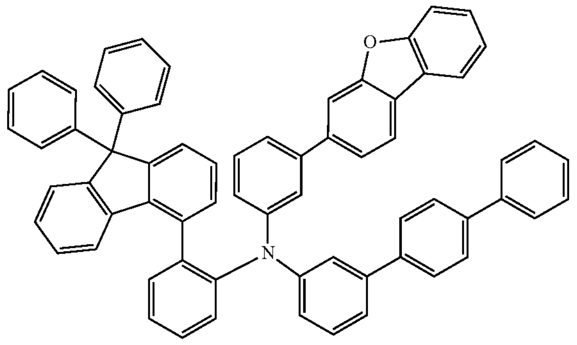
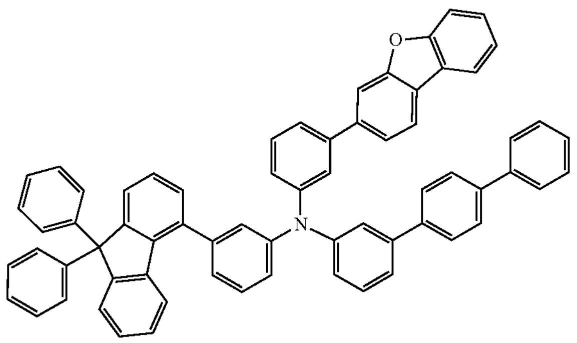
-continued
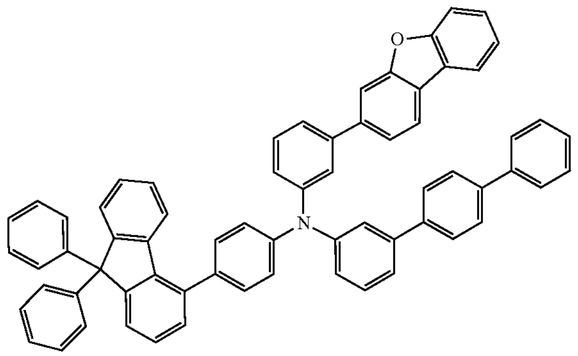
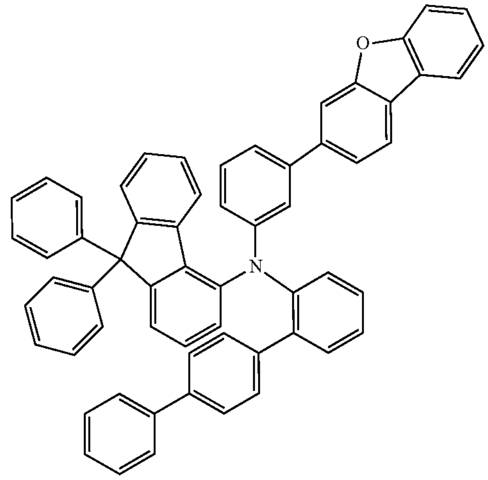
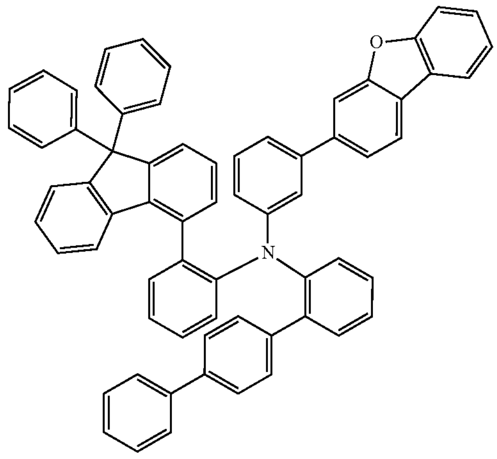
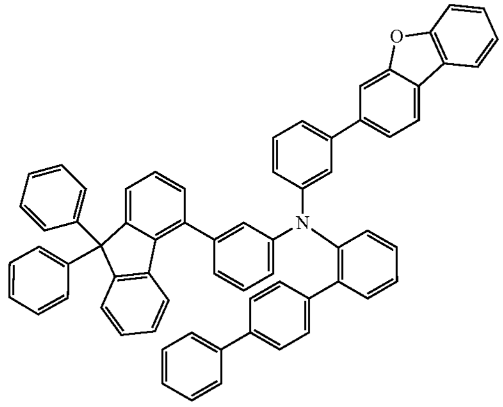

-continued
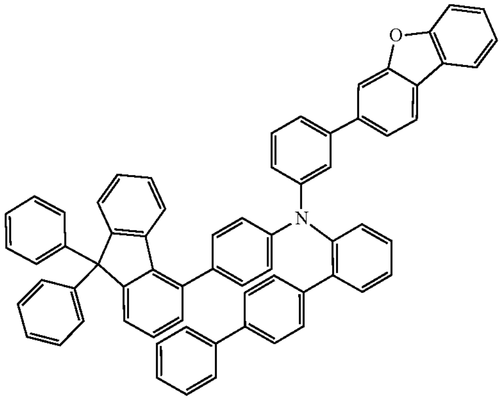
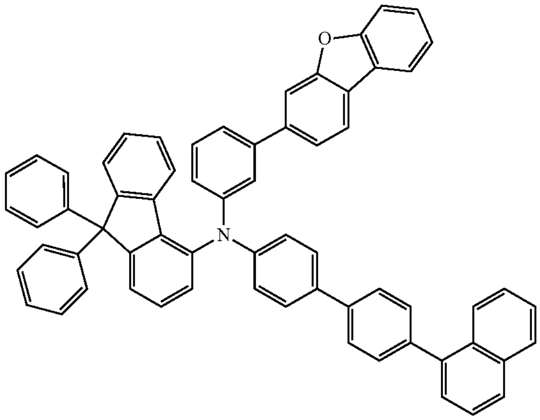
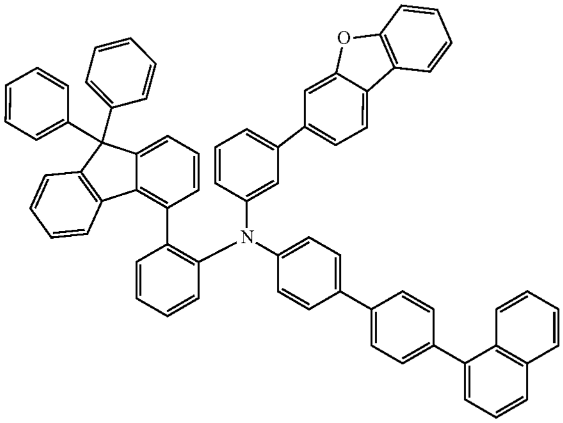
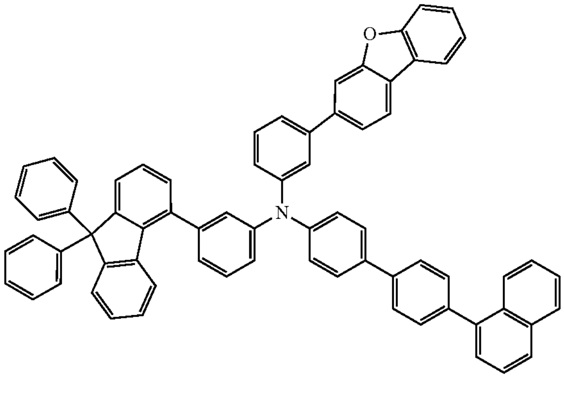
-continued
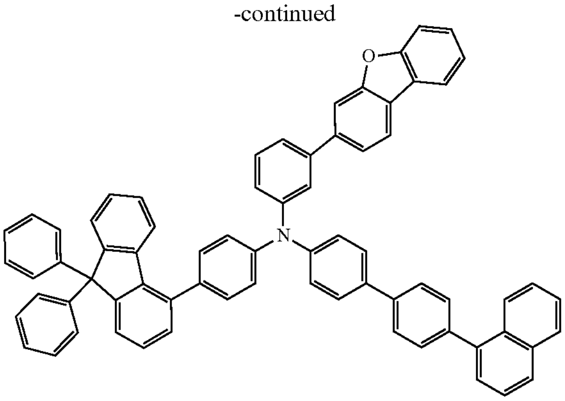
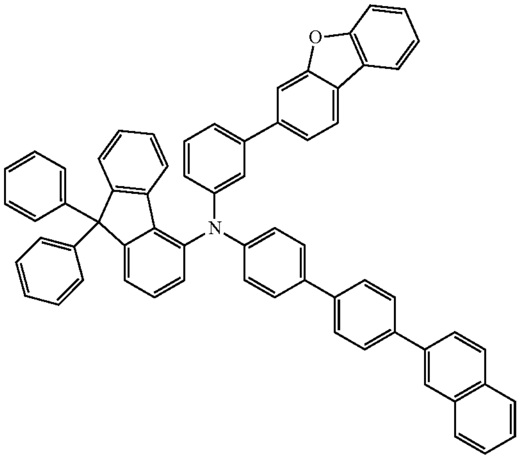
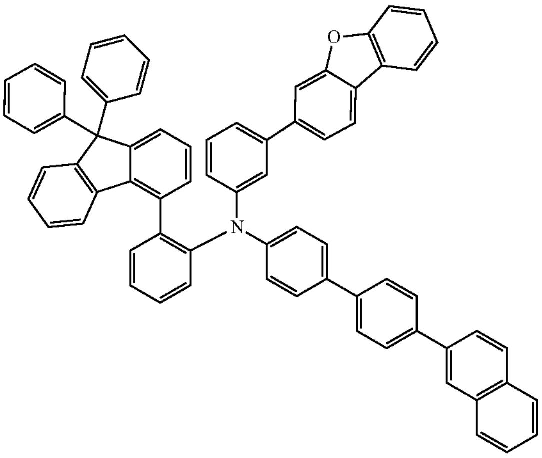
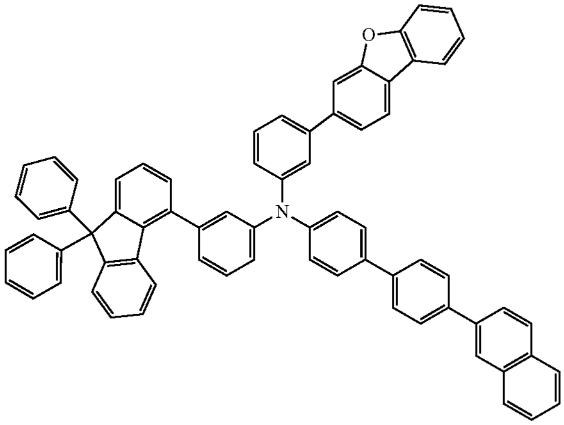

-continued
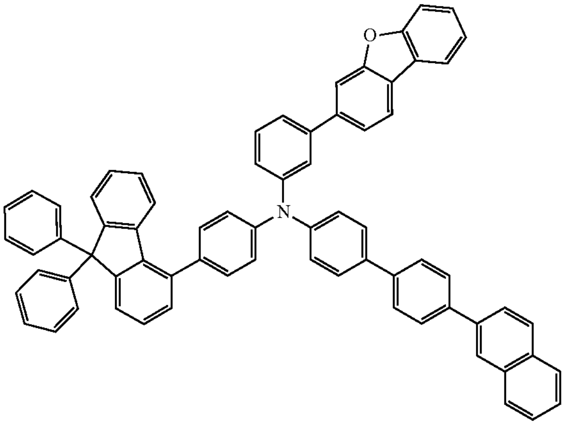
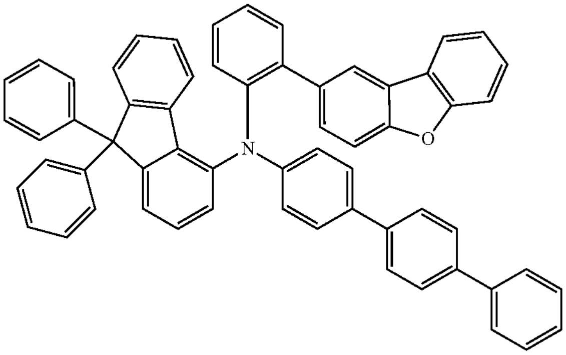
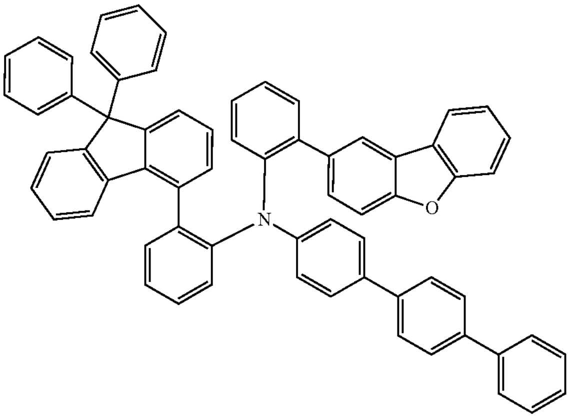
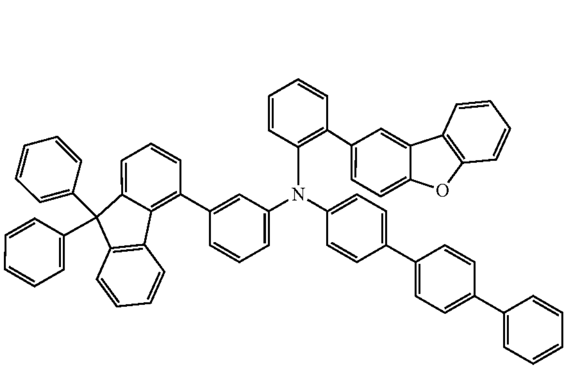
-continued
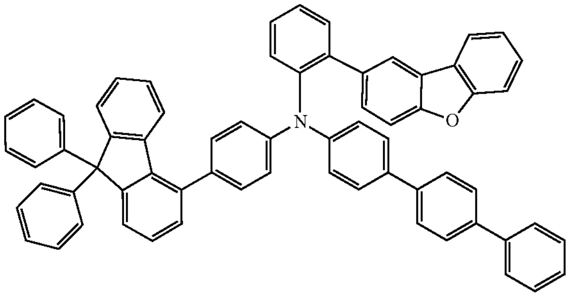
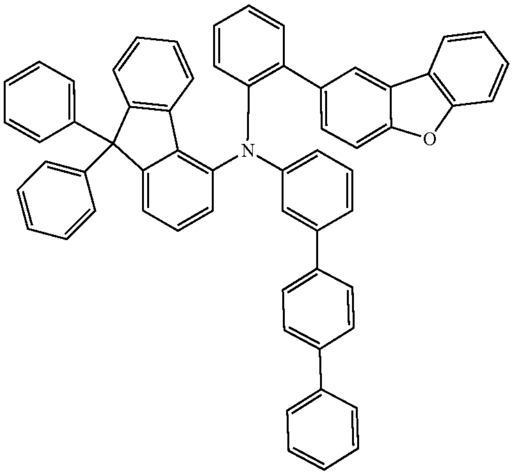
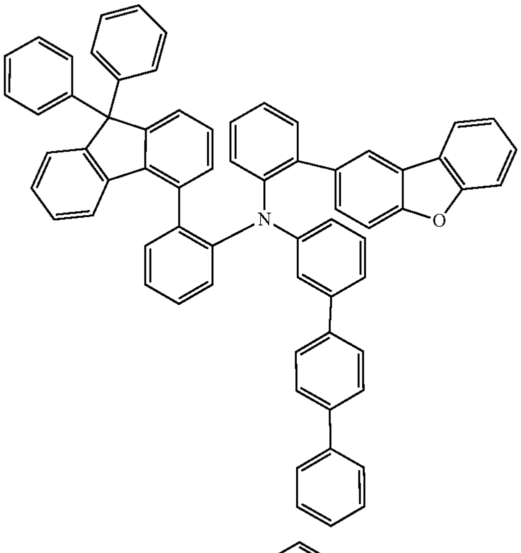
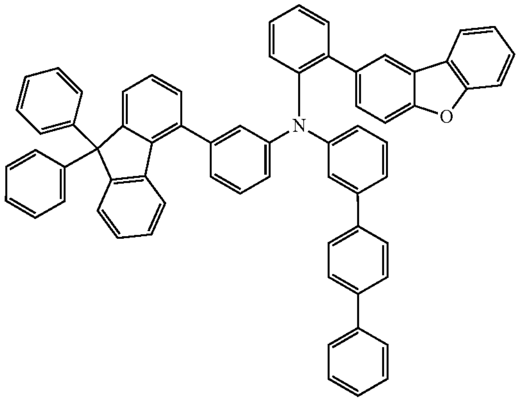

-continued
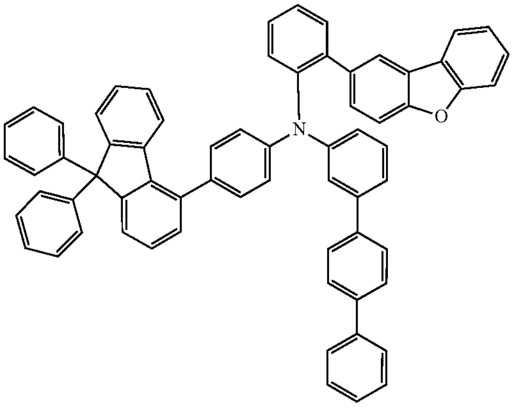
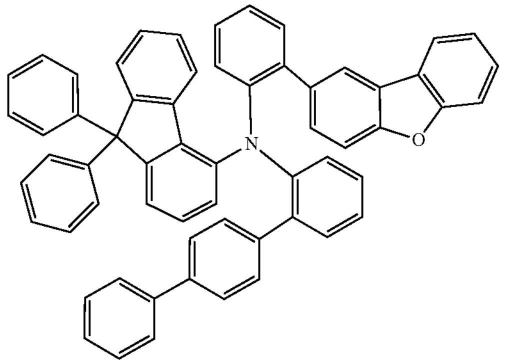
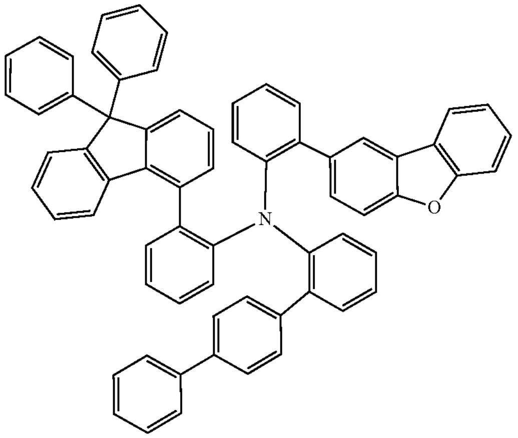
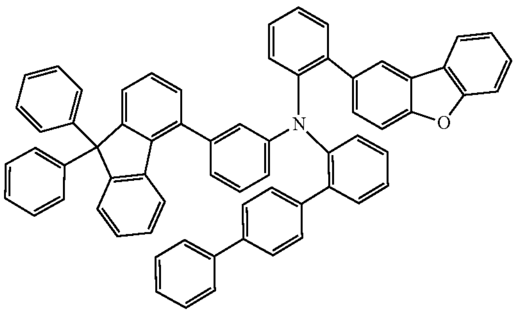
-continued
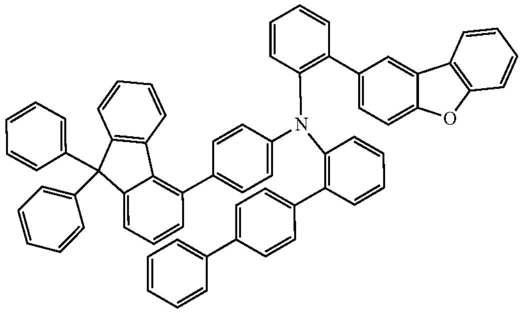
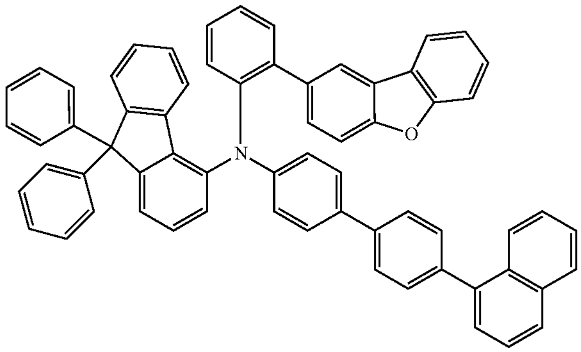
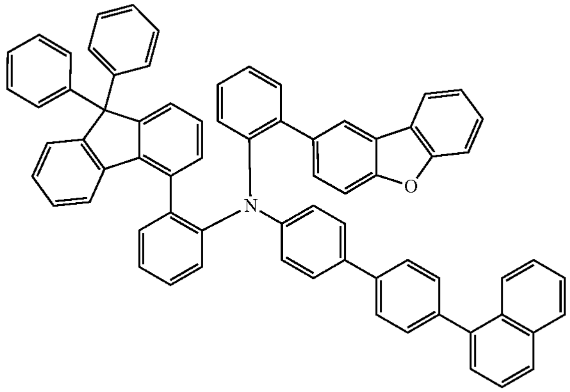
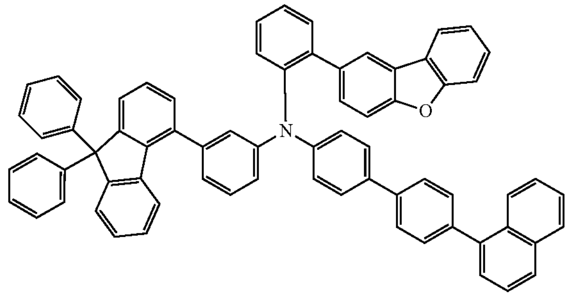
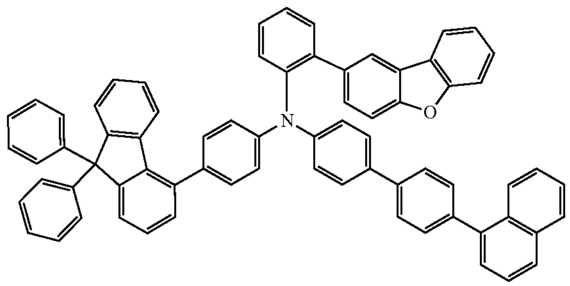

-continued
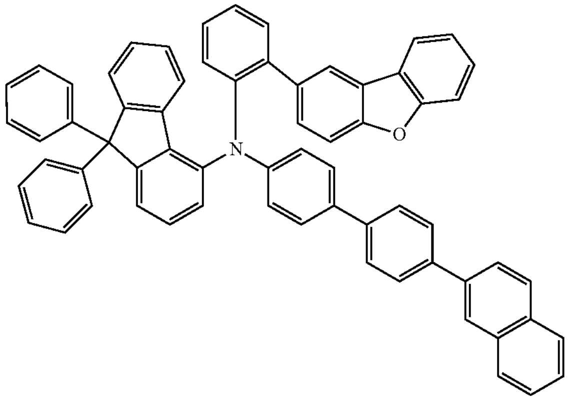
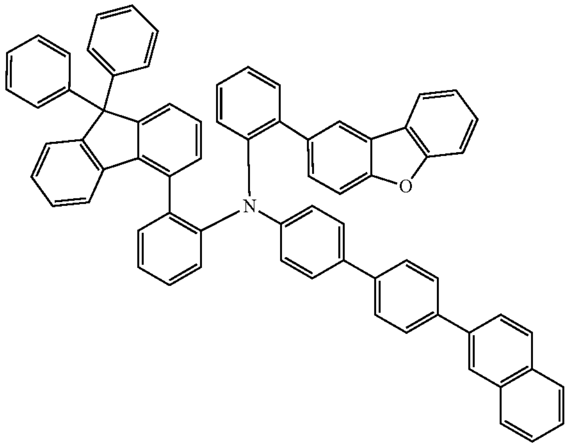
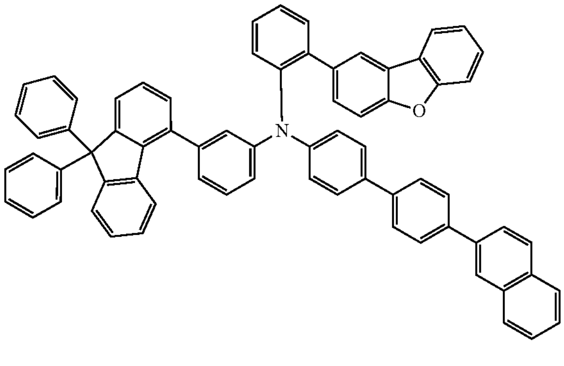
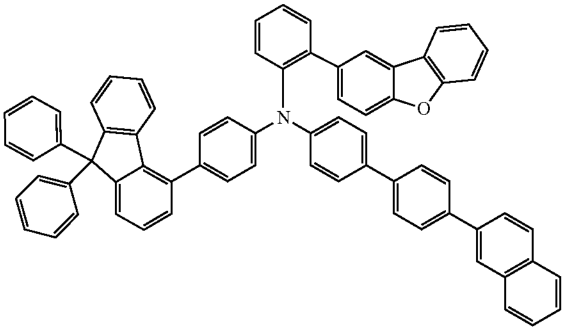
-continued
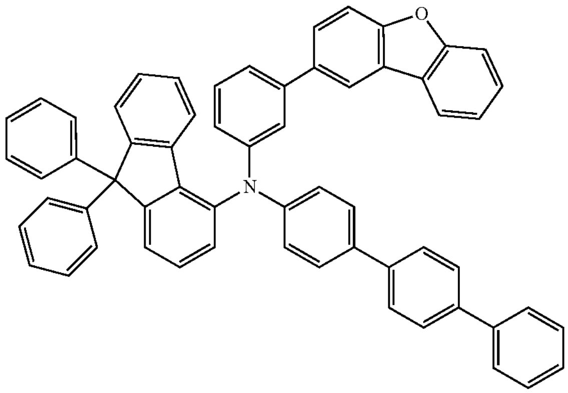
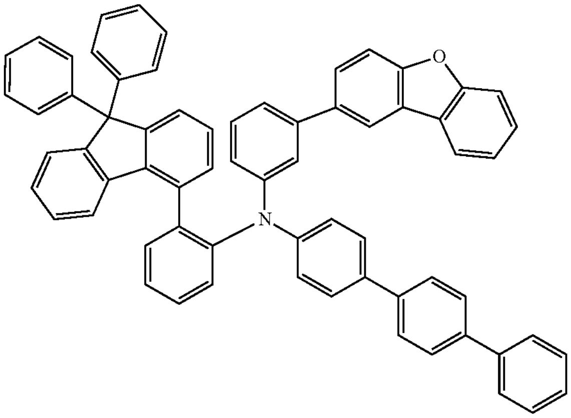
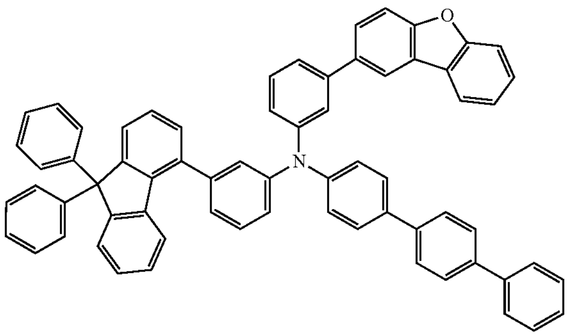
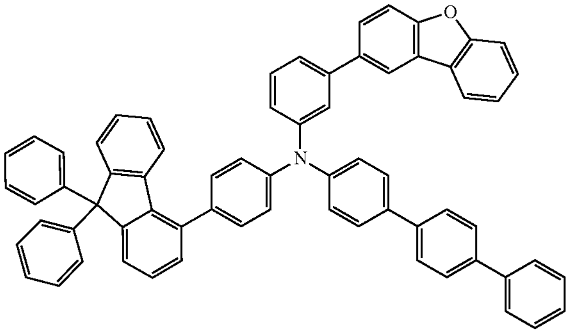

-continued
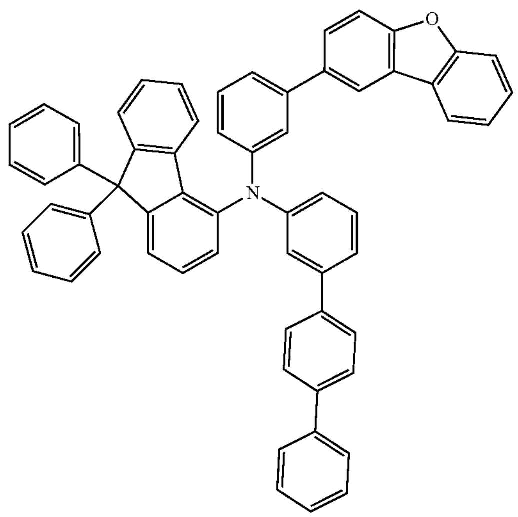
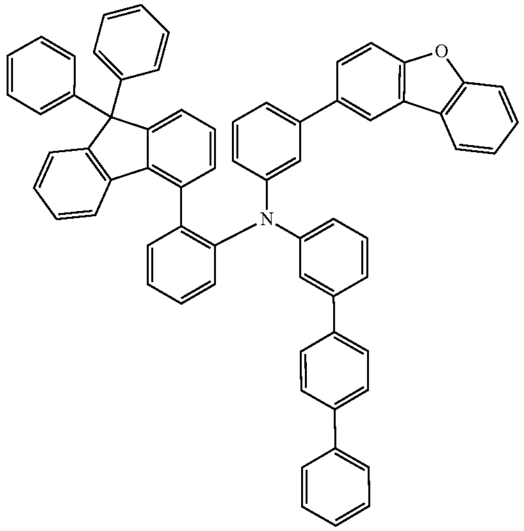
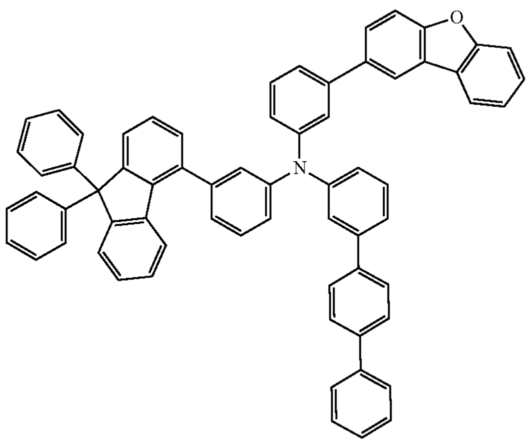
-continued
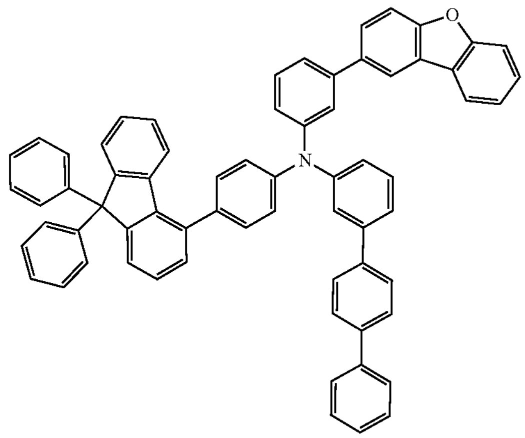
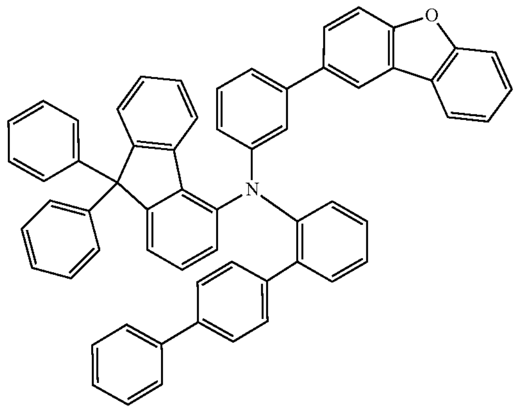
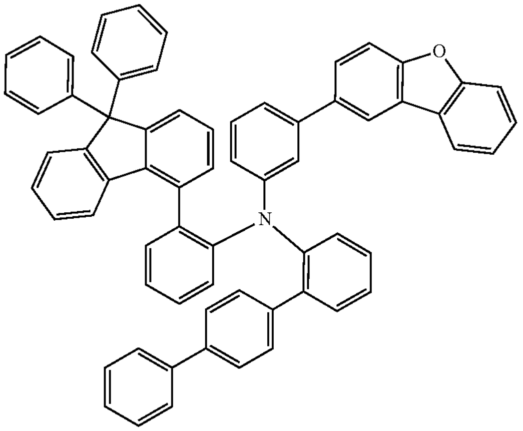
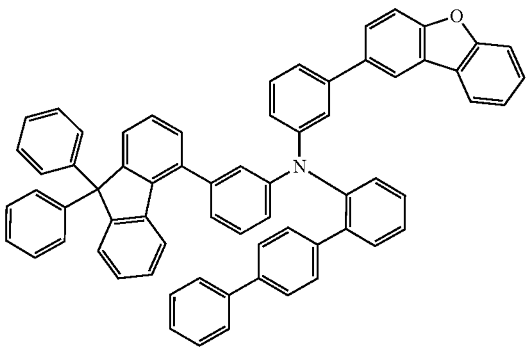

-continued
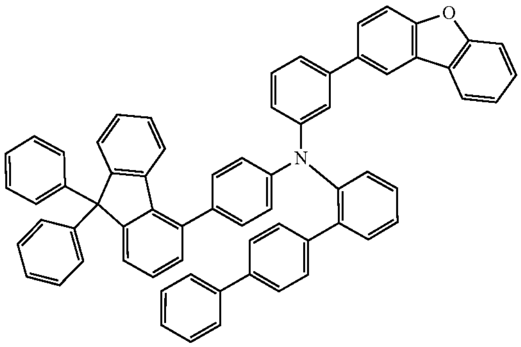
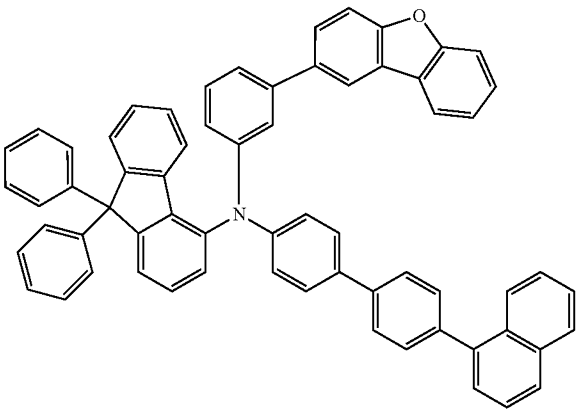
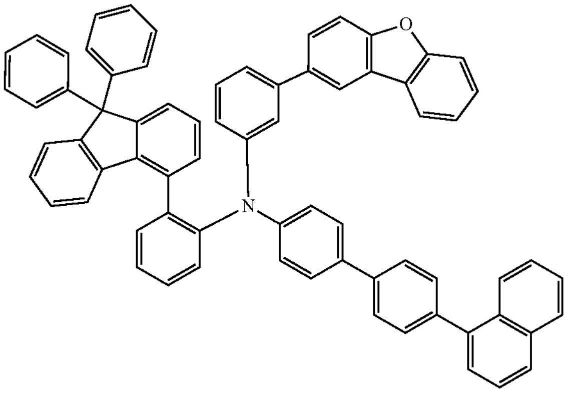
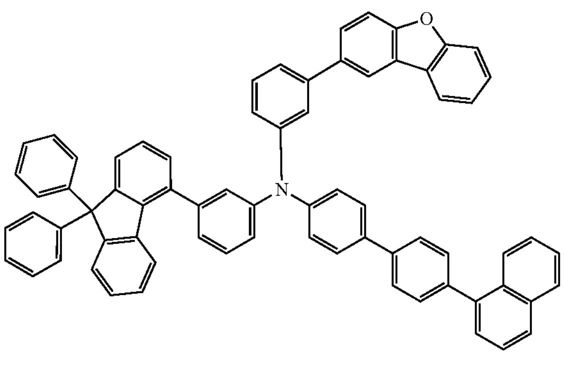
-continued
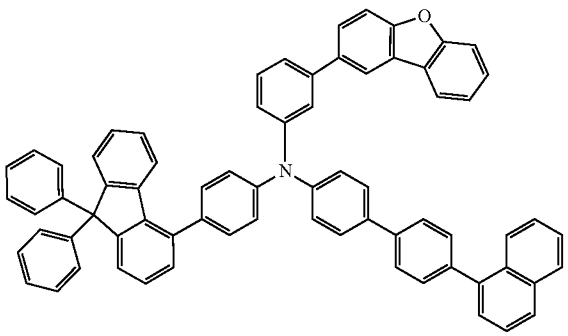
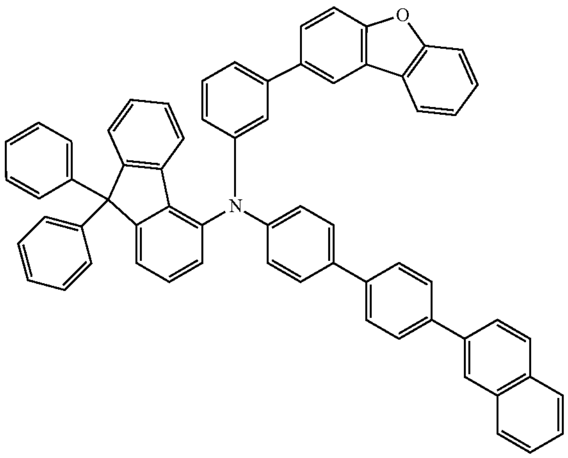
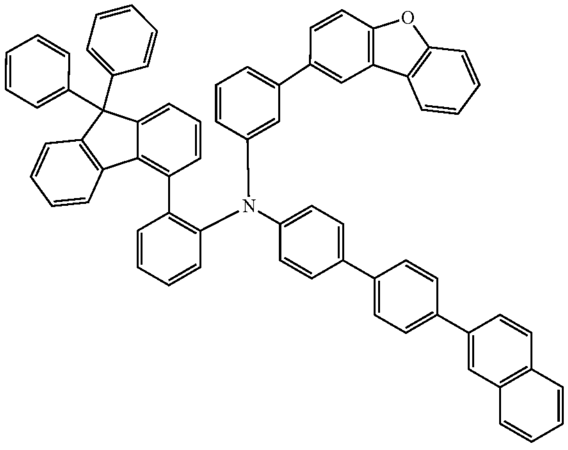
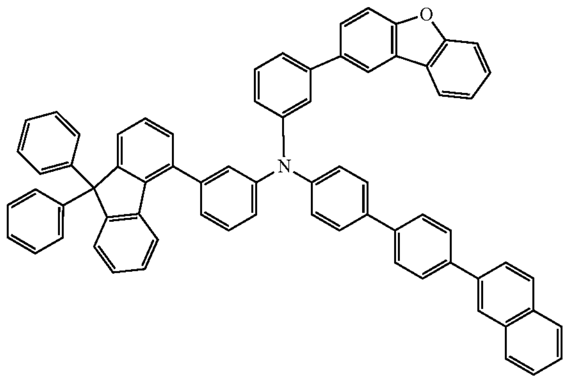

-continued
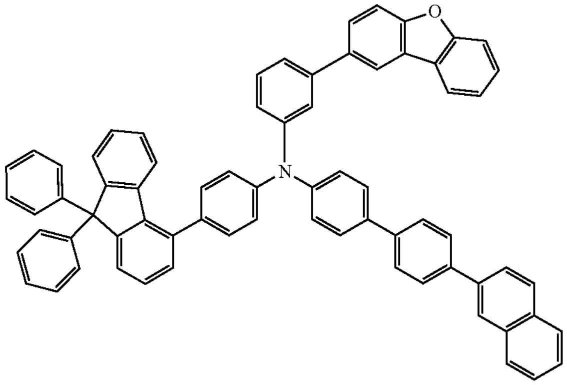
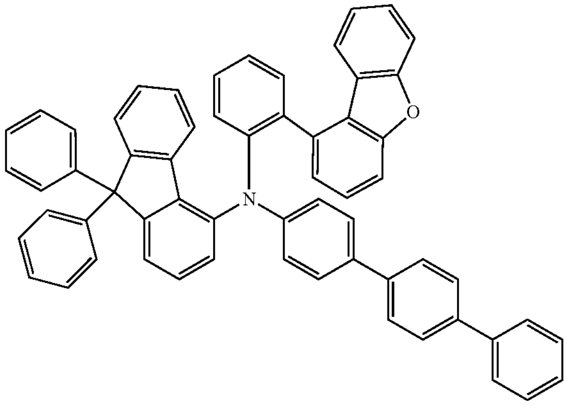
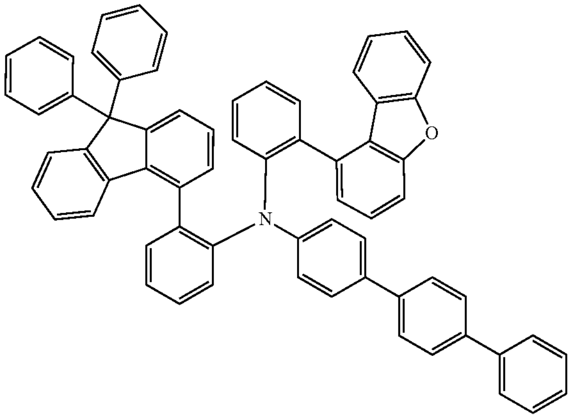
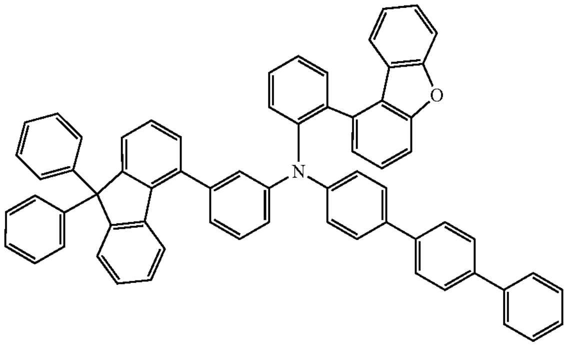
-continued
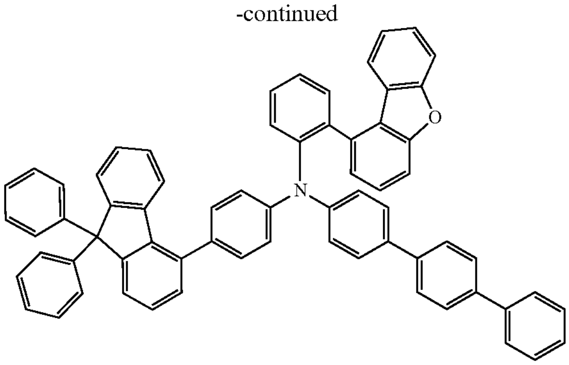
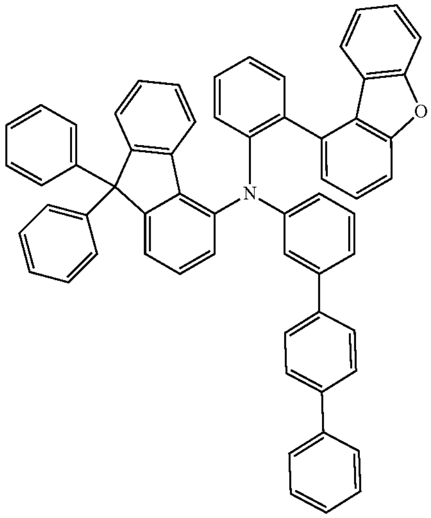
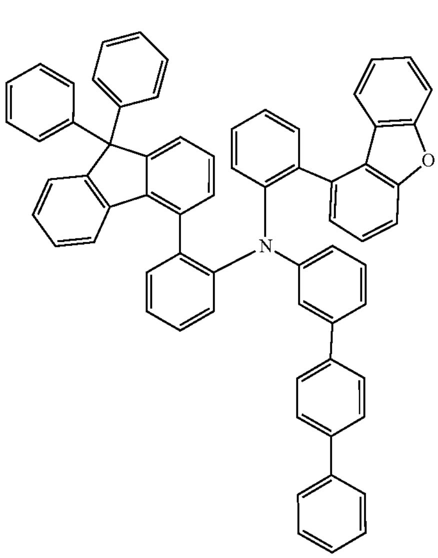

-continued
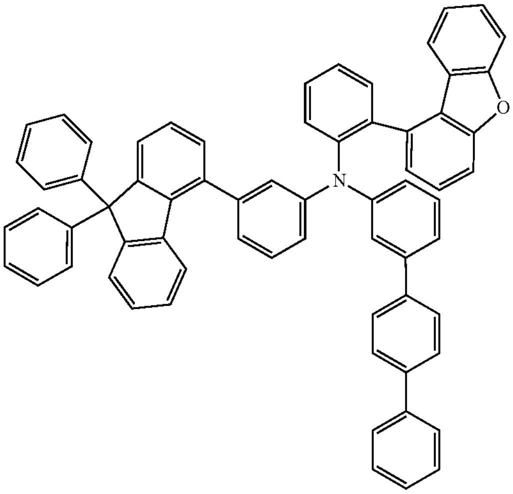
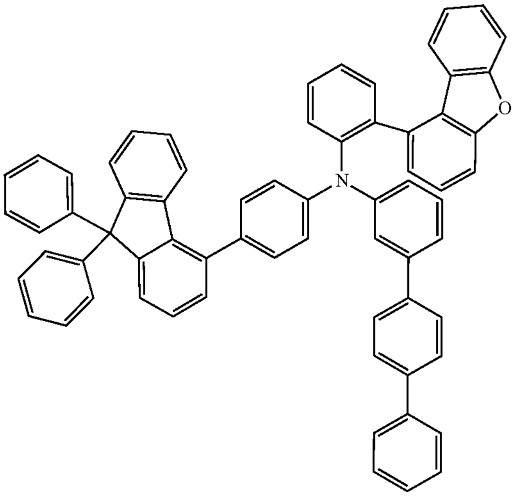
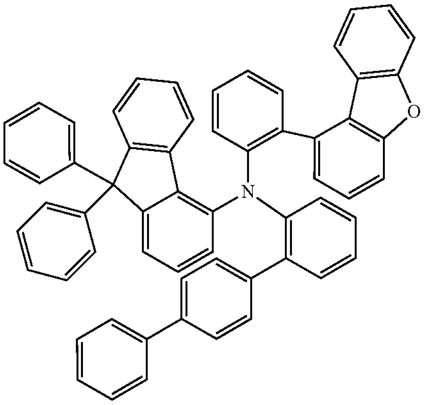
-continued
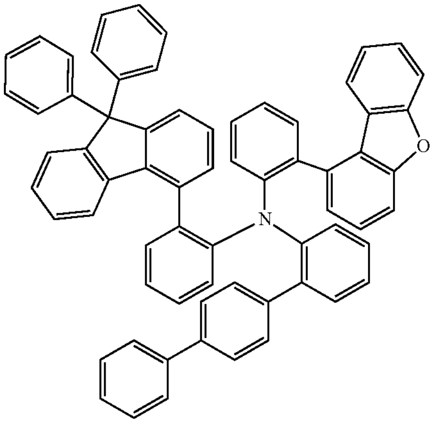
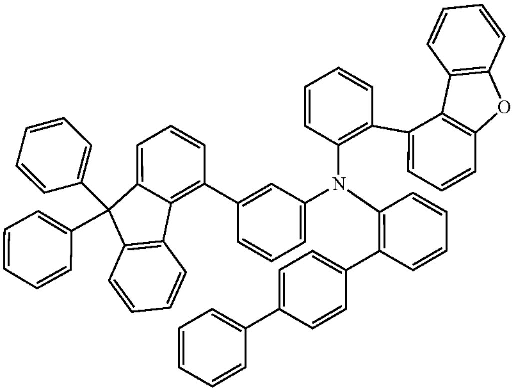
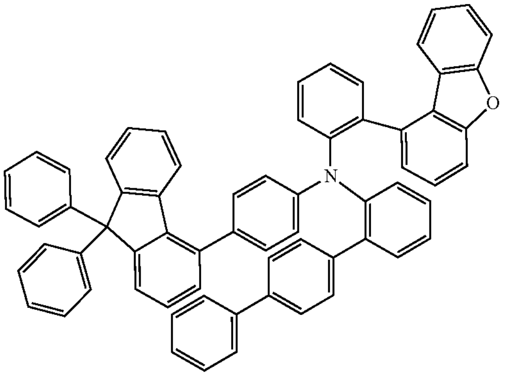
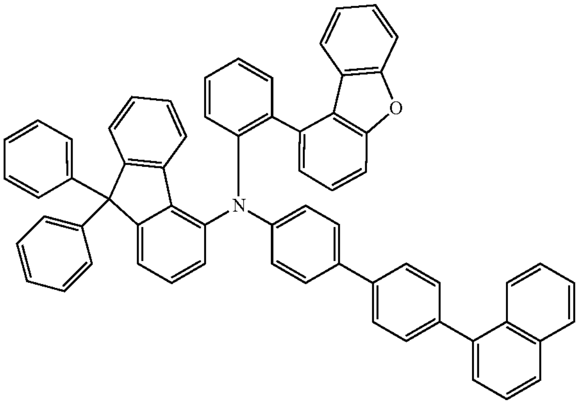

-continued
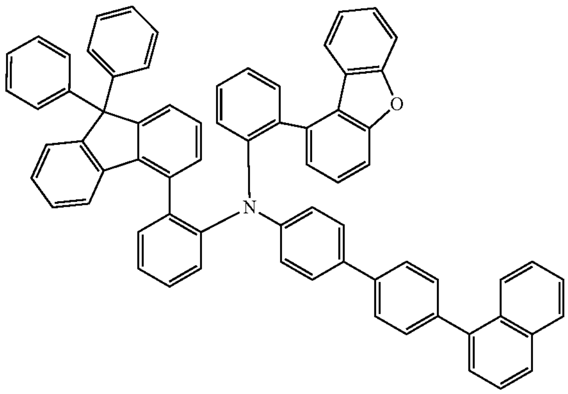
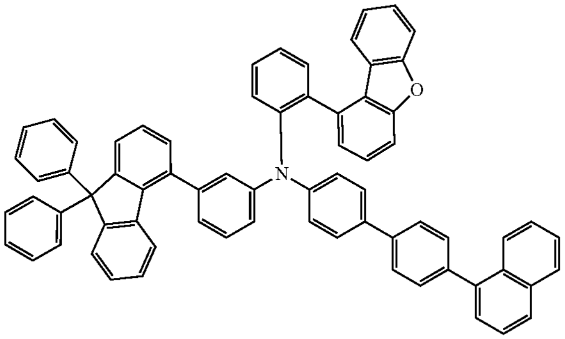
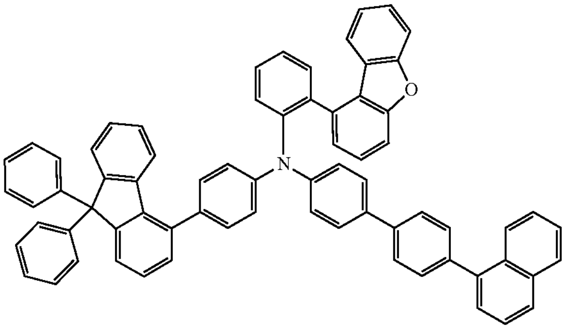
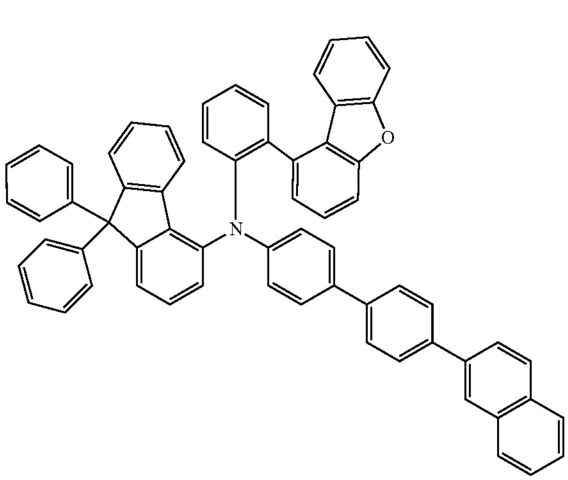
-continued
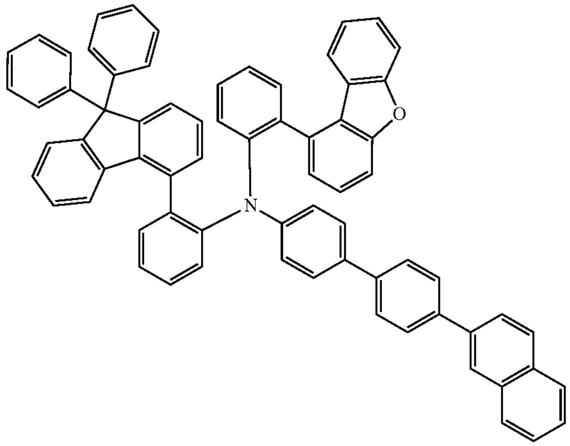
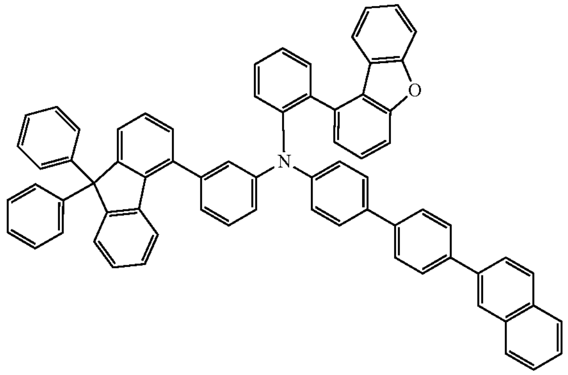
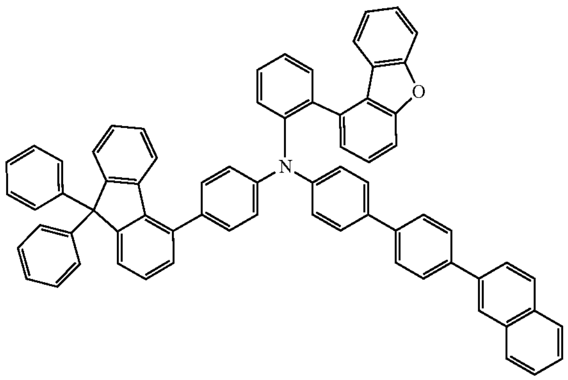

-continued
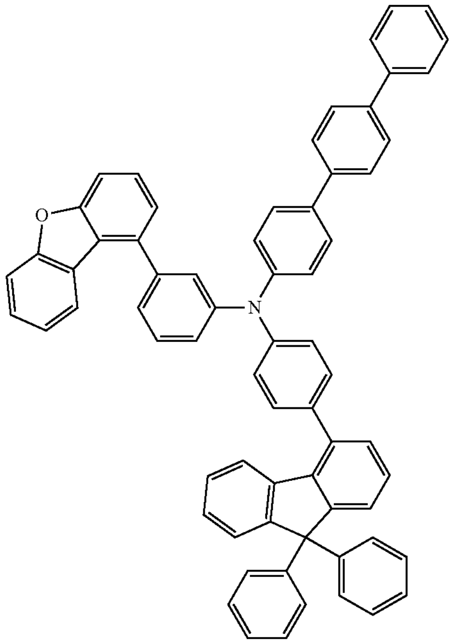
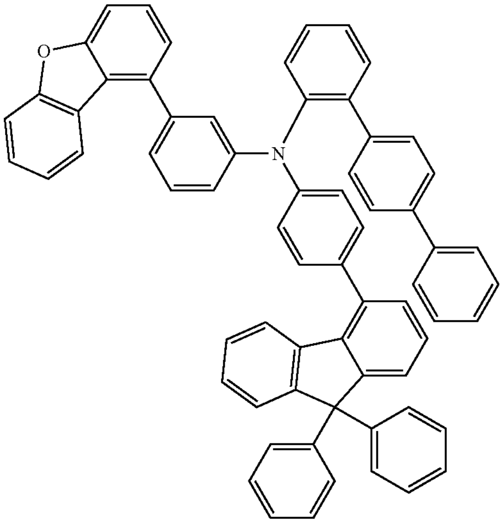
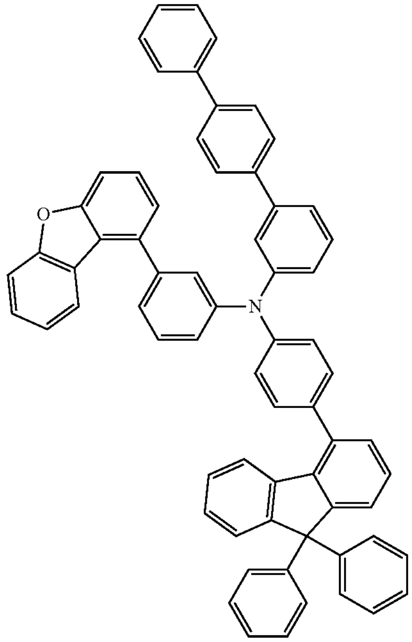
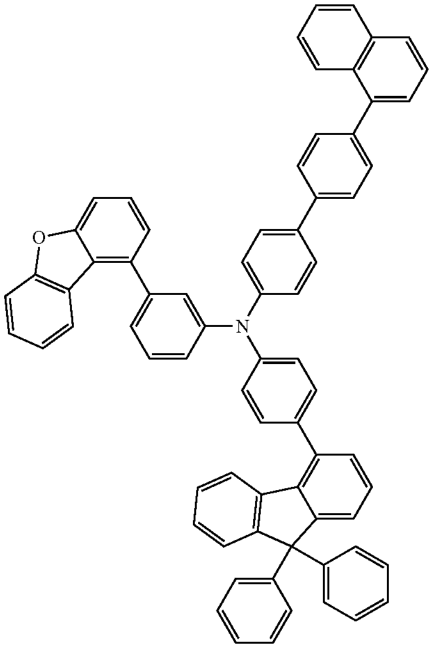

-continued
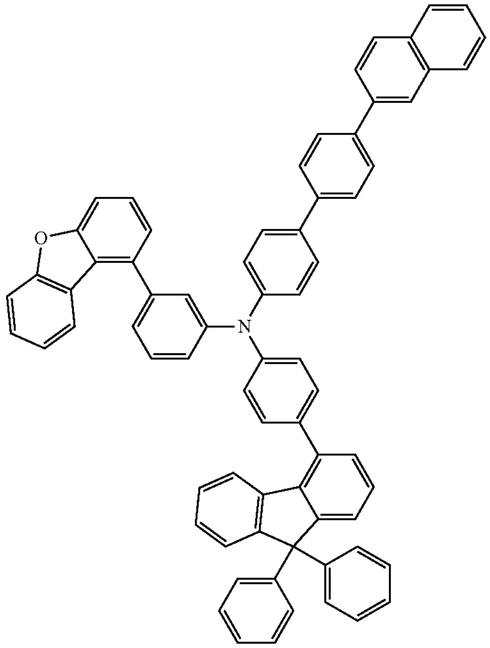
-continued
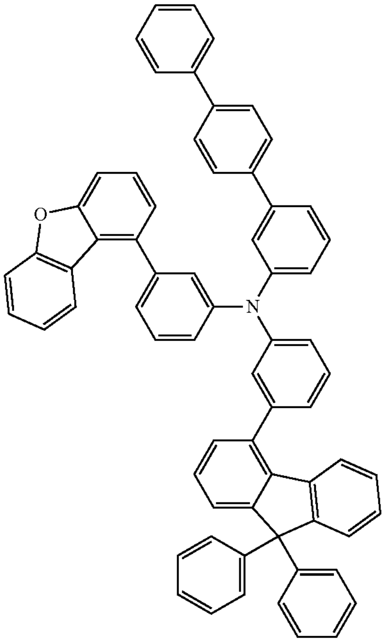
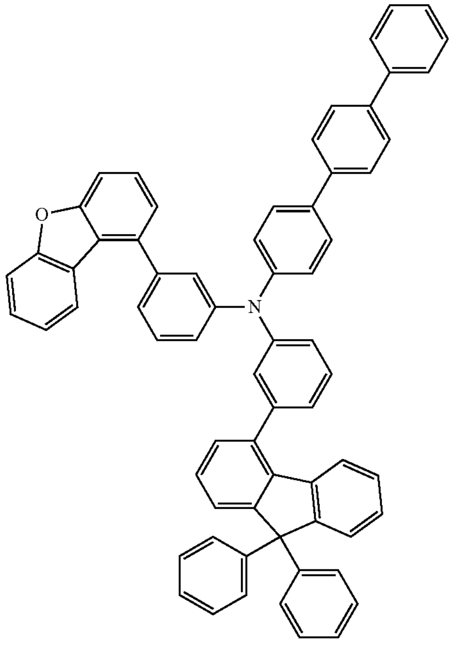
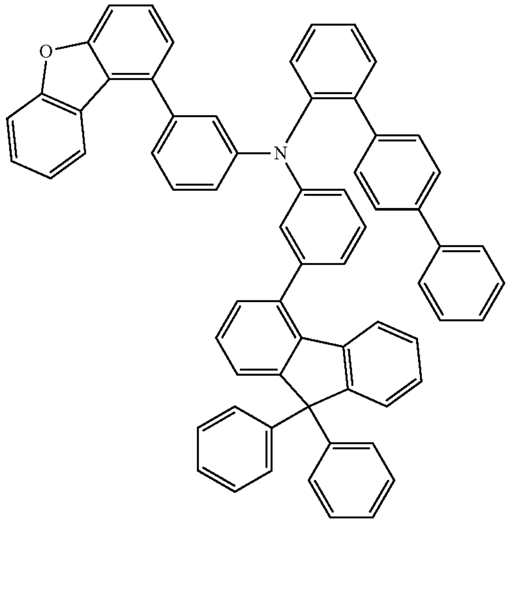

-continued
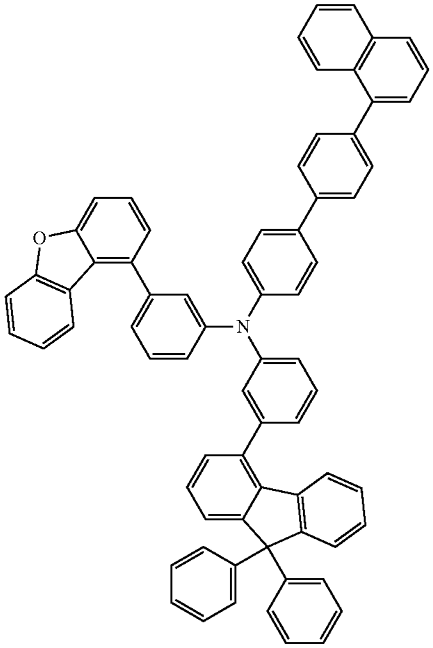
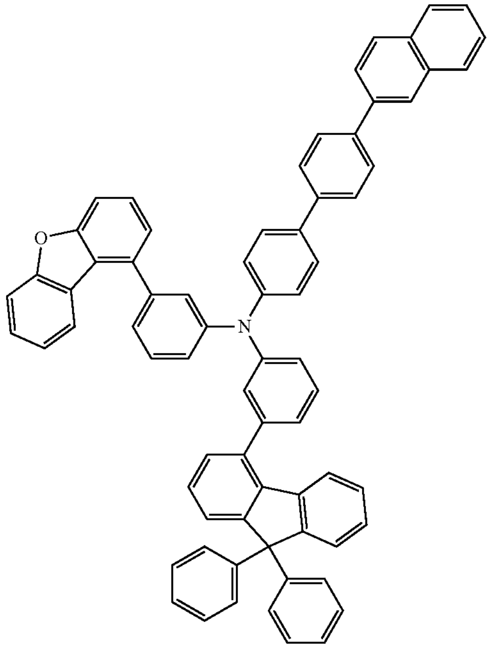
-continued
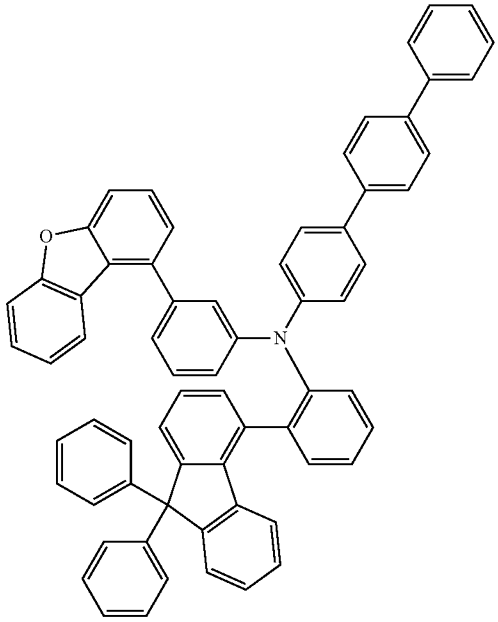
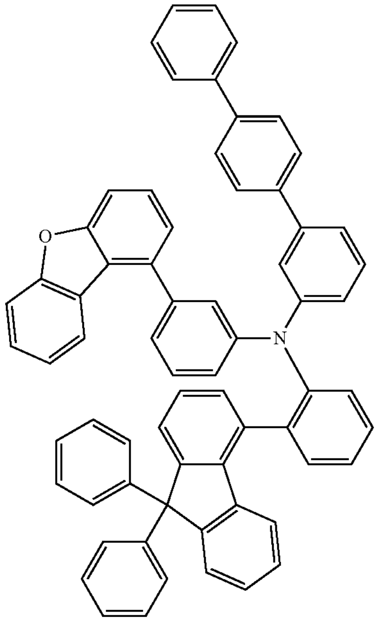
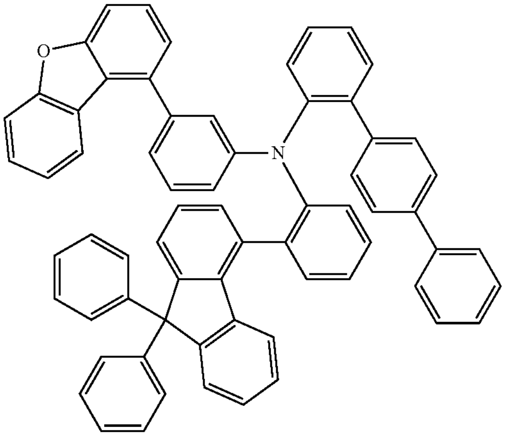

-continued
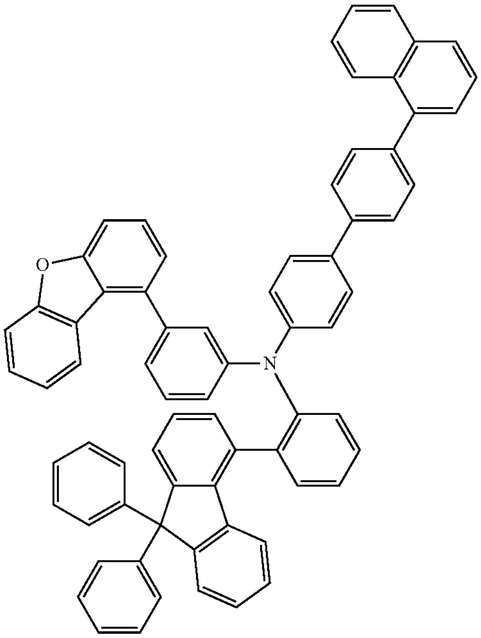
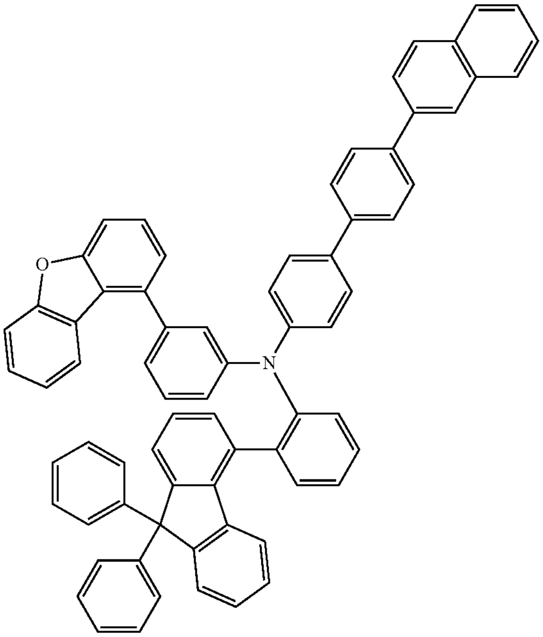
-continued
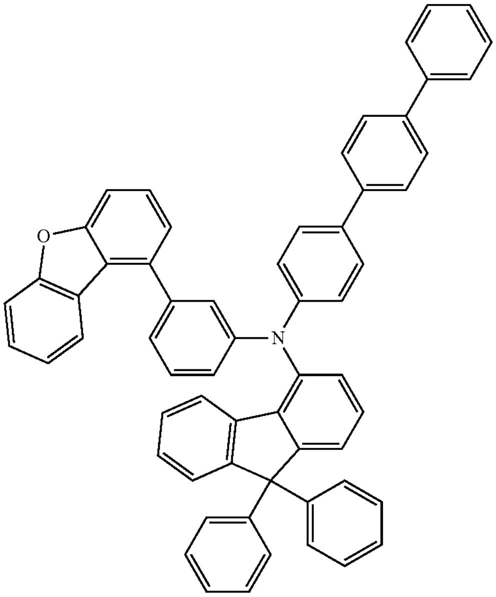
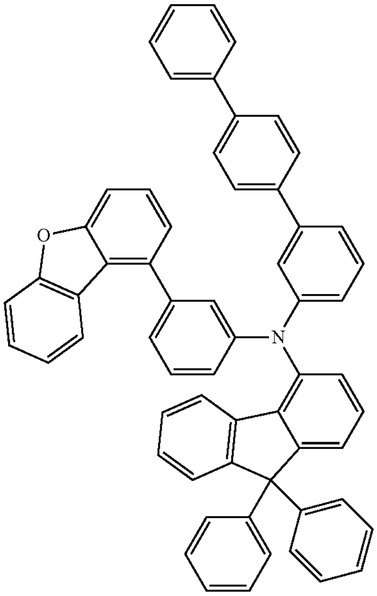
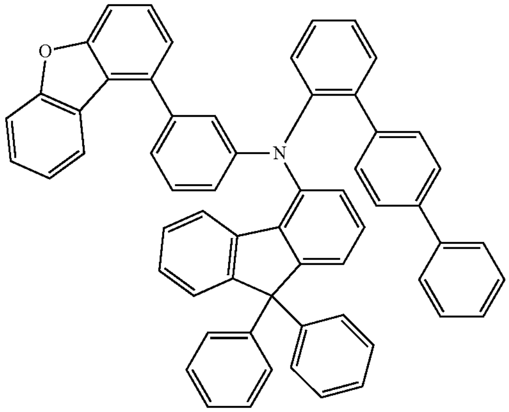

-continued

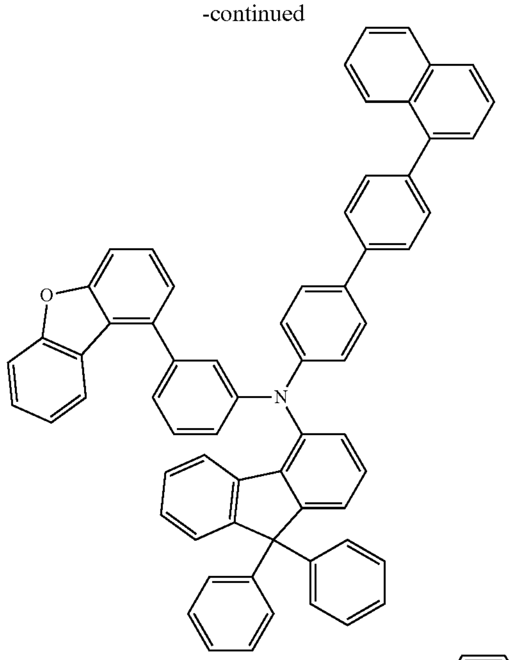

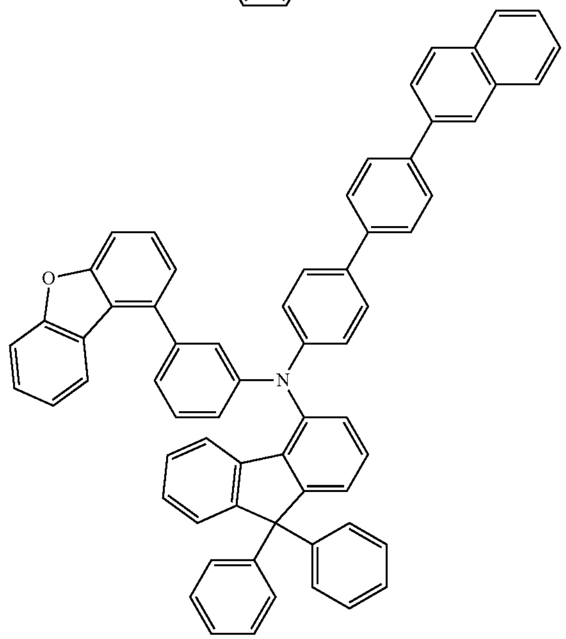

Material for Organic EL Device

The material for organic EL device comprises Compound (1). The content of Compound (1) in the material for organic EL device is, for example, 1% by mass or more (inclusive of 100%), preferably 10% by mass or more (inclusive of 100%), more preferably 50% by mass or more (inclusive of 100%), still more preferably 80% by mass or more (inclusive of 100%), and particularly preferably 90% by mass or more (inclusive of 100%). The material for organic EL device is useful for the production of an organic EL device.

Organic EL Device

The organic EL device of the invention will be described below.

The organic EL device comprises a cathode, an anode, and an organic layer disposed between the cathode and the anode. The organic layer comprises a light emitting layer and at least one layer of the organic layer comprises Compound (1).

Examples of the organic layer which comprises Compound (1) include a hole transporting region formed between an anode and a light emitting layer, such as a hole transporting layer, a hole injecting layer, an electron blocking layer, and an exciton blocking layer, a light emitting layer, a space layer, and an electron transporting region formed between a cathode and a light emitting layer, such as an electron transporting layer, an electron injecting layer, and a hole blocking layer, although not limited thereto. The compound (1) is used for the production of a fluorescent or phosphorescent EL device preferably as a material for a hole transporting region or a light emitting layer, more preferably as a material for a hole transporting region, and still more preferably as a material for a hole transporting layer, an electron blocking layer or an exciton blocking layer.

The organic EL device of the invention may be any of a fluorescent or phosphorescent single color emitting device, a white-emitting device of fluorescent-phosphorescent hybrid type, a simple-type emitting device having a single emission unit, and a tandem emitting device having two or more emission units, with a fluorescent device being preferred. The "emission unit" referred to herein is the smallest unit for emitting light by the recombination of injected holes and injected electrons, which comprises an organic layer, wherein at least one layer is a light emitting layer.

Representative device structures of the simple-type organic EL device are shown below:

(1) Anode/Emission Unit/Cathode

The emission unit may be a multi-layered structure comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the simple-type emission unit are shown below, wherein the layers in parentheses are optional:

(a) (Hole injecting layer/)Hole transporting layer/Fluorescent emitting layer(/Electron transporting layer/Electron injecting layer);

(b) (Hole injecting layer/)Hole transporting layer/Phosphorescent emitting layer(/Electron transporting layer/Electron injecting layer);

(c) (Hole injecting layer/)Hole transporting layer/First fluorescent emitting layer/Second fluorescent emitting layer(/Electron transporting layer/Electron injecting layer);

(d) (Hole injecting layer/)Hole transporting layer/First phosphorescent emitting layer/Second phosphorescent emitting layer(/Electron transporting layer/Electron injecting layer);

(e) (Hole injecting layer/)Hole transporting layer/Phosphorescent emitting layer/Space layer/Fluorescent emitting layer(/Electron transporting layer/Electron injecting layer);

(f) (Hole injecting layer/)Hole transporting layer/First phosphorescent emitting layer/Second phosphorescent emitting layer/Space layer/Fluorescent emitting layer(/Electron transporting layer/Electron injecting layer);

(g) (Hole injecting layer/)Hole transporting layer/First phosphorescent emitting layer/Space layer/Second phosphorescent emitting layer/Space layer/Fluorescent emitting layer(/Electron transporting layer/Electron injecting layer);

(h) (Hole injecting layer/)Hole transporting layer/Phosphorescent emitting layer/Space layer/First fluorescent emitting layer/Second fluorescent emitting layer(/Electron transporting layer/Electron injecting layer);

(i) (Hole injecting layer/)Hole transporting layer/Electron blocking layer/Fluorescent emitting layer(/Electron transporting layer/Electron injecting layer);

(j) (Hole injecting layer/)Hole transporting layer/Electron blocking layer/Phosphorescent emitting layer(/Electron transporting layer/Electron injecting layer);

(k) (Hole injecting layer/)Hole transporting layer/Exciton blocking layer/Fluorescent emitting layer(/Electron transporting layer/Electron injecting layer);

(l) (Hole injecting layer/)Hole transporting layer/Exciton blocking layer/Phosphorescent emitting layer(/Electron transporting layer/Electron injecting layer);

(m) (Hole injecting layer/)First hole transporting layer/Second hole transporting layer/Fluorescent emitting layer(/Electron transporting layer/Electron injecting layer);

(n) (Hole injecting layer/)First hole transporting layer/Second hole transporting layer/Phosphorescent emitting layer(/Electron transporting layer/Electron injecting layer);

(o) (Hole injecting layer/)First hole transporting layer/Second hole transporting layer/Fluorescent emitting layer/First electron transporting layer/Second electron transporting layer(/Electron injecting layer);

(p) (Hole injecting layer/)First hole transporting layer/Second hole transporting layer/Phosphorescent emitting layer/First electron transporting layer/Second electron transporting layer(/Electron injecting layer);

(q) (Hole injecting layer/)Hole transporting layer/Fluorescent emitting layer/Hole blocking layer(/Electron transporting layer/Electron injecting layer);

(r) (Hole injecting layer/)Hole transporting layer/Phosphorescent emitting layer/Hole blocking layer(/Electron transporting layer/Electron injecting layer);

(s) (Hole injecting layer/)Hole transporting layer/Fluorescent emitting layer/Exciton blocking layer(/Electron transporting layer/Electron injecting layer); and (t) (Hole injecting layer/)Hole transporting layer/Phosphorescent emitting layer/Exciton blocking layer(/Electron transporting layer/Electron injecting layer).

The emission colors of phosphorescent emitting layers or fluorescent emitting layers may be different. For example, the emission unit (f) may be (Hole injecting layer)/Hole transporting layer/First phosphorescent emitting layer (red emission)/Second phosphorescent emitting layer (green emission)/Space layer/Fluorescent emitting layer (blue emission)/Electron transporting layer.

An electron blocking layer may be disposed between each light emitting layer and the hole transporting layer or between each light emitting layer and the space layer, if necessary. Also, a hole blocking layer may be disposed between each light emitting layer and the electron transporting layer, if necessary. With such an electron blocking layer or a hole blocking layer, electrons and holes are confined in the light emitting layer to increase the charge recombination in the light emitting layer, thereby improving the emission efficiency.

Representative device structure of the tandem-type organic EL device is shown below:

(2) Anode/First Emission Unit/Intermediate Layer/Second Emission Unit/Cathode.

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer supplies electrons to the first emission unit and holes to the second emission unit and may be formed by known materials.

FIG. 1 is a schematic illustration showing the structure of an example of the organic EL device of the invention, wherein the organic EL device 1 comprises a substrate 2, an anode 3, a cathode 4, and an emission unit 10 disposed between the anode 3 and the cathode 4. The emission unit 10 comprises a light emitting layer 5. A hole transporting region 6 (for example, a hole injecting layer or a hole transporting layer) is disposed between the light emitting layer 5 and the anode 3, and an electron transporting region 7 (for example, an electron injecting layer or an electron transporting layer) is disposed between the light emitting layer 5 and the cathode 4. An electron blocking layer (not shown) may be disposed on the anode 3 side of the light emitting layer 5, and a hole blocking layer (not shown) may be disposed on the cathode 4 side of the light emitting layer 5. With these blocking layers, electrons and holes are confined in the light emitting layer 5 to increase the exciton generation in the light emitting layer 5.

Figure 2:
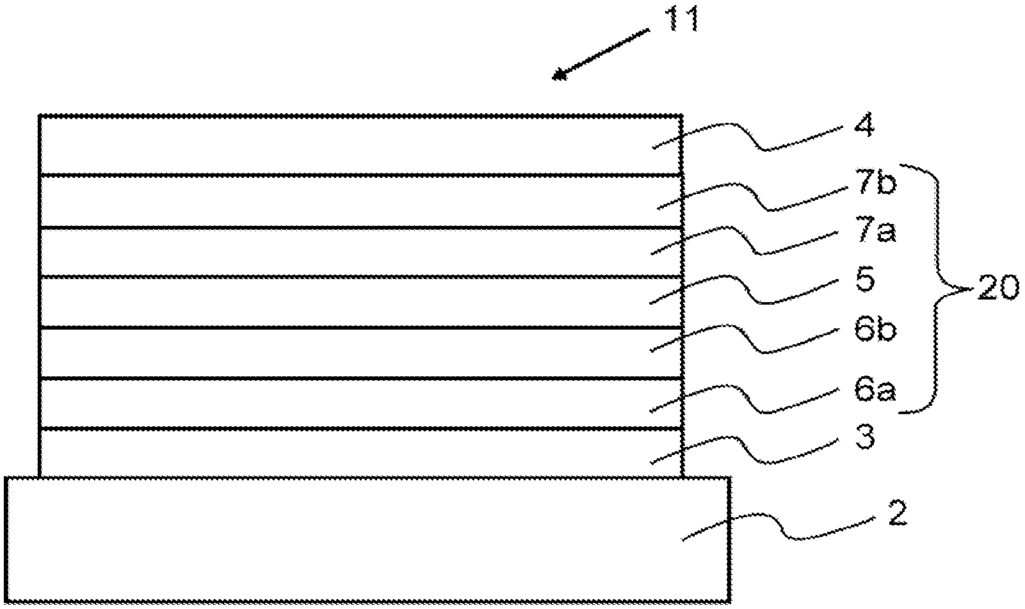
FIG. 2 is a schematic view showing another example of the layered structure of an organic EL device in an embodiment of the invention.

FIG. 2 is a schematic illustration showing the structure of another example of the organic EL device, wherein the organic EL device 11 comprises a substrate 2, an anode 3, a cathode 4, and an emission unit 20 disposed between the anode 3 and the cathode 4. The emission unit 20 comprises a light emitting layer 4. The hole transporting region disposed between the anode 3 and the light emitting layer 5 is formed by a first hole transporting layer 6*a* and a second hole transporting layer 6*b*. The electron transporting region disposed between the light emitting layer 5 and the cathode 4 is formed by a first electron transporting layer 7*a* and a second electron transporting layer 7*b*.

In the present invention, a host is referred to as a fluorescent host when combinedly used with a fluorescent dopant (fluorescent emitting material) and as a phosphorescent host when combinedly used with a phosphorescent dopant (phosphorescent emitting material). Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be used as a material for a fluorescent emitting layer. The same applies to the fluorescent host.

Substrate

The substrate is a support for the emitting device and made of, for example, glass, quartz, and plastics. The substrate may be a flexible substrate, for example, a plastic substrate made of polycarbonate, polyarylate, polyether sulfone, polypropylene, polyester, polyvinyl fluoride, or polyvinyl chloride. An inorganic deposition film is also usable.

Anode

The anode is formed on the substrate preferably from a metal, an alloy, an electrically conductive compound, and a mixture thereof, each having a large work function, for example, 4.0 eV or more. Examples of the material for the anode include indium oxide-tin oxide (ITO: indium tin oxide), indium oxide-tin oxide doped with silicon or silicon oxide, indium oxide-zinc oxide, indium oxide doped with tungsten oxide and zinc oxide, and graphene. In addition, gold (Au), platinum (Pt), nickel (Ni), tungsten (W), chromium (Cr), molybdenum (Mo, iron (Fe), cobalt (Co), copper (Cu), palladium (Pd), titanium (Ti), and a nitride of the above metal (for example, titanium nitride) are also usable.

These anode materials are made into a film generally by a sputtering method. For example, a film of indium oxide-zinc oxide is formed by sputtering an indium oxide target doped with 1 to 10 wt % of zinc oxide, and a film of indium oxide doped with tungsten oxide and zinc oxide is formed by sputtering an indium oxide target doped with 0.5 to 5 wt % of tungsten oxide and 0.1 to 1 wt % of zinc oxide. In addition, a vacuum vapor deposition method, a coating method, an inkjet method, and a spin coating method are usable.

A hole injecting layer to be optionally formed in contact with the anode is formed from a material which is capable of easily injecting holes independently of the work function of the anode. Therefore, the anode can be formed by a material generally known as an electrode material, for example, a metal, an alloy, an electroconductive compound, a mixture thereof, and a group 1 element and a group 2 element of the periodic table.

A material having a small work function belonging to a group 1 or a group 2 of the periodic table, for example, an alkali metal, such as lithium (Li) and cesium (Cs), an alkaline earth metal, such as magnesium (Mg), calcium (Ca), and strontium (Sr), and an alloy thereof, such as MgAg and AlLi, are also usable as an anode material. In addition, a rare earth metal, such as europium and ytterbium, and an alloy thereof are also usable. The alkali metal, the alkaline earth metal, and the alloy thereof is made into the anode by a vacuum vapor deposition or a sputtering method. When a silver paste is used, a coating method and an inkjet method are usable.

Hole Injecting Layer

The hole injecting layer comprises a material having a high hole injecting ability (hole injecting material). The compound (1) may be used in a hole injecting layer alone or in combination with the material described below.

Examples of the hole injecting material other than Compound (1) include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

The following low molecular aromatic amine compound is also usable as the hole injecting layer material: 4,4',4"-tris(N,N-diphenylamino)triphenylamine (TDATA), 4,4',4"-tris[N-(3-methylphenyl)-N-phenylamino]triphenylamine (MTDATA), 4,4'-bis[N-(4-diphenylaminophenyl)-N-phenylamino]biphenyl (DPAB), 4,4'-bis(N-{4-[N'-(3-methylphenyl)-N'-phenylamino]phenyl}-N-phenylamino)biphenyl (DNTPD), 1,3,5-tris[N-(4-diphenylaminophenyl)-N-phenylamino]benzene (DPA3B), 3-[N-(9-phenylcarbazole-3-yl)-N-phenylamino]-9-phenylcarbazole (PCzPCA1), 3,6-bis[N-(9-phenylcarbazole-3-yl)-N-phenylamino]-9-phenylcarbazole (PCzPCA2), and 3-[N-(1-naphthyl)-N-(9-phenylcarbazole-3-yl)amino]-9-phenylcarbazole (PCzPCN1).

A macromolecular compound, such as an oligomer, a dendrimer, a polymer, is also usable as the hole injecting layer material. Examples thereof include poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacrylamide](PTPDMA), and poly[N,N'-bis(4-butylphenyl)-N,N'-bis(phenyl)benzidine] (Poly-TPD). A macromolecular compound doped with an acid, such as poly(3,4-ethylenedioxythiophene)/poly(styrenesulfonic acid) (PEDOT/PSS) and polyaniline/poly(styrenesulfonic acid) (PAni/PSS), is also usable.

In addition, an acceptor material, such as a hexaazatriphenylene (HAT) compound represented by formula (K), is preferably used in combination with Compound (1):

(K)

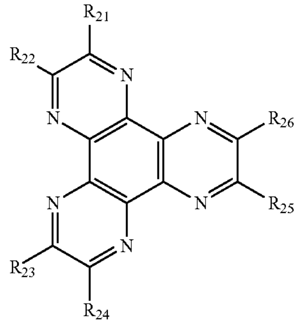

wherein:

$R_{21}$ to $R_{26}$ are each independently a cyano group, $-CONH_2$, a carboxyl group, or $-COOR_{27}$ wherein $R_{27}$ is an alkyl group having 1 to 20 carbon atoms or a cycloalkyl group having 3 to 20 ring carbon atoms, or adjacent two selected from $R_{21}$ and $R_{22}$, $R_{23}$ and $R_{24}$, and $R_{25}$ and $R_{26}$ may be bonded to each other to form a group represented by —CO—O—CO—.

Examples of $R_{27}$ include a methyl group, an ethyl group, a n-propyl group, an isopropyl group, a n-butyl group, an isobutyl group, a t-butyl group, a cyclopentyl group, and a cyclohexyl group.

Hole Transporting Layer

The hole transporting layer comprises a material having a high hole transporting ability (hole transporting material). The compound (1) is preferably used in a hole transporting layer alone or in combination with the compound described below.

Examples of the hole transporting material other than Compound (1) includes an aromatic amine compound, a carbazole derivative, and an anthracene derivative.

Examples of the aromatic amine compound include 4,4'-bis[N-(1-naphthyl)-N-phenylamino]biphenyl (NPB), N,N'-bis(3-methylphenyl)-N,N'-diphenyl-[1,1'-biphenyl]-4,4'-diamine (TPD), 4-phenyl-4'-(9-phenylfluorene-9-yl) triphenylamine (BAFLP), 4,4'-bis[N-(9,9-dimethylfluorene-2-yl)-N-phenylamino]biphenyl (DFLDPBi), 4,4',4"-tris(N,N-diphenylamino)triphenylamine (TDATA), 4,4',4"-tris[N-(3-methylphenyl)-N-phenylamino]triphenylamine (MTDATA), and 4,4'-bis[N-(spiro-9,9'-bifluorene-2-yl)-N-phenylamino]biphenyl (BSPB). The above compounds have a hole mobility of $10^{-6}$ $cm^2/Vs$ or more.

Examples of the carbazole derivative include 4,4'-di(9-carbazolyl)biphenyl (CBP), 9-[4-(9-carbazolyl)phenyl]-10-phenylanthracene (CzPA), and 9-phenyl-3-[4-(10-phenyl-9-anthryl)phenyl]-9H-carbazole (PCzPA).

Examples of the anthracene derivative include 2-t-butyl-9,10-di(2-naphthyl)anthracene (t-BuDNA), 9,10-di(2-naphthyl)anthracene (DNA), and 9,10-diphenylanthracene (DPAnth).

In addition, a macromolecular compound, such as poly (N-vinylcarbazole) (PVK) and poly(4-vinyltriphenylamine) (PVTPA) are usable.

Compounds other than those mentioned above are also usable, if their hole transporting ability is higher than their electron transporting ability.

The hole transporting layer may be a single layer or a multi-layer of two or more layers. For example, the hole transporting layer may be a two-layered structure comprising a first hole transporting layer (anode side) and a second hole transporting layer (cathode side). In an embodiment of the invention, a hole transporting layer of a single-layered structure is preferably in contact with a light emitting layer and a hole transporting layer in a multi-layered structure which is closest to a cathode, for example, the second hole transporting layer in the two-layered structure mentioned above, is preferably in contact with a light emitting layer. In another embodiment of the invention, an electron blocking layer may be disposed between the light emitting layer and the hole transporting layer of the single-layered structure or between the light emitting layer and the hole transporting layer in the multi-layered structure which is closest to the light emitting layer.

In the two-layered structure of the hole transporting layer, Compound (1) may be included in one or both of the first hole transporting layer and the second hole transporting layer. The compound (1) included in the first hole transporting layer and Compound (1) included in the second hole transporting layer are different.

In an embodiment of the invention, Compound (1) is preferably used in only the first hole transporting layer. In another embodiment, Compound (1) is preferably used in only the second hole transporting layer. In still another embodiment, Compound (1) is preferably used in both the first hole transporting layer and the second hole transporting layer.

Dopant Material of Light Emitting Layer

The light emitting layer comprises a highly light-emitting material (dopant material) and may be formed from a various kind of materials. For example, a fluorescent emitting material and a phosphorescent emitting material are usable as the dopant material. The fluorescent emitting material is a compound capable of emitting light from a singlet excited state, and the phosphorescent emitting material is a compound capable of emitting light from a triplet excited state.

Examples of blue fluorescent emitting material usable in the light emitting layer include a pyrene derivative, a styrylamine derivative, a chrysene derivative, a fluoranthene derivative, a fluorene derivative, a diamine derivative, and a triarylamine derivative, such as N,N'-bis[4-(9H-carbazole-9-yl)phenyl]-N,N'-diphenylstilbene-4,4'-diamine (YGA2S), 4-(9H-carbazole-9-yl)-4'-(10-phenyl-9-anthryl)triphenylamine (YGAPA), and 4-(10-phenyl-9-anthryl)-4'-(9-phenyl-9H-carbazole-3-yl)triphenylamine (PCBAPA).

Examples of green fluorescent emitting material usable in the light emitting layer include an aromatic amine derivative, such as N-(9,10-diphenyl-2-anthryl)-N,9-diphenyl-9H-carbazole-3-amine (2PCAPA), N-[9,10-bis(1,1'-biphenyl-2-yl)-2-anthryl]-N,9-diphenyl-9H-carbazole-3-amine (2PCABPhA), N-(9,10-diphenyl-2-anthryl)-N,N',N'-triphenyl-1,4-phenylenediamine (2DPAPA), N-[9,10-bis(1,1'-biphenyl-2-yl)-2-anthryl]-N,N',N'-triphenyl-1,4-phenylenediamine (2DPABPhA), N-[9,10-bis(1,1'-biphenyl-2-yl)]-N-[4-(9H-carbazole-9-yl)phenyl]-N-phenylanthracene-2-amine (2YGABPhA), and N,N,9-triphenylanthracene-9-amine (DPhAPhA).

Examples of red fluorescent emitting material usable in the light emitting layer include a tetracene derivative and a diamine derivative, such as N,N,N',N'-tetrakis(4-methylphenyl)tetracene-5,11-diamine (p-mPhTD) and 7,14-diphenyl-N,N,N',N'-tetrakis(4-methylphenyl)acenaphtho[1,2-a]fluoranthene-3,10-diamine (p-mPhAFD).

Examples of blue phosphorescent emitting material usable in the light emitting layer include a metal complex, such as an iridium complex, an osmium complex, and a platinum complex. Examples thereof include bis[2-(4',6'-difluorophenyl)pyridinato-N,C2']iridium(III) tetrakis(1-pyrazolyl)borato (FIro), bis[2-(4',6'-difluorophenyl)pyridinato-N,C2']iridium(III) picolinato (FIrpic), bis[2-(3',5'-bistrifluoromethylphenyl)pyridinato-N,C2']iridium(III) picolinato ($Ir(CFsppy)_2(pic)$), and bis[2-(4',6'-difluorophenyl)pyridinato-N,C2']iridium(III) acetylacetonato (FIracac).

Examples of green phosphorescent emitting material usable in the light emitting layer include an iridium complex, such as tris(2-phenylpyridinato-N,C2')iridium(III) (Ir(ppy)s), bis(2-phenylpyridinato-N,C2')iridium(III) acetylacetonato ($Ir(ppy)_2(acac)$), bis(1,2-diphenyl-1H-benzimidazolato)iridium(III) acetylacetonato ($Ir(pbi)_2(acac)$), and bis(benzo[h]quinolinato)iridium(III) acetylacetonato ($Ir(bzq)_2(acac)$).

Examples of red phosphorescent emitting material usable in the light emitting layer include a metal complex, such as an iridium complex, a platinum complex, a terbium complex, and a europium complex. Examples thereof include an organometallic complex, such as bis[2-(2'-benzo[4,5-a]thienyl)pyridinato-N,C3']iridium(III) acetylacetonato ($Ir(btp)_2(acac)$), bis(1-phenylisoquinolinato-N,C2')iridium(III) acetylacetonato ($Ir(piq)_2(acac)$), (acetylacetonato)bis[2,3-bis(4-fluorophenyl)quinoxalinato]iridium(III) ($Ir(Fdpq)_2(acac)$), and 2,3,7,8,12,13,17,18-octaethyl-21H,23H-porphyrin platinum(II) (PtOEP).

A rare earth metal complex, such as tris(acetylacetonato)(monophenanthroline)terbium(III) ($Tb(acac)_3(Phen)$), tris(1,3-diphenyl-1,3-propanedionato)(monophenanthroline)europium(III) ($Eu(DBM)_3(Phen)$), and tris[1-(2-thenoyl)-3,3,3-trifluoroacetonato](monophenanthroline)europium(III) ($Eu(TTA)_3(Phen)$), emits light from the rare earth metal ion (electron transition between different multiple states), and therefore, usable as a phosphorescent emitting material.

Host Material for Light Emitting Layer

The light emitting layer may be a layer wherein the above dopant material is dispersed in another material (host material). The compound (1) may be used as a host material or a co-host material of a fluorescent or phosphorescent light emitting layer, although other materials are usable. The host material preferably has a lowest unoccupied molecular orbital level (LUMO level) higher than that of the dopant material and a highest occupied molecular orbital level (HOMO level) lower than that of the dopant material.

The host material other Compound (1) may include, for example, (1) a metal complex, such as an aluminum complex, a beryllium complex, and a zinc complex;

(2) a heterocyclic compound, such as an oxadiazole derivative, a benzimidazole derivative, and a phenanthroline derivative;

(3) a fused aromatic compound, such as a carbazole derivative, an anthracene derivative, a phenanthrene derivative, a pyrene derivative, and a chrysene derivative; and (4) an aromatic amine compound, such as a triarylamine derivative and a fused aromatic polycyclic amine derivative.

Examples thereof include:

a metal complex, such as tris(8-quinolinolato)aluminum (III) (Alq), tris(4-methyl-8-quinolinolato)aluminum (III) ($Almg_3$), bis(10-hydroxybenzo[h]quinolinato)beryllium(II) ($BeBq_2$), bis(2-methyl-8-quinolinolato)(4-phenylphenolato)aluminum(III) (BAlq), bis(8- quinolinolato)zinc(II) (Znq), bis[2-(2-benzoxazolyl) phenolato]zinc(II) (ZnPBO), and bis[2-(2-benzothiazolyl)phenolato]zinc(II) (ZnBTZ);

a heterocyclic compound, such as 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-biphenylyl)-4-phenyl-5-(4-tert-butylphenyl)-1,2,4-triazole (TAZ), 2,2',2"-(1,3,5-benzenetriyl)tris(1-phenyl-1H-benzimidazole) (TPBI), bathophenanthroline (BPhen), and bathocuproin (BCP);

a fused aromatic compound, such as 9-[4-(10-phenyl-9-anthryl)phenyl]-9H-carbazole (CzPA), 3,6-diphenyl-9-[4-(10-phenyl-9-anthryl)phenyl]-9H-carbazole (DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (t-BuDNA), 9,9'-bianthryl (BANT), 9,9'-(stilbene-3,3'-diyl)diphenanthrene (DPNS), 9,9'-(stilbene-4,4'-diyl) diphenanthrene (DPNS2), 3,3',3"-(benzene-1,3,5-triyl) tripyrene (TPB3), 9,10-diphenylanthracene (DPAnth), and 6,12-dimethoxy-5,11-diphenylchrysene; and an aromatic amine compound, such as N,N-diphenyl-9-[4-(10-phenyl-9-anthryl)phenyl]-9H-carbazole-3-amine (CzA1PA), 4-(10-phenyl-9-anthryl)triphenylamine (DPhPA), N,9-diphenyl-N-[4-(10-phenyl-9-anthryl)phenyl]-9H-carbazole-3-amine (PCAPA), N,9-diphenyl-N-{4-[4-(10-phenyl-9-anthryl)phenyl] phenyl}-9H-carbazole-3-amine (PCAPBA), N-(9,10-diphenyl-2-anthryl)-N,9-diphenyl-9H-carbazole-3-amine (2PCAPA), 4,4'-bis[N-(1-anthryl)-N-phenylamino]biphenyl (NPB or α-NPD), N,N'-bis(3-methylphenyl)-N,N'-diphenyl-[1,1'-biphenyl]-4,4'-diamine (TPD), 4,4'-bis[N-(9,9-dimethylfluorene-2-yl)-N-phenylamino]biphenyl (DFLDPBi), and 4,4'-bis [N-(spiro-9,9'-bifluorene-2-yl)-N-phenylamino] biphenyl (BSPB).

The host material may be used alone or in combination of two or more.

In particular, as a host material for a blue fluorescent device, the following anthracene compound is preferably used.

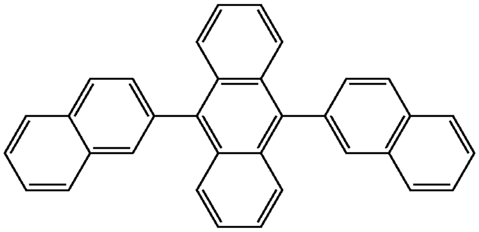

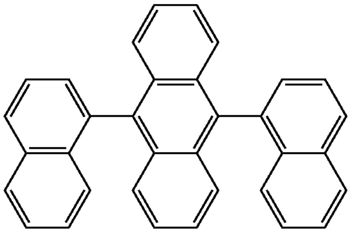

-continued

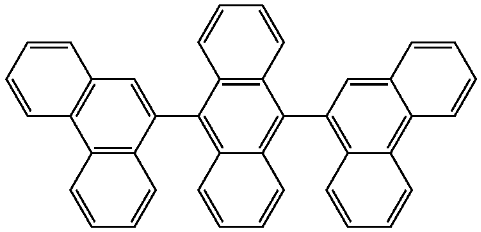

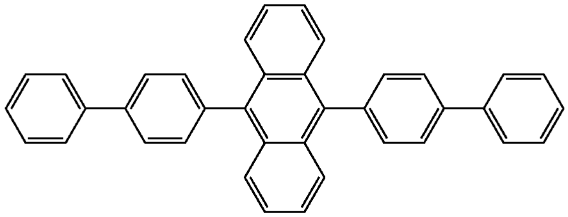

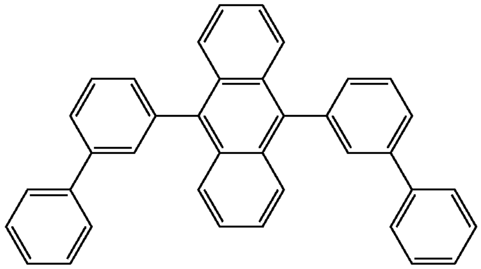

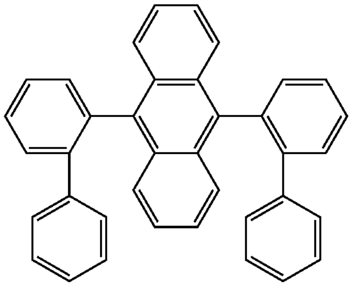

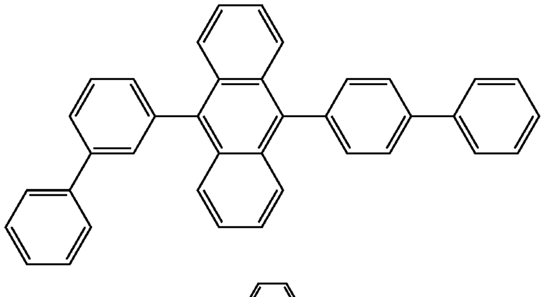

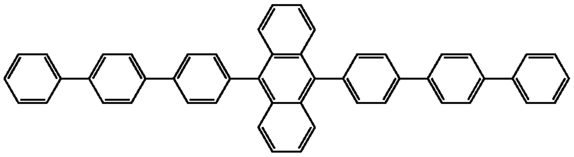

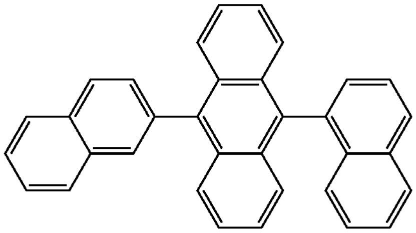

-continued
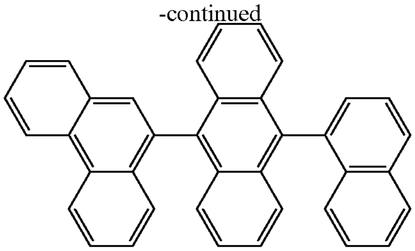
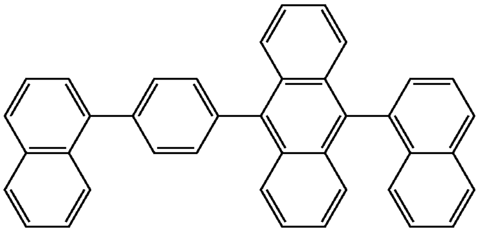
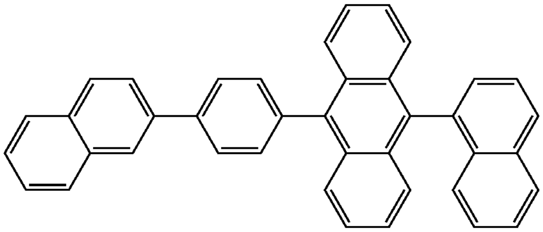
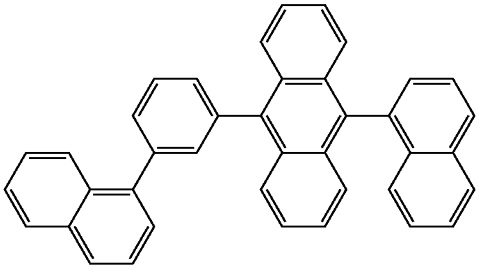
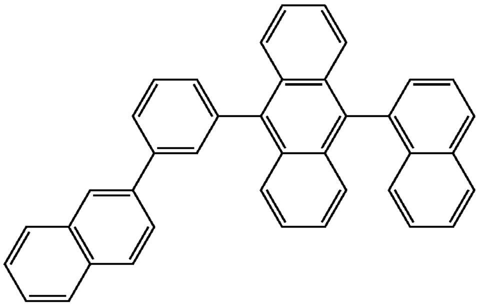
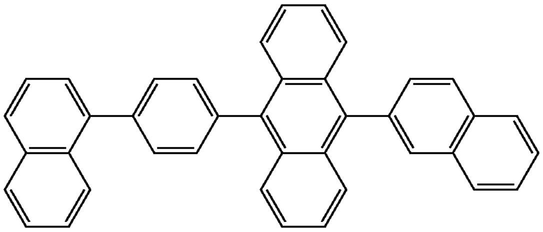
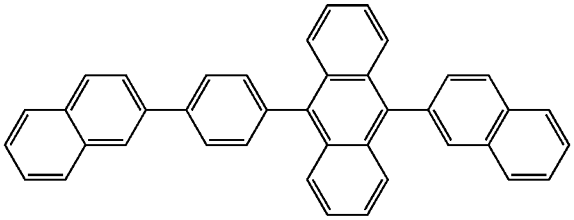
-continued
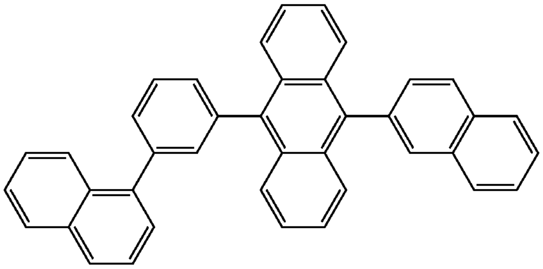
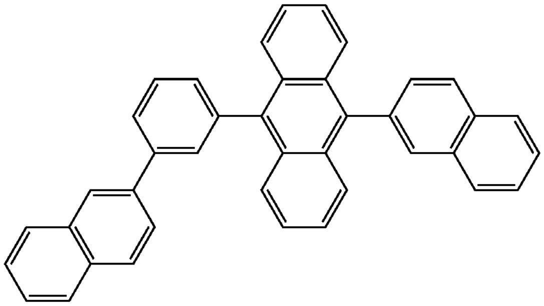
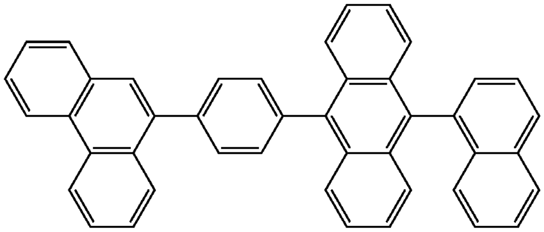
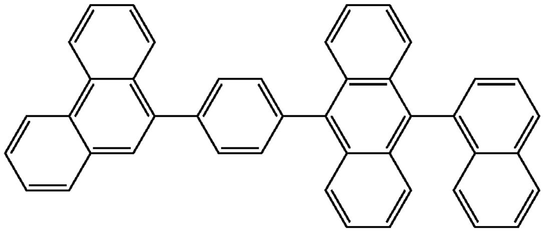
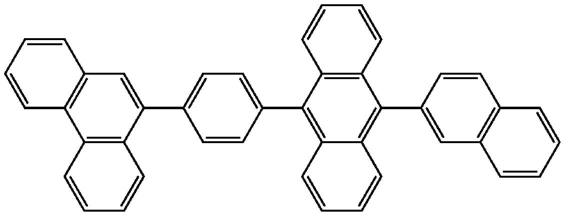
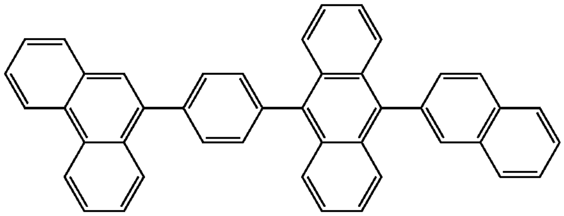

-continued
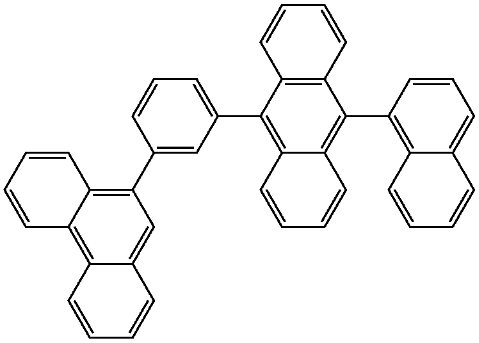
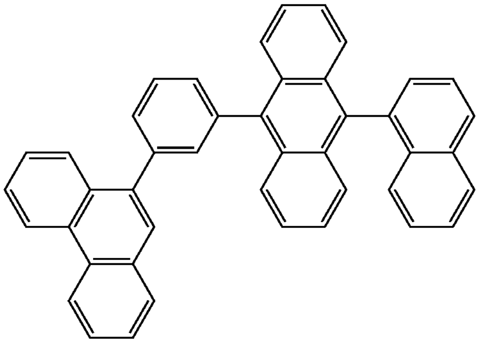
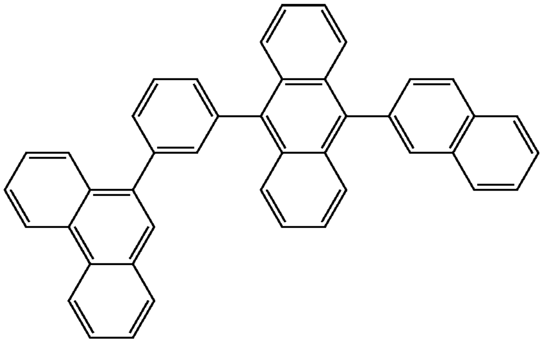
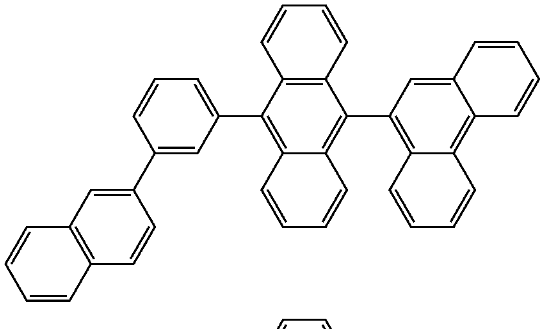
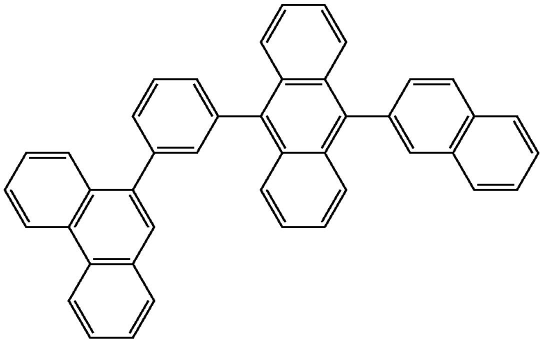
-continued
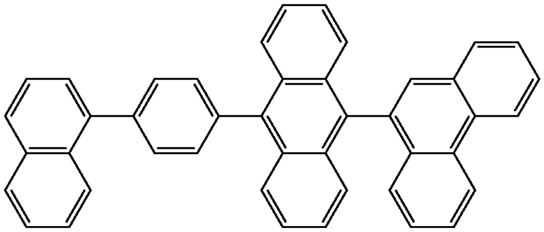
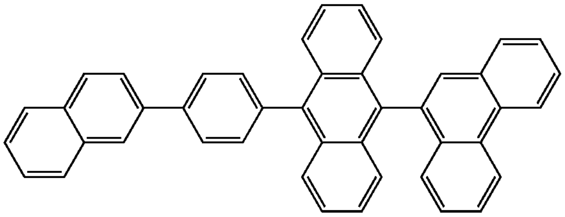
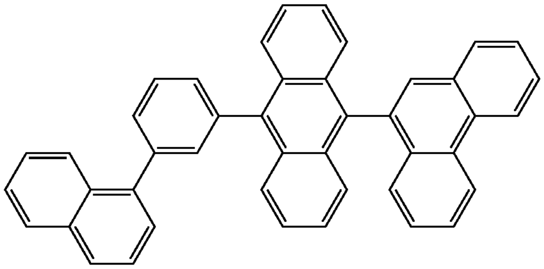
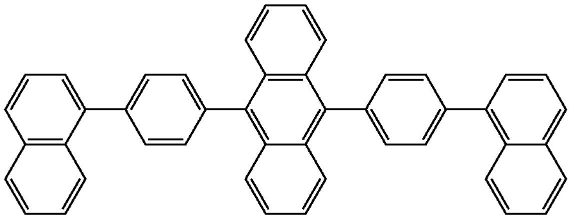
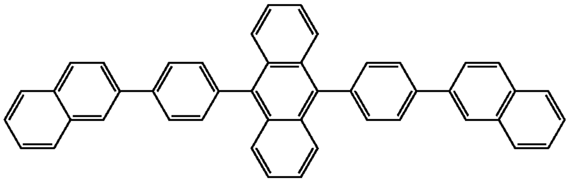
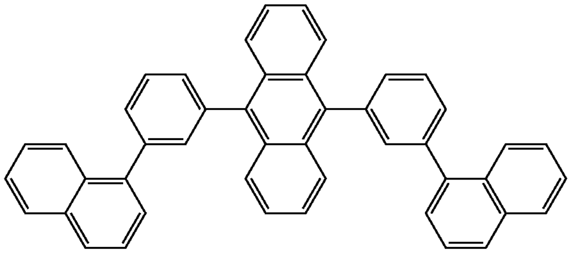
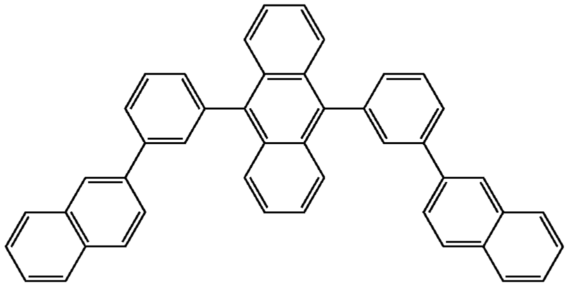

-continued
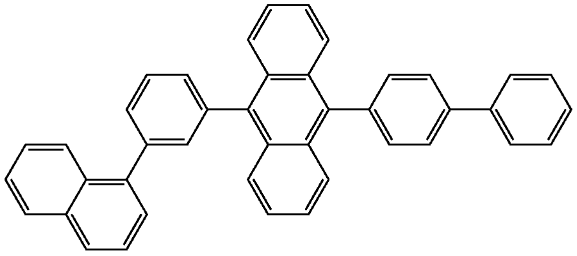
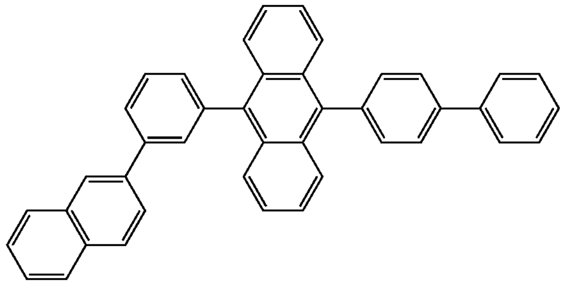
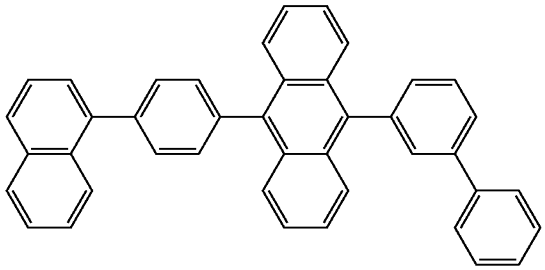
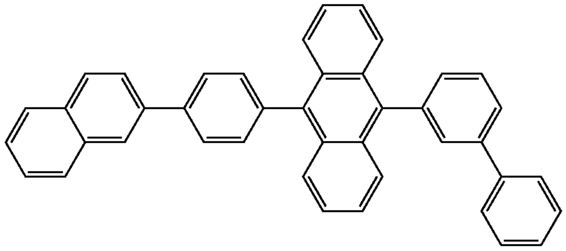
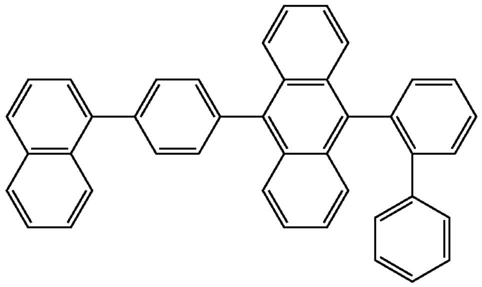
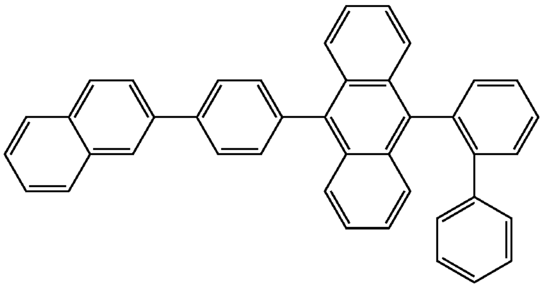
-continued
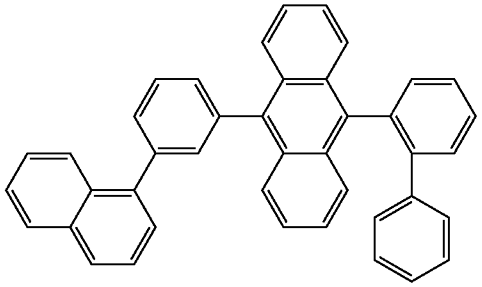
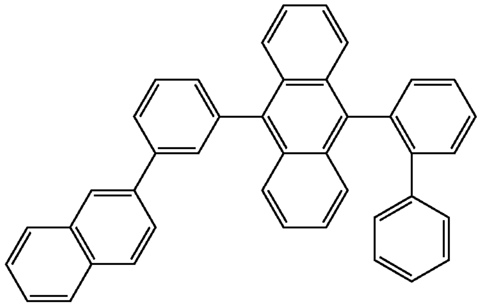
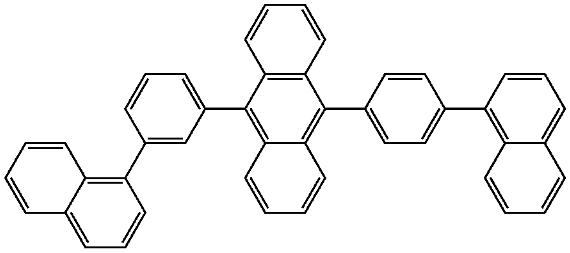
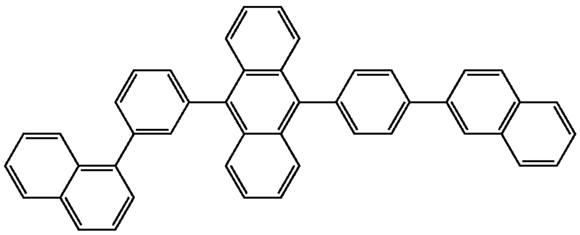
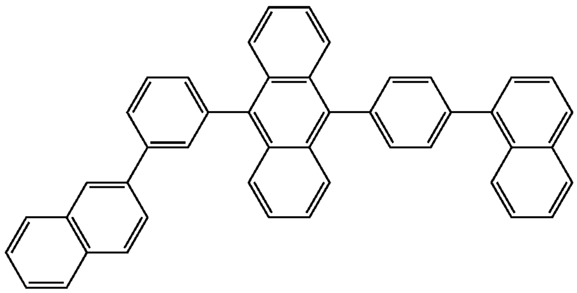
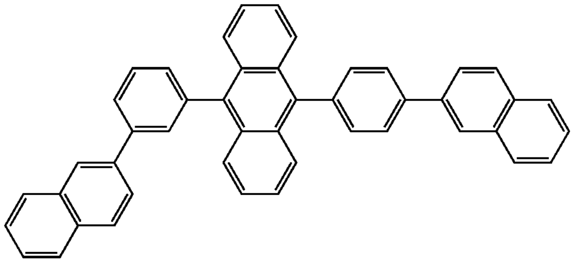

-continued
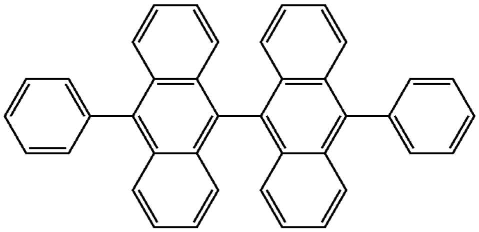
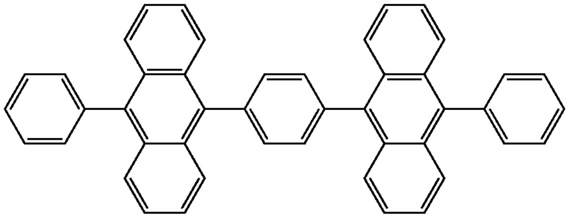
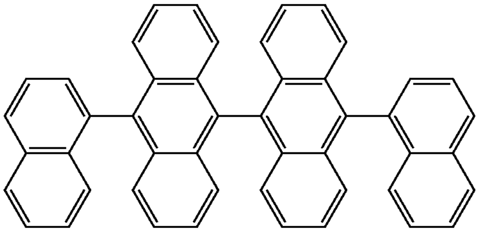
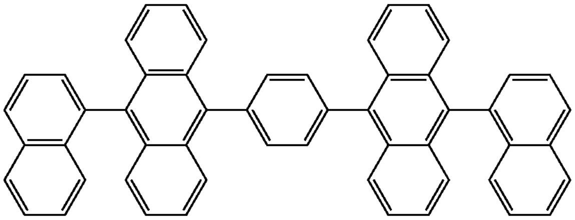
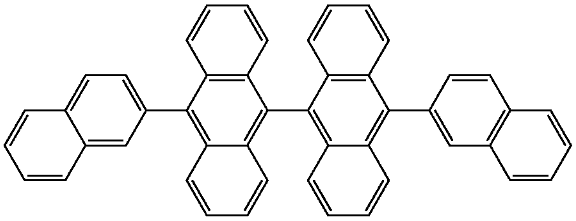
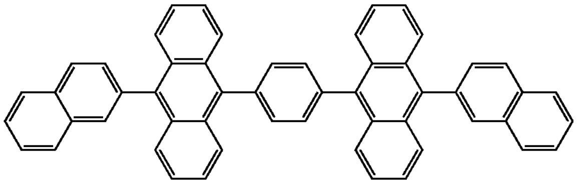
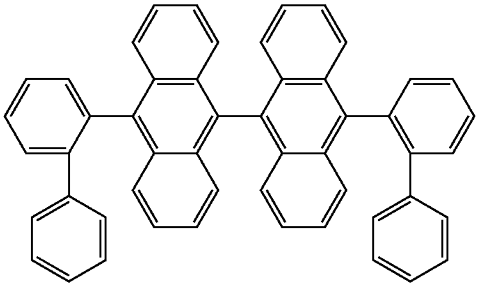
-continued
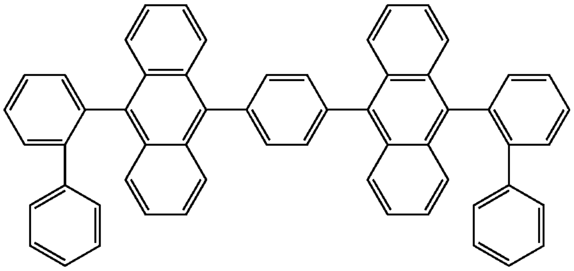
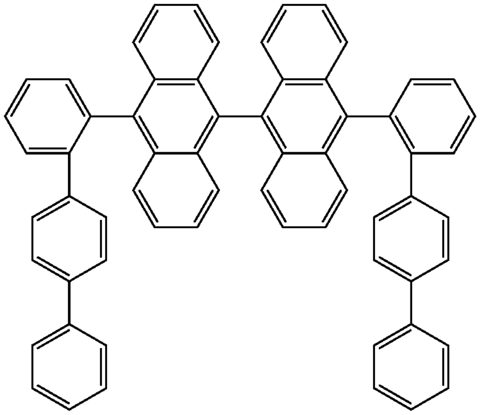
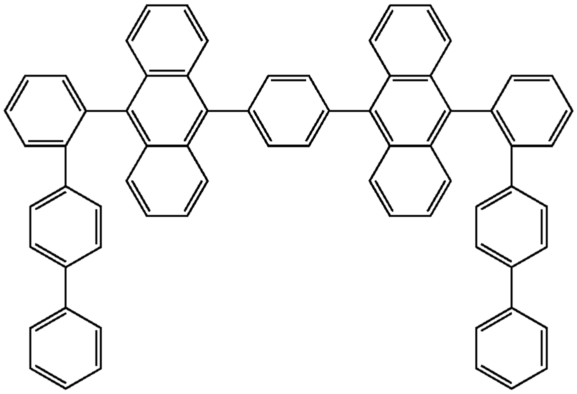
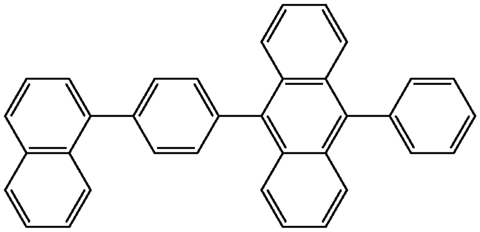
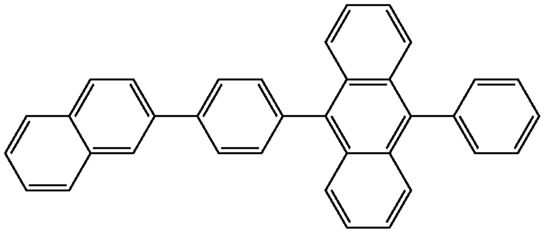

-continued
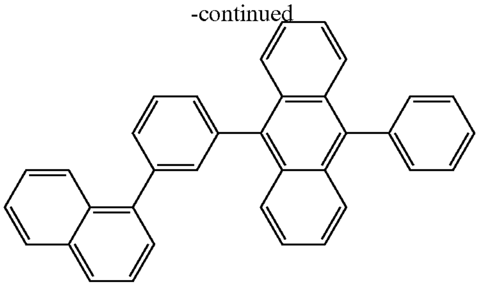
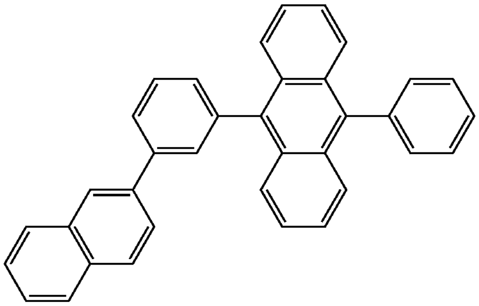
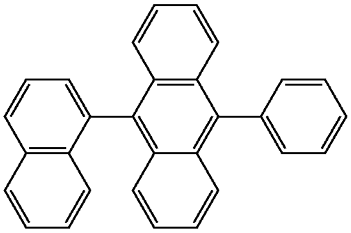
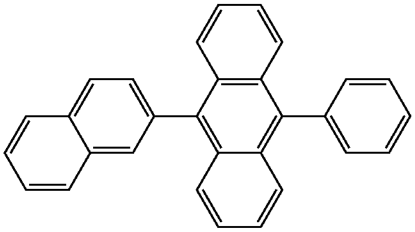
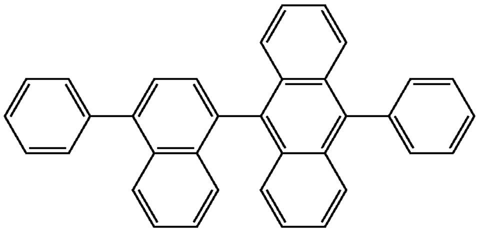
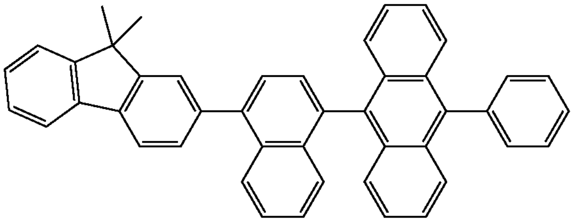
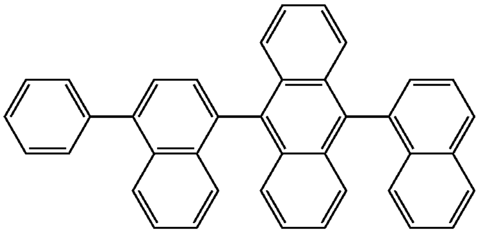
-continued
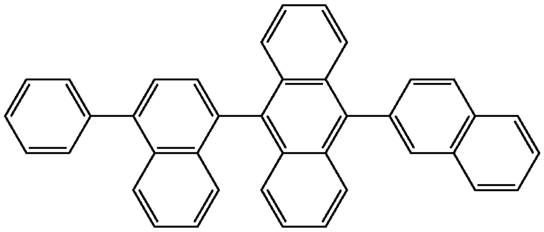
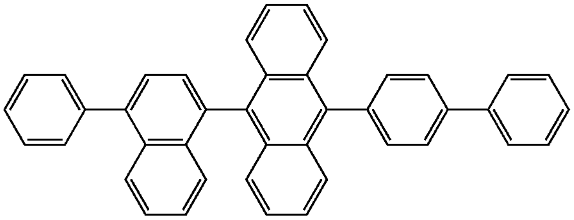
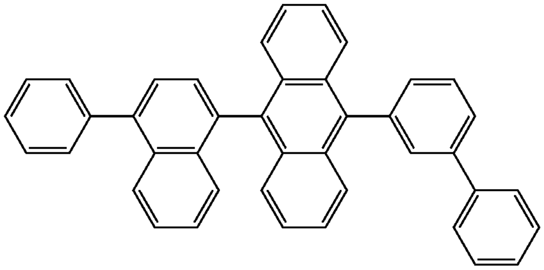
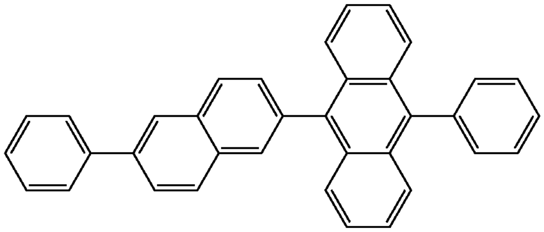
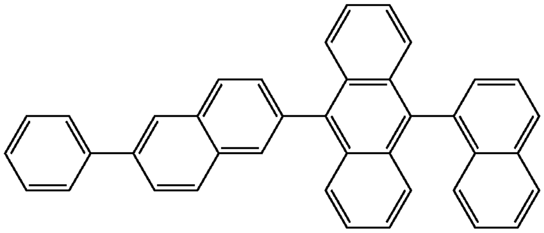
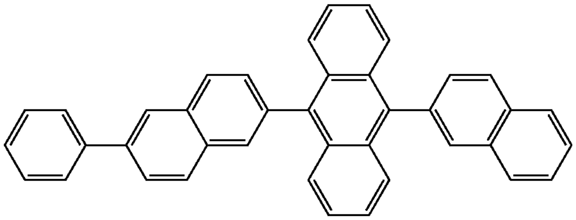
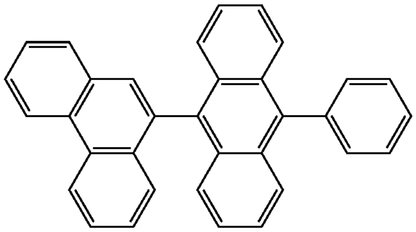

-continued
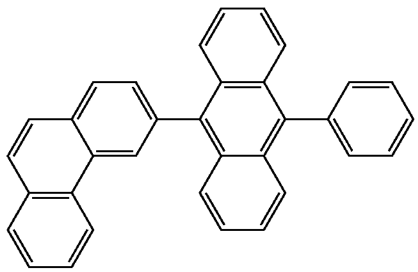
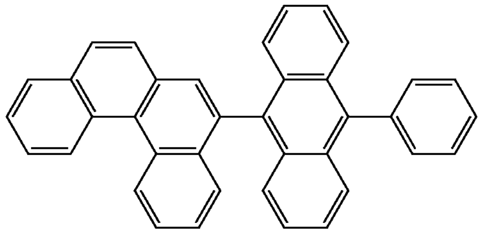
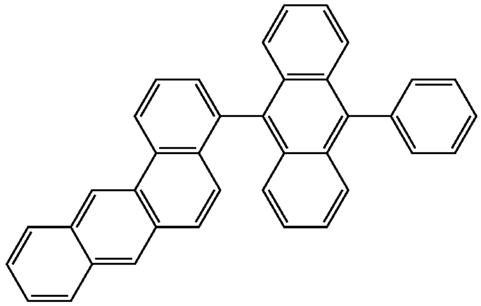
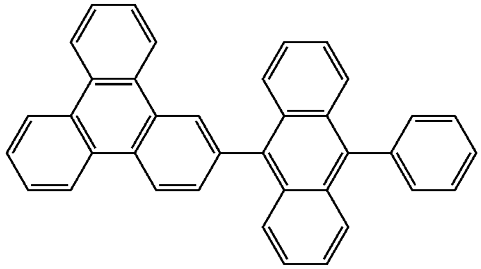
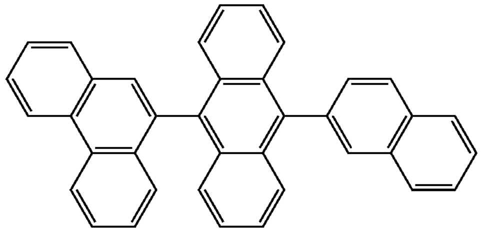
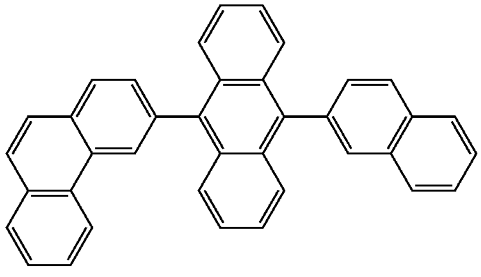
-continued
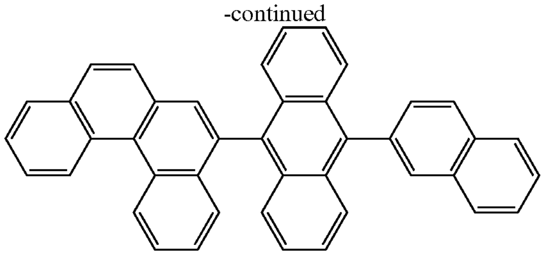
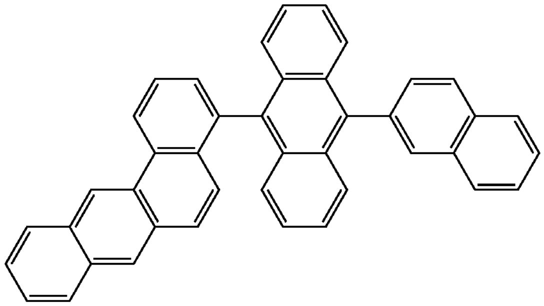
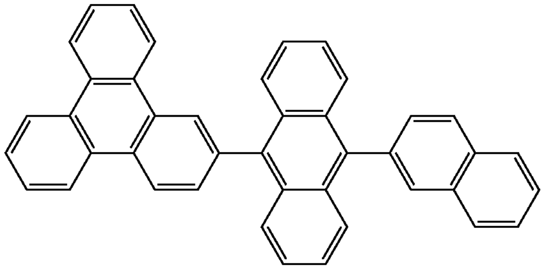
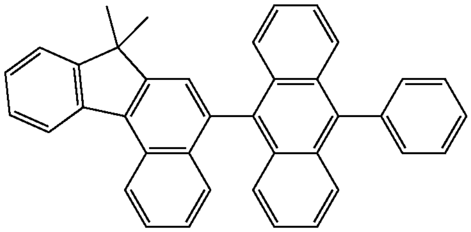
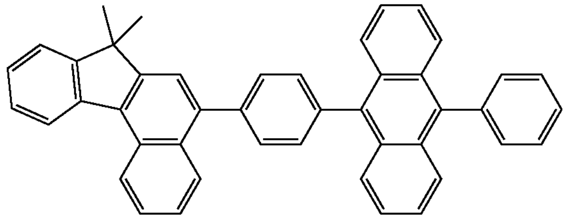
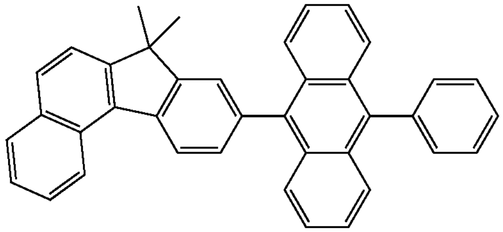
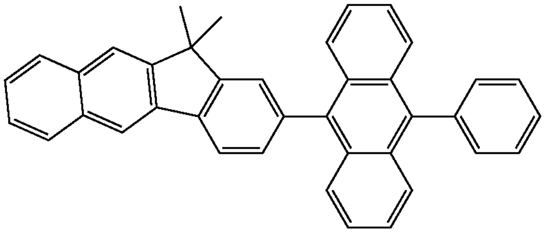

-continued
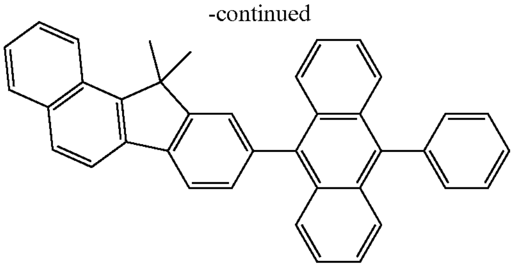
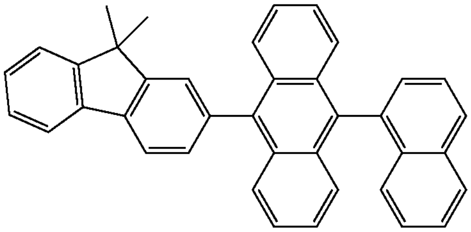
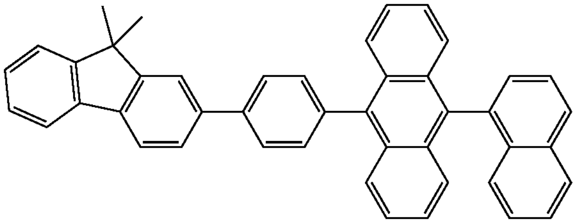
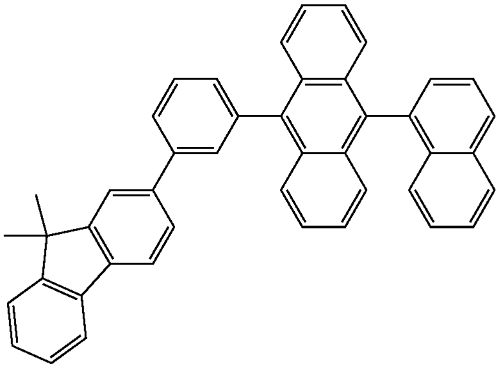
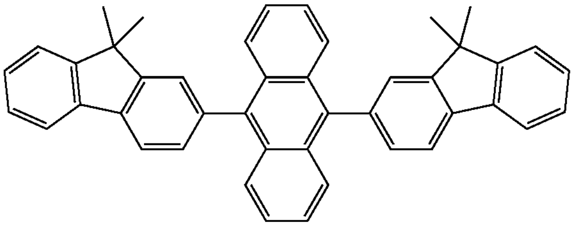
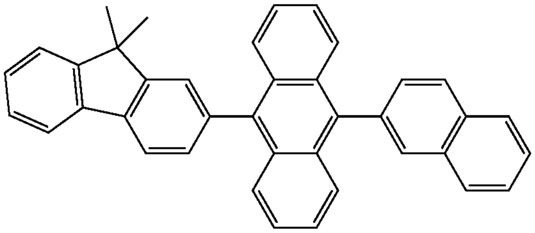
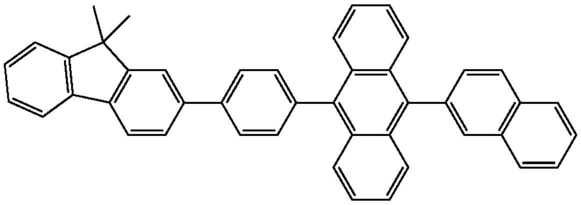
-continued
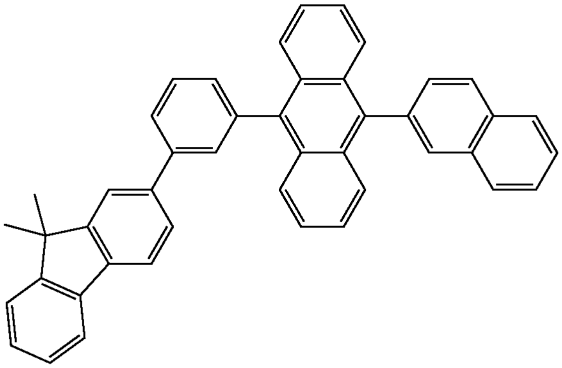
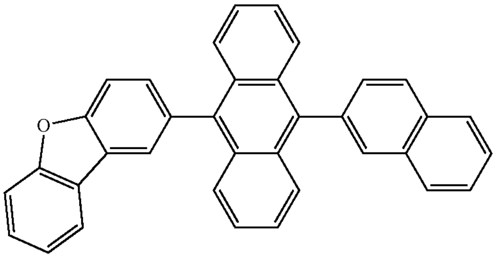
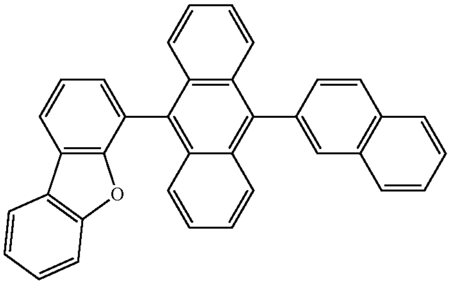
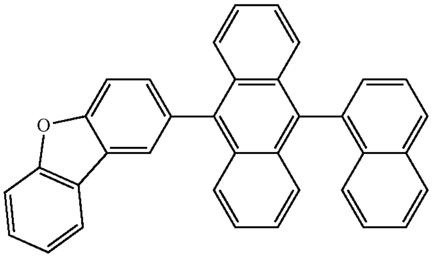
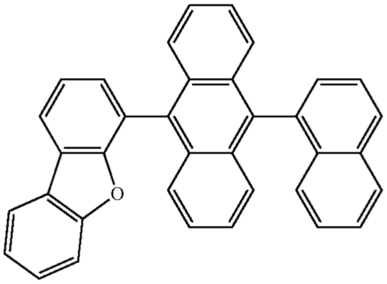
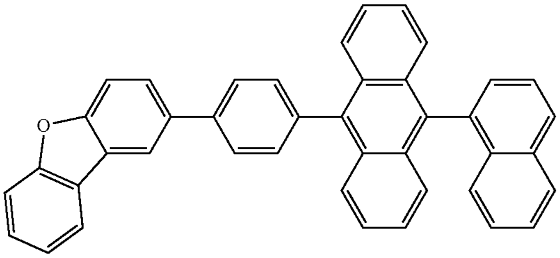

-continued
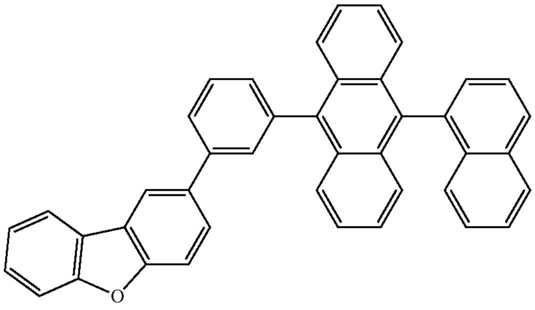
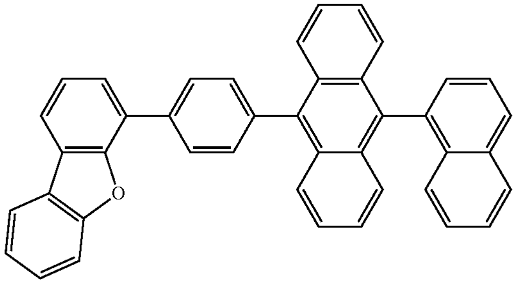
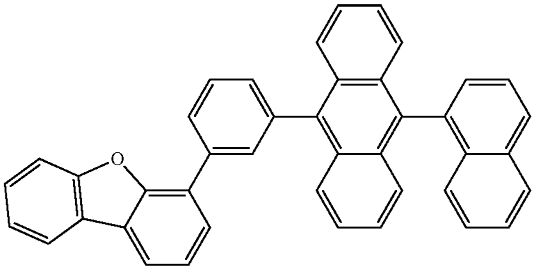
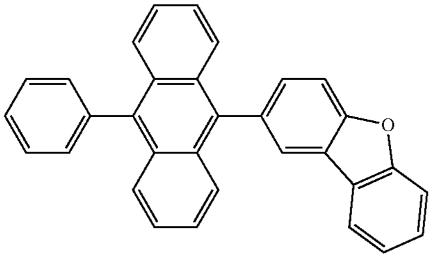
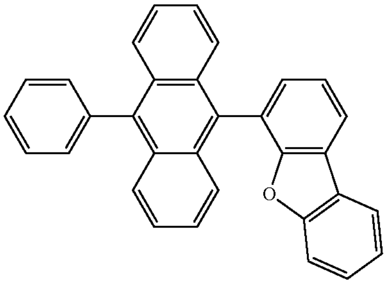
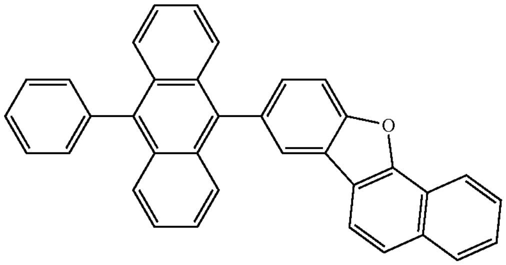
-continued
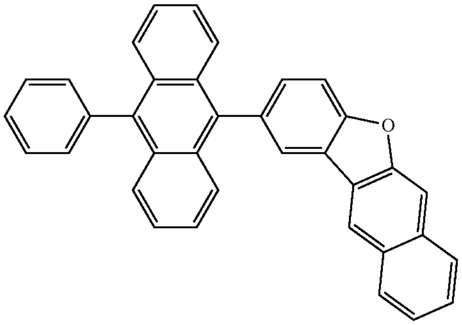
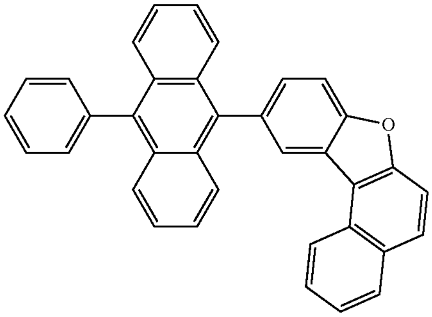
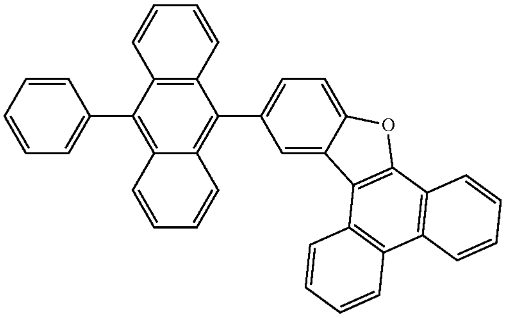
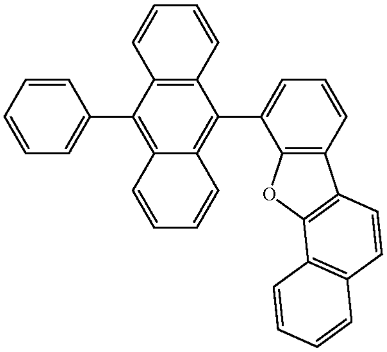
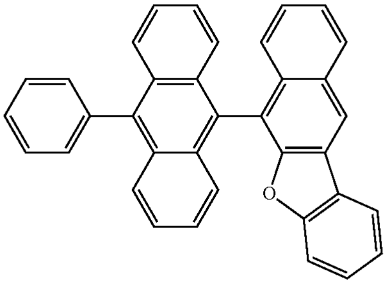

-continued
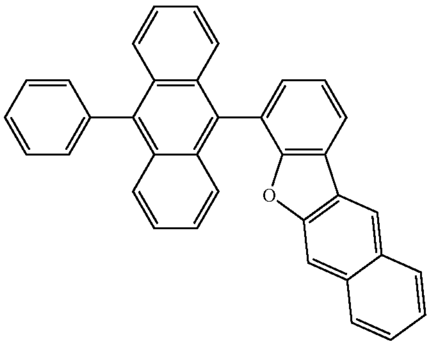
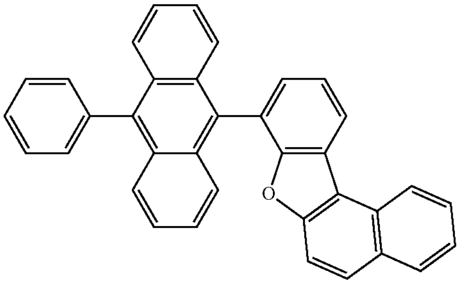
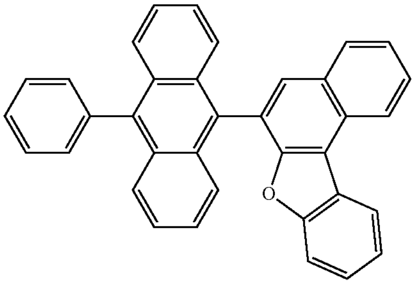
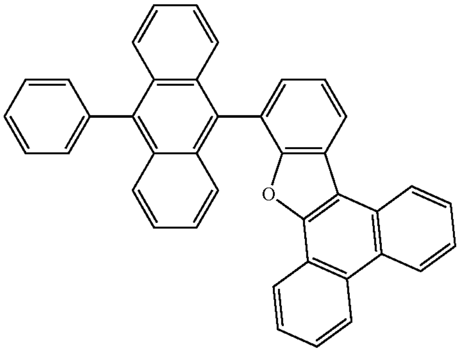
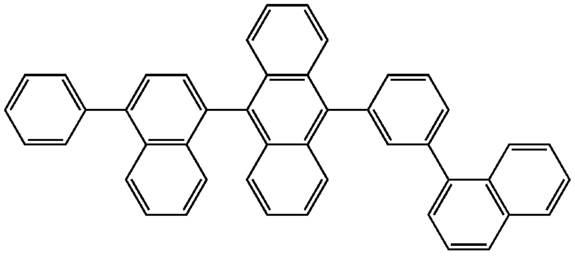
-continued
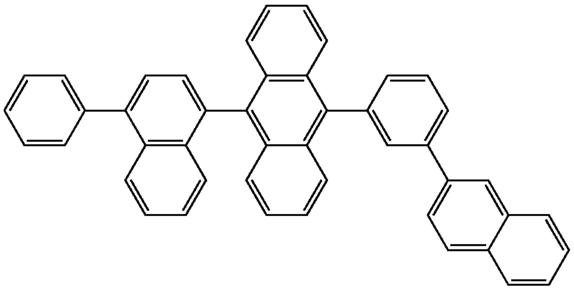
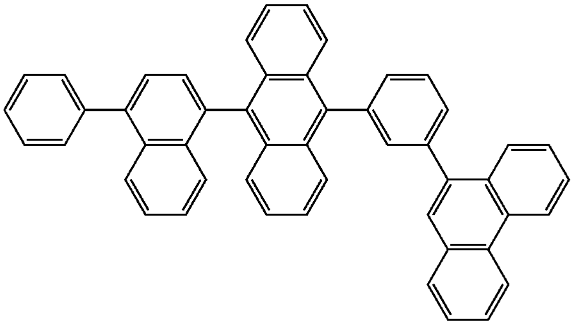
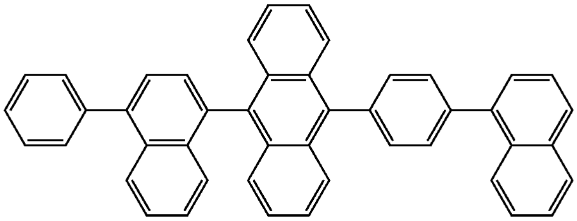
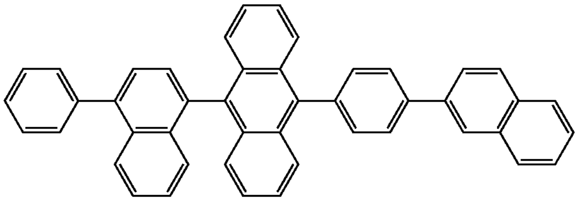
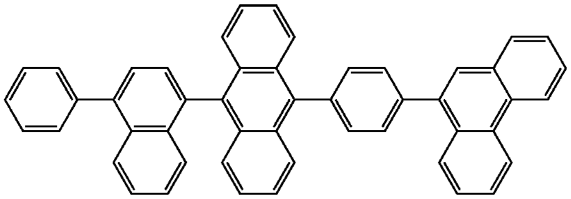
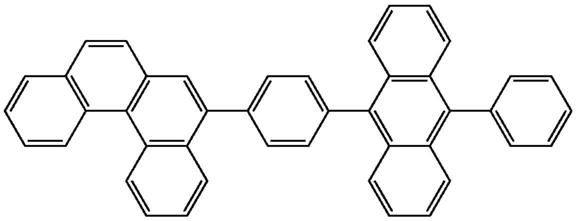

-continued

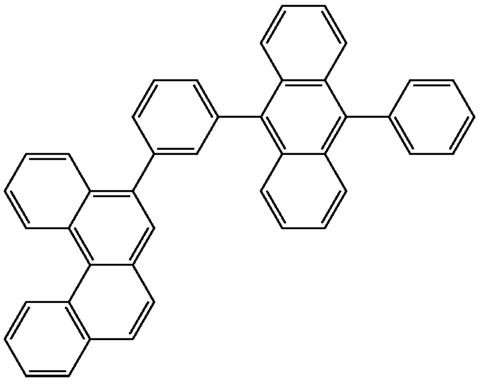

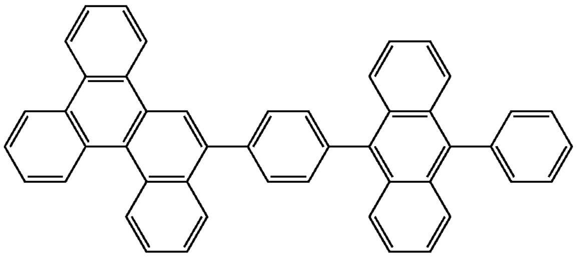

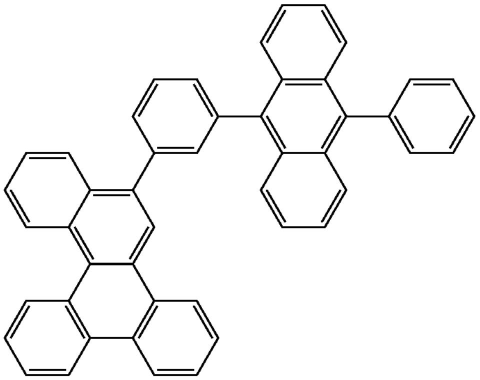

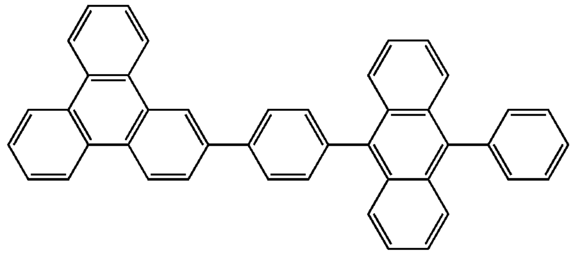

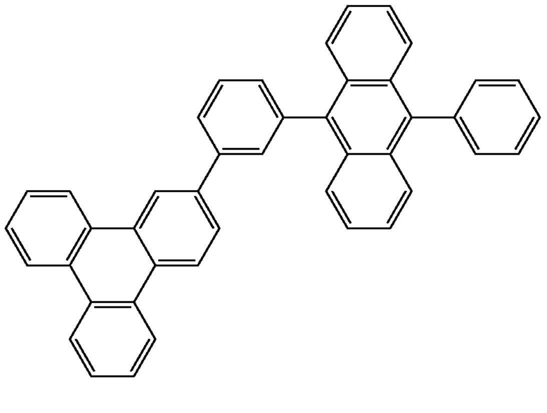

Electron Transporting Layer

The electron transporting layer comprises a material having a high electron transporting ability (electron transporting material). The electron transporting layer may be formed, for example, by (1) a metal complex, such as an aluminum complex, a beryllium complex, and a zinc complex;

(2) a heteroaromatic compound, such as an imidazole derivative, a benzimidazole derivative, an azine derivative, a carbazole derivative, and a phenanthroline derivative; and (3) a macromolecular compound.

Examples of the metal complex include tris(8-quinolinolato)aluminum (III) (Alq), tris(4-methyl-8-quinolinolato) aluminum ($Almq_3$), bis(10-hydroxybenzo[h]quinolinato)beryllium ($BeBq_2$), bis(2-methyl-8-quinolinato)(4-phenylphenolato)aluminum (III) (BAlq), bis(8-quinolinato) zinc(II) (Znq), bis[2-(2-benzoxazolyl)phenolato]zinc(II) (ZnPBO), and bis[2-(2-benzothiazolyl)phenolato]zinc(II) (ZnBTZ).

Examples of the heteroaromatic compound include 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-tert-butylphenyl)-4-phenyl-5-(4-biphenylyl)-1,2,4-triazole (TAZ), 3-(4-tert-butylphenyl)-4-(4-ethylphenyl)-5-(4-biphenylyl)-1,2,4-triazole (p-EtTAZ), bathophenanthroline (BPhen), bathocuproine (BCP), and 4,4'-bis(5-methylbenzoxazole-2-yl)stilbene (BzOs).

Examples of the macromolecular compound include poly [(9,9-dihexylfluorene-2,7-diyl)-co-(pyridine-3,5-diyl)](PF-Py), and poly[(9,9-dioctylfluorene-2,7-diyl)-co-(2,2'-bipyridine-6,6'-diyl)](PF-BPy).

The above compounds have an electron mobility of $10^{-6}$ $cm^2/Vs$ or more. Materials other than those mentioned above are also usable in the electron transporting layer if their electron transporting ability is higher than their hole transporting ability.

The electron transporting layer may be a single layer or a multi-layer of two or more layers. For example, the electron transporting layer may be a two-layered structure comprising a first electron transporting layer (anode side) and a second electron transporting layer (cathode side). Each of two or more electron transporting layers is formed by the electron transporting material mentioned above.

Electron Injecting Layer

The electron injecting layer is a layer comprising a material having a high electron injecting ability, for example, an alkali metal, an alkaline earth metal, and a compound of these metals, such as lithium (Li), cesium (Cs), calcium (Ca), lithium fluoride (LiF), cesium fluoride (CsF), calcium fluoride ($CaF_2$), and an oxide of lithium ($LiO_x$). In addition, an electron transporting material which is doped with an alkali metal, an alkaline earth metal or a compound thereof, for example, Alq doped with magnesium (Mg), is also usable. By using such a material, electrons are efficiently injected from the cathode.

A composite material comprising an organic compound and an electron donor is also usable in the electron injecting layer. Such a composite material is excellent in the electron injecting ability and the electron transporting ability, because the organic compound receives electrons from the electron donor. The organic compound is preferably a compound excellent in transporting the received electrons. Examples thereof include the materials for the electron transporting layer mentioned above, such as the metal complex and the aromatic heterocyclic compound. Any compound capable of giving its electron to the organic compound is usable as the electron donor. Preferred examples thereof are an alkali metal, an alkaline earth metal, and a rare earth metal, such as lithium, cesium, magnesium, calcium, erbium, and ytterbium; an alkali metal oxide and an alkaline earth metal oxide, such as, lithium oxide, calcium oxide, and barium oxide; a Lewis base, such as magnesium oxide; and an organic compound, such as tetrathiafulvalene (TTF).

Cathode

The cathode is formed preferably from a metal, an alloy, an electrically conductive compound, or a mixture thereof, each having a small work function, for example, a work function of 3.8 eV or less. Examples of the material for the cathode include an element belonging to a group 1 or group 2 of the periodic table, i.e., an alkali metal, such as lithium (Li) and cesium (Cs), an alkaline earth metal, such as magnesium (Mg), calcium (Ca), and strontium (Sr), an alloy containing these metals (for example, MgAg and AlLi), a rare earth metal, such as europium (Eu) and ytterbium (Yb), and an alloy containing a rare earth metal.

The alkali metal, the alkaline earth metal, and the alloy thereof is made into the cathode by a vacuum vapor deposition or a sputtering method. A coating method and an inkjet method are usable when a silver paste is used.

When the electron injecting layer is formed, the material for the cathode is selected irrespective of whether the work function is large or small and various electroconductive materials, such as Al, Ag, ITO, graphene, and indium oxide-tin oxide doped with silicon or silicon oxide, are usable. These electroconductive materials are made into films by a sputtering method, an inkjet method, and a spin coating method.

Insulating Layer

Since electric field is applied to the ultra-thin films of organic EL devices, the pixel defects due to leak and short circuit tends to occur. To prevent the defects, an insulating thin film layer may be interposed between the pair of electrodes.

Examples of the material for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. These materials may be used in combination or may be used in each layer of stacked layers.

Space Layer

For example, in an organic EL device having a fluorescent emitting layer and a phosphorescent emitting layer, a space layer is disposed between the fluorescent emitting layer and the phosphorescent emitting layer to prevent the diffusion of excitons generated in the phosphorescent emitting layer to the fluorescent emitting layer or to control the carrier (charge) balance. The space layer may be disposed between two or more phosphorescent emitting layers.

Since the space layer is disposed between the light emitting layers, a material combining the electron transporting ability and the hole transporting ability is preferably used for forming the space layer. To prevent the diffusion of triplet energy in the adjacent phosphorescent emitting layer, the triplet energy of the material for the space layer is preferably 2.6 eV or more. The materials described with respect to the hole transporting layer are usable as the material for the space layer.

Blocking Layer

A blocking layer, such as an electron blocking layer, a hole blocking layer, and an exciton blocking layer, may be provided in the portion adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The exciton blocking layer prevents the diffusion of excitons generated in the light emitting layer to adjacent layers and has a function of confining the excitons in the light emitting layer.

Each layer of the organic EL device is formed by a known method, such as a vapor deposition method and a coating method. For example, each layer is formed by a known vapor deposition method, such as a vacuum vapor deposition method and a molecular beam evaporation method (MBE method), and a known coating method using a solution of a compound for forming a layer, such as a dipping method, a spin coating method, a casting method, a bar coating method, and a roll coating method.

The thickness of each layer is not particularly limited and preferably 5 nm to 10 μm, more preferably 10 nm to 0.2 μm, because an excessively small thickness may cause defects such as pin holes and an excessively large thickness may require a high driving voltage.

The organic EL device can be used in an electronic device, for example, as display parts, such as organic EL panel module, display devices of television sets, mobile phones, personal computer, etc., and light emitting sources of lighting equipment and vehicle lighting equipment.

EXAMPLES

The present invention will be described below in more details with reference to the examples. However, it should be noted that the scope of the invention is not limited thereto.

Synthesis Example 1: Synthesis of Compound 1

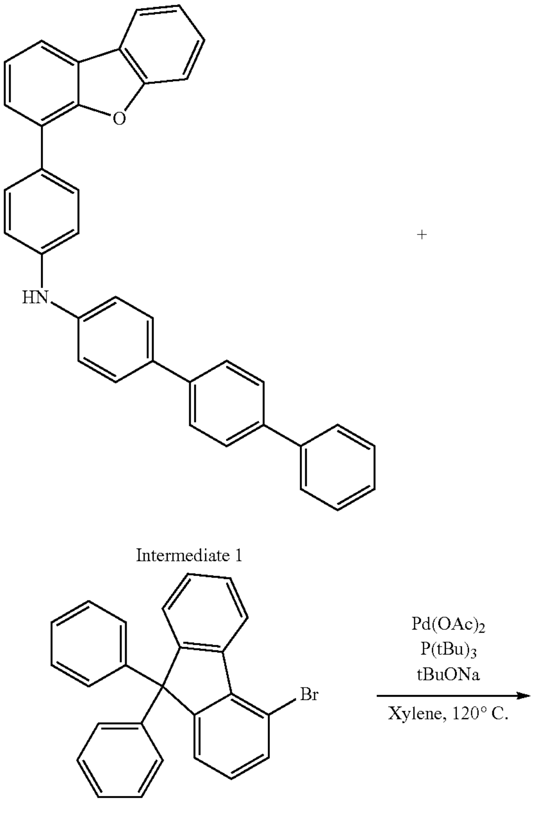

Intermediate 1

-continued

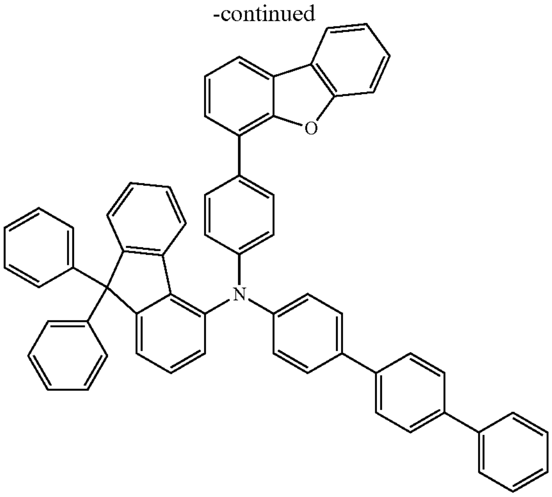

Compound 1

Under argon atmosphere, a mixture of palladium(II) acetate (0.34 g, 1.52 mmol), tri-t-butylphosphine (0.61 g, 3.04 mmol), and xylene (700 mL) was stirred at room temperature for 30 min. Into the mixture, Intermediate 1 (37 g, 76 mmol) synthesized by the method described in WO 2010/061824, 4-bromo-9,9-diphenylfluorene (33.2 g, 83 mmol), and sodium t-butoxide (8.75 g, 91 mmol) were added. The temperature was raised to 120° C. and the mixture was stirred for 30 min. After cooling to room temperature, methanol (100 mL) was added to the reaction mixture, which was then stirred and the generated solid was collected by filtration. The obtained solid was purified by silica gel column chromatography and recrystallization to obtain a white solid (38.5 g).

The obtained product was identified as the compound 1 by the result of mass spectrometric analysis (m/e=803 to the molecular weight of 803.32). The yield was 63%.

Example 1

Production of Organic EL Device

A 25 mm×75 mm×1.1 mm glass substrate having ITO transparent electrode (product of Geomatec Company) was ultrasonically cleaned in isopropyl alcohol for 5 min and then UV/ozone cleaned for 30 min. The thickness of ITO transparent electrode was 130 nm.

The cleaned glass substrate having the ITO transparent electrode was mounted to a substrate holder of a vacuum vapor deposition apparatus. First, the compound HI-1 was vapor-deposited so as to cover the ITO transparent electrode to form a hole injecting layer with a thickness of 5 nm.

On the hole injecting layer, the compound HT-1 (first hole transporting layer material) was vapor-deposited to form a first hole transporting layer with a thickness of 80 nm.

On the first hole transporting layer, the compound 1 synthesized in Synthesis Example 1 (second hole transporting layer material) was vapor-deposited to form a second hole transporting layer with a thickness of 10 nm.

Then, on the second hole transporting layer, the compound BH-1 (host material) and the compound BD-1 (dopant material) were vapor co-deposited to form a light emitting layer with a thickness of 25 nm. The concentration of the compound BD-1 was 4.0% by mass.

On the light emitting layer, the compound ET-1 (first electron transporting layer material) was vapor-deposited to form a first electron transporting layer with a thickness of 10 nm.

On the first electron transporting layer, the compound ET-2 (second electron transporting layer material) was vapor-deposited to form a second electron transporting layer with a thickness of 15 nm.

On the second electron transporting layer, LiF was vapor-deposited to form an electron injecting electrode (cathode) with a thickness of 1 nm.

Then, metallic Al was vapor-deposited on the electron injecting electrode to form a metallic cathode with a thickness of 80 nm. The organic EL device was thus produced.

HI-1

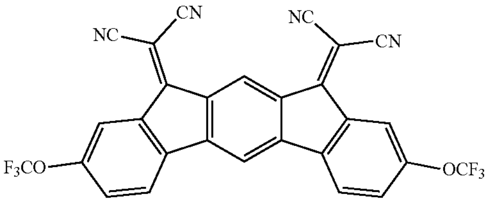

HT-1

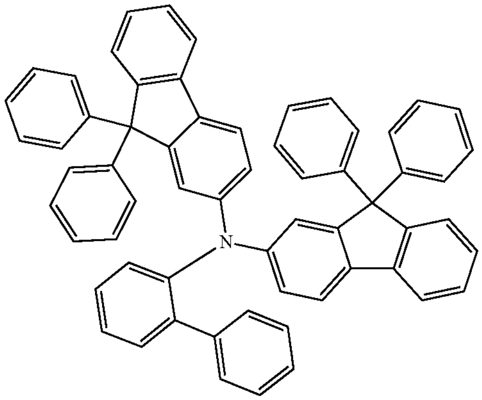

BH-1

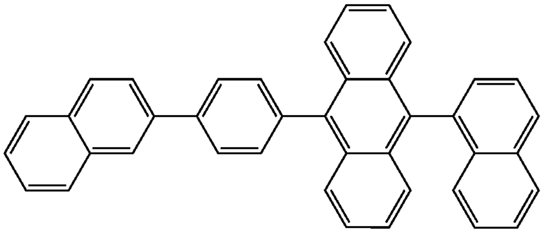

BD-1

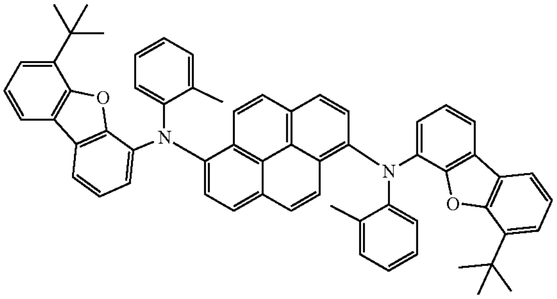

-continued

ET-1

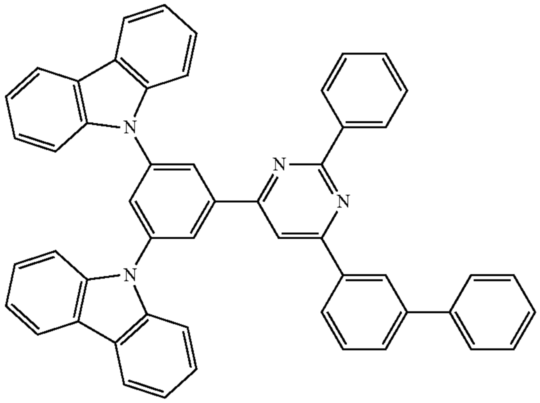

ET-2

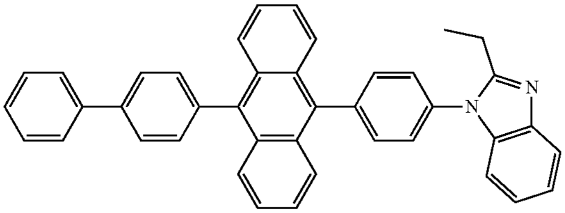

Measurement of External Quantum Efficiency

The organic EL device thus produced was operated at room temperature by a constant direct current at a current density of 10 mA/cm$^2$ to measure the luminance by a spectroradiometer (CS-1000 manufactured by Minolta). The external quantum efficiency (%) was determined by the result of the measurement. The result is shown in Table 1.

Measurement of Device Lifetime

The organic EL device thus produced was operated at room temperature by a direct current at a current density of 50 mA/cm$^2$ to measure the time taken until the luminance was reduced to 90% of the initial luminance. The result was taken as 90% lifetime (LT90) and shown in Table 1.

Comparative Examples 1 and 2

Each organic EL device was produced in the same manner as in Example 1 except for using, in place of Compound 1, Comparative compound 1 (the compound of formula 140 described in Patent Literature 1) or Comparative compound 2 (the compound described in Patent Literature 3, page 20) as the second hole transporting layer material. The organic EL device was measured for the external quantum efficiency and the device lifetime in the same manner as in Example 1. The results are shown in Table 1.

Compound 1

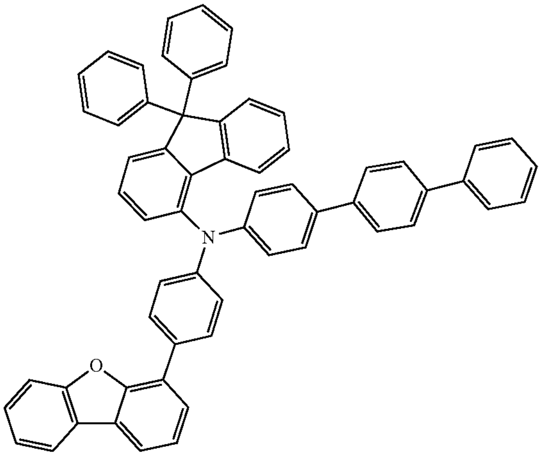

Comparative compound 1

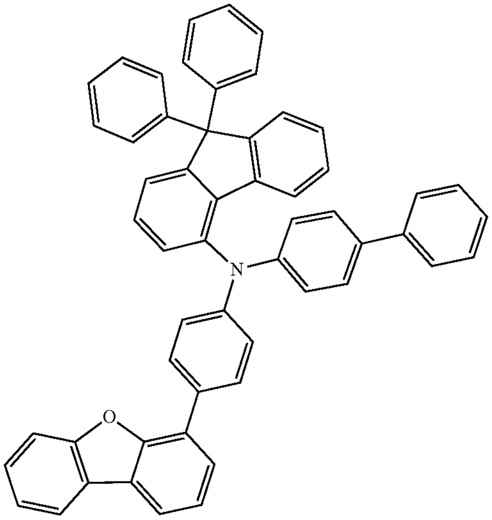

Comparative compound 2

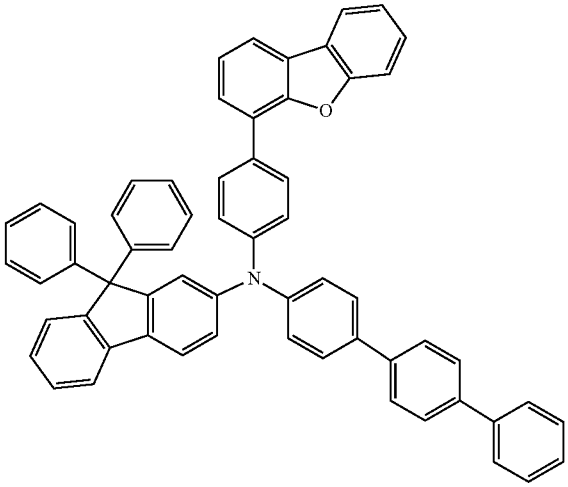

TABLE 1

| | Second hole transporting layer material | External quantum efficiency (%) | 90% Lifetime (h) |
|---|---|---|---|
| Example 1 | Compound 1 | 10.0 | 260 |
| Comparative Example 1 | Comparative Compound 1 | 10.0 | 210 |
| Comparative Example 2 | Comparative Compound 2 | 8.5 | 180 |

The comparison of Example 1 with Comparative Example 1 shows that the device lifetime is significantly improved by Compound 1 of the invention which corresponds to the compound derived from Comparative Compound 1 by replacing its biphenyl group with a terphenyl group.

The comparison of Example 1 with Comparative Example 2 shows that both the external quantum efficiency and the device lifetime are significantly improved by Compound 1 of the invention which corresponds to the compound derived from Comparative Compound 2 by replacing its 9,9-diphenylfluorene-2-yl group with a 9,9-diphenylfluorene-4-yl group.

Thus, the results show that Compound 1 improves the efficiency and the lifetime simultaneously.

Synthesis Example 2: Synthesis of Compound 2

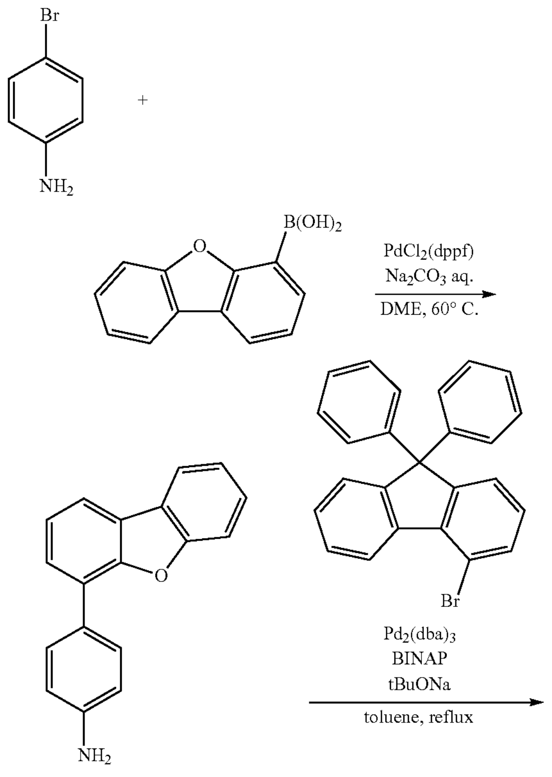

Intermediate 2-1

-continued

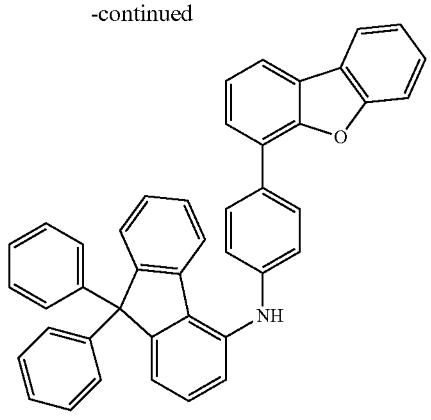

Intermediate 2

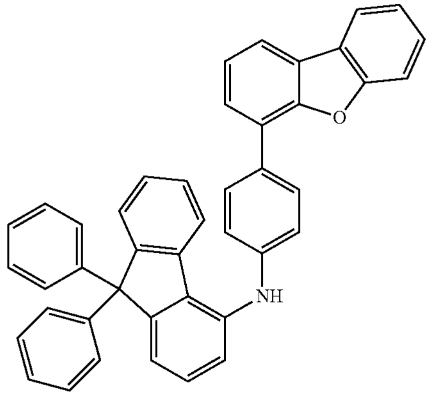

Intermediate 2

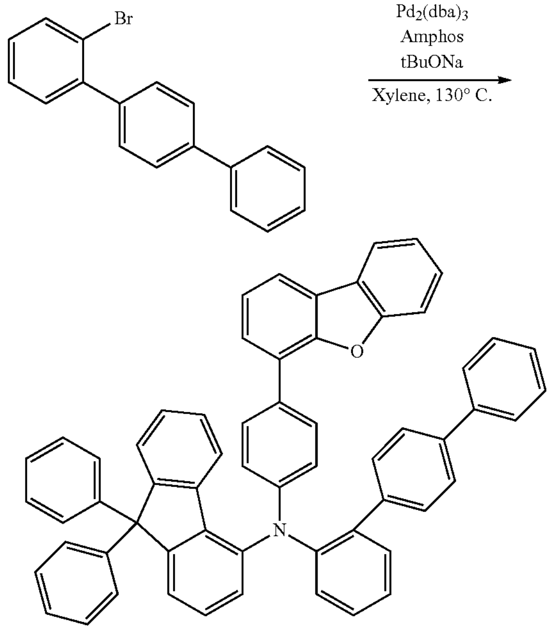

Compound 2

(2-1) Synthesis of Intermediate 2-1

Under argon atmosphere, a mixture of 4-bromoaniline (20 g, 116 mmol), dibenzofuran-4-ylboronic acid (27.1 g, 128 mmol), a dichloromethane adduct of [1,1'-bis(diphenylphosphino)ferrocene]palladium(II) dichloride (3.8 g, 4.65 mmol), a 2 M aqueous solution of sodium carbonate (174 mL, 349 mmol), and 1,2-dimethoxyethane (DME) (460 mL) was stirred under heating at 60° C. overnight. The reaction mixture was cooled to room temperature and then passed through a silica gel column. The obtained solution was concentrated under reduced pressure. The residue was recrystallized to obtain Intermediate 2-2 (23.4 g). The yield was 78%.

(2-2) Synthesis of Intermediate 2

Under argon atmosphere, a mixture of 4-bromo-9,9-diphenylfluorene (8.94 g, 22.51 mmol), Intermediate 2-1 (6.42 g, 24.76 mmol), tris(dibenzylideneacetone)dipalladium(0) (0.412 g, 0.45 mmol), 2,2'-bis(diphenylphosphino)-1,1'-binaphthyl (BINAP) (0.561 g, 0.90 mmol), sodium t-butoxide (4.33 g, 45 mmol), and toluene (330 mL) was refluxed under heating for 2 h. The reaction mixture was cooled to room temperature and then passed through a silica gel column. The obtained solution was concentrated under reduced pressure. The obtained reside was purified by silica gel column chromatography and recrystallization to obtain Intermediate 2 (5.3 g). The yield was 41%.

(2-3) Synthesis of Compound 2

Under argon atmosphere, a mixture of Intermediate 2 (7.09 g, 12.32 mmol), 2-bromo-1,1':4',1"-terphenyl (3.81 g, 12.32 mmol), tris(dibenzylideneacetone)dipalladium(0) (0.226 g, 0.246 mmol), Amphos (0.261 g, 0.985 mmol), sodium t-butoxide (3.55 g, 36.9 mmol), and xylene (400 mL) was stirred at 130° C. overnight. The reaction mixture was cooled to room temperature and then passed through a silica gel column. The obtained solution was concentrated under reduced pressure. The obtained reside was purified by recrystallization to obtain a white solid (3.0 g).

The obtained product was identified as Compound 2 by the result of mass spectrometric analysis (m/e=803 to the molecular weight of 803.32). The yield was 29%.

Synthesis Example 3: Synthesis of Compound 3

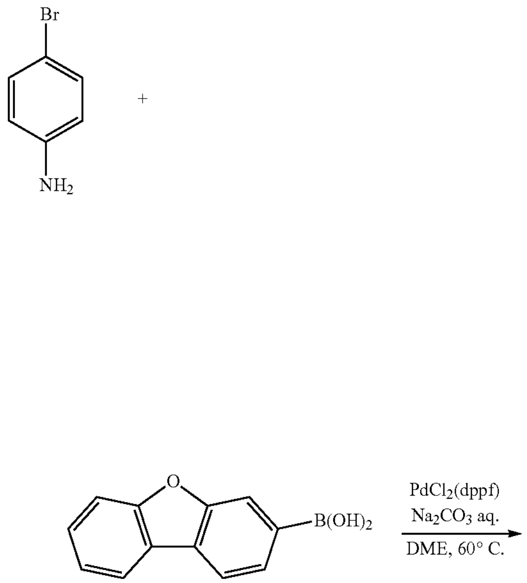

-continued

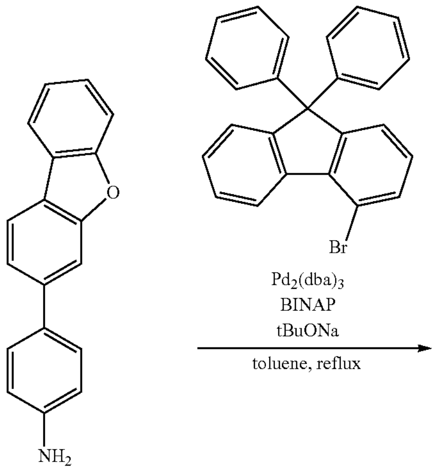

Intermediate 3-1

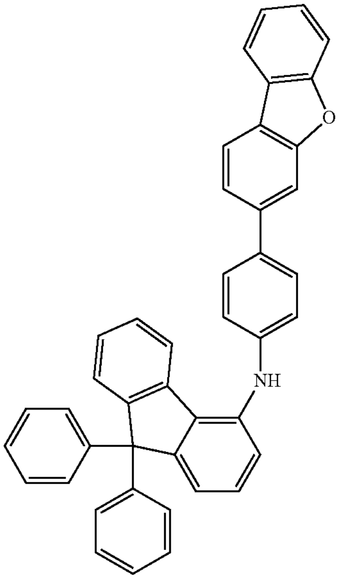

Intermediate 3

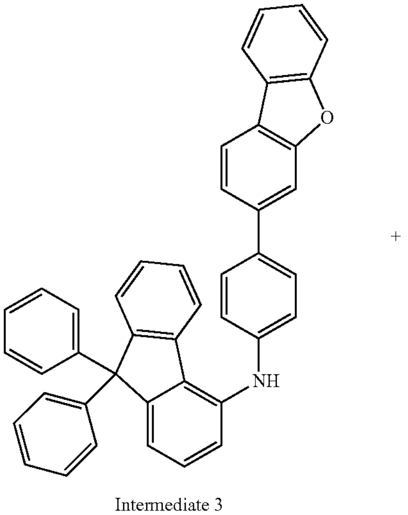

Intermediate 3

-continued

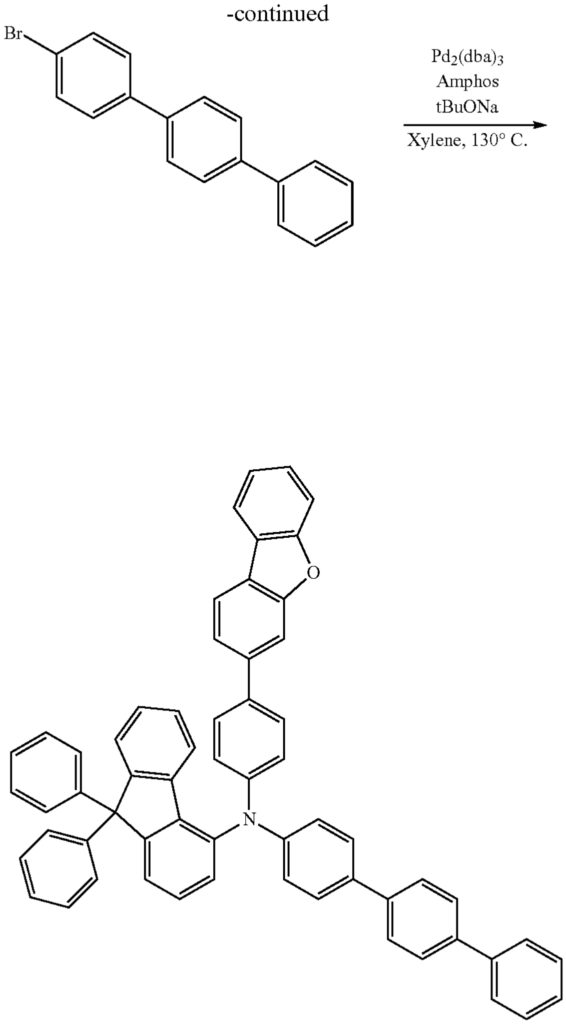

Compound 3

(3-1) Synthesis of Intermediate 3

Intermediate 3 was synthesized in the same manner as in the steps (2-1) to (2-2) of Synthesis Example 2 except for using in the step (2-1) dibenzofuran-3-ylboronic acid synthesized by the method described in WO 2018/164239 in place of dibenzofuran-4-ylboronic acid.

(3-2) Synthesis of Compound 3

The step (2-3) of Synthesis Example 2 was repeated except for using Intermediate 3 in place of Intermediate 2 and using 4-bromo-1,1':4',1"-terphenyl in place of 2-bromo-1,1':4',1"-terphenyl to obtain a white solid. The obtained product was identified as Compound 3 by the result of mass spectrometric analysis (m/e=803 to the molecular weight of 803.32). The yield was 55%.

Synthesis Example 4: Synthesis of Compound 4

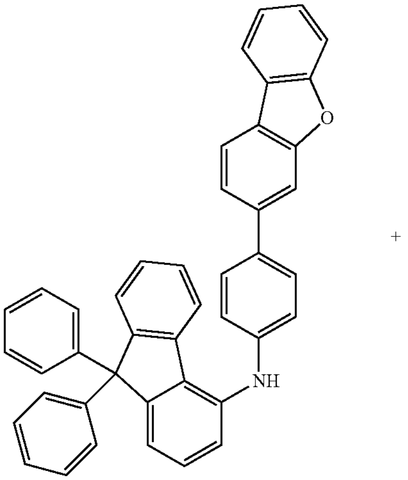

Intermediate 3

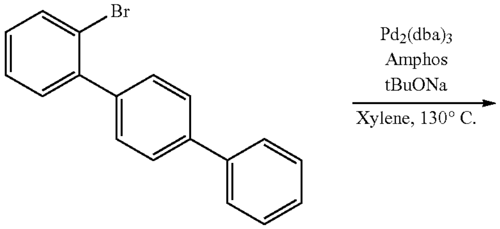

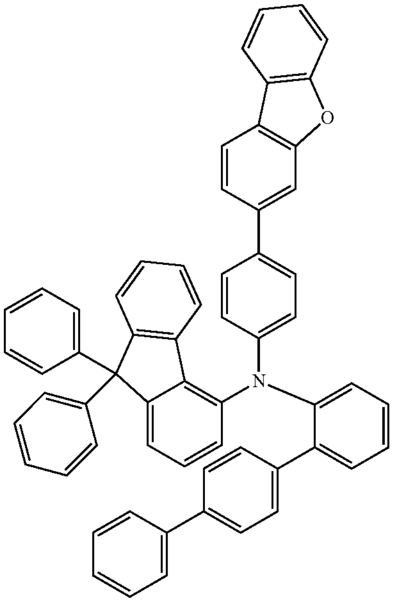

Compound 4

The step (2-3) of Synthesis Example 2 was repeated except for using Intermediate 3 in place of Intermediate 2 to obtain a white solid.

The obtained product was identified as Compound 4 by the result of mass spectrometric analysis (m/e=803 to the molecular weight of 803.32). The yield was 35%.

Synthesis Example 5: Synthesis of Compound 5

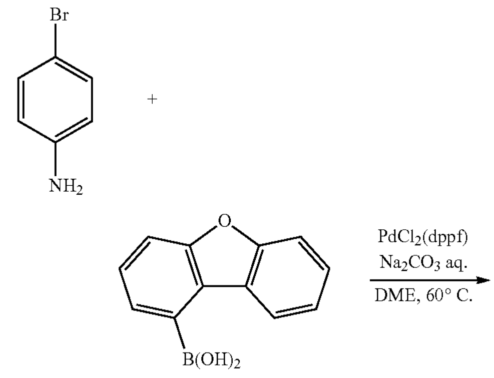

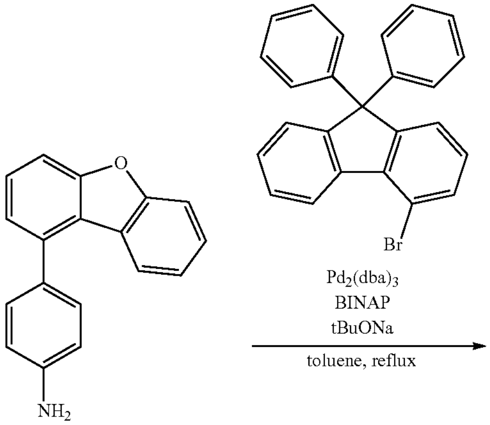

Intermediate 4-1

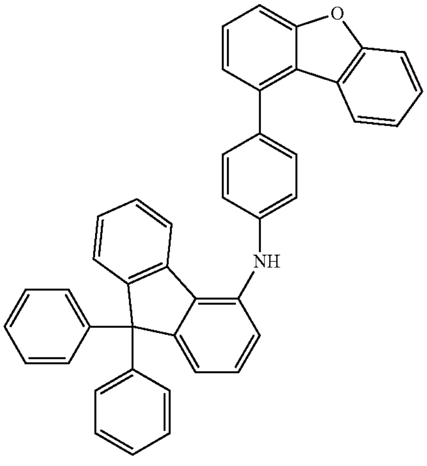

Intermediate 4

-continued

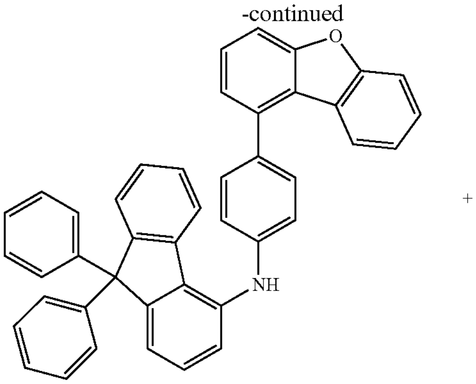

Intermediate 4

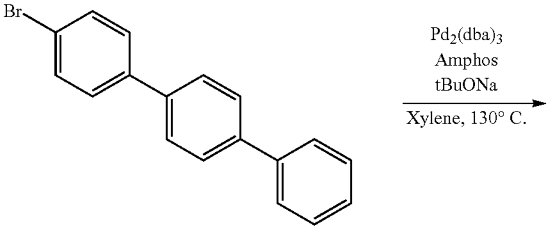

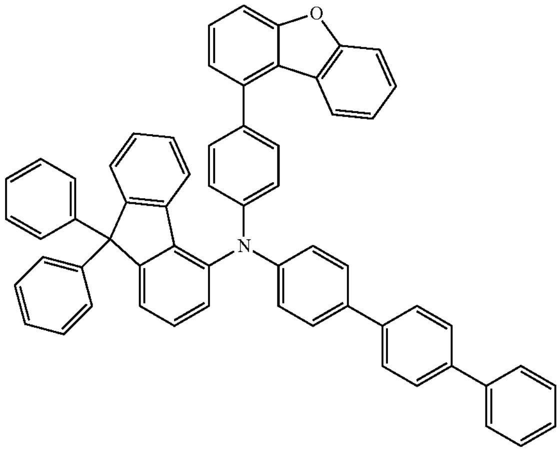

Compound 5

(5-1) Synthesis of Intermediate 4

Intermediate 4 was synthesized in the same manner as in the steps (2-1) and (2-2) of Synthesis Example 2 except for using in the step (2-1) dibenzofuran-1-ylboronic acid synthesized by the method described in WO 2018/164201 in place of dibenzofuran-4-ylboronic acid.

(5-2) Synthesis of Compound 5

The step (2-3) of Synthesis Example 2 was repeated except for using Intermediate 4 in place of Intermediate 2 and using 4-bromo-1,1':4',1"-terphenyl in place of 2-bromo-1,1':4',1"-terphenyl to obtain a white solid.

The obtained product was identified as Compound 5 by the result of mass spectrometric analysis (m/e=803 to the molecular weight of 803.32). The yield was 60%.

Synthesis Example 6: Synthesis of Compound 6

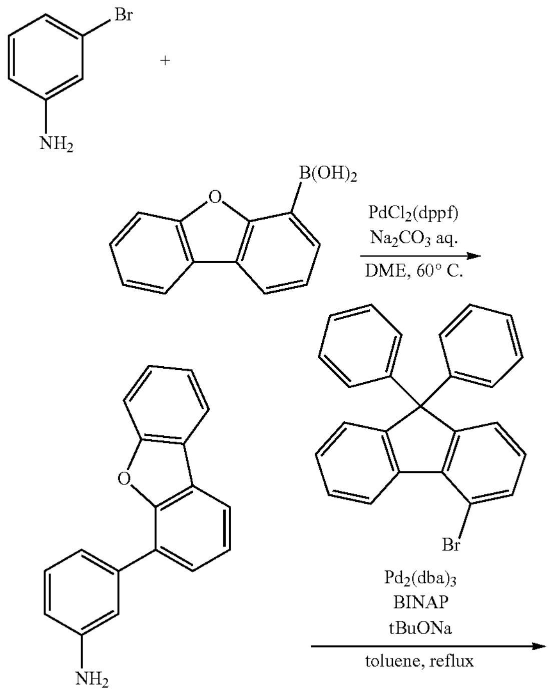

Intermediate 5-1

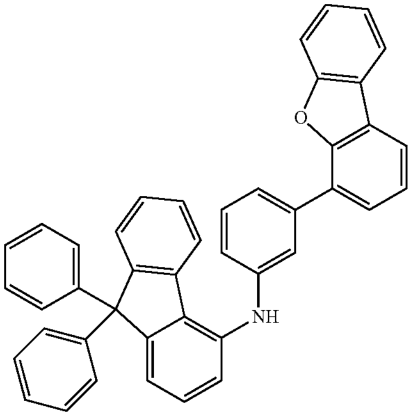

Intermediate 5

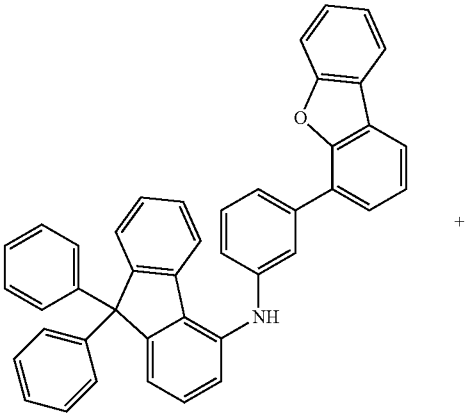

Intermediate 5

-continued

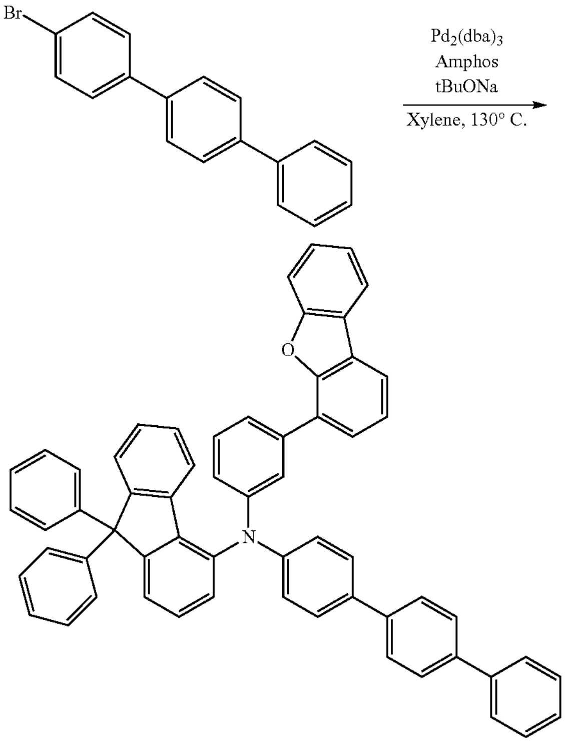

Compound 6

(6-1) Synthesis of Intermediate 5

Intermediate 5 was synthesized in the same manner as in the steps (2-1) to (2-2) except for using 3-bromoaniline in the step (2-1) in place of 4-bromoaniline.

(6-2) Synthesis of Compound 6

The step (2-3) of Synthesis Example 2 was repeated except for using Intermediate 5 in place of Intermediate 2 and using 4-bromo-1,1':4',1"-terphenyl in place of 2-bromo-1,1':4',1"-terphenyl to obtain a white solid.

The obtained product was identified as Compound 6 by the result of mass spectrometric analysis (m/e=803 to the molecular weight of 803.32). The yield was 57%.

Synthesis Example 7: Synthesis of Compound 7

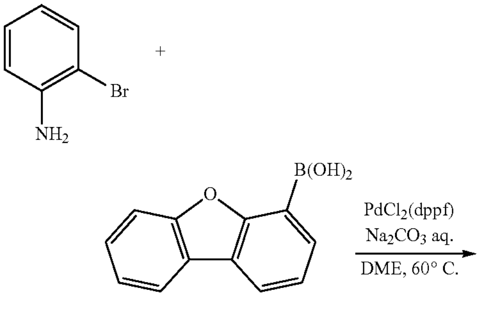

-continued

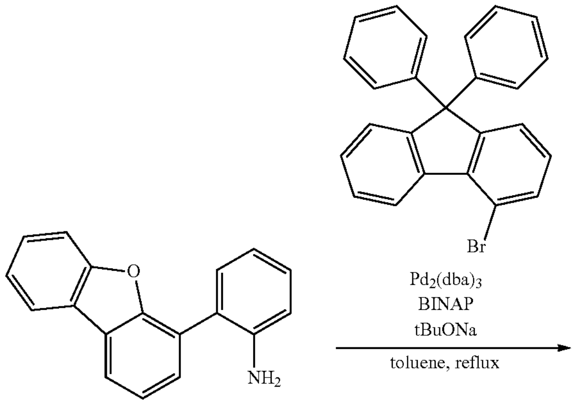

Intermediate 6-1

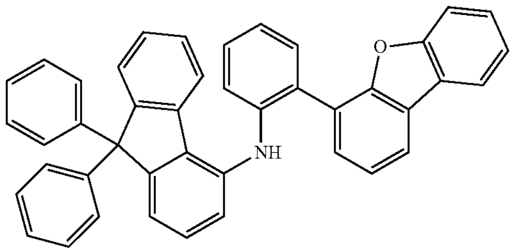

Intermediate 6

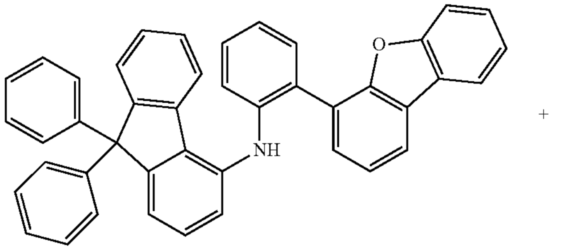

Intermediate 6

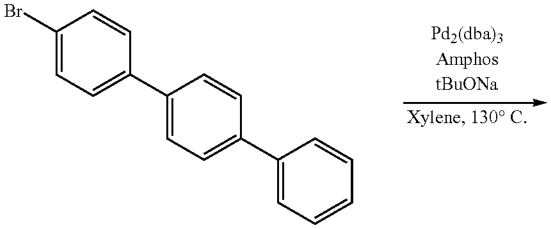

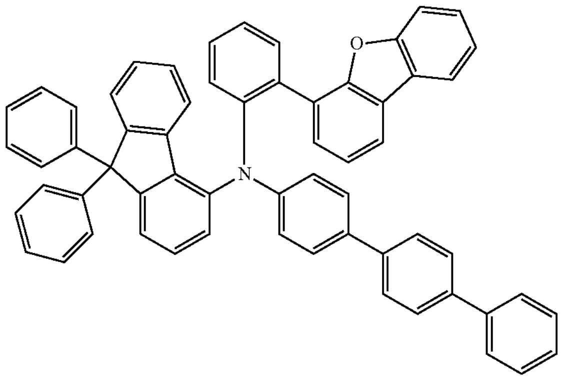

Compound 7

(7-1) Synthesis of Intermediate 6

Intermediate 6 was synthesized in the same manner as in the steps (2-1) to (2-2) of Synthesis Example 2 except for using 2-bromoaniline in the step (2-1) in place of 4-bromoaniline.

(7-2) Synthesis of Compound 7

The step (2-3) of Synthesis Example 2 was repeated except for using Intermediate 6 in place of Intermediate 2 and using 4-bromo-1,1':4',1"-terphenyl in place of 2-bromo-1,1':4',1"-terphenyl to obtain a white solid. The obtained product was identified as Compound 7 by the result of mass spectrometric analysis (m/e=803 to the molecular weight of 803.32). The yield was 42%.

Synthesis Example 8: Synthesis of Compound 8

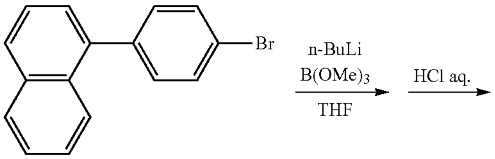

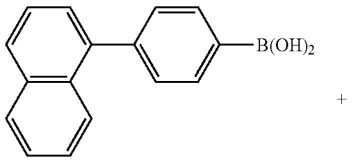

Intermediate 7-1

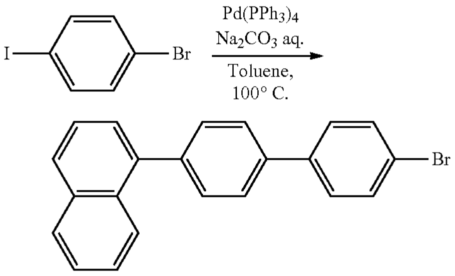

Intermediate 7

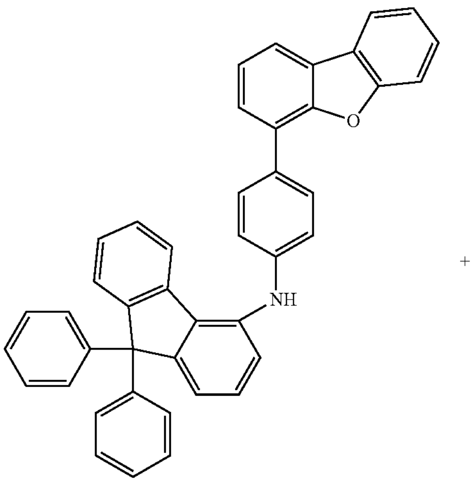

Intermediate 2

-continued

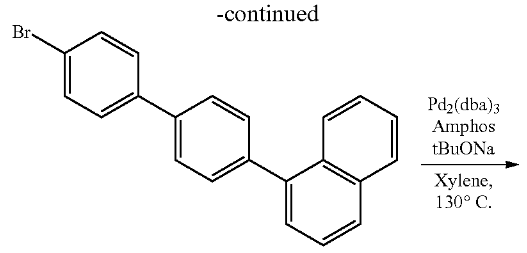

Intermediate 7

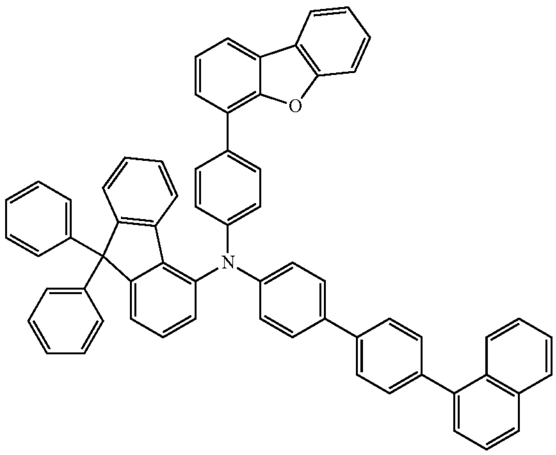

Compound 8

(8-1) Synthesis of Intermediate 7-1

Under argon atmosphere, a solution of 1-(4-bromophenyl) naphthalene (7.08 g, 25 mmol) in THF (125 mL) was cooled in a dry ice/acetone bath. After adding a 1.6 M hexane solution of n-butyllithium (17.2 mL, 27.5 mmol) dropwise, the solution was stirred for 2 h. After adding a solution of trimethyl borate (3.35 mL, 30 mmol) in THF (10 mL) dropwise, the solution was stirred for one hour and the temperature was raised to room temperature by removing the dry ice/acetone bath. After cooling in an iced water and then adding a 2 M hydrochloric acid, the reaction solution was heated to room temperature and stirred for one hour. The obtained solution was extracted with ethyl acetate. The organic layer was washed with water, dried over anhydrous sodium sulfate, and concentrated under reduced pressure. The obtained residue was crystallized to obtain Intermediate 7-1 (4.03 g). The yield was 65%.

(8-2) Synthesis of Intermediate 7

Under argon atmosphere, a mixture of Intermediate 7-1 (3.72 g, 15 mmol), 4-bromoiodobenzene (4.24 g, 15 mmol), tetrakis(triphenylphosphine)palladium(0) (347 mg, 0.30 mmol), a 2 M aqueous solution of sodium carbonate (22.5 mL), and toluene (45 mL) was stirred at 100° C. for 7 h. After returned to room temperature, water was added, the resultant solution was extracted with toluene, and the obtained toluene layer was dried over anhydrous sodium sulfate and concentrated under reduced pressure. The obtained residue was purified by silica gel column chromatography to obtain Intermediate 7 (2.96 g). The yield was 55%.

(8-3) Synthesis of Compound 8

The step (2-3) of Synthesis Example 2 was repeated except for using Intermediate 7 in place of 2-bromo-1,1':4',1"-terphenyl to obtain a white solid.

The obtained product was identified as Compound 8 by the result of mass spectrometric analysis (m/e=853 to the molecular weight of 853.33). The yield was 65%.

Synthesis Example 9: Synthesis of Compound 9

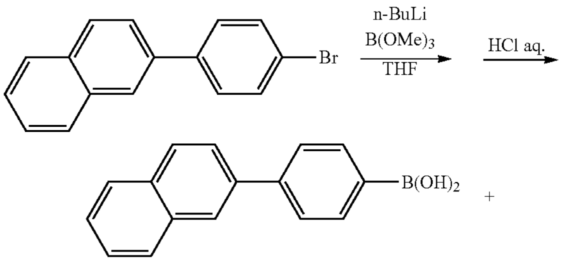

Intermediate 8-1

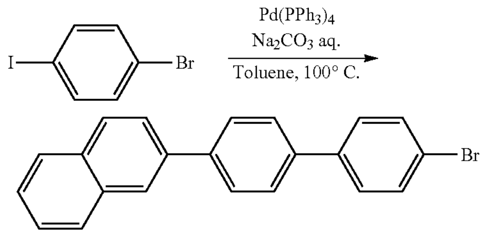

Intermediate 8

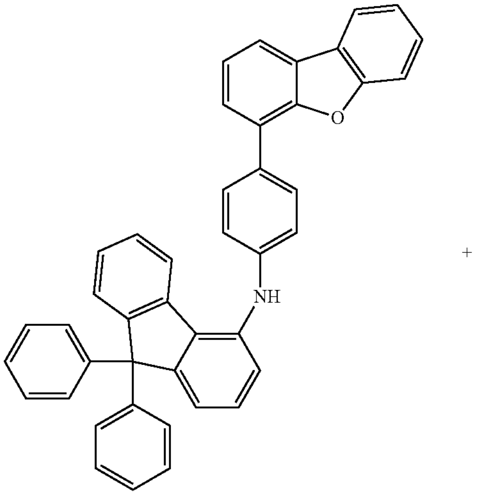

Intermediate 2

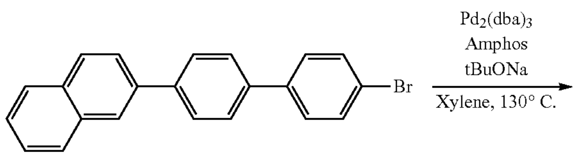

Intermediate 8

-continued

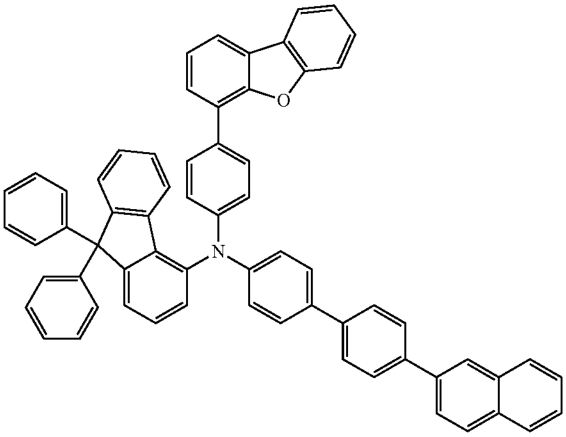

Compound 9

(9-1) Synthesis of Intermediate 8

Intermediate 8 was synthesized in the same manner as in the steps (8-1) to (8-2) of Synthesis Example 8 except for using 2-(4-bromophenyl)naphthalene in the step (8-1) in place of 1-(4-bromophenyl)naphthalene.

(9-2) Synthesis of Compound 9

The step (8-3) of Synthesis Example 8 was repeated except for using Intermediate 8 in place of Intermediate 7 to obtain a white solid. The obtained product was identified as Compound 9 by the result of mass spectrometric analysis (m/e=853 to the molecular weight of 853.33). The yield was 62%.

Synthesis Example 10; Synthesis of Compound 10

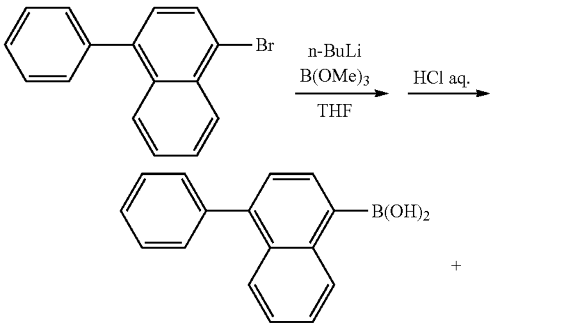

Intermediate 8-1

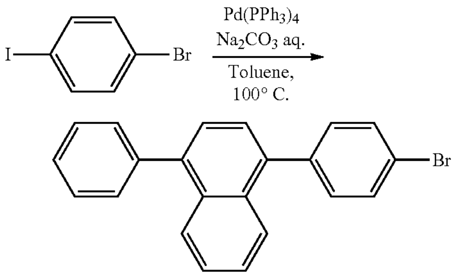

Intermediate 8

-continued

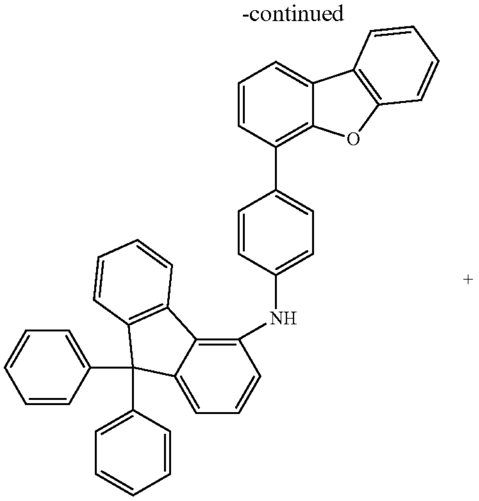

Intermediate 2

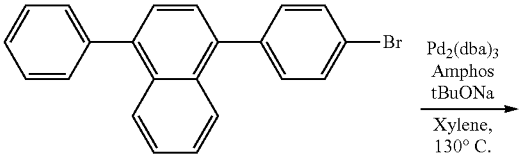

Intermediate 9

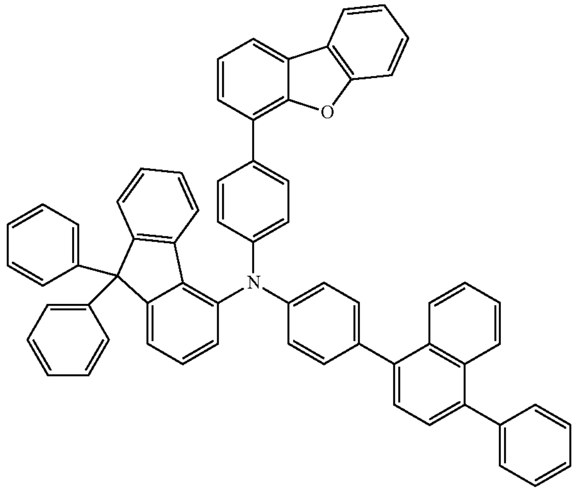

Compound 10

(10-1) Synthesis of Intermediate 9

Intermediate 9 was synthesized in the same manner as in the steps (8-1) to (8-2) of Synthesis Example 8 except for using in the step (8-1) 1-bromo-4-phenylnaphthalene synthesized by the method described in WO 2007/102361 in place of 1-(4-bromophenyl)naphthalene.

(10-2) Synthesis of Compound 10

The step (8-3) of Synthesis Example 8 was repeated except for using Intermediate 9 in place of Intermediate 7 to obtain a white solid.

The obtained product was identified as Compound 10 by the result of mass spectrometric analysis (m/e=853 to the molecular weight of 853.33). The yield was 52%.

Synthesis Example 11 Synthesis of Compound 11

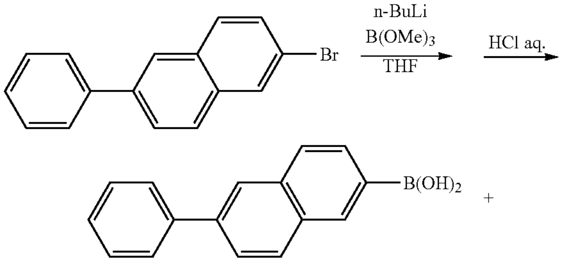

Intermediate 10-1

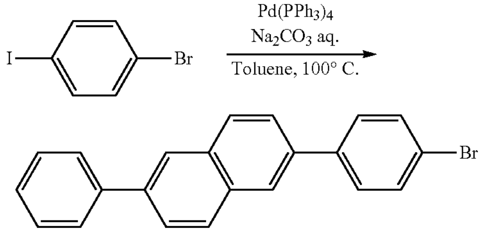

Intermediate 10

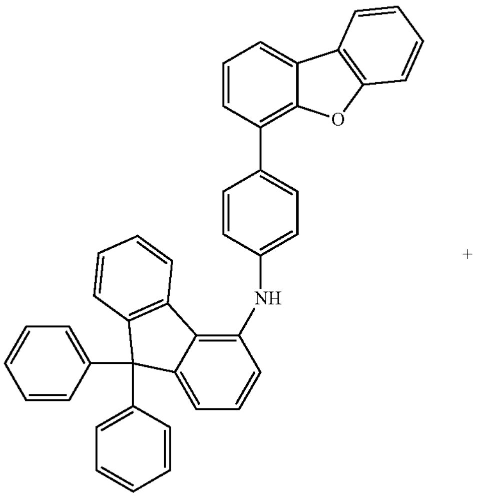

Intermediate 2

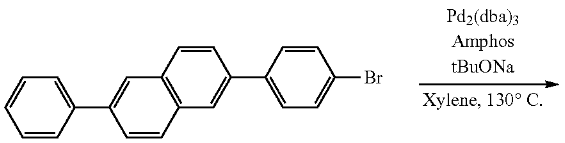

Intermediate 10

-continued

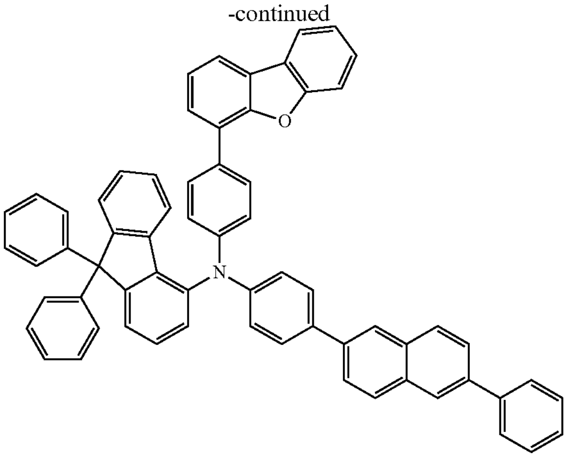

Compound 11

(11-1) Synthesis of Intermediate 10

Intermediate 10 was synthesized in the same manner as in the steps (8-1) to (8-2) of Synthesis Example 8 except for using in the step (8-1) 2-bromo-6-phenylnaphthalene synthesized by the method described in WO 2009/008311 in place of 1-(4-bromophenyl)naphthalene.

(11-2) Synthesis of Compound 11

The step (8-3) of Synthesis Example 8 was repeated except for using Intermediate 10 in place of Intermediate 7 to obtain a white solid.

The obtained product was identified as Compound 11 by the result of mass spectrometric analysis (m/e=853 to the molecular weight of 853.33). The yield was 58%.

Synthesis Example 12: Synthesis of Compound 12

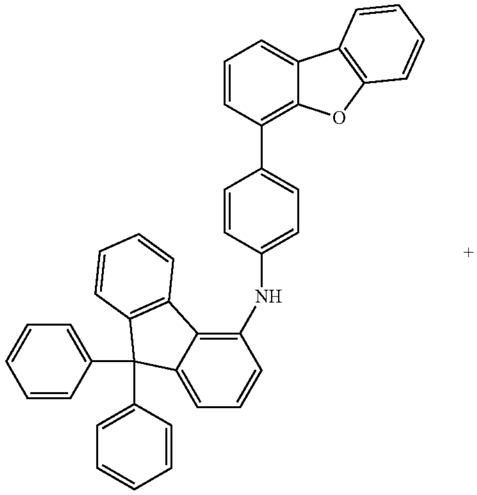

Intermediate 2

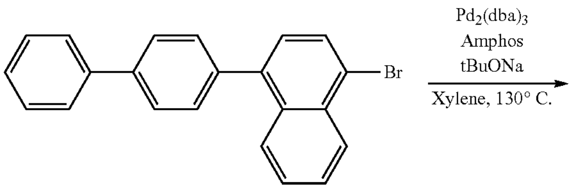

-continued

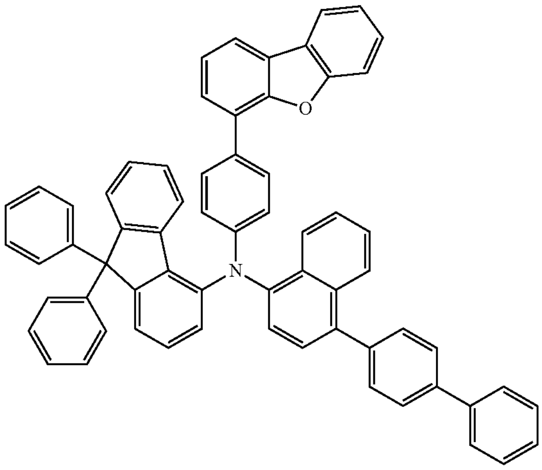

Compound 12

The step (2-3) of Synthesis Example 2 was repeated except for using 1-[1,1'-biphenyl-4-yl]-4-bromonaphthalene synthesized by the method described in WO 2007/102361 in place of 2-bromo-1,1':4',1"-terphenyl to obtain a white solid.

The obtained product was identified as Compound 12 by the result of mass spectrometric analysis (m/e=853 to the molecular weight of 853.33). The yield was 28%.

Synthesis Example 13: Synthesis of Compound 13

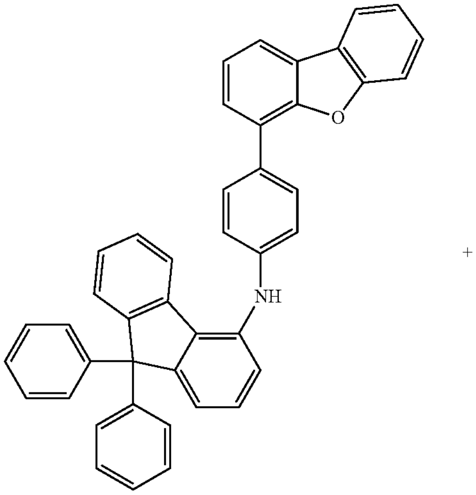

Intermediate 2

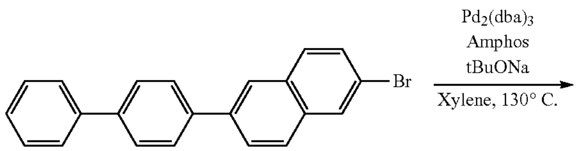

-continued

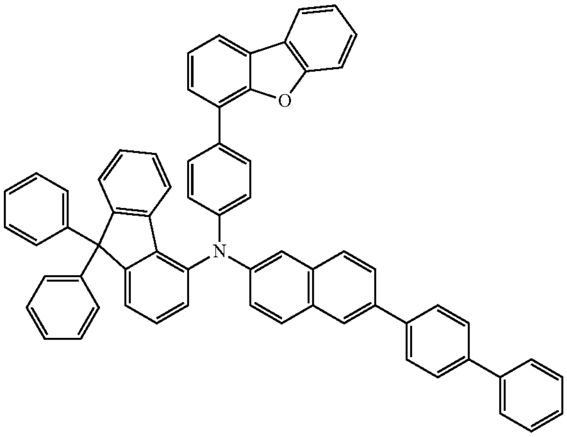

Compound 13

The step (2-3) of Synthesis Example 2 was repeated except for using 2-[1,1'-biphenyl-4-yl]-6-bromonaphthalene in place of 2-bromo-1,1':4',1"-terphenyl to obtain a white solid.

The obtained product was identified as Compound 13 by the result of mass spectrometric analysis (m/e=853 to the molecular weight of 853.33). The yield was 48%.

Synthesis Example 14: Synthesis of Compound 14

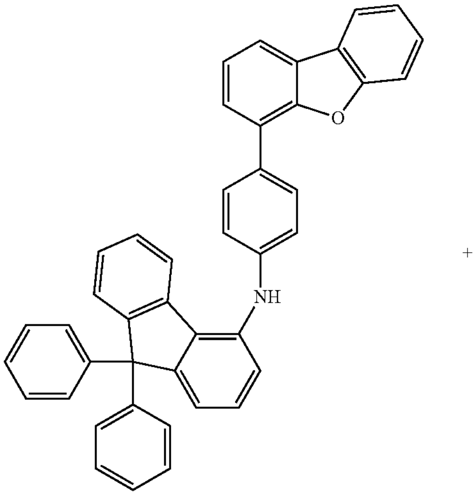

Intermediate 2

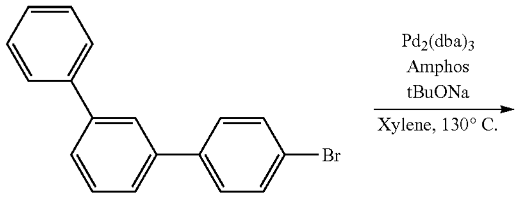

-continued

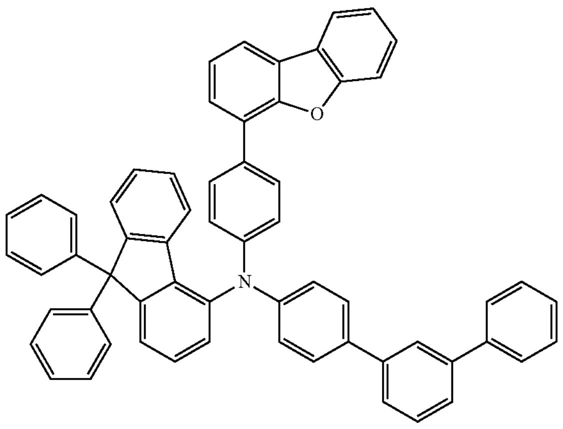

Compound 14

The step (2-3) of Synthesis Example 2 was repeated except for using 4-bromo-1,1':3',1"-terphenyl in place of 2-bromo-1,1':4',1"-terphenyl to obtain a white solid.

The obtained product was identified as Compound 14 by the result of mass spectrometric analysis (m/e=803 to the molecular weight of 803.32). The yield was 59%.

Synthesis Example 15: Synthesis of Compound 15

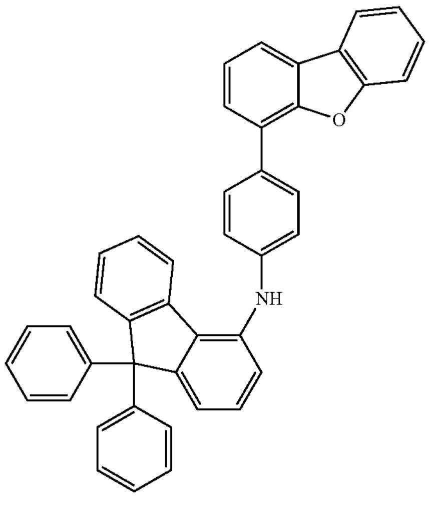

Intermediate 2

+

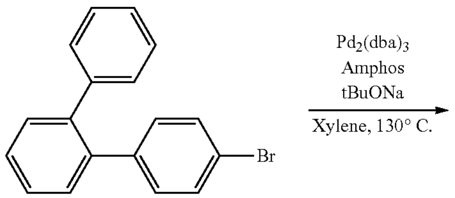

-continued

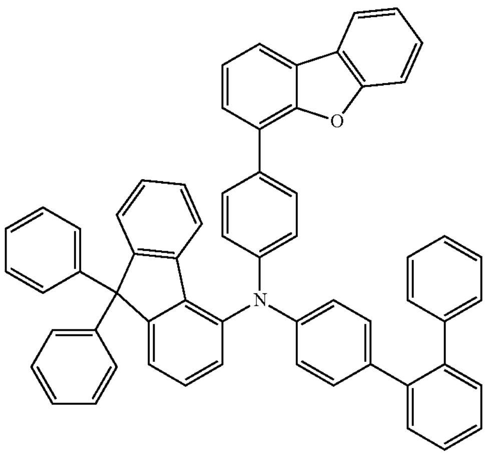

Compound 15

The step (2-3) of Synthesis Example 2 was repeated except for using 4-bromo-1,1':2',1"-terphenyl in place of 2-bromo-1,1':4',1"-terphenyl to obtain a white solid.

The obtained product was identified as Compound 15 by the result of mass spectrometric analysis (m/e=803 to the molecular weight of 803.32). The yield was 60%.

Synthesis Example 16: Synthesis of Compound 16

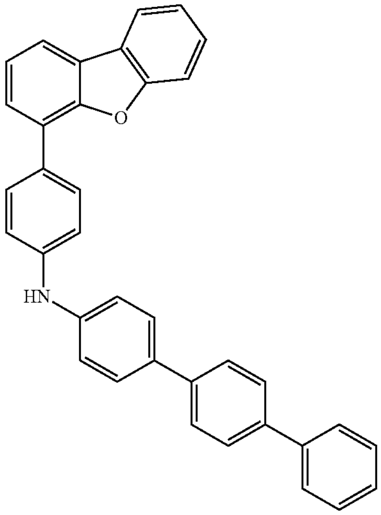

Intermediate 1

+

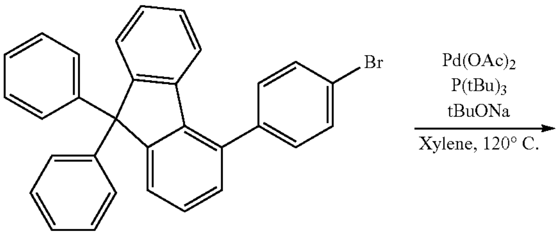

-continued

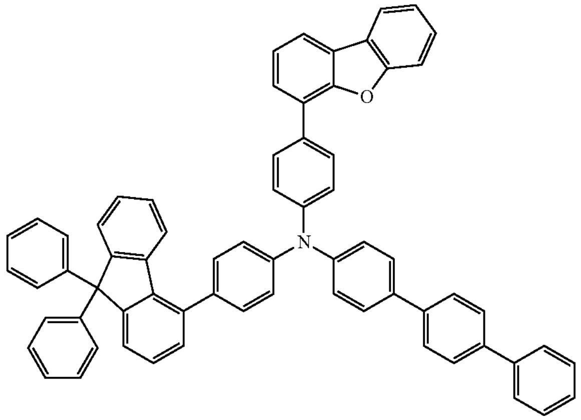

Compound 16

The procedure of Synthesis Example 1 was repeated except for using 4-(4-bromophenyl)-9,9-diphenylfluorene in place of 4-bromo-9,9-diphenylfluorene to obtain a white solid.

The obtained product was identified as Compound 16 by the result of mass spectrometric analysis (m/e=879 to the molecular weight of 879.35). The yield was 55%.

Synthesis Example 17: Synthesis of Compound 17

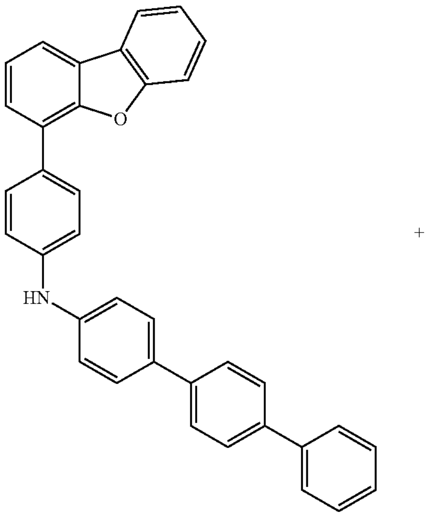

Intermediate 1

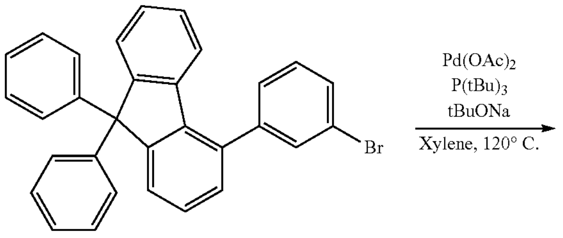

-continued

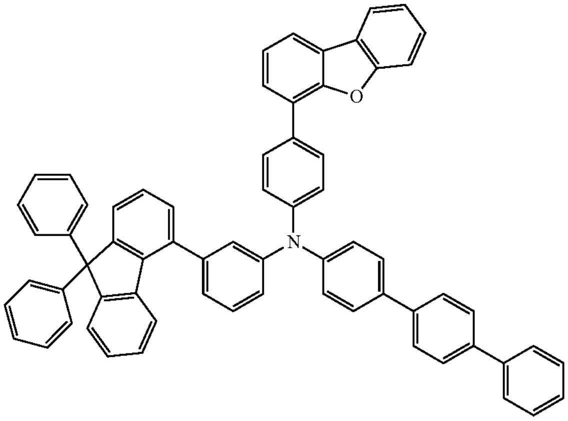

Compound 17

The procedure of Synthesis Example 1 was repeated except for using 4-(3-bromophenyl)-9,9-diphenylfluorene in place of 4-bromo-9,9-diphenylfluorene to obtain a white solid.

The obtained product was identified as Compound 17 by the result of mass spectrometric analysis (m/e=879 to the molecular weight of 879.35). The yield was 52%.

Synthesis Example 18: Synthesis of Compound 18

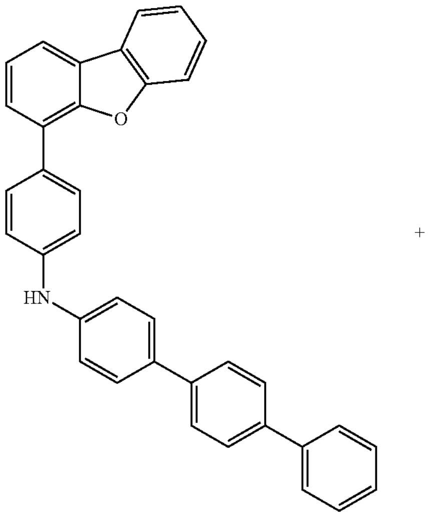

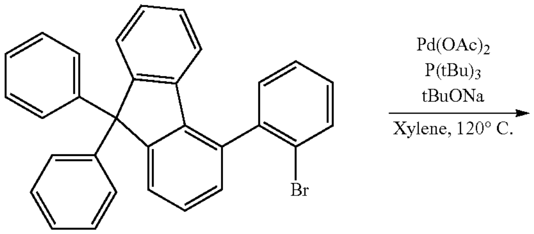

-continued

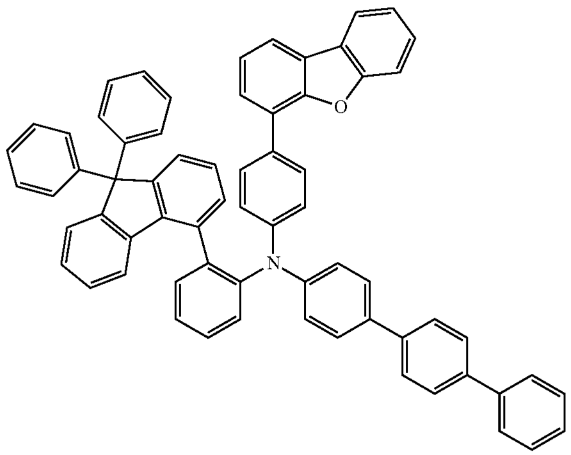

Intermediate 1 Compound 18

The procedure of Synthesis Example 1 was repeated except for using 4-(2-bromophenyl)-9,9-diphenylfluorene in place of 4-bromo-9,9-diphenylfluorene to obtain a white solid.

The obtained product was identified as Compound 18 by the result of mass spectrometric analysis (m/e=879 to the molecular weight of 879.35). The yield was 50%.

Examples 2 to 16

Each organic EL device was produced in the same manner as in Example 1 except for using each of Compounds 3 to 16 and 18 as the second hole transporting layer material in place of Compound 1. Each of the organic EL devices was measured for the external quantum efficiency and the device lifetime in the same manner as in Example 1. The results are shown in Table 2.

Compound 3

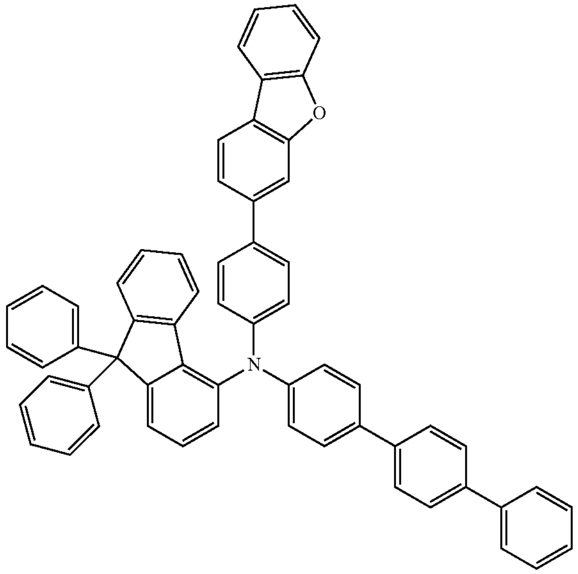

-continued

Compound 4

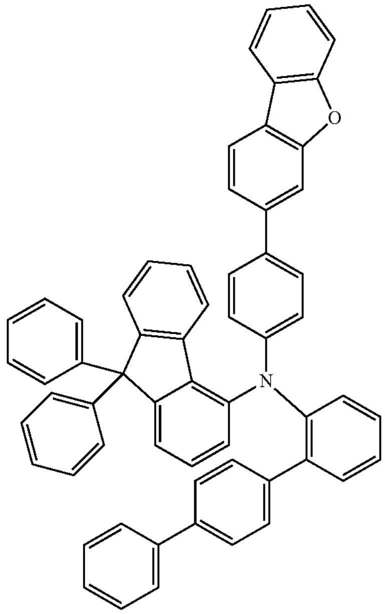

Compound 5

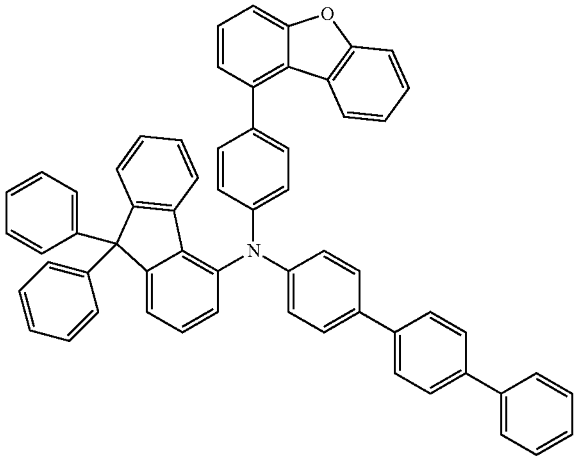

Compound 6

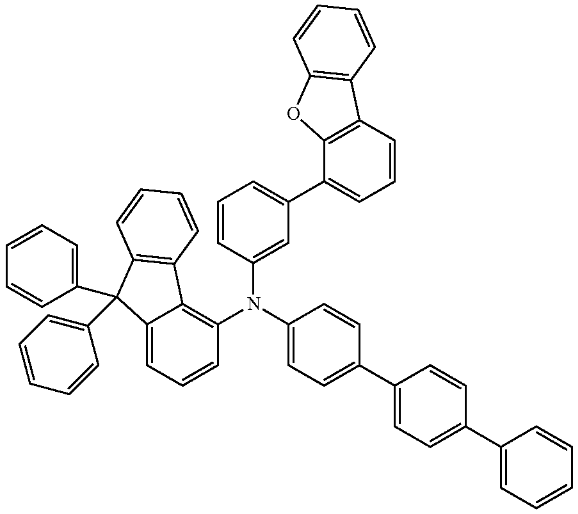

-continued
Compound 7
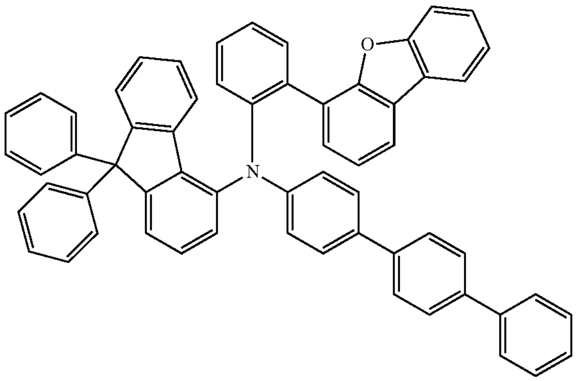
Compound 8
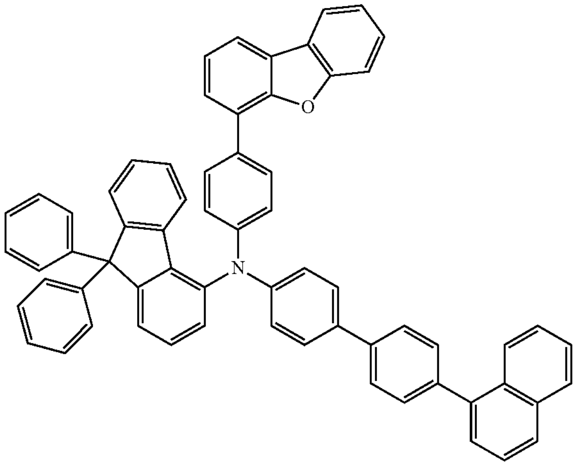
Compound 9
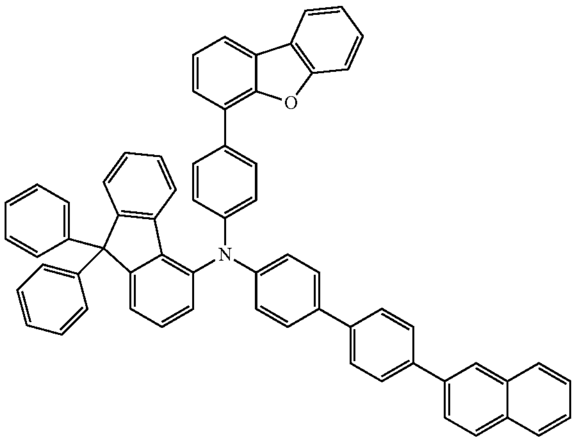
-continued
Compound 10
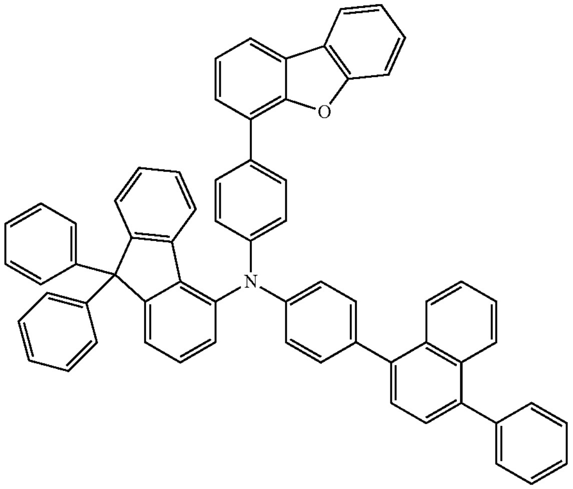
Compound 11
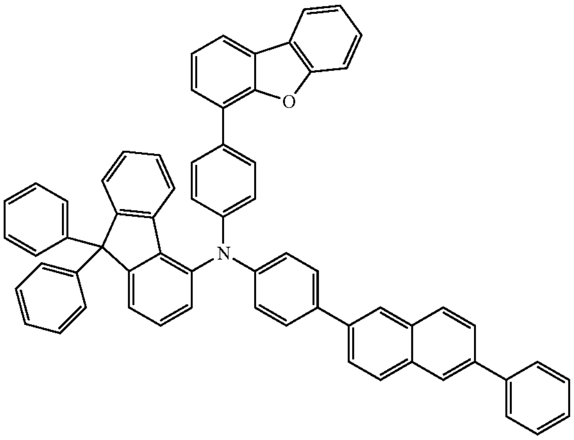
Compound 12
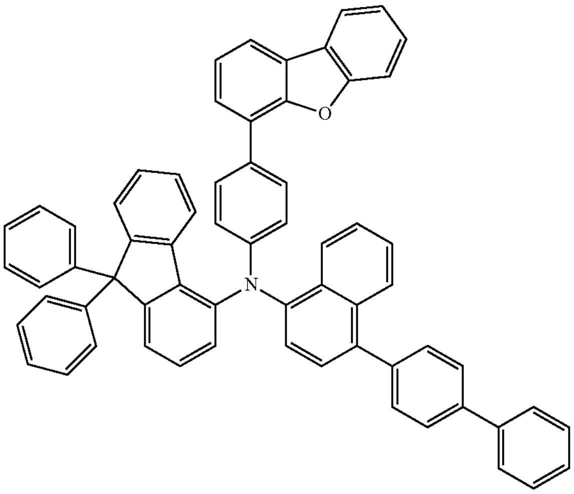

-continued

Compound 13

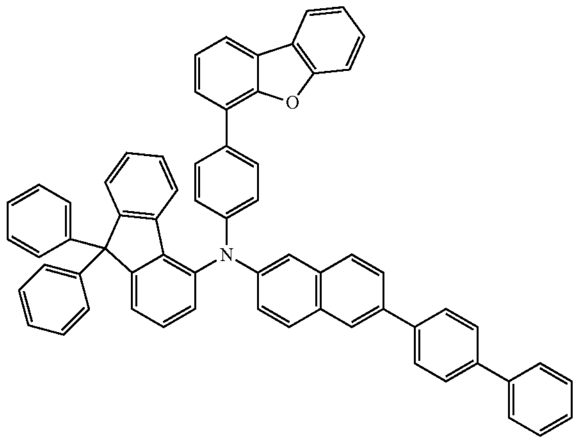

Compound 14

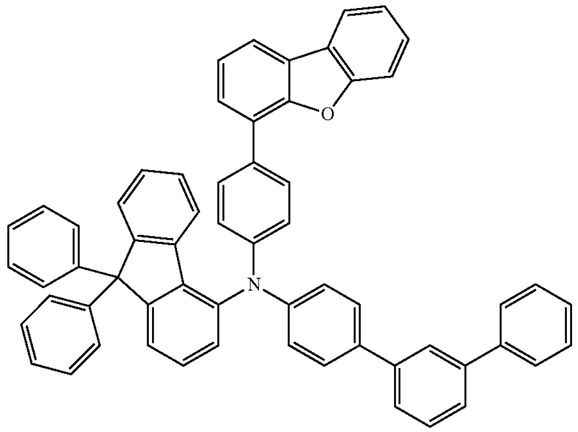

Compound 15

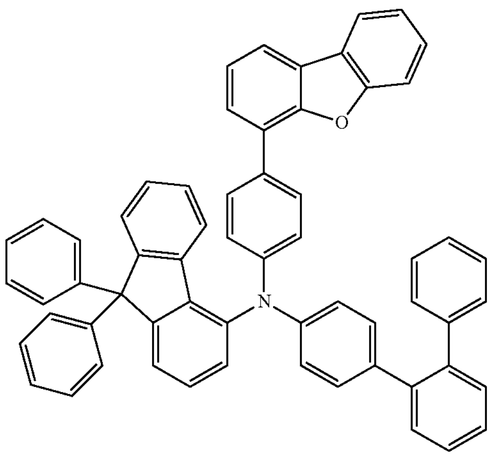

-continued

Compound 16

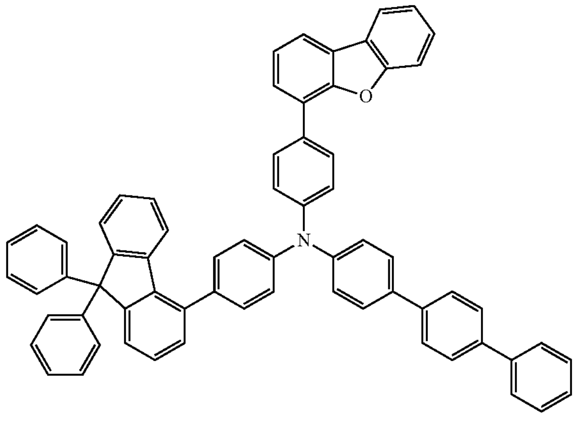

Compound 18

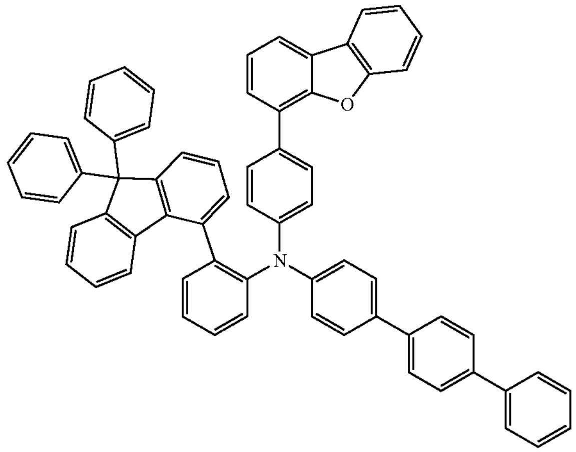

TABLE 2

| | Second hole transporting layer material | External quantum efficiency (%) | 90% Lifetime (h) |
|---|---|---|---|
| Example 2 | Compound 3 | 10.1 | 250 |
| Example 3 | Compound 4 | 10.2 | 240 |
| Example 4 | Compound 5 | 10.3 | 240 |
| Example 5 | Compound 6 | 10.0 | 245 |
| Example 6 | Compound 7 | 10.0 | 250 |
| Example 7 | Compound 8 | 10.1 | 240 |
| Example 8 | Compound 9 | 10.2 | 235 |
| Example 9 | Compound 10 | 10.1 | 240 |
| Example 10 | Compound 11 | 10.2 | 245 |
| Example 11 | Compound 12 | 10.3 | 240 |
| Example 12 | Compound 13 | 10.2 | 240 |
| Example 13 | Compound 14 | 10.0 | 250 |
| Example 14 | Compound 15 | 10.1 | 250 |
| Example 15 | Compound 16 | 10.2 | 255 |
| Example 16 | Compound 18 | 10.2 | 240 |

The results of Examples 2 to 16 show that the compounds wherein at least one of the 1,1':4',1"-terphenyl-4-yl group, the 4-(4-dibenzofuranyl)phenyl group, and the 9,9-diphenylfluorene-4-yl group in Compound 1 is replaced by another group included in the definition of formula (1) have the external quantum efficiency and the device lifetime that are similar to those of Compound 1.

REFERENCE SIGNS LIST

1, 11: Organic EL device
2: Substrate
3: Anode
4: Cathode
5: Light emission layer
6: Hole transporting region (hole transporting layer)
6*a*: First hole transporting layer
6*b*: Second hole transporting layer
7: Electron transporting region (electron transporting layer)
7*a*: First electron transporting layer
7*b*: Second electron transporting layer
10, 20: Emission unit

The invention claimed is:

1. A compound selected from the group consisting of Compound 1, Compound 3, Compound 5, Compound 6, Compound 7, Compound 8, Compound 9, Compound 10, Compound 11, Compound 12, Compound 13, Compound 14, Compound 15, Compound 16, Compound 17, and Compound 18:

Compound 1

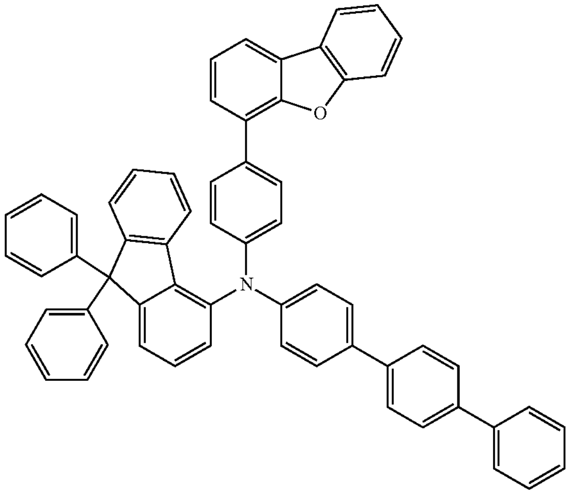

Compound 3

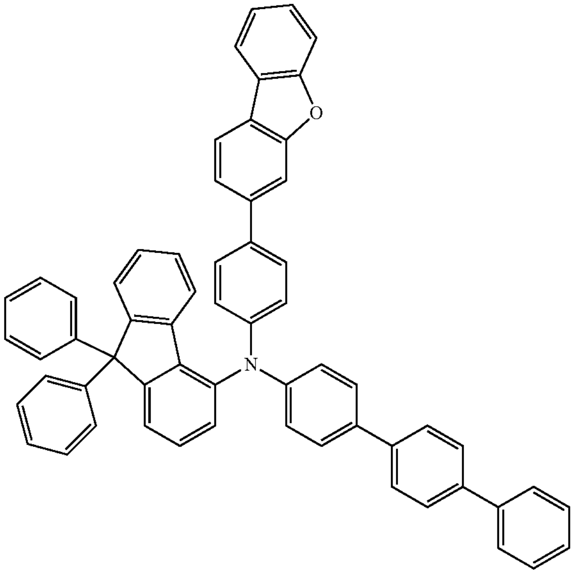

-continued

Compound 5

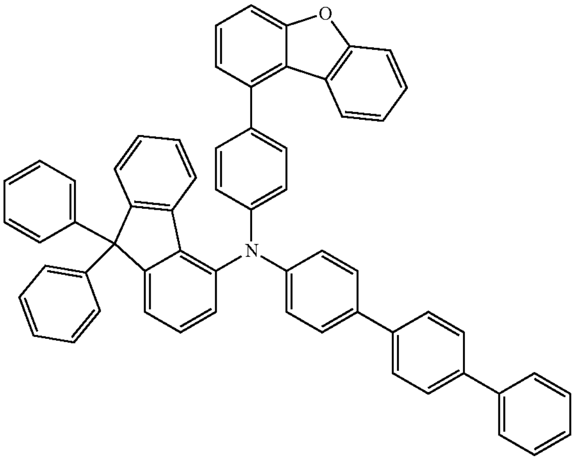

Compound 6

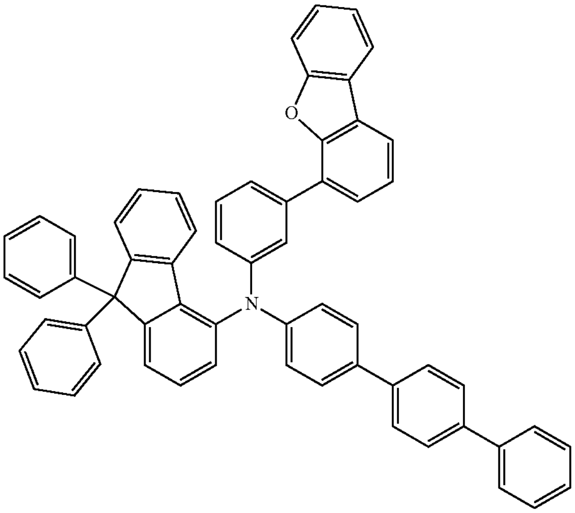

Compound 7

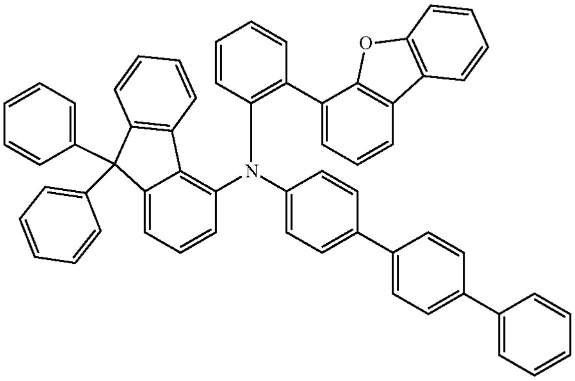

-continued
Compound 8
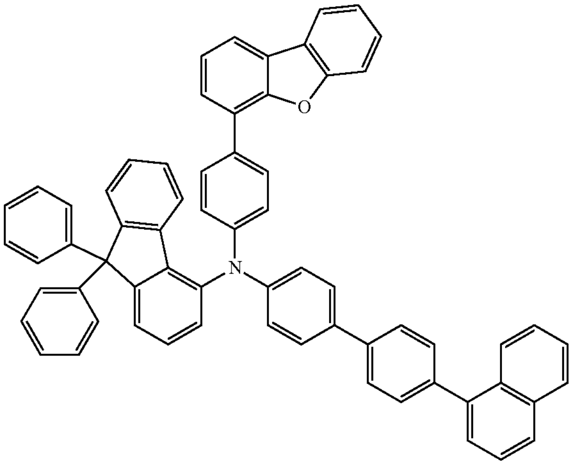
Compound 9
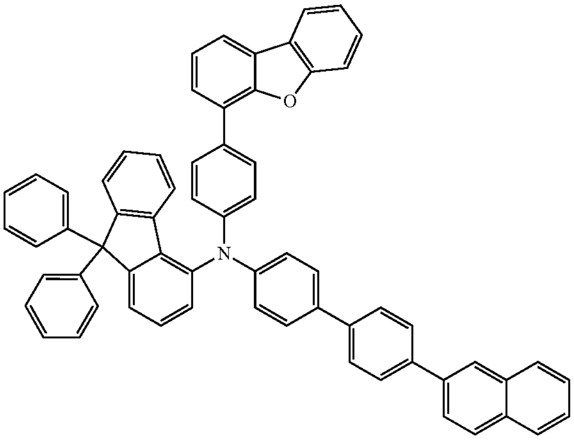
Compound 10
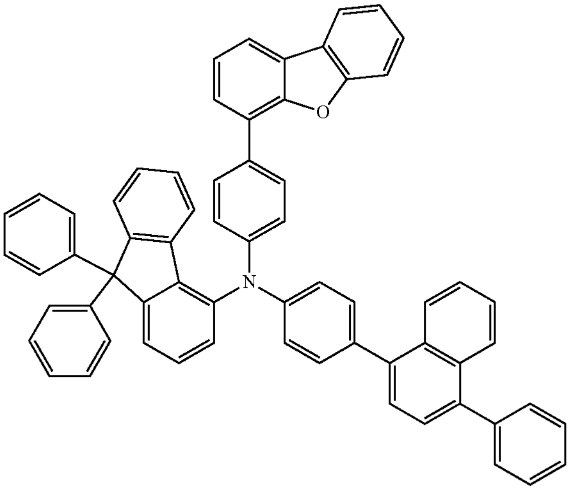
-continued
Compound 11
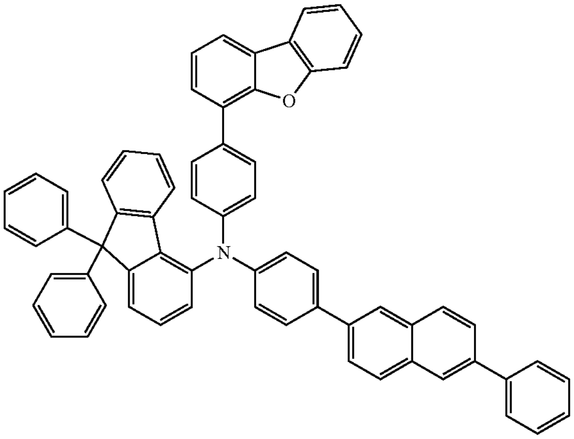
Compound 12
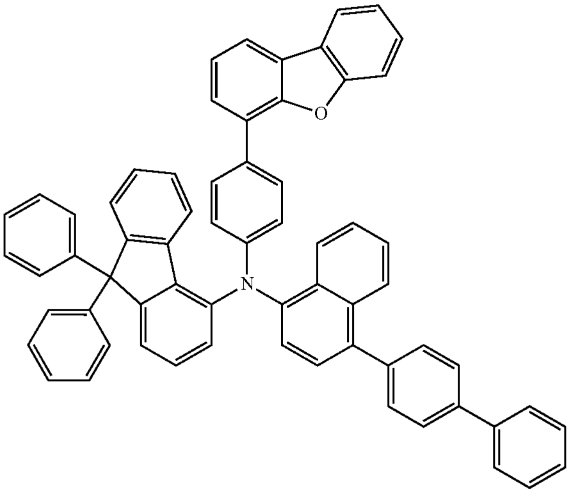
Compound 13
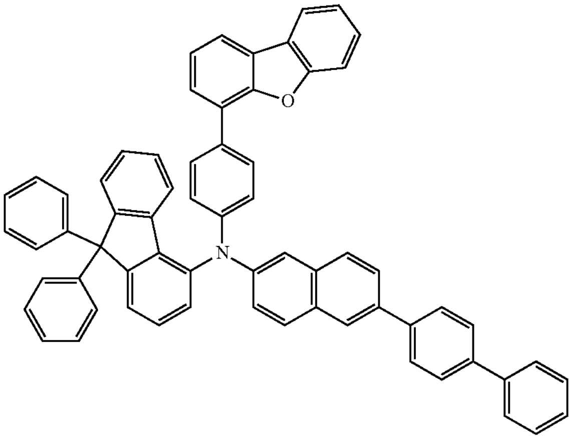

-continued

Compound 14

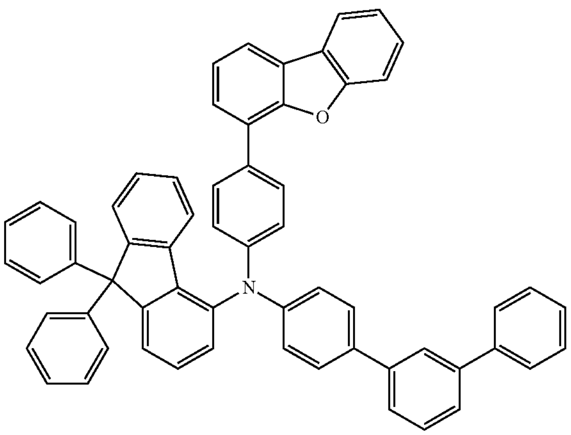

Compound 15

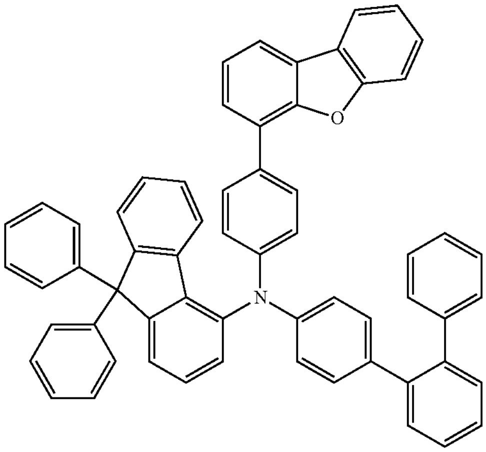

Compound 16

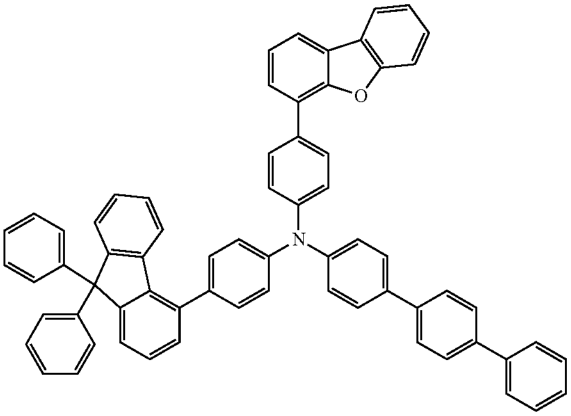

-continued

Compound 17

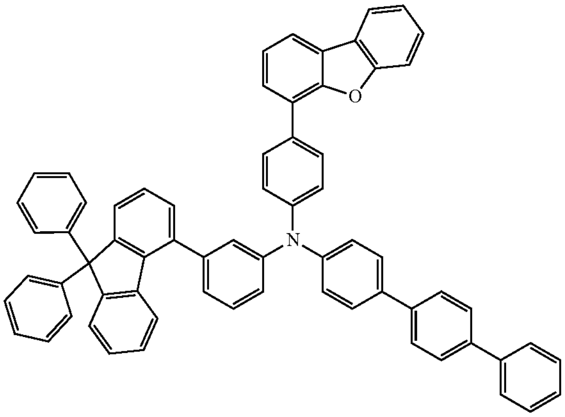

Compound 18

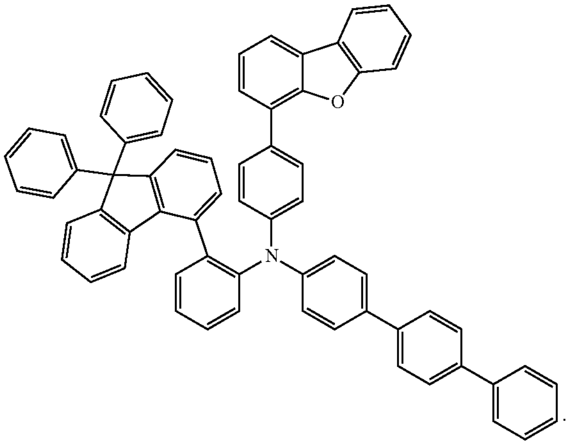

2. An organic electroluminescence device comprising:
an anode;
a cathode; and
an organic layer between the anode and the cathode,
wherein the organic layer comprises a light emitting layer and at least one layer of the organic layer comprises the compound according to claim 1.

3. The organic electroluminescence device according to claim 2, wherein the organic layer comprises a hole transporting region between the anode and the light emitting layer and the hole transporting region comprises the compound.

4. The organic electroluminescence device according to claim 3, wherein the hole transporting region comprises a first hole transporting layer at anode side and a second hole transporting layer at cathode side and the first hole transporting layer, the second hole transporting, or both comprise the compound.

5. The organic electroluminescence device according to claim 4, wherein the first hole transporting layer comprises the compound.

6. The organic electroluminescence device according to claim 4, wherein the second hole transporting layer comprises the compound.

7. The organic electroluminescence device according to claim 6, wherein the second hole transporting layer is in contact with the light emitting layer.

8. The organic electroluminescence device according to claim 2, wherein the light emitting layer comprises a fluorescent dopant material.

9. The organic electroluminescence device according to claim 2, wherein the light emitting layer comprises a phosphorescent dopant material.

10. An electronic device comprising:
the organic electroluminescence device according to claim 2.

11. The compound according to claim 1, wherein the compound is Compound 1.

12. A compound represented by one selected from the group consisting of formula (3a-1), formula (3a-2) and formula (3a-3)

(3a-1)

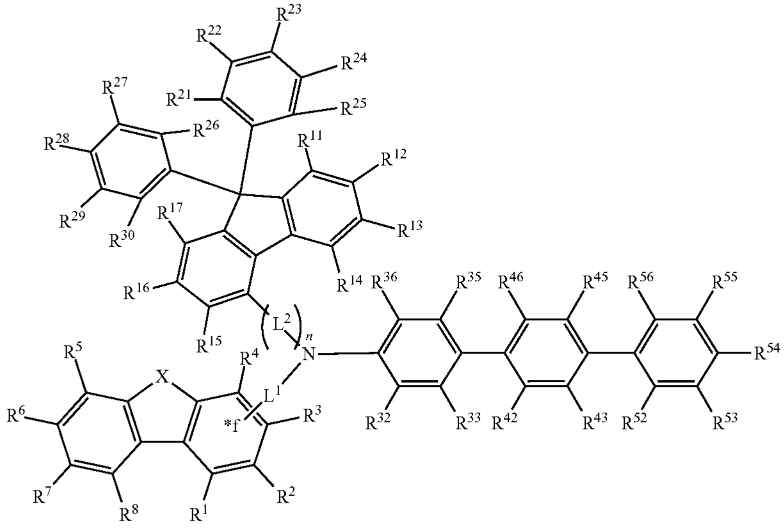

(3a-2)

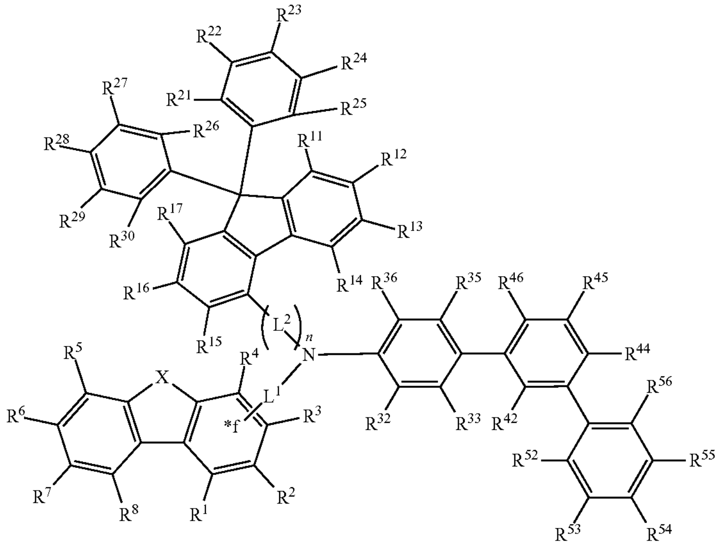

-continued (3a-3)

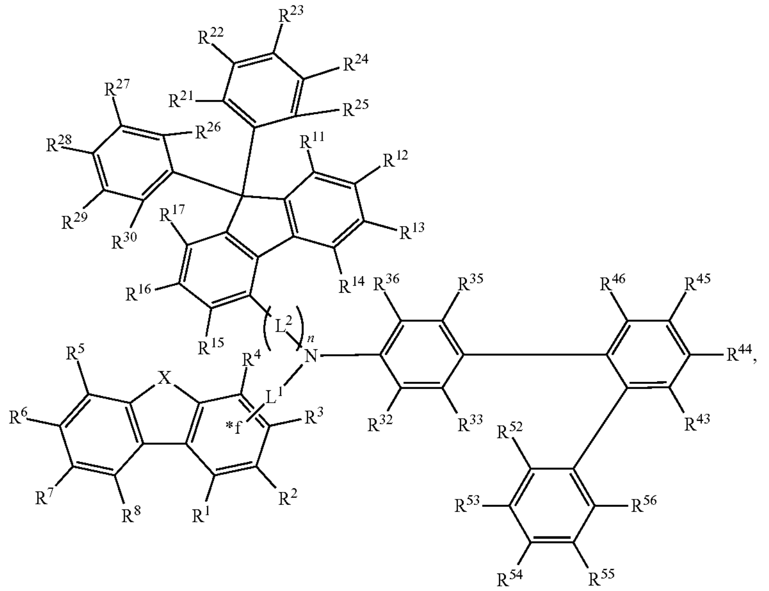

where X is an oxygen atom;

one selected from $R^1$ to $R^4$ is a single bond bonded to *f;

$R^5$ to $R^8$ and $R^1$ to $R^4$ not the single bond bonded to *f are hydrogen atoms;

$R^{11}$ to $R^{17}$ and $R^{21}$ to $R^{30}$ are hydrogen atoms;

$L^1$ and $L^2$ are each independently an unsubstituted phenylene group;

n is 0 or 1, when n is 0, $-(L^2)_0-$ is a single bond; and $R^{32}$, $R^{33}$, $R^{35}$, $R^{36}$, $R^{42}$ to $R^{46}$, and $R^{52}$ to $R^{56}$ are hydrogen atoms.

13. The compound according to claim 12, wherein the compound is represented by formula (3a-1).

14. The compound according to claim 13, wherein n is 1.

15. The compound according to claim 14, wherein $R^4$ is a single bond bonded to *f.

16. The compound according to claim 12, wherein n is 0.

17. The compound according to claim 16, wherein $R^1$ is a single bond bonded to *f.

18. The compound according to claim 16, wherein $R^3$ is a single bond bonded to *f.

19. The compound according to claim 16, wherein $R^4$ is a single bond bonded to *f.

20. The compound according to claim 12, wherein the compound is represented by formula (3a-2) or (3a-3), and n is 0.

21. A compound represented by formula (4a-1) or (4a-2)

(4a-1)

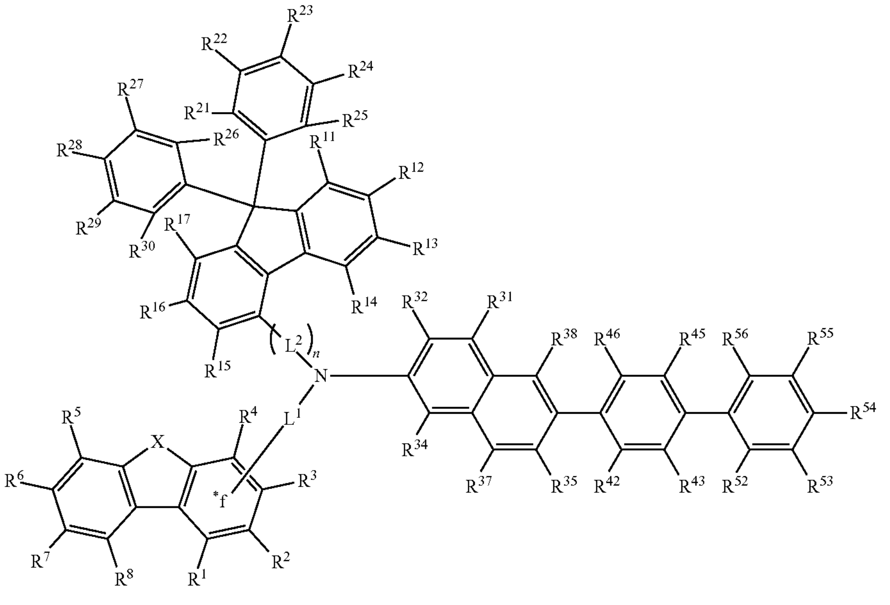

-continued (4a-2)

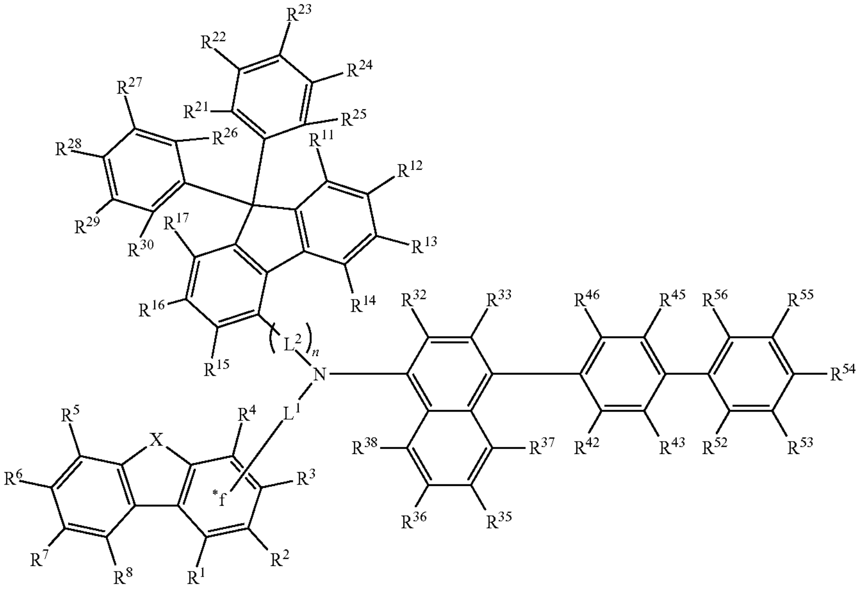

where X is an oxygen atom;

one selected from $R^1$ to $R^4$ is a single bond bonded to *f;

$R^5$ to $R^8$ and $R^1$ to $R^4$ not the single bond bonded to *f are hydrogen atoms;

$R^{11}$ to $R^{17}$ and $R^{21}$ to $R^{30}$ are hydrogen atoms;

$L^1$ and $L^2$ are each independently an unsubstituted phenylene group;

n is 0 or 1, when n is 0, $-(L^2)_0-$ is a single bond; and $R^{31}$ to $R^{38}$, $R^{42}$, $R^{43}$, $R^{45}$, $R^{46}$, and $R^{52}$ to $R^{56}$ are hydrogen atoms.

22. The compound according to claim 21, wherein n is 0, and $R^4$ is a single bond bonded to *f.

23. A compound represented by formula (5a-1) or (5a-2)

(5a-1)

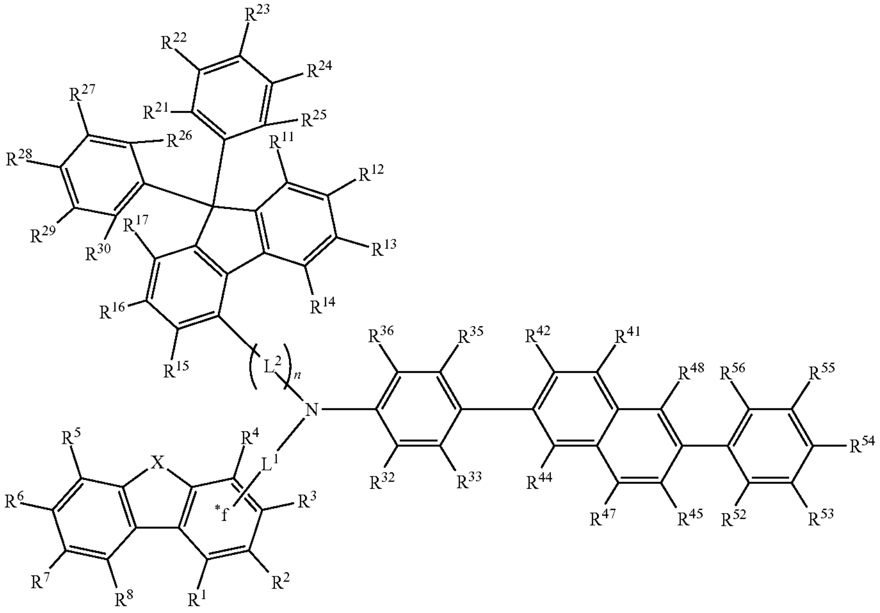

-continued (5a-2)

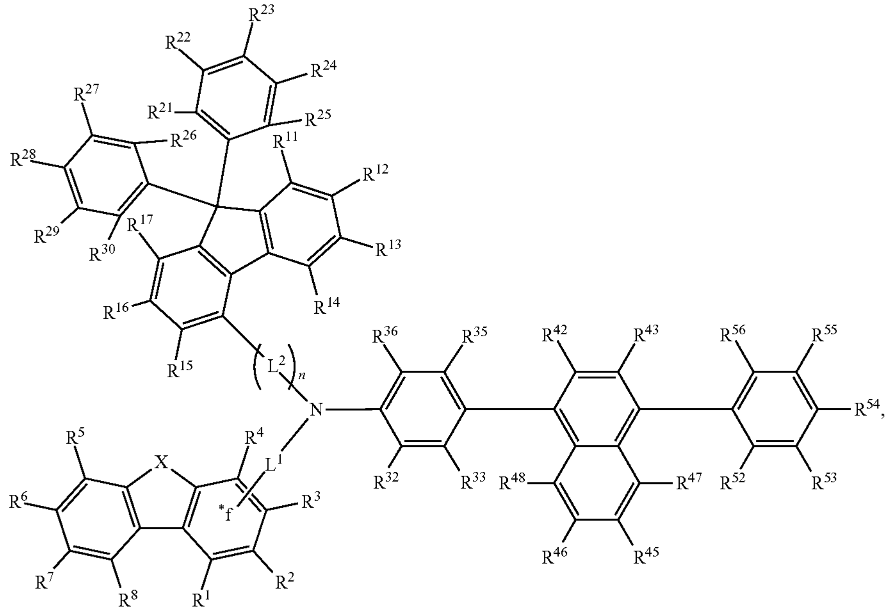

where X is an oxygen atom;

one selected from $R^1$ to $R^4$ is a single bond bonded to *f;

$R^5$ to $R^8$ and $R^1$ to $R^4$ not the single bond bonded to *f are hydrogen atoms;

$R^{11}$ to $R^{17}$ and $R^{21}$ to $R^{30}$ are hydrogen atoms;

$L^1$ and $L^2$ are each independently an unsubstituted phenylene group;

n is 0 or 1, when n is 0, $-(L^2)_0-$ is a single bond; and $R^{32}$, $R^{33}$, $R^{35}$, $R^{36}$, $R^{41}$ to $R^{48}$, and $R^{52}$ to $R^{56}$ are hydrogen atoms.

24. The compound according to claim 23, wherein n is 0, and $R^4$ is a single bond bonded to *f.

25. A compound represented by formula (6a-1) or (6a-2)

(6a-1)

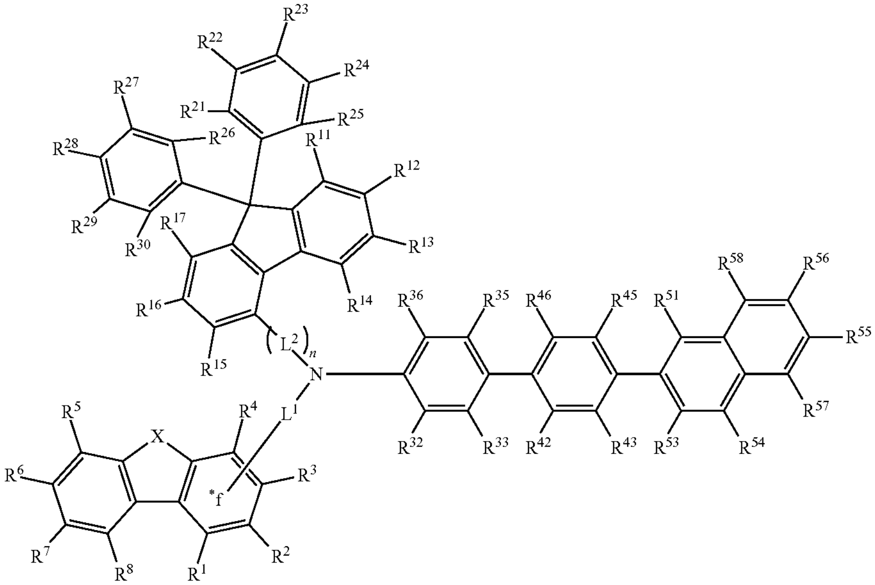

-continued (6a-2)

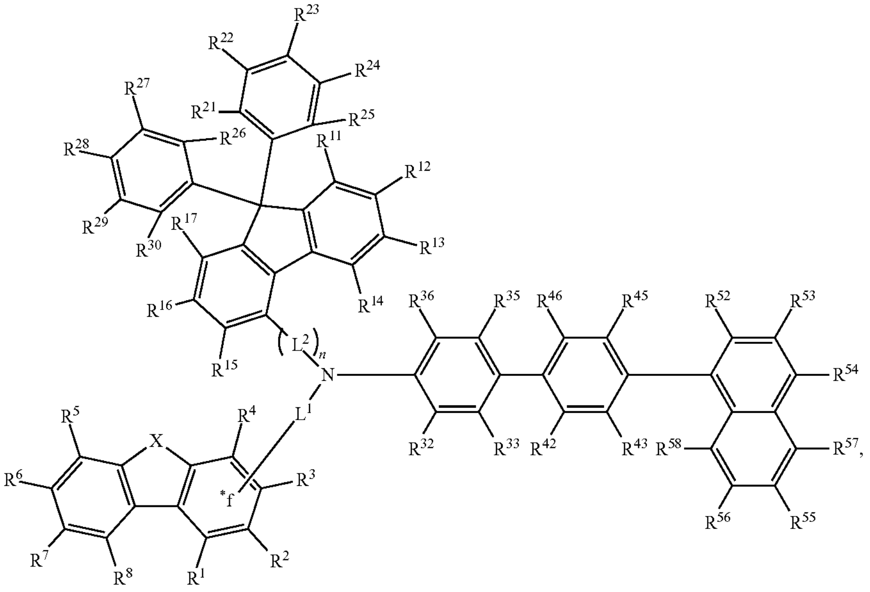

where X is an oxygen atom;

one selected from $R^1$ to $R^4$ is a single bond bonded to *f;

$R^5$ to $R^8$ and $R^1$ to $R^4$ not the single bond bonded to *f are hydrogen atoms;

$R^{11}$ to $R^{17}$ and $R^{21}$ to $R^{30}$ are hydrogen atoms;

$L^1$ and $L^2$ are each independently an unsubstituted phenylene group;

n is 0 or 1, when n is 0, $-(L^2)_0-$ is a single bond; and $R^{32}$, $R^{33}$, $R^{35}$, $R^{36}$, $R^{42}$, $R^{43}$, $R^{45}$, $R^{46}$, and $R^{51}$ to $R^{58}$ are hydrogen atoms.

26. The compound according to claim 25, wherein n is 0, and $R^4$ is a single bond bonded to *f.

* * * * *